United States Patent
Zhou et al.

(10) Patent No.: US 10,130,615 B2
(45) Date of Patent: Nov. 20, 2018

(54) BENZOMORPHAN ANALOGS AND THE USE THEREOF

(71) Applicant: Purdue Pharma L.P., Stamford, CT (US)

(72) Inventors: Xiaoming Zhou, Monmouth Junction, NJ (US); Laykea Tafesse, Robbinsville, NJ (US); John J. Engel, Linden, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 15/511,360

(22) PCT Filed: Sep. 17, 2015

(86) PCT No.: PCT/US2015/050617
§ 371 (c)(1),
(2) Date: Mar. 15, 2017

(87) PCT Pub. No.: WO2016/044546
PCT Pub. Date: Mar. 24, 2016

(65) Prior Publication Data
US 2017/0290816 A1    Oct. 12, 2017

Related U.S. Application Data

(60) Provisional application No. 62/051,320, filed on Sep. 17, 2014.

(51) Int. Cl.
| | | |
|---|---|---|
| C07D 221/26 | (2006.01) | |
| A61K 31/435 | (2006.01) | |
| C07D 401/12 | (2006.01) | |
| A61K 31/485 | (2006.01) | |

(52) U.S. Cl.
CPC .......... *A61K 31/435* (2013.01); *A61K 31/485* (2013.01); *C07D 221/26* (2013.01); *C07D 401/12* (2013.01)

(58) Field of Classification Search
CPC .................................................. C07D 221/26
See application file for complete search history.

(56) References Cited

U.S. PATENT DOCUMENTS

| | | | | |
|---|---|---|---|---|
| 3,341,538 A | * | 9/1967 | Block | C07D 221/26 514/823 |
| 3,480,638 A | * | 11/1969 | Clarke, Jr. | C07D 211/70 546/216 |

FOREIGN PATENT DOCUMENTS

WO    WO 2013167963 A1 * 11/2013 ........... C07D 221/26

OTHER PUBLICATIONS

Jorgenson, M. , J. Org Chem. 1962 vol. 27 pp. 3224-3228.*

* cited by examiner

*Primary Examiner* — Heidi Reese
(74) *Attorney, Agent, or Firm* — Purdue Pharma L.P.; Alan L. Koller; Weiying Yang

(57) ABSTRACT

In one aspect, the invention provides compounds of Formula (I) or (II): (I) or (II) and pharmaceutically acceptable salts and solvates thereof, wherein $R^1$, $R^{2a}$, $R^{2b}$, $R^3$, $R^4$, Z and G are defined as set forth in the disclosure. The invention also provides compounds of Formulae A and B and pharmaceutically acceptable salts and solvates thereof. Other aspects of the invention include the use of compounds of Formulae I, II, A, and B, and pharmaceutically acceptable salts and solvates thereof for the treatment of disorders responsive to modulation of one or more opioid receptors. In certain embodiments, the Compounds of the Invention are useful for treating pain.

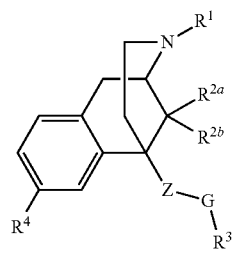

(I) or (II)

23 Claims, No Drawings

BENZOMORPHAN ANALOGS AND THE USE THEREOF

CROSS-REFERENCE TO RELATED APPLICATIONS

This application is the U.S. national phase, pursuant to 35 U.S.C. § 371, of PCT International Application Ser. No. PCT/US2015/050617, filed on Sep. 17, 2015, designating the United States and published in English on Mar. 24, 2016 as PCT Publication No. WO 2016/044546 A1, claiming priority to U.S. Provisional Application Ser. No. 62/051,320, filed on Sep. 17, 2014. The contents of the afore-mentioned patent applications are incorporated herein by their entirety.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Although the term "narcotic" is often used to refer to opioids, the term is not specifically applicable to opioids. The term "narcotic", derived from the Greek word for "stupor", originally referred to any drug that induced sleep, only later being associated with opioids (Gutstein, Howard B., Akil, Huda, "Chapter 21. Opioid Analgesics" (Chapter 21), Brunton, L L, Lazo, J S, Parker, K l: Goodman & Gilman's The Pharmacological Basis of Therapeutics, 11$^{th}$ Edition: http://www.accessmedicine.com/content.aspx?aID=940653). In the legal context, the term "narcotic" refers to a variety of mechanistically unrelated substances with abuse or addictive potential (Gutstein, Howard B., Akil, Huda, "Chapter 21. Opioid Analgesics" (Chapter 21), Brunton L L, Lazo J S, Parker K l: Goodman & Gilman's The Pharmacological Basis of Therapeutics, 11$^{th}$ Edition: http://www.accessmedicine.com/content.aspx?aID=940653). Thus, the term "narcotic" not only refers to opioids, but also refers to such drugs as cocaine, methamphetamine, ecstasy, etc., which exert their pharmacological effects via different receptors than opioids. Furthermore, because the term "narcotic" refers to such a wide variety of unrelated drugs, many of which do not possess analgesic properties, it cannot be assumed that a drug that has "narcotic" properties is necessarily analgesic. For example, drugs such as ecstasy and methamphetamine are not analgesic, and are not used to treat pain.

Until recently, there was evidence of three major classes of opioid receptors in the central nervous system (CNS), with each class having subtype receptors. These receptor classes are known as $\mu$, $\delta$ and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This newly discovered receptor was classified as an opioid receptor based only on structural grounds, as the receptor did not exhibit pharmacological homology. It was initially demonstrated that non-selective ligands having a high affinity for $\mu$, $\delta$ and $\kappa$ receptors had low affinity for the ORL-1 receptor. This characteristic, along with the fact that an endogenous ligand had not yet been discovered, led to the ORL-1 receptor being designated as an "orphan receptor".

Subsequent research led to the isolation and structure of the endogenous ligand of the ORL-1 receptor. This ligand, nociceptin (also known as orphanin FQ (OFQ)), is a seventeen amino acid peptide structurally similar to members of the opioid peptide family. (C. Altier et al., "ORL-1 receptor-mediated internalization of N-type calcium channels." *Nature Neuroscience*, 2005, 9:31).

The discovery of the ORL-1 receptor and its endogenous ligand presents an opportunity for the discovery of novel compounds that can be administered for pain management or other syndromes influenced by this receptor.

Many publications in the ORL-1/nociceptin field provide evidence that activation of ORL-1 receptors in the brain can inhibit opioid-mediated analgesia (e.g., D. Barlocco et al., "The opioid-receptor-like 1 (ORL-1) as a potential target for new analgesics." *Eur. J. Med. Chem.*, 2000, 35:275; J. S. Mogil et al., "Orphanin FQ is a functional anti-opioid peptide." *Neurosci.*, 1996, 75:333; K. Lutfy et al., "Tolerance develops to the inhibitory effect of orphanin FQ on morphine-induced antinociception in the rat." *NeuroReport*, 1999, 10:103; M. M. Morgan et al., "Antinociception mediated by the periaqueductal gray is attenuated by orphanin FQ." *NeuroReport*, 1997, 8:3431; and J. Tian et al., "Involvement of endogenous Orphanin FQ in electroacupuncture-induced analgesia." *NeuroReport*, 1997, 8:497).

A growing body of evidence supports a more generalized regulatory role for ORL-1 against the actions of the $\mu$ receptor, possibly contributing to the development of $\mu$-agonist tolerance in patients being treated with classical opiates (e.g., J. Tian et al., "Functional studies using antibodies against orphanin FQ/nociceptin." *Peptides*, 2000, 21:1047; and H. Ueda et al., "Enhanced Spinal Nociceptin Receptor Expression Develops Morphine Tolerance and Dependence." *J. Neurosci.*, 2000, 20:7640). Moreover, ORL-1 activation appears to have an inhibitory effect on the rewarding properties of several drugs of abuse, including $\mu$ agonists.

Use of opioid analgesics often leads to constipation as a side effect. Constipation associated with the use of opioid analgesics is presumed to occur primarily and mechanistically as a result of the action of mu opioid agonists directly upon mu opioid receptors located in the bowel (Wood & Galligan (2004), Function of opioids in the enteric nervous system. *Neurogastroenterology & Motility* 16 (Suppl.2): 17-28). Stimulation of the mu opioid receptors in the bowel causes inhibition of normal gastrointestinal (GI) motility, leading to constipation. The effect of $\mu$ opioid agonist on $\mu$ opioid receptors in the bowel can be observed via the action of lope amide (Imodium™) in treating diarrhea. Lope amide is a potent $\mu$ opioid agonist that is administered orally, but which has little to no absorption into the blood stream. As a result, lope amide exerts its action locally upon the $\mu$ opioid receptors in the bowel, and these results in inhibition of GI motility, which treats diarrhea.

There has been recent interest in developing combinations of $\mu$ receptor agonists and antagonists having defined bio distribution properties that might serve to limit opioid-induced constipation. For example, the co-administration of an orally bio-available μ opioid receptor agonist (such as morphine, codeine, oxycodone or hydromorphone) together with a potent μopioid receptor antagonist (such as N-methyl naloxone or N-methyl naltrexone) that is not orally bio-available may serve to prevent or reduce the constipation otherwise associated with mu opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

Benzo orphan analog compounds including, such as 3,11,11-trimethyl-1,2,3,4,5,6-hexahydro-2,6-methanobenzo[d]azocine-6,8-diol and 8-methoxy-3,11,11-trimethyl-1,2,3,4,5,6-hexahydro-2,6-methanobenzo[d]azocin-6-ol, having analgesic activity have been described (e.g. U.S. Pat. Nos. 4,425,353; 4,406,904; 4,366,325; and WO 2013/167963 A1).

BRIEF SUMMARY OF THE INVENTION

The invention provides novel benzo orphan analogs useful for treating a variety of conditions, including pain (such as, acute pain, chronic pain, or surgical pain) and constipation. In certain embodiments, the invention provides compounds of Formulae I, II, A, and B, provided below, and pharmaceutically acceptable salts, prodrugs and solvates thereof, that exhibit affinity for one or more of ORL-1, μ, δ, and/or κ opioid receptors. Such compounds, pharmaceutically acceptable salts, prodrugs and solvates are collectively referred to hereinafter as "Compounds of the Invention" (each is individually referred to hereinafter as a "Compound of the Invention").

In one aspect, the invention provides compounds of Formula I, and pharmaceutically acceptable salts or solvates thereof:

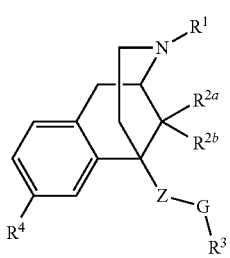

I wherein $R^1$ is —$(C_1$-$C_{10})$alkyl optionally substituted by —$(C_3$-$C_{12})$cycloalkyl;

$R^{2a}$ and $R^{2b}$ are, each independently, hydrogen or —$(C_1$-$C_5)$alkyl;

Z is —$(CH_2)_m$— optionally substituted with 1 or 2 independently selected —$(C_1$-$C_6)$alkyl;

G is selected from the group consisting of —$N(R^d)$, —O—, —$C(O)$—, —$N(R^a)C(O)N(R^a)$, $N(R^a)S(O)_2N(R^b)$, and —$C(O)N(R^c)$;

$R^3$ is selected from the group consisting of hydrogen, —$(C_1$-$C_{10})$alkyl, —$(C_3$-$C_{12})$cycloalkyl, —$C(=O)$ $(C_1$-$C_6)$alkyl, —$C(=O)$ $(C_3$-$C_{12})$cycloalkyl, -(3- to 12-membered)heterocyclo, -(6- to 14-membered)aryl, —$(C_1$-$C_6)$alkyl-(6- to 14-membered)aryl, -(5- to 12-membered)heteroaryl, —$(C_1$-$C_6)$alkyl-(5- to 12-membered)heteroaryl, —$S(O)_2$—$(C_1$-$C_6)$alkyl, —$S(O)_2$—$(C_3$-$C_{12})$cycloalkyl, —$S(O)_2$-(6- to 14-membered)aryl, and -(7- to 12-membered)bicycloheterocyclo; each of which is optionally substituted with one, two, or three substituents independently selected from the group consisting of (=O), halo, —$(C_1$-$C_6)$alkyl, $(C_1$-$C_6)$alkoxy, $COOR^6$, —$NHC(O)(C_1$-$C_6)$alkyl, —$C(O)R^5$, —$NH_2$, (alkyl)amino, (dialkyl)amino, $(C_3$-$C_{12})$cycloalkyl, —$(C_6$-$C_{14})$bicycloalkyl, —$(C_1$-$C_6)$alkyl$(C_6$-$C_{14})$bicycloalkyl, -(3- to 8-membered)heterocyclo, -(6- to 14-membered)aryl, -(5- to 12-membered)heteroaryl, aryloxy, carboxamido, —$C(O)NH(C_1$-$C_6)$alkyl, —$SO_2NH_2$, —$N(R^a)SO_2(C_1$-$C_6)$alkyl, —$SO_2N(R^a)(C_1$-$C_6)$alkyl, —$N(R^a)SO_2$-(6- to 14-membered)aryl, -(7- to 12-membered)bicycloheterocyclo, and $(C_1$-$C_6)$alkyl-(7- to 12-membered)-bicycloheterocyclo; wherein each of the —$(C_1$-$C_6)$alkyl, $(C_3$-$C_{12})$cycloalkyl, —$(C_6$-$C_{14})$bicycloalkyl, —$(C_1$-$C_6)$alkyl$(C_6$-$C_{14})$bicycloalkyl, -(3- to 8-membered)heterocyclo, -(6- to 14-membered)aryl, -(5- to 12-membered)heteroaryl, aryloxy, $N(R^a)SO_2(C_1$-$C_6)$alkyl, —$SO_2N(R^a)(C_1$-$C_6)$alkyl, —$N(R^a)SO_2$-(6- to 14-membered)aryl, -(7- to 12-membered)bicycloheterocyclo, and —$(C_1$-$C_6)$alkyl-(7- to 12-membered)bicycloheterocyclo is further optionally substituted by one or two substituents independently selected from the group consisting of —$(C_1$-$C_3)$alkyl, —$(C_1$-$C_3)$alkoxy, halogen, and carboxamido;

or $R^3$ and $R^d$, together with the nitrogen atom to which they are attached, form a (4- to 8-membered)heterocyclo, which is further optionally substituted by one to three independently selected $R^7$ groups;

Each of $R^a$ independently is hydrogen, —$(C_1$-$C_5)$alkyl, or —$(C_3$-$C_{12})$cycloalkyl;

$R^b$, and $R^c$, each independently, are hydrogen, —$(C_1$-$C_5)$alkyl, or —$(C_3$-$C_{12})$cycloalkyl;

$R^d$ is H or —$(C_1$-$C_6)$alkyl; or $R^d$ and $R^3$, together with the nitrogen atom to which they are attached, form a (4- to 8-membered)heterocyclo, which is further optionally substituted by one to three independently selected $R^7$ groups;

$R^4$ is hydrogen, OH, halo, —$(C_1$-$C_5)$alkyl, —$C(O)NH_2$, —$(C_1$-$C_5)$alkoxy, —$(C_2$-$C_5)$alkenyl, $(C_2$-$C_5)$alkynyl, or —$(CH_2)_n$—O—$(CH_2)_n$—$CH_3$; wherein each of the —$(C_1$-$C_5)$alkyl, —$C(O)NH_2$, —$(C_1$-$C_5)$alkoxy, —$(C_2$-$C_5)$alkenyl, —$(C_2$-$C_5)$alkynyl, and —$(CH_2)_n$—O—$(CH_2)_n$—$CH_3$, is optionally substituted by one to three independently selected $R^7$ groups;

$R^5$ is selected from the group consisting of hydrogen, —OH, —$NH_2$, —$(C_1$-$C_6)$alkyl, —$(C_2$-$C_5)$alkenyl, —$(C_2$-$C_5)$alkynyl, —$(C_1$-$C_6)$alkoxy, and —$(C_3$-$C_8)$cycloalkyl, each of —$NH_2$, —$(C_1$-$C_6)$alkyl, —$(C_2$-$C_5)$alkenyl, —$(C_2$-$C_5)$alkynyl, —$(C_1$-$C_6)$alkoxy, and —$(C_3$-$C_8)$cycloalkyl is optionally substituted with 1, 2, or 3 independently selected $R^6$ groups; or $R^6$ is selected from the group consisting of hydrogen, —$(C_1$-$C_6)$alkyl, —$(C_2$-$C_6)$alkenyl, $(C_2$-$C_6)$alkynyl, —$(C_3$-$C_{12})$cycloalkyl, —$(C_4$-$C_{12})$cycloalkenyl, $((C_3$-$C_{12})$cycloalkyl)-$(C_1$-$C_6)$alkyl-, and $((C_4$-$C_{12})$cycloalkenyl)-$(C_1$-$C_6)$alkyl-;

each $R^7$ is independently selected from the group consisting of —OH, (=O), —$NH_2$, halo, $(C_1$-$C_6)$alkyl, —$(C_1$-$C_6)$alkyl-(6- to 14-membered)aryl, —$(C_2$-$C_{10})$alkenyl, —$(C_2$-$C_{10})$alkynyl, $(C_1$-$C_6)$alkoxy, —$(C_3$-$C_{12})$cycloalkyl, —$C(O)$OH, —$C(O)O(C_1$-$C_6)$alkyl, carboxamido, $C(O)NH(C_1$-$C_6)$alkyl, —$NHC(O)(C_1$-$C_6)$alkyl, —$S(O)_2NH_2$, —$(CH_2)_n$—O—$(CH_2)_n$—$CH_3$, -(3- to 8-membered)heterocyclo, -(7- to 12-membered)bicycloheterocyclo, and —$N(R^a)SO_2$-(6- to 14-membered)aryl; wherein each of the —$(C_1$-$C_6)$alkyl, —$(C_1$-$C_6)$alkyl-(6- to 14-membered)aryl, -(3- to 8-membered)heterocyclo, -(7- to 12-membered)bicycloherocyclo, and —N(R$^a$)SO$_2$-(6- to 14-membered)aryl is optionally substituted by one to three substituents independently selected from the group of (=O), —(C$_1$-C$_3$)alkyl, —NH$_2$, halogen, and phenyl optionally substituted by halogen; and wherein the -(3- to 8-membered)heterocyclo is further optionally fused together with a phenyl group;

m is 1, 2, 3, 4, 5, or 6;
n is 0, 1, 2, 3, 4, 5, or 6;
provided that
(i) when G is —O—, and R$^3$ is optionally-substituted -(5- to 12-membered)heteroaryl or optionally-substituted -(6- to 14-membered)aryl, then R$^1$ is unsubstituted —(C$_1$-C$_{10}$)alkyl;
(ii) when G is —O—, and R$^3$ is H or —CH$_2$Ph, then Z is —CH$_2$CH$_2$—;
(iv) when -G-R$^3$ is —C(O)NH$_2$, then R$^1$ is —(C$_1$-C$_{10}$)alkyl that is either unsubstituted or substituted by cyclobutyl;

further provided that said compound is not
a) 4-((6S,11R)-3-(cyclopropylmethyl)-8-methoxy-11-methyl-2,3,4,5-tetrahydro-2,6-methanobenzo[d]azocin-6(1H)-yl)-N-isobutylbutan-1-amine (Compound E1);
b) 4-((2R,6R,11R)-8-hydroxy-3-isopropyl-11-methyl-2,3,4,5-tetrahydro-2,6-methanobenzo[d]azocin-6(1H)-yl)butanamide (Compound E2);
c) 4-((2R,6R,11R)-8-hydroxy-3-isobutyl-11-methyl-2,3,4,5-tetrahydro-2,6-methanobenzo[d]azocin-6(1H)-yl)butanamide (Compound E3);
d) 3-((2-((2R,6R,11R)-3-(cyclopropylmethyl)-8-methoxy-11-methyl-2,3,4,5-tetrahydro-2,6-methanobenzo[d]azocin-6(1H)-yl)ethyl)carbamoyl)benzoic acid (Compound E4);
e) 4-((2-((2R,6R,11R)-3-(cyclopropylmethyl)-8-methoxy-11-methyl-2,3,4,5-tetrahydro-2,6-methanobenzo[d]azocin-6(1H)-yl)ethyl)carbamoyl)benzoic acid (Compound E5);
f) methyl 3-((2-((2R,6R,11R)-3-(cyclopropylmethyl)-8-methoxy-11-methyl-2,3,4,5-tetrahydro-2,6-methanobenzo[d]azocin-6(1H)-yl)ethyl)-carbamoyl)-benzoate (Compound E6);
g) N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-2-(dimethylamino)acetamide (Compound E7); or
h) 2-amino-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)acetamide (Compound E8).

Another aspect of the invention provides compounds of Formula II, and pharmaceutically acceptable salts or solvates thereof:

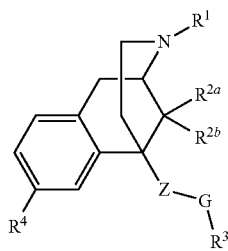

II wherein
R$^1$ is —(C$_1$-C$_{10}$)alkyl optionally substituted by —(C$_3$-C$_{12}$)cycloalkyl;
R$^{2a}$ and R$^{2b}$, are each independently, hydrogen or —(C$_1$-C$_5$)alkyl;
Z is —(CH$_2$)$_m$— optionally substituted with 1 or 2 independently selected —(C$_1$-C$_6$)alkyl;
G is selected from the group consisting of —N(R$^d$), —O—, —N(R$^a$)C(O)N(R$^a$), —C(O), N(R$^a$)S(O)$_2$N(R$^b$), and —C(O)N(R$^c$);
R$^3$ is selected from the group consisting of hydrogen, —(C$_1$-C$_{10}$)alkyl, —(C$_3$-C$_{12}$)cycloalkyl, —C(=O) (C$_1$-C$_6$)alkyl, —C(=O) (C$_3$-C$_{12}$)cycloalkyl, -(3- to 12-membered)heterocyclo, -(6- to 14-membered)aryl, —(C$_1$-C$_6$)alkyl-(6- to 14-membered)aryl, -(5- to 12-membered)heteroaryl, —(C$_1$-C$_6$)alkyl-(5- to 12-membered)heteroaryl, —S(O)$_2$—(C$_1$-C$_6$)alkyl, —S(O)$_2$—(C$_3$-C$_{12}$)cycloalkyl, —S(O)$_2$-(6- to 14-membered)aryl, and -(7- to 12-membered)bicycloheterocyclo; each of which is optionally substituted with one, two, or three substituents independently selected from the group consisting of (=O), halo, —(C$_1$-C$_6$)alkyl, (C$_1$-C$_6$)alkoxy, —COOR$^6$, —NHC(O)(C$_1$-C$_6$)alkyl, —C(O)R$^5$, —NH$_2$, (alkyl)amino, (dialkyl)amino, (C$_3$-C$_{12}$)cycloalkyl, —(C$_6$-C$_{14}$)bicycloalkyl, —(C$_1$-C$_6$)alkyl(C$_6$-C$_{14}$)bicycloalkyl, -(3- to 8-membered)-heterocyclo, -(6- to 14-membered)aryl, -(5- to 12-membered)heteroaryl, aryloxy, carboxamido, —C(O)NH(C$_1$-C$_6$)alkyl, —SO$_2$NH$_2$, —N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and (C$_1$-C$_6$)alkyl-(7- to 12-membered)bicycloheterocyclo; wherein each of the —(C$_1$-C$_6$)alkyl, —(C$_3$-C$_{12}$)cycloalkyl, —(C$_6$-C$_{14}$)bicycloalkyl, —(C$_1$-C$_6$)alkyl(C$_6$-C$_{14}$)bicycloalkyl, -(3- to 8-membered)heterocyclo, -(6- to 14-membered)aryl, -(5- to 12-membered)heteroaryl, aryloxy, N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo is further optionally substituted by one or two substituents independently selected from the group consisting of —(C$_1$-C$_3$)alkyl, —(C$_1$-C$_3$)alkoxy, halogen, and carboxamido;
or R$^3$ and R$^d$, together with the nitrogen atom to which they are attached, form a (4- to 8-membered)heterocyclo, which is further optionally substituted by one to three independently selected R$^7$ groups;
Each of R$^a$ independently is hydrogen, —(C$_1$-C$_5$)alkyl, or —(C$_3$-C$_{12}$)cycloalkyl;
R$^b$, and R$^c$, each independently, are hydrogen, —(C$_1$-C$_5$)alkyl, or —(C$_3$-C$_{12}$)cycloalkyl;
R$^d$ is H or —(C$_1$-C$_6$)alkyl; or R$^d$ and R$^3$, together with the nitrogen atom to which they are attached, form a (4- to 8-membered)heterocyclo, which is further optionally substituted by one to three independently selected R$^7$ groups;
R$^4$ is hydrogen, OH, halo, —(C$_1$-C$_5$)alkyl, —C(O)NH$_2$, —(C$_1$-C$_5$)alkoxy, —(C$_2$-C$_5$)alkenyl, (C$_2$-C$_5$)alkynyl, or —(CH$_2$)$_n$—O—(CH$_2$)$_n$—CH$_3$; wherein each of the —(C$_1$-C$_5$)alkyl, —C(O)NH$_2$, —(C$_1$-C$_5$)alkoxy, —(C$_2$-C$_5$)alkenyl, —(C$_2$-C$_5$)alkynyl, and —(CH$_2$)$_n$—O—(CH$_2$)$_n$—CH$_3$, is optionally substituted by one to three independently selected R$^7$ groups;
R$^5$ is selected from the group consisting of hydrogen, —OH, —NH$_2$, —(C$_1$-C$_6$)alkyl, —(C$_2$-C$_5$)alkenyl, —(C$_2$-C$_5$)alkynyl, —(C$_1$-C$_6$)alkoxy, and —(C$_3$-C$_8$)cycloalkyl, each of —NH$_2$, —(C$_1$-C$_6$)alkyl, —(C$_2$-C$_5$)alkenyl, —(C$_2$-C$_5$)alkynyl, —(C$_1$-C$_6$)alkoxy, and —(C$_3$-C$_8$)cycloalkyl is optionally substituted with 1, 2, or 3 independently selected R$^6$ groups; or $R^6$ is selected from the group consisting of hydrogen, —$(C_1-C_6)$alkyl, —$(C_2-C_6)$alkenyl, $(C_2-C_6)$alkynyl, $(C_3-C_{12})$cycloalkyl, —$(C_4-C_{12})$cycloalkenyl, $((C_3-C_{12})$cycloalkyl)-$(C_1-C_6)$alkyl-, and $((C_4-C_{12})$cycloalkenyl)-$(C_1-C_6)$alkyl-;

each $R^7$ is independently selected from the group consisting of —OH, (=O), —$NH_2$, halo, $(C_1-C_6)$alkyl, —$(C_1-C_6)$alkyl-(6- to 14-membered)aryl, —$(C_2-C_{10})$alkenyl, —$(C_2-C_{10})$alkynyl, $(C_1-C_6)$alkoxy, —$(C_3-C_{12})$cycloalkyl, —C(O)OH, —C(O)O$(C_1-C_6)$alkyl, carboxamido, C(O)NH$(C_1-C_6)$alkyl, —NHC(O)$(C_1-C_6)$alkyl, —S(O)$_2$NH$_2$, —$(CH_2)_n$—O—$(CH_2)_n$—$CH_3$, -(3- to 8-membered)heterocyclo, -(7- to 12-membered)bicycloheterocyclo, and —N($R^a$)SO$_2$-(6- to 14-membered)aryl; wherein each of the —$(C_1-C_6)$alkyl, —$(C_1-C_6)$alkyl-(6- to 14-membered)aryl, -(3- to 8-membered)heterocyclo, -(7- to 12-membered)bicycloheterocyclo, and —N($R^a$)SO$_2$-(6- to 14-membered)aryl is optionally substituted by one to three substituents independently selected from the group of (=O), —$(C_1-C_3)$alkyl, —$NH_2$, halogen, and phenyl optionally substituted by halogen; and wherein the -(3- to 8-membered)heterocyclo is further optionally fused together with a phenyl group;

m is 1, 2, 3, 4, 5, or 6; and n is 0, 1, 2, 3, 4, 5, or 6;

provided that (i) when G is —O—, and $R^3$ is optionally-substituted -(5- to 12-membered)heteroaryl or optionally-substituted -(6- to 14-membered)aryl, then $R^1$ is unsubstituted —$(C_1-C_{10})$alkyl;

(ii) when G is —O—, and $R^3$ is H or —$CH_2$Ph, then Z is —$CH_2CH_2$—;

(iii) when -G-$R^3$ is —C(O)NH$_2$, then $R^1$ is —$(C_1-C_{10})$alkyl that is either unsubstituted or substituted by cyclobutyl; and (iv) when $R^1$ is cyclopropylmethyl, $R^4$ is methoxy, Z is —$(CH_2)_2$—, one of $R^{2a}$ and $R^{2b}$ is H, and the other is methyl, and G is —NHC(O), then $R^3$ is $(C_1-C_6)$alkyl, -(3- to 12-membered)heterocyclo, or —$(C_1-C_6)$alkyl-(6- to 14-membered)aryl; each of which is substituted with one, two, or three substituents independently selected from the group consisting of (=O), halo, —$NH_2$, —$(C_1-C_6)$alkyl, $(C_1-C_6)$alkoxy, —COOR$^6$, —NHC(O)$(C_1-C_6)$alkyl, —C(O)$R^5$, —$(C_3-C_{12})$cycloalkyl, -(3- to 8-membered)-heterocyclo, -(6- to 14-membered)aryl, -(5- to 12-membered)heteroaryl, aryloxy, carboxamido, —C(O)NH$(C_1-C_6)$alkyl, —SO$_2$NH$_2$, —N($R^a$)SO$_2$$(C_1-C_6)$alkyl, —SO$_2$N($R^a$)$(C_1-C_6)$alkyl, —N($R^a$)SO$_2$-(6- to 14-membered)aryl, -(7- to 12-membered)bicycloheterocyclo, and $(C_1-C_6)$alkyl-(7- to 12-membered)bicycloheterocyclo; wherein each of the —$(C_1-C_6)$alkyl, —$(C_3-C_{12})$cycloalkyl, -(3- to 8-membered)heterocyclo, -(6- to 14-membered)aryl, -(5- to 12-membered)heteroaryl, aryloxy, —N($R^a$)SO$_2$$(C_1-C_6)$alkyl, —SO$_2$N($R^a$)$(C_1-C_6)$alkyl, —N($R^a$)SO$_2$-(6- to 14-membered)aryl, -(7- to 12-membered)bicycloheterocyclo, and —$(C_1-C_6)$alkyl-(7- to 12-membered)bicycloheterocyclo is further optionally substituted by one or two substituents independently selected from the group consisting of —$(C_1-C_3)$alkyl, —$(C_1-C_3)$alkoxy, halogen, and carboxamido;

(v) when $R^1$ is unsubstituted —$(C_1-C_{10})$alkyl, then $R^1$ is a straight —$(C_1-C_{10})$alkyl chain;

(vi) when G is —N($R^a$), and $R^3$ is —$(C_1-C_{10})$alkyl optionally substituted by —$(C_1-C_6)$alkyl, then $R^4$ is —OH; and (vii) when $R^1$ is cyclopropylmethyl, Z is —$(CH_2)_2$—, and $R^3$ is a) —$(C_1-C_{10})$alkyl substituted by —$NH_2$ or (dialkyl)amino; or b) —C(=O) $(C_1-C_6)$alkyl substituted by —$NH_2$ or (dialkyl)amino; then $R^4$ is methoxy.

In certain embodiments of Formula I or II, the invention provides compounds of Formula A and B, and pharmaceutically acceptable salts or solvates thereof.

In another aspect, the invention provides the use of Compounds of the Invention as synthesis intermediates.

In another aspect, the invention provides the use of Compounds of the Invention as modulators of one or more opioid receptors. Specifically, the present disclosure provides the use of Compounds of the Invention as modulators of μ, δ, κ, and/or ORL-1 opioid receptors, and especially modulators of μ and/or κ opioid receptors.

Another aspect of the invention provides a method of treating or preventing a disorder responsive to the modulation of one or more opioid receptors in a patient, comprising administering to the patient an effective amount of a Compound of the Invention.

In still another aspect, the invention provides use of a Compound of the Invention as an analgesic to treat or prevent pain; or as an agent to treat or prevent withdrawal from alcohol or drug addiction; or as an agent to treat or prevent addictive disorders; or as an agent to treat a pruritic condition; or as an agent to treat or prevent constipation; or as an agent to treat or prevent diarrhea (each of pain, alcohol withdrawal, drug withdrawal, addictive disorders, pruritis, constipation, and diarrhea being a "Condition").

The invention further provides methods of treating or preventing a Condition, comprising administering to a patient in need thereof a therapeutically effective amount of a Compound of the Invention. In certain embodiments, the Condition is pain (including acute pain, chronic pain and surgical pain). In one embodiment, the Compounds of the Invention are useful for treating or preventing chronic pain (which includes, but is not limited to, neuropathic pain, postoperative pain, and inflammatory pain).

In another aspect, the present disclosure provides a pharmaceutical composition comprising a therapeutically effective amount of a Compound of the Invention and one or more pharmaceutically acceptable carriers. Such compositions are useful for treating or preventing a Condition in a patient.

In another aspect, the present disclosure provides the Compounds of the Invention for use in treatment or prevention of a disorder responsive to the modulation of one or more opioid receptors. In certain embodiments, the disorder is responsive to modulation of the μ-opioid receptor or the κ-opioid receptor, or to modulation of a combination thereof.

In another aspect, the present disclosure provides a method of modulating one or more opioid receptors in a patient in need of said modulation, comprising administering to the patient an opioid receptor modulating amount of a Compound of the Invention.

In another aspect, the present disclosure provides the Compounds of the Invention for use in the treatment or prevention of one or more Conditions in a patient in need of said treatment or prevention.

In still another aspect, the present disclosure provides the Compounds of the Invention for use in the treatment or prevention of pain in a patient, such as acute pain, chronic pain (which includes but is not limited to, neuropathic pain, postoperative pain, and inflammatory pain), or surgical pain.

In yet another aspect, the present disclosure provides the Compounds of the Invention for use in modulation of one or more opioid receptors in a patient.

In another aspect, the present disclosure provides use of the Compounds of the Invention in the manufacture of a medicament for treating or preventing a disorder responsive to the modulation of one or more opioid receptors.

In another aspect, the present disclosure provides use of the Compounds of the Invention in the manufacture of a medicament for modulating of one or more opioid receptors in a patient. In certain embodiments, µ- or κ-opioid receptors are modulated, or both the µ- and κ-opioid receptors are modulated.

In another aspect, the present disclosure provides the Compounds of the Invention for use as a medicament.

In another aspect, the present disclosure provides use of a Compound of the Invention in the manufacture of a medicament for treating or preventing a Condition in a patient.

In another aspect, the present disclosure provides use of a Compound of the Invention in the manufacture of a medicament for treating or preventing pain in a patient, such as acute pain, chronic pain, or surgical pain.

In another aspect, the present disclosure provides a pharmaceutical composition, comprising a Compound of the Invention for treating or preventing a disorder responsive to the modulation of one or more opioid receptors.

The invention further provides methods for preparing a pharmaceutical composition, comprising admixing a Compound of the Invention and a pharmaceutically acceptable carrier to form the pharmaceutical composition.

In another aspect, the invention provides radiolabeled Compounds of the Invention, especially $^1$H, $^{11}$C and $^{14}$C radiolabeled Compounds of the Invention, and the use of such compounds as radioligands to detect binding to an opioid receptor in screening assays.

In another aspect, the invention provides a method for screening a candidate compound for the ability to bind to an opioid receptor, comprising a) introducing a fixed concentration of a radiolabeled Compound of the Invention to the receptor under conditions that permit binding of the radiolabeled compound to the receptor to form a complex; b) titrating the complex with a candidate compound; and c) determining the binding of the candidate compound to said receptor.

In a further aspect, the invention relates to a kit, comprising a sterile container containing an effective amount of a Compound of the Invention and instructions for therapeutic use.

In a further aspect, the invention provides a method of making the Compounds of the Invention.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

DETAILED DESCRIPTION OF THE INVENTION

In one aspect, the invention provides benzomorphan analogs, and pharmaceutically acceptable salts, prodrugs, and solvates thereof (also referred to as the "Compounds of the Invention"). In certain embodiments, the benzomorphan analogs of the invention are useful for treating one or more Conditions, such as pain or constipation. Certain Compounds of the Invention may provide a reduced liability for developing analgesic tolerance and physical dependence.

Certain compounds of the invention are novel compounds that are expected to have antagonist activity at the ORL-1 receptor that is greater than compounds currently available, e.g., JTC-801 (described in WO 99/48492; and Shinkai et al., "4-aminoquinolines: Novel nociceptin antagonists with analgesic activity", *J. Med. Chem.*, 2000, 43:4667-4677) and J-113397 (described in WO 98/54168; and Kawamoto et al., "Discovery of the first potent and selective small molecule opioid receptor-like (ORL-1) antagonist: 1-[(3R,4R)-1-cyclooctylmethyl-3-hydroxymethyl-4-piperidyl]-3-ethyl-1,3-dihydro-2H-benzimidazol-2-one (J-113397)", *J. Med. Chem.*, 1999, 42:5061-6063).

In certain embodiments, the invention provides benzomorphan analogs useful for treating or preventing constipation, such as, µ opioid receptor-induced constipation.

One aspect of the invention provides compounds of Formula I, and pharmaceutically acceptable salts or solvates thereof:

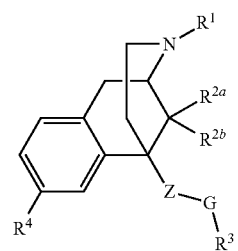

I wherein
$R^1$ is —$(C_1-C_{10})$alkyl optionally substituted by —$(C_3-C_{12})$cycloalkyl;
$R^{2a}$ and $R^{2b}$ are, each independently, hydrogen or —$(C_1-C_5)$alkyl;
Z is —$(CH_2)_m$— optionally substituted with 1 or 2 independently selected —$(C_1-C_6)$alkyl;
G is selected from the group consisting of —N($R^a$), —O—, —C(O), —N($R^a$)C(O)N($R^a$), N($R^a$)S(O)$_2$N($R^b$), and —C(O)N($R^c$)—;
$R^3$ is selected from the group consisting of hydrogen, —$(C_1-C_{10})$alkyl, —$(C_3-C_{12})$cycloalkyl, —C(=O) $(C_1-C_6)$alkyl, —C(=O) $(C_3-C_{12})$cycloalkyl, -(3- to 12-membered) heterocyclo, -(6- to 14-membered)aryl, —$(C_1-C_6)$alkyl-(6- to 14-membered)aryl, -(5- to 12-membered)heteroaryl, —$(C_1-C_6)$alkyl-(5- to 12-membered)heteroaryl, —S(O)$_2$—$(C_1-C_6)$alkyl, —S(O)$_2$—$(C_3-C_{12})$cycloalkyl, —S(O)$_2$-(6- to 14-membered)aryl, and -(7- to 12-membered)bicycloheterocyclo; each of which is optionally substituted with one, two, or three substituents independently selected from the group consisting of (=O), halo, —$(C_1-C_6)$alkyl, $(C_1-C_6)$alkoxy, —COOR$^6$, —NHC(O)$(C_1-C_6)$alkyl, —C(O)R$^5$, —NH$_2$, (alkyl)amino, (dialkyl)amino, $(C_3-C_{12})$cycloalkyl, —$(C_6-C_{14})$bicycloalkyl, —$(C_1-C_6)$alkyl$(C_6-C_{14})$bicycloalkyl, -(3- to 8-membered)heterocyclo, -(6- to 14-membered)aryl, -(5- to 12-membered)heteroaryl, aryloxy, carboxamido, —C(O)NH$(C_1-C_6)$alkyl, —SO$_2$NH$_2$, —N($R^a$)SO$_2$$(C_1-C_6)$alkyl, —SO$_2$N($R^a$)$(C_1-C_6)$alkyl, —N($R^a$)SO$_2$-(6- to 14-membered)aryl, -(7- to 12-membered)bicycloheterocyclo, and $(C_1-C_6)$alkyl-(7- to 12-membered)bicycloheterocyclo; wherein each of the —$(C_1-C_6)$alkyl, —$(C_3-C_{12})$cycloalkyl, —$(C_6-C_{14})$bicycloalkyl, —$(C_1-C_6)$alkyl$(C_6-C_{14})$bicycloalkyl, -(3- to 8-membered)heterocyclo, -(6- to 14-membered)aryl, -(5- to 12-membered)heteroaryl, aryloxy, N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo is further optionally substituted by one or two substituents independently selected from the group consisting of —(C$_1$-C$_3$)alkyl, —(C$_1$-C$_3$)alkoxy, halogen, and carboxamido;

or R$^3$ and R$^d$, together with the nitrogen atom to which they are attached, form a (4- to 8-membered)heterocyclo, which is further optionally substituted by one to three independently selected R$^7$ groups;

Each of R$^a$ independently is hydrogen, —(C$_1$-C$_5$)alkyl, or —(C$_3$-C$_{12}$)cycloalkyl;

R$^b$, and R$^c$, each independently, are hydrogen, —(C$_1$-C$_5$)alkyl, or —(C$_3$-C$_{12}$)cycloalkyl;

R$^d$ is H or —(C$_1$-C$_6$)alkyl; or R$^d$ and R$^3$, together with the nitrogen atom to which they are attached, form a (4- to 8-membered)heterocyclo, which is further optionally substituted by one to three independently selected R$^7$ groups;

R$^4$ is hydrogen, OH, halo, —(C$_1$-C$_5$)alkyl, —C(O)NH$_2$, —(C$_1$-C$_5$)alkoxy, —(C$_2$-C$_5$)alkenyl, (C$_2$-C$_5$)alkynyl, or —(CH$_2$)$_n$—O—(CH$_2$)$_n$—CH$_3$; wherein each of the —(C$_1$-C$_5$)alkyl, —C(O)NH$_2$, —(C$_1$-C$_5$)alkoxy, —(C$_2$-C$_5$)alkenyl, —(C$_2$-C$_5$)alkynyl, and —(CH$_2$)$_n$—O—(CH$_2$)$_n$—CH$_3$, is optionally substituted by one to three independently selected R$^7$ groups;

R$^5$ is selected from the group consisting of hydrogen, —OH, —NH$_2$, —(C$_1$-C$_6$)alkyl, —(C$_2$-C$_5$)alkenyl, —(C$_2$-C$_5$)alkynyl, —(C$_1$-C$_6$)alkoxy, and —(C$_3$-C$_8$)cycloalkyl, each of —NH$_2$, —(C$_1$-C$_6$)alkyl, —(C$_2$-C$_5$)alkenyl, —(C$_2$-C$_5$)alkynyl, —(C$_1$-C$_6$)alkoxy, and —(C$_3$-C$_8$)cycloalkyl is optionally substituted with 1, 2, or 3 independently selected R$^6$ groups; or R$^6$ is selected from the group consisting of hydrogen, —(C$_1$-C$_6$)alkyl, —(C$_2$-C$_6$)alkenyl, (C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each R$^7$ is independently selected from the group consisting of —OH, (=O), —NH$_2$, halo, (C$_1$-C$_6$)alkyl, —(C$_1$-C$_6$)alkyl-(6- to 14-membered)aryl, —(C$_2$-C$_{10}$)alkenyl, —(C$_2$-C$_{10}$)alkynyl, (C$_1$-C$_6$)alkoxy, —(C$_3$-C$_{12}$)cycloalkyl, —C(O)OH, —C(O)O(C$_1$-C$_6$)alkyl, carboxamido, C(O)NH(C$_1$-C$_6$)alkyl, —NHC(O)(C$_1$-C$_6$)alkyl, —S(O)$_2$NH$_2$, —(CH$_2$)$_n$—O—(CH$_2$)$_n$—CH$_3$, -(3- to 8-membered)heterocyclo, -(7- to 12-membered)bicycloheterocyclo, and —N(R$^a$)SO$_2$-(6- to 14-membered)aryl; wherein each of the —(C$_1$-C$_6$)alkyl, —(C$_1$-C$_6$)alkyl-(6- to 14-membered)aryl, -(3- to 8-membered)heterocyclo, -(7- to 12-membered)bicycloheterocyclo, and —N(R$^a$)SO$_2$-(6- to 14-membered)aryl is optionally substituted by one to three substituents independently selected from the group of (=O), —(C$_1$-C$_3$)alkyl, —NH$_2$, halogen, and phenyl optionally substituted by halogen; and wherein the -(3- to 8-membered)heterocyclo is further optionally fused together with a phenyl group;

m is 1, 2, 3, 4, 5, or 6; and n is 0, 1, 2, 3, 4, 5, or 6;

provided that (i) when G is —O—, and R$^3$ is optionally-substituted -(5- to 12-membered)heteroaryl or optionally-substituted -(6- to 14-membered)aryl, then R$^1$ is unsubstituted —(C$_1$-C$_{10}$)alkyl;

(ii) when G is —O—, and R$^3$ is H or —CH$_2$Ph, then Z is —CH$_2$CH$_2$—;

(iii) when -G-R$^3$ is —C(O)NH$_2$, then R$^1$ is —(C$_1$-C$_{10}$)alkyl that is either unsubstituted or substituted by cyclobutyl;

and further provided that said compound of Formula I is NOT any compound selected from the group consisting of Compound E1 to Compound E8 as provided in TABLE 1 as follows:

TABLE 1

| Cpd # | Structure | Chemical name |
|---|---|---|
| E1 | 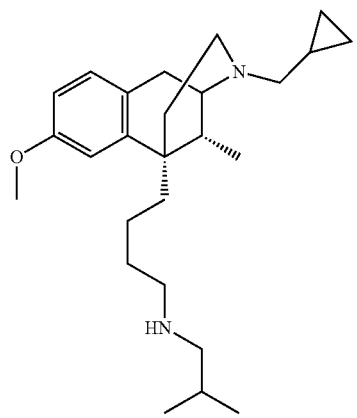 [SMILES: COc1ccc2c(c1)[C@@]1(CCCCNCC(C)C)CCN(CC3CC3)C(C2)[C@@H]1C] | 4-((6S,11R)-3-(cyclopropylmethyl)-8-methoxy-11-methyl-2,3,4,5-tetrahydro-2,6-methanobenzo[d]azocin-6(1H)-yl)-N-isobutylbutan-1-amine |

TABLE 1-continued

| Cpd # | Structure | Chemical name |
|---|---|---|
| E2 | 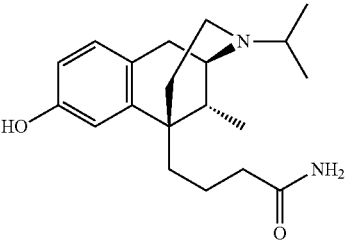 [SMILES: CC(C)N1CC[C@@]2(CCCC(N)=O)c3cc(O)ccc3C[C@@H]1[C@@H]2C] | 4-((2R,6R,11R)-8-hydroxy-3-isopropyl-11-methyl-2,3,4,5-tetrahydro-2,6-methano-benzo[d]azocin-6(1H)-yl)butanamide |
| E3 | 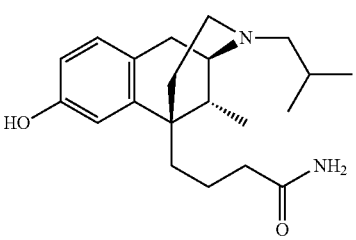 [SMILES: CC(C)CN1CC[C@@]2(CCCC(N)=O)c3cc(O)ccc3C[C@@H]1[C@@H]2C] | 4-((2R,6R,11R)-8-hydroxy-3-isobutyl-11-methyl-2,3,4,5-tetrahydro-2,6-methanobenzo[d]azocin-6(1H)-yl)butanamide |
| E4 | 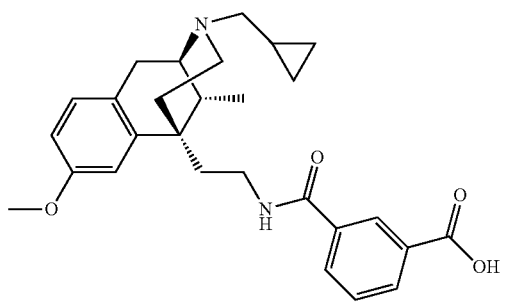 | 3-((2-((2R,6R,11R)-3-(cyclopropyl-methyl)-8-methoxy-11-methyl-2,3,4,5-tetrahydro-2,6-methanobenzo[d]azocin-6(1H)-yl)ethyl)carbamoyl)benzoic acid |
| E5 | 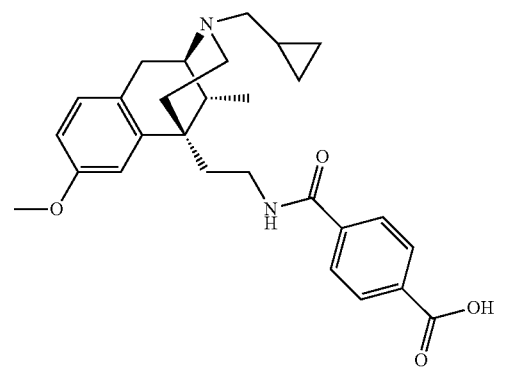 | 4-((2-((2R,6R,11R)-3-(cyclopropyl-methyl)-8-methoxy-11-methyl-2,3,4,5-tetrahydro-2,6-methanobenzo[d]azocin-6(1H)-yl)ethyl)carbamoyl)benzoic acid |
| E6 | 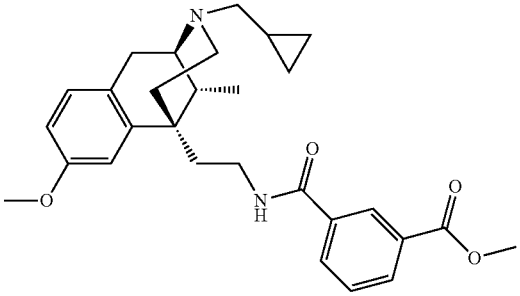 | methyl 3-((2-((2R,6R,11R)-3-(cyclopropylmethyl)-8-methoxy-11-methyl-2,3,4,5-tetrahydro-2,6-methanobenzo[d]azocin-6(1H)-yl)ethyl)carbamoyl)benzoate |

TABLE 1-continued

| Cpd # | Structure | Chemical name |
|---|---|---|
| E7 | 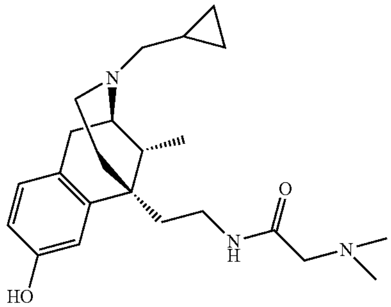 | N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-2-(dimethylamino)acetamide |
| E8 | 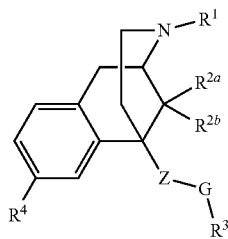 | 2-amino-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)acetamide |

In another aspect, the invention provides compounds of Formula II, and pharmaceutically acceptable salts or solvates thereof:

II wherein $R^1$ is —($C_1$-$C_{10}$)alkyl optionally substituted by —($C_3$-$C_{12}$)cycloalkyl;

$R^{2a}$ and $R^{2b}$, are each independently, hydrogen or —($C_1$-$C_5$)alkyl;

Z is —$(CH_2)_m$— optionally substituted with 1 or 2 independently selected —($C_1$-$C_6$)alkyl;

G is selected from the group consisting of —N($R^d$), —O—, —N($R^a$)C(O)N($R^a$), —C(O), N($R^a$)S(O)$_2$N($R^b$), and —C(O)N($R^c$);

$R^3$ is selected from the group consisting of hydrogen, —($C_1$-$C_{10}$)alkyl, —($C_3$-$C_{12}$)cycloalkyl, —C(=O) ($C_1$-$C_6$)alkyl, —C(=O) ($C_3$-$C_{12}$)cycloalkyl, -(3- to 12-membered)heterocyclo, -(6- to 14-membered)aryl, —($C_1$-$C_6$)alkyl-(6- to 14-membered)aryl, -(5- to 12-membered)heteroaryl, —($C_1$-$C_6$)alkyl-(5- to 12-membered)heteroaryl, —S(O)$_2$—($C_1$-$C_6$)alkyl, —S(O)$_2$—($C_3$-$C_{12}$)cycloalkyl, —S(O)$_2$-(6- to 14-membered)aryl, and -(7- to 12-membered)bicycloheterocyclo; each of which is optionally substituted with one, two, or three substituents independently selected from the group consisting of (=O), halo, —($C_1$-$C_6$)alkyl, ($C_1$-$C_6$)alkoxy, —COOR$^6$, —NHC(O)($C_1$-$C_6$)alkyl, —C(O)R$^5$, —NH$_2$, (alkyl)amino, (dialkyl)amino, ($C_3$-$C_{12}$)cycloalkyl, —($C_6$-$C_{14}$)bicycloalkyl, —($C_1$-$C_6$)alkyl($C_6$-$C_{14}$)bicycloalkyl, -(3- to 8-membered)-heterocyclo, -(6- to 14-membered)aryl, -(5- to 12-membered)heteroaryl, aryloxy, carboxamido, —C(O)NH($C_1$-$C_6$)alkyl, —SO$_2$NH$_2$, —N($R^a$)SO$_2$($C_1$-$C_6$)alkyl, —SO$_2$N($R^a$)($C_1$-$C_6$)alkyl, —N($R^a$)SO$_2$-(6- to 14-membered)aryl, -(7- to 12-membered)bicycloheterocyclo, and ($C_1$-$C_6$)alkyl-(7- to 12-membered)bicycloheterocyclo; wherein each of the —($C_1$-$C_6$)alkyl, —($C_3$-$C_{12}$)cycloalkyl, —($C_6$-$C_{14}$)bicycloalkyl, —($C_1$-$C_6$)alkyl($C_6$-$C_{14}$)bicycloalkyl, -(3- to 8-membered)heterocyclo, -(6- to 14-membered)aryl, -(5- to 12-membered)heteroaryl, aryloxy, N($R^a$)SO$_2$($C_1$-$C_6$)alkyl, —SO$_2$N($R^a$)($C_1$-$C_6$)alkyl, —N($R^a$)SO$_2$-(6- to 14-membered)aryl, -(7- to 12-membered)bicycloheterocyclo, and —($C_1$-$C_6$)alkyl-(7- to 12-membered)bicycloheterocyclo is further optionally substituted by one or two substituents independently selected from the group consisting of —($C_1$-$C_3$)alkyl, —($C_1$-$C_3$)alkoxy, halogen, and carboxamido;

or $R^3$ and $R^d$, together with the nitrogen atom to which they are attached, form a (4- to 8-membered)heterocyclo, which is further optionally substituted by one to three independently selected $R^7$ groups;

Each of $R^a$ independently is hydrogen, —($C_1$-$C_5$)alkyl, or —($C_3$-$C_{12}$)cycloalkyl;

$R^b$, and $R^c$, each independently, are hydrogen, —($C_1$-$C_5$)alkyl, or —($C_3$-$C_{12}$)cycloalkyl;

$R^d$ is H or —($C_1$-$C_6$)alkyl; or $R^d$ and $R^3$, together with the nitrogen atom to which they are attached, form a (4- to 8-membered)heterocyclo, which is further optionally substituted by one to three independently selected $R^7$ groups;

$R^4$ is hydrogen, OH, halo, —($C_1$-$C_5$)alkyl, —C(O)NH$_2$, —($C_1$-$C_5$)alkoxy, —($C_2$-$C_5$)alkenyl, ($C_2$-$C_5$)alkynyl, or —$(CH_2)_n$—O—$(CH_2)_n$—$CH_3$; wherein each of the —($C_1$-$C_5$)alkyl, —C(O)NH$_2$, —($C_1$-$C_5$)alkoxy, —($C_2$-$C_5$)alkenyl, —($C_2$-$C_5$)alkynyl, and —$(CH_2)_n$—O—$(CH_2)_n$—$CH_3$, is optionally substituted by one to three independently selected $R^7$ groups;

$R^5$ is selected from the group consisting of hydrogen, —OH, —$NH_2$, —($C_1$-$C_6$)alkyl, —($C_2$-$C_5$)alkenyl, —($C_2$-$C_5$)alkynyl, —($C_1$-$C_6$)alkoxy, and —($C_3$-$C_8$)cycloalkyl, each of —$NH_2$, —($C_1$-$C_6$)alkyl, —($C_2$-$C_5$)alkenyl, —($C_2$-$C_5$)alkynyl, —($C_1$-$C_6$)alkoxy, and —($C_3$-$C_8$)cycloalkyl is optionally substituted with 1, 2, or 3 independently selected $R^6$ groups; or $R^6$ is selected from the group consisting of hydrogen, —($C_1$-$C_6$)alkyl, —($C_2$-$C_6$)alkenyl, ($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each $R^7$ is independently selected from the group consisting of —OH, (=O), —$NH_2$, halo, ($C_1$-$C_6$)alkyl, —($C_1$-$C_6$)alkyl-(6- to 14-membered)aryl, —($C_2$-$C_{10}$)alkenyl, —($C_2$-$C_{10}$)alkynyl, ($C_1$-$C_6$)alkoxy, —($C_3$-$C_{12}$)cycloalkyl, —C(O)OH, —C(O)O($C_1$-$C_6$)alkyl, carboxamido, C(O)NH($C_1$-$C_6$) alkyl, —NHC(O)($C_1$-$C_6$)alkyl, —S(O)$_2$NH$_2$, —$(CH_2)_n$—O—$(CH_2)_n$—$CH_3$, -(3- to 8-membered)heterocyclo, -(7- to 12-membered)bicycloheterocyclo, and —N($R^a$)SO$_2$-(6- to 14-membered)aryl; wherein each of the —($C_1$-$C_6$)alkyl, —($C_1$-$C_6$)alkyl-(6- to 14-membered)aryl, -(3- to 8-membered)heterocyclo, -(7- to 12-membered)bicycloheterocyclo, and —N($R^a$)SO$_2$-(6- to 14-membered)aryl is optionally substituted by one to three substituents independently selected from the group of (=O), —($C_1$-$C_3$)alkyl, —$NH_2$, halogen, and phenyl optionally substituted by halogen; and wherein the -(3- to 8-membered)heterocyclo is further optionally fused together with a phenyl group;

m is 1, 2, 3, 4, 5, or 6; and n is 0, 1, 2, 3, 4, 5, or 6;

provided that (i) when G is —O—, and $R^3$ is optionally-substituted -(5- to 12-membered)heteroaryl or optionally-substituted -(6- to 14-membered)aryl, then $R^1$ is unsubstituted —($C_1$-$C_{10}$)alkyl;

(ii) when G is —O—, and $R^3$ is H or —$CH_2$Ph, then Z is —$CH_2CH_2$—;

(iii) when -G-$R^3$ is —C(O)NH$_2$, then $R^1$ is —($C_1$-$C_{10}$)alkyl that is either unsubstituted or substituted by cyclobutyl; and (iv) when $R^1$ is cyclopropylmethyl, $R^4$ is methoxy, Z is —$(CH_2)_2$—, one of $R^{2a}$ and $R^{2b}$ is H, and the other is methyl, and G is —NHC(O)—, then $R^3$ is —($C_1$-$C_6$)alkyl, -(3- to 12-membered)heterocyclo, or —($C_1$-$C_6$)alkyl-(6- to 14-membered)aryl; each of which is substituted with one, two, or three substituents independently selected from the group consisting of (=O), halo, —$NH_2$, —($C_1$-$C_6$)alkyl, ($C_1$-$C_6$)alkoxy, —COOR$^6$, —NHC(O)($C_1$-$C_6$)alkyl, —C(O)$R^5$, —($C_3$-$C_{12}$)cycloalkyl, -(3- to 8-membered)-heterocyclo, -(6- to 14-membered)aryl, -(5- to 12-membered)heteroaryl, aryloxy, carboxamido, —C(O)NH($C_1$-$C_6$)alkyl, —SO$_2$NH$_2$, —N($R^a$)SO$_2$($C_1$-$C_6$)alkyl, —SO$_2$N($R^a$) ($C_1$-$C_6$)alkyl, —N($R^a$)SO$_2$-(6- to 14-membered)aryl, -(7- to 12-membered)bicycloheterocyclo, and ($C_1$-$C_6$) alkyl-(7- to 12-membered)bicycloheterocyclo; wherein each of the —($C_1$-$C_6$)alkyl, —($C_3$-$C_{12}$)cycloalkyl, -(3- to 8-membered)heterocyclo, -(6- to 14-membered)aryl, -(5- to 12membered)heteroaryl, aryloxy, —N($R^a$)SO$_2$($C_1$-$C_6$)alkyl, —SO$_2$N($R^a$)($C_1$-$C_6$)alkyl, —N($R^a$)SO$_2$-(6- to 14-membered)aryl, -(7- to 12-membered) bicycloheterocyclo, and —($C_1$-$C_6$)alkyl-(7- to 12-membered)bicycloheterocyclo is further optionally substituted by one or two substituents independently selected from the group consisting of —($C_1$-$C_3$)alkyl, —($C_1$-$C_3$)alkoxy, halogen, and carboxamido;

(v) when $R^1$ is unsubstituted —($C_1$-$C_{10}$)alkyl, then $R^1$ is a straight —($C_1$-$C_{10}$)alkyl chain;

(vi) when G is —N($R^a$), and $R^3$ is —($C_1$-$C_{10}$)alkyl optionally substituted by —($C_1$-$C_6$)alkyl, then $R^4$ is OH; and (vii) when $R^1$ is cyclopropylmethyl, Z is —$(CH_2)_2$—, and $R^3$ is a) —($C_1$-$C_{10}$)alkyl substituted by —$NH_2$ or (dialkyl) amino; or b) —C(=O) ($C_1$-$C_6$)alkyl substituted by —$NH_2$ or (dialkyl)amino; then $R^4$ is methoxy.

In certain embodiments, the invention provides compounds of Formula A, and pharmaceutically acceptable salts or solvates thereof:

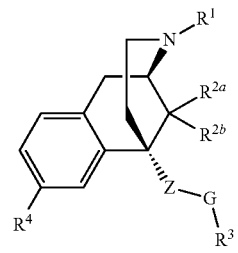

A wherein $R^1$, $R^{2a}$, $R^{2b}$, $R^3$, $R^4$, Z, and G are as above defined in connection with Formula I or II.

Another embodiment of the invention provides compounds of Formula B, and pharmaceutically acceptable salts or solvates thereof:

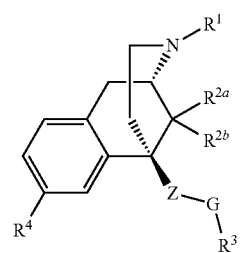

B wherein $R^1$, $R^{2a}$, $R^{2b}$, $R^3$, $R^4$, Z, and G are as above defined in connection with Formula I or II.

In one embodiment, Compounds of the Invention are compounds represented by any one of Formulae I, II, A, and B, delineated supra., and the pharmaceutically acceptable salts or solvates thereof, wherein Z is optionally-substituted —$(CH_2)_m$—. One embodiment provides that Z is unsubstituted —$(CH_2)_m$—. In certain instances, m is 1, 2, 3, or 4. As one example, Z is $CH_2CH_2$—. Another example provides that Z is —$CH_2CH_2CH_2CH_2$—. A further example provides that Z is —$CH_2CH_2CH_2$—.

In a separate embodiment, Compounds of the Invention are compounds represented by any one of Formulae I, II, A, and B, delineated supra., and the pharmaceutically acceptable salts or solvates thereof, wherein G is —N($R^a$)C(O)N ($R^a$). In certain circumstances, each of $R^a$ independently is hydrogen or —($C_1$-$C_5$)alkyl. One embodiment provides that $R^a$ is hydrogen.

In certain embodiments of the invention, G is —N(R$^a$)C(O)N(R$^a$), and R$^3$ is a moiety selected from the group consisting of —(C$_3$-C$_{12}$)cycloalkyl, -(3- to 12-membered)heterocyclo, -(6- to 14-membered)aryl, —(C$_1$-C$_6$)alkyl-(6- to 14-membered)aryl, -(5- to 12-membered)heteroaryl, —(C$_1$-C$_6$)alkyl-(5- to 12-membered)heteroaryl, and —S(O)$_2$-(6- to 14-membered)aryl; each of which is optionally substituted with one or two substituents independently selected from the group consisting of (=O), halo, —(C$_1$-C$_6$)alkyl, (C$_1$-C$_6$)alkoxy, —COOR$^6$, —NHC(O)(C$_1$-C$_6$)alkyl, —C(O)R$^5$, —NH$_2$, (alkyl)amino, (dialkyl)amino, (C$_3$-C$_{12}$)cycloalkyl, -(3- to 8-membered)heterocyclo, -(6- to 14-membered)aryl, -(5- to 12-membered)heteroaryl, aryloxy, carboxamido, —C(O)NH(C$_1$-C$_6$)alkyl, —SO$_2$NH$_2$, N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo; wherein each of —(C$_1$-C$_6$)alkyl, —(C$_3$-C$_{12}$)cycloalkyl, -(3- to 8-membered)heterocyclo, -(6- to 14-membered)aryl, -(5- to 12-membered)heteroaryl, aryloxy, —N(R$^a$)SO$_2$(C$_1$-C$_6$)alkyl, SO$_2$N(R$^a$)(C$_1$-C$_6$)alkyl, N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo is further optionally substituted by one or two substituents independently selected from the group consisting of —(C$_1$-C$_3$)alkyl, —(C$_1$-C$_3$)alkoxy, halogen, and carboxamido.

In certain instances, G is —N(R$^a$)C(O)N(R$^a$), and R$^3$ is selected from the group consisting of -(6- to 14-membered)aryl, —(C$_1$-C$_6$)alkyl-(6- to 14-membered)aryl, and —S(O)$_2$-(6- to 14-membered)aryl, each of which is optionally substituted with a substituent selected from the group consisting of —(C$_1$-C$_6$)alkyl, halo, —COOR$^6$, —NHC(O)(C$_1$-C$_6$)alkyl, —NH$_2$, -(6- to 14-membered)aryl, aryloxy, carboxamido, and —SO$_2$NH$_2$.

For example, Compounds of the Invention include those represented by each of the above-delineated embodiments, wherein G is —N(R$^a$)C(O)N(R$^a$), and R$^3$ is selected from the group consisting of -phenyl, —(C$_1$-C$_3$)alkyl-phenyl, and —S(O)$_2$-phenyl; each of which is optionally substituted with a substituent selected from the group consisting of halo, —COOR$^6$, phenyl, and -OPh. Certain embodiments provide that R$^6$ is hydrogen or —(C$_1$-C$_3$)alkyl.

In a further embodiment, Compounds of the Invention are compounds represented by any one of Formulae I, II, A, and B, delineated supra., and the pharmaceutically acceptable salts or solvates thereof, wherein G is —O—.

One embodiment of the invention provides that G is —O—; and R$^3$ is selected from the group consisting of hydrogen, —(C$_1$-C$_{10}$)alkyl, —(C$_3$-C$_{12}$)cycloalkyl, -(3- to 12-membered)heterocyclo, -(6- to 14-membered)aryl, —(C$_1$-C$_6$)alkyl-(6- to 14-membered)-aryl, -(5- to 12-membered)heteroaryl, —(C$_1$-C$_6$)alkyl-(5- to 12-membered)-heteroaryl, and -(7- to 12-membered)bicycloheterocyclo, each of which (except hydrogen) is optionally substituted with one or two substituents independently selected from the group consisting of (=O), halo, —(C$_1$-C$_6$)alkyl, —(C$_1$-C$_6$)alkoxy, —COOR$^6$, —NHC(O)(C$_1$-C$_6$)alkyl, —C(O)R$^5$, —NH$_2$, (alkyl)amino, (dialkyl)amino, —(C$_3$-C$_{12}$)cycloalkyl, -(3- to 8-membered)heterocyclo, -(6- to 14-membered)aryl, -(5- to 12-membered)heteroaryl, aryloxy, carboxamido, C(O)NH(C$_1$-C$_6$)alkyl, —SO$_2$NH$_2$, —N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo; wherein each of —(C$_1$-C$_6$)alkyl, —(C$_3$-C$_{12}$)cycloalkyl, -(3- to 8-membered)heterocyclo, -(6- to 14-membered)aryl, -(5- to 12-membered)heteroaryl, aryloxy, N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)-bicycloheterocyclo is further optionally substituted by one or two substituents independently selected from the group consisting of —(C$_1$-C$_3$)alkyl, —(C$_1$-C$_3$)alkoxy, halogen, and carboxamido.

Another embodiment of the invention provides that G is —O—; and R$^3$ is selected from the group consisting of hydrogen, —(C$_1$-C$_{10}$)alkyl, -(6- to 14-membered)aryl, —(C$_1$-C$_6$)alkyl-(6- to 14-membered)aryl, -(5- to 12-membered)-heteroaryl, and —(C$_1$-C$_6$)alkyl-(5- to 12-membered)heteroaryl, each of which (except hydrogen) is optionally substituted with a substituent selected from the group consisting of —(C$_1$-C$_6$)alkyl, halo, —COOR$^6$, NHC(O)(C$_1$-C$_6$)alkyl, —NH$_2$, -(6- to 14-membered)aryl, aryloxy, carboxamido, and —SO$_2$NH$_2$.

In yet another embodiment, Compounds of the Invention are compounds represented by any one of Formulae I, II, A, and B, delineated supra., and the pharmaceutically acceptable salts or solvates thereof, wherein G is —O—; and R$^3$ is selected from the group consisting of hydrogen, —(C$_1$-C$_3$)alkyl, phenyl, —(C$_1$-C$_3$)alkyl-phenyl, pyridyl, pyrimidyl, —(C$_1$-C$_3$)alkyl-pyridyl, and —(C$_1$-C$_3$)alkyl-pyrimidyl, each of which (except hydrogen) is optionally substituted with a substituent selected from the group consisting of —(C$_1$-C$_3$)alkyl, halo, —COOH, —C(O)O(C$_1$-C$_6$)alkyl, carboxamido, and —SO$_2$NH$_2$.

Alternatively, the invention provides compounds represented by any one of Formulae I, II, A, and B, delineated supra., and the pharmaceutically acceptable salts or solvates thereof, wherein G is —N(R$^d$). In one embodiment, R$^d$ is H. In another embodiment, R$^d$ is (C$_1$-C$_3$)alkyl.

In other embodiments, the invention provides compounds represented by any one of Formulae I, II, A, and B, delineated supra., and the pharmaceutically acceptable salts or solvates thereof, wherein G is —N(R$^d$); and R$^3$ is selected from the group consisting of —(C$_1$-C$_{10}$)alkyl, —(C$_3$-C$_{12}$)cycloalkyl, —C(=O) (C$_1$-C$_6$)alkyl, (C$_1$-C$_6$)alkyl-(6- to 14-membered)aryl, —(C$_1$-C$_6$)alkyl-(5- to 12- membered)heteroaryl, S(O)$_2$—(C$_1$-C$_6$)alkyl, —S (O)$_2$-(C$_3$-C$_{12}$)cycloalkyl, and -(7- to 12-membered)bicycloheterocyclo; each of which is optionally substituted with one or two substituents independently selected from the group consisting of halo, —(C$_1$-C$_6$)alkyl, —COOR$^6$, —NHC(O)(C$_1$-C$_6$)alkyl, —C(O)R$^5$, —NH$_2$, (alkyl)amino, (dialkyl)amino, —(C$_3$-C$_{12}$)cycloalkyl, -(3- to 8-membered)heterocyclo, -(6- to 14-membered)aryl, -(5- to 12-membered)heteroaryl, aryloxy, carboxamido, —C(O)NH(C$_1$-C$_6$)alkyl, —SO$_2$NH$_2$, N(R$^a$)SO$_2$(C$_1$-C$_6$)alkyl, SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo; wherein each of —(C$_1$-C$_6$)alkyl, —(C$_3$-C$_{12}$)cycloalkyl, -(3- to 8-membered)heterocyclo, -(6- to 14-membered)aryl, -(5- to 12-membered)heteroaryl, aryloxy, —N(R$^a$)SO$_2$(C$_1$-C$_6$)alkyl, SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo is further optionally substituted by one or two substituents independently selected from the group consisting of —(C$_1$-C$_3$)alkyl, —(C$_1$-C$_3$)alkoxy, halogen, and carboxamido.

In separate embodiments, the invention provides compounds represented by any one of Formulae I, II, A, and B, delineated supra., and the pharmaceutically acceptable salts or solvates thereof, wherein G is —N(R$^d$), and R$^3$ is selected from the group consisting of —(C$_1$-C$_6$)alkyl, —C(=O)(C$_1$-C$_6$)alkyl, —(C$_1$-C$_6$)alkyl-(6- to 14-membered)aryl, —(C$_1$-C$_6$)alkyl-(5- to 12-membered)heteroaryl, —S(O)$_2$—(C$_1$-C$_6$)alkyl, —S(O)$_2$—(C$_3$-C$_{12}$)cycloalkyl, and -(7- to 12-membered)bicycloheterocyclo; each of which is optionally substituted with one or two substituents independently selected from the group consisting of halo, —COOR$^6$, carboxamido, NH$_2$, (alkyl)amino, (dialkyl)amino, -(3- to 8-membered)heterocyclo, -(6- to 14-membered)aryl, —SO$_2$NH$_2$, and —(C$_1$-C$_6$)alkyl-(7- to 12-membered)bicycloheterocyclo optionally substituted by one or two same or different —(C$_1$-C$_3$)alkyl.

Still further, the invention provides compounds represented by any one of Formulae I, II, A, and B, delineated supra., and the pharmaceutically acceptable salts or solvates thereof, wherein G is —N(R$^d$), and R$^3$ is selected from the group consisting of —(C$_1$-C$_6$)alkyl, —C(=O)(C$_1$-C$_3$)alkyl, —(C$_1$-C$_3$)alkyl-phenyl, —(C$_1$-C$_3$)alkyl-(5- to 6-membered)heteroaryl, —S(O)$_2$—(C$_1$-C$_3$)alkyl, —S(O)$_2$—(C$_3$-C$_6$)cycloalkyl, and -(7- to 12-membered)bicycloheterocyclo; each of which is optionally substituted with one or two substituents independently selected from the group consisting of halo, —COOR$^6$, carboxamido, —NH$_2$, (di(C$_1$-C$_3$)alkyl)amino, -(5- to 6-membered)heterocyclo, phenyl, —SO$_2$NH$_2$, and —(C$_1$-C$_3$)alkyl-(7- to 12-membered)bicycloheterocyclo optionally substituted by one or two same or different —(C$_1$-C$_3$)alkyl. Certain embodiments provide that R$^6$ is hydrogen or —(C$_1$-C$_3$)alkyl.

In yet another embodiment, the invention provides compounds represented by any one of Formulae I, II, A, and B, delineated supra., and the pharmaceutically acceptable salts or solvates thereof, wherein G is —N(R$^d$), and R$^d$ and R$^3$, together with the nitrogen atom to which they are attached, form a (4- to 8-membered)heterocyclo, which is further optionally substituted by one to three independently selected R$^7$ groups.

For example, R$^7$ can be each independently selected from the group consisting of (=O), (C$_1$-C$_6$)alkyl, —(C$_1$-C$_6$)alkyl-(6- to 14-membered)aryl, —C(O)OH, —N(R$^a$)SO$_2$-(6- to 14-membered)aryl, —(CH$_2$)$_n$—O—(CH$_2$)$_n$—CH$_3$, -(3- to 8-membered)heterocyclo, and -(7- to 12-membered)bicycloheterocyclo, and wherein each of the —(C$_1$-C$_6$)alkyl-(6- to 14-membered)aryl, -(3- to 8-membered)heterocyclo, —N(R$^a$)SO$_2$-(6- to 14-membered)aryl, and -(7- to 12-membered)bicycloheterocyclo is optionally substituted by one or two substituents independently selected from the group of (=O), —(C$_1$-C$_3$)alkyl, —NH$_2$, halogen, and phenyl optionally substituted by halogen; and wherein the -(3- to 8-membered)heterocyclo can further optionally fuse together with a phenyl group.

In a specific embodiment, the invention provides compounds represented by any one of Formulae I, II, A, and B, delineated supra., and the pharmaceutically acceptable salts or solvates thereof, wherein G is —N(R$^d$), and R$^d$ and R$^3$, together with the nitrogen atom to which they are attached, form a (5 to 6-membered)heterocyclo substituted by —N(R$^a$)SO$_2$-(6- to 14-membered)aryl, wherein the —N(R$^a$)SO$_2$-(6- to 14-membered)aryl is optionally substituted by halo. One embodiment provides that R$^a$ is —(C$_3$-C$_6$)cycloalkyl.

In an alternative embodiment, the Compounds of the Invention are those represented by any one of Formulae I, II, A, and B, delineated supra., and the pharmaceutically acceptable salts or solvates thereof, wherein G is —N(R$^d$), and R$^d$ and R$^3$, together with the nitrogen atom to which they are attached, form a (5- to 6-membered)heterocyclo substituted by optionally-substituted (C$_1$-C$_3$)alkyl-(6- to 14-membered)aryl. In one embodiment, the said —(C$_1$-C$_3$)alkyl-(6- to 14-membered)aryl is further optionally substituted by one or two substituents independently selected from the group consisting of halogen and phenyl optionally substituted by halogen.

For example, in accordance with the preceding embodiments, G is —N(R$^d$); and R$^d$ and R$^3$, together with the nitrogen atom to which they are attached, can form

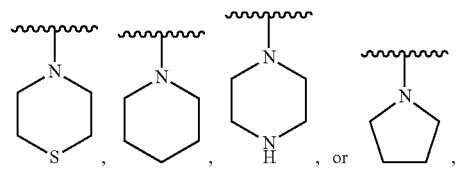

each of the above heterocyclos is optionally substituted by one or two substituents independently selected from the group consisting of (=O), —(C$_1$-C$_3$)alkyl-phenyl, —C(O)OH, N(R$^a$)SO$_2$-phenyl, —(CH$_2$)$_n$—O—(CH$_2$)$_n$—CH$_3$, and -(5- to 6-membered)heterocyclo, and wherein each of the —(C$_1$-C$_3$)alkyl-phenyl, —N(R$^a$)SO$_2$-phenyl, and -(5- to 6-membered)heterocyclo is optionally substituted by one or two substituents independently selected from the group of halogen and phenyl optionally substituted by halogen; and wherein the -(5- to 6-membered)heterocyclo is further optionally fused together with a phenyl group.

In yet another embodiment, the invention provides compounds represented by any one of Formulae I, II, A, and B, delineated supra., and the pharmaceutically acceptable salts or solvates thereof, wherein G is —C(O)N(R$^c$). It is understood by one skilled in the art that the moiety "—C(O)N(R$^c$)" can be directly attached to R$^3$ either through the N or C atom. R$^c$ can be, for example, H or —(C$_1$-C$_3$)alkyl.

One embodiment provides compounds represented by any one of Formulae I, II, A, and B, delineated supra., and the pharmaceutically acceptable salts or solvates thereof, wherein G is —C(O)N(R$^c$), and R$^3$ is selected from the group consisting of hydrogen, —(C$_1$-C$_{10}$)alkyl, -(3- to 12-membered)heterocyclo, -(6- to 14-membered)aryl, and —(C$_1$-C$_6$)alkyl-(6-to 14-membered)aryl; wherein each of —(C$_1$-C$_{10}$)alkyl, -(3- to 12-membered)heterocyclo, -(6-to 14-membered)aryl, and —(C$_1$-C$_6$)alkyl-(6- to 14-membered)aryl is optionally substituted with one, two, or three substituents independently selected from the group consisting of (=O), halo, —(C$_1$-C$_6$)alkyl, —(C$_1$-C$_6$)alkoxy, —COOR$^6$, —NHC(O)(C$_1$-C$_6$)alkyl, —C(O)R$^5$, —NH$_2$, (alkyl)amino, (dialkyl)amino, —(C$_3$-C$_{12}$)cycloalkyl, -(3- to 8-membered)heterocyclo, -(6- to 14-membered)aryl, -(5- to 12-membered)heteroaryl, aryloxy, carboxamido, C(O)NH(C$_1$-C$_6$)alkyl, —SO$_2$NH$_2$, —N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)bicycloheterocyclo; wherein each of the —(C$_1$-C$_6$)alkyl, —(C$_3$-C$_{12}$)cycloalkyl, -(3- to 8-membered)heterocyclo, -(6- to 14-membered)aryl, -(5- to 12-membered)heteroaryl, aryloxy, —N(R$^a$)SO$_2$(C$_1$-C$_6$)alkyl, —SO$_2$N(R$^a$)(C$_1$-C$_6$)alkyl, —N(R$^a$)SO$_2$-(6- to 14-membered)aryl, -(7- to 12-membered)bicycloheterocyclo, and —(C$_1$-C$_6$)alkyl-(7- to 12-membered)-bicycloheterocyclo is further optionally substituted by one or two substituents independently selected from the group consisting of —(C$_1$-C$_3$)alkyl, —(C$_1$-C$_3$)alkoxy, halogen, and carboxamido.

In still another embodiment, the invention includes compounds represented by any one of Formulae I, II, A, and B, delineated supra., and the pharmaceutically acceptable salts or solvates thereof, wherein G is —C(O)N($R^c$), and $R^3$ is selected from the group consisting of hydrogen, —($C_1$-$C_6$)alkyl, -(5- to 6-membered)heterocyclo, phenyl, and —($C_1$-$C_3$)alkyl-phenyl, wherein each of the —($C_1$-$C_6$)alkyl, -(5- to 6-membered)heterocyclo, phenyl, and —($C_1$-$C_3$)alkyl-phenyl is optionally substituted with one or two substituents independently selected from the group consisting of (=O), halo, —NHC(O)($C_1$-$C_3$)alkyl, —C(O)$R^5$, —COO$R^6$, —$NH_2$, —$SO_2NH_2$, and carboxamido. $R^5$ can be, for instance, —($C_1$-$C_3$)alkyl. In certain embodiments, $R^6$ is H or ($C_1$-$C_3$)alkyl.

Further, the invention also includes compounds represented by any one of Formulae I, II, A, and B, delineated supra., and the pharmaceutically acceptable salts or solvates thereof, wherein G is —C(O). Certain embodiments provide that $R^3$ is -(3- to 12-membered)heterocyclo optionally substituted by —N($R^a$)$SO_2$-(6- to 14-membered)aryl, wherein the —N($R^a$)$SO_2$-(6- to 14-membered)aryl is further optionally substituted by one or two substituents independently selected from the group consisting of —($C_1$-$C_3$)alkyl, —($C_1$-$C_3$)alkoxy, halogen, and carboxamido. In a specific embodiment, $R^3$ is -(5- to 6-membered)heterocyclo substituted by N($R^a$)$SO_2$-phenyl, wherein the —N($R^a$)$SO_2$-phenyl is further optionally substituted by —($C_1$-$C_3$)alkyl or halogen. For example, $R^a$ can be —($C_3$-$C_6$)cycloalkyl in any of the preceding embodiments.

Another embodiment in accordance with Formulae I, II, A, and B, delineated supra., provides that G is —N($R^a$)S(O)$_2$N($R^b$). Each of $R^a$ and $R^b$ as used herein, independently can be hydrogen or —($C_1$-$C_3$)alkyl. In certain instances, $R^3$ is optionally-substituted —($C_1$-$C_{10}$)alkyl including, such as unsubstituted —($C_1$-$C_6$)alkyl.

In certain embodiments, the Compounds of the Invention include exemplified compounds provided in TABLE 2, and their pharmaceutically acceptable salts and solvates thereof.

TABLE 2

| Cpd # | Structure | Chemical name |
|---|---|---|
| 1 | 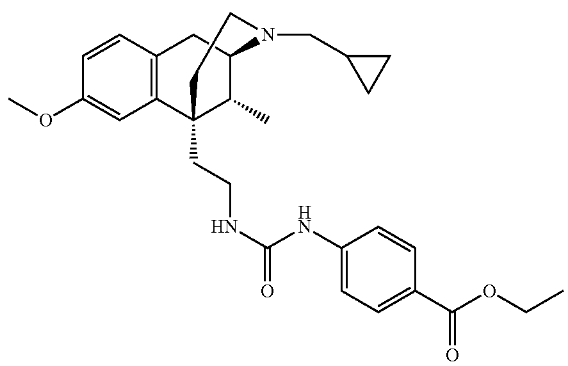 | Ethyl 4-(3-(2-((2R,6R,11R)-3-(cyclopropylmethyl)-8-methoxy-11-methyl-2,3,4,5-tetrahydro-2,6-methanobenzo[d]azocin-6(1H)-yl)ethyl)ureido)benzoate |
| 2 | 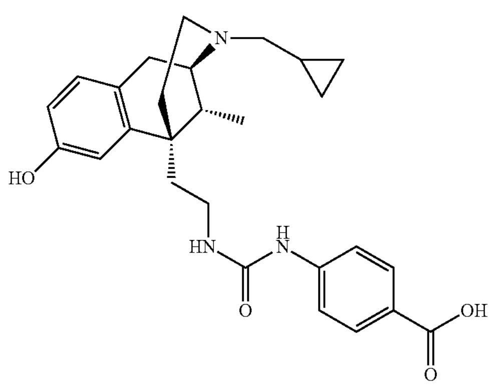 [SMILES: C[C@H]1[C@H]2Cc3ccc(O)cc3[C@]1(CCNC(=O)Nc1ccc(C(=O)O)cc1)CCN2CC1CC1] | 4-(3-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)ureido)benzoic acid |
| 3 | 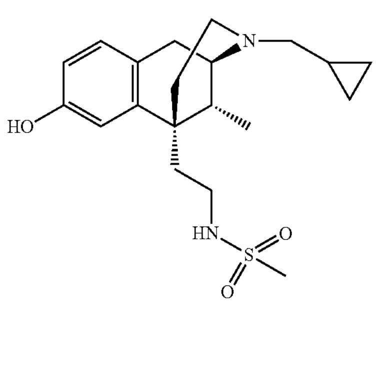 | N-(2-((2R,6S,11R)-3-(cyclopropylmethyl)-8-hydroxy-11-methyl-2,3,4,5-tetrahydro-2,6-methanobenzo[d]azocin-6(1H)-yl)ethyl)methanesulfonamide |

TABLE 2-continued

| Cpd # | Structure | Chemical name |
|---|---|---|
| 4 | 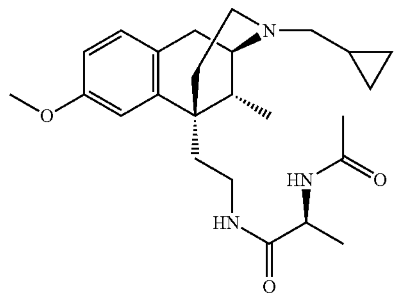 | (S)-2-acetamido-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)propanamide |
| 5 | 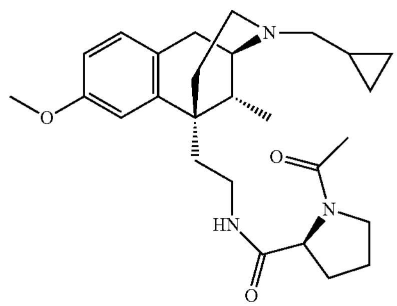 | (S)-1-acetyl-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)pyrrolidine-2-carboxamide |
| 6 | 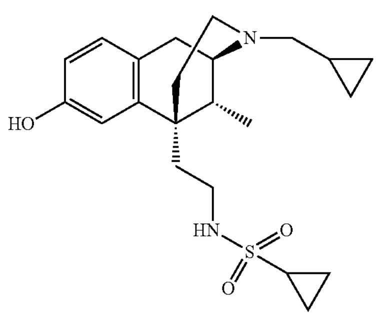 | N-(2-((2R,6S,11R)-3-(cyclopropyl-methyl)-8-hydroxy-11-methyl-2,3,4,5-tetrahydro-2,6-methanobenzo[d]azocin-6(1H)-yl)ethyl)-cyclopropanesulfonamide |
| 7 | 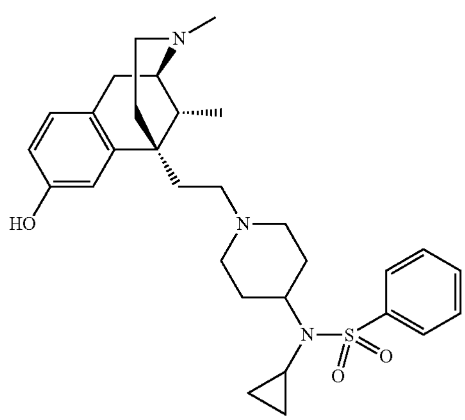 | N-cyclopropyl-N-(1-(2-((2R,6R,11R)-8-hydroxy-3,11-dimethyl-2,3,4,5-tetrahydro-2,6-methanobenzo[d]azocin-6(1H)-yl)ethyl)piperidin-4-yl)benzenesulfonamide |

TABLE 2-continued
| Cpd # | Structure | Chemical name |
|---|---|---|
| 8 | 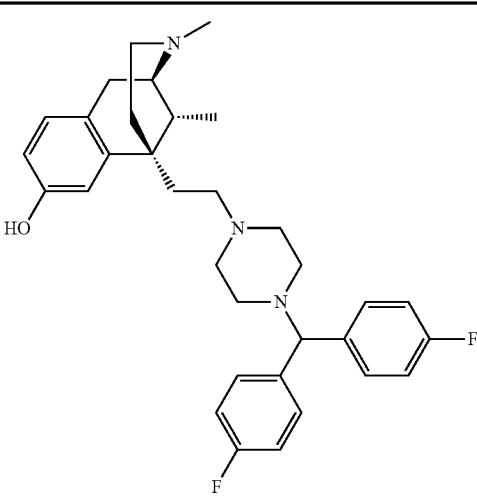 | (2R,6R,11R)-6-(2-(4-(bis(4-fluorophenyl)methyl)piperazin-1-yl)ethyl)-3,11-dimethyl-1,2,3,4,5,6-hexahydro-2,6-methanobenzo[d]azocin-8-ol |
| 9 | 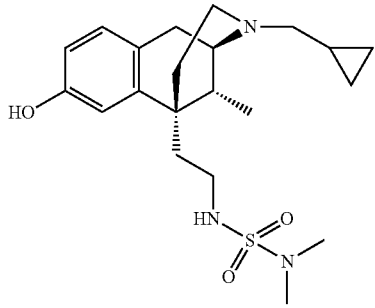 | |
| 10 | 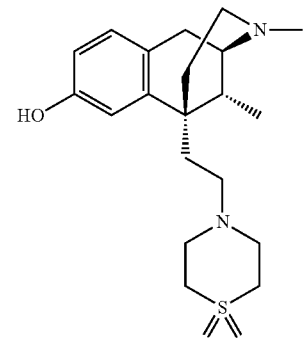 | 4-(2-((2R,6R,11R)-8-hydroxy-3,11-dimethyl-2,3,4,5-tetrahydro-2,6-methanobenzo[d]azocin-6(1H)-yl)-ethyl)thiomorpholine 1,1-dioxide |
| 11 | 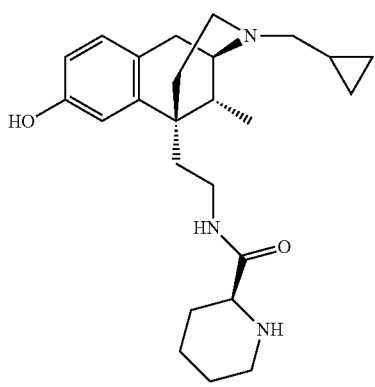 | (S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)piperidine-2-carboxamide |

TABLE 2-continued

| Cpd # | Structure | Chemical name |
|---|---|---|
| 12 | 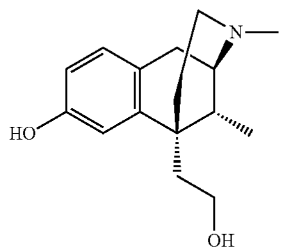 | (2R,6S,11R)-6-(2-hydroxyethyl)-3,11-dimethyl-1,2,3,4,5,6-hexahydro-2,6-methanobenzo[d]azocin-8-ol |
| 13 | 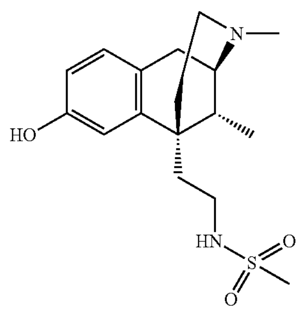 | N-(2-((2R,6S,11R)-8-hydroxy-3,11-dimethyl-2,3,4,5-tetrahydro-2,6-methanobenzo[d]azocin-6(1H)-yl)ethyl)methanesulfonamide |
| 14 | 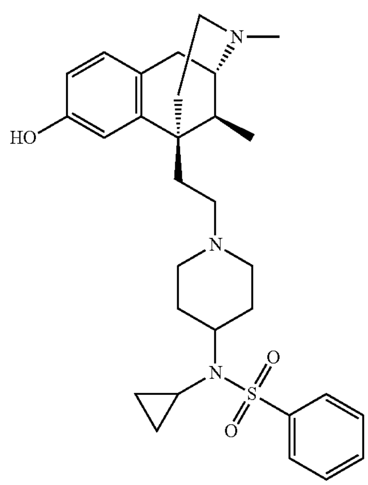 | N-cyclopropyl-N-(1-(2-((2S,6S,11S)-8-hydroxy-3,11-dimethyl-2,3,4,5-tetrahydro-2,6-methanobenzo[d]azocin-6(1H)-yl)ethyl)piperidin-4-yl)-benzenesulfonamide |
| 15 | 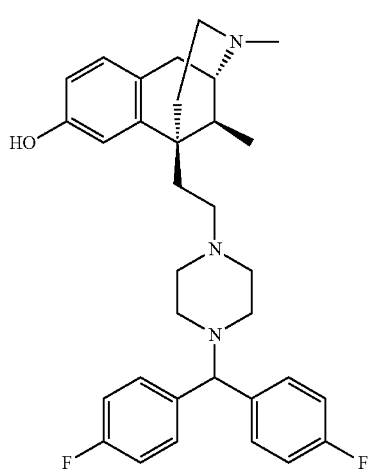 | (2S,6S,11S)-6-(2-(4-(bis(4-fluoro-phenyl)methyl)piperazin-1-yl)ethyl)-3,11-dimethyl-1,2,3,4,5,6-hexahydro-2,6-methanobenzo[d]azocin-8-ol |

TABLE 2-continued

| Cpd # | Structure | Chemical name |
|---|---|---|
| 16 | 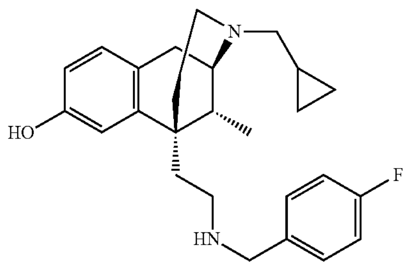 | (2R,6R,11R)-3-(cyclopropylmethyl)-6-(2-((4-fluorobenzyl)amino)ethyl)-11-methyl-1,2,3,4,5,6-hexahydro-2,6-methanobenzo[d]azocin-8-ol |
| 17 | 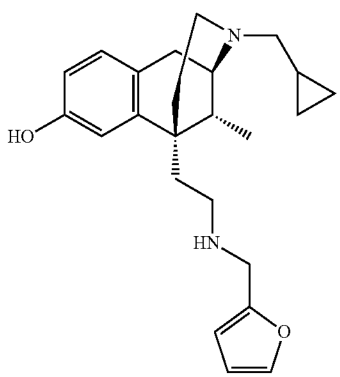 | (2R,6R,11R)-3-(cyclopropylmethyl)-6-(2-((furan-2-ylmethyl)amino)ethyl)-11-methyl-1,2,3,4,5,6-hexahydro-2,6-methanobenzo[d]azocin-8-ol |
| 18 | 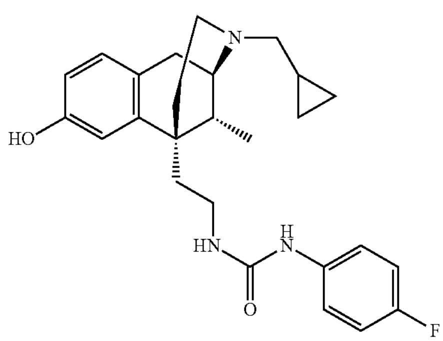 | 1-(2-((2R,6R,11R)-3-(cyclopropyl-methyl)-8-hydroxy-11-methyl-2,3,4,5-tetrahydro-2,6-methanobenzo[d]azocin-6(1H)-yl)ethyl)-3-(4-fluorophenyl)urea |
| 19 | 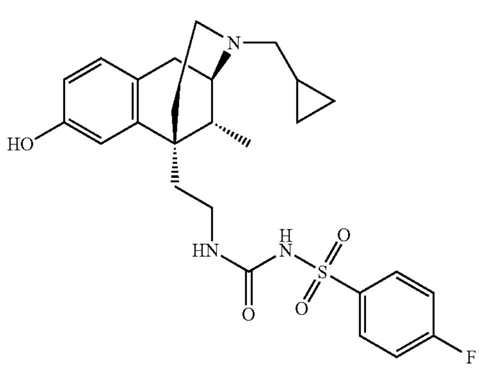 | N-((2-((2R,6R,11R)-3-(cyclopropyl-methyl)-8-hydroxy-11-methyl-2,3,4,5-tetrahydro-2,6-methanobenzo[d]azocin-6(1H)-yl)ethyl)carbamoyl)-4-fluoro-benzenesulfonamide |

TABLE 2-continued

| Cpd # | Structure | Chemical name |
|---|---|---|
| 20 | 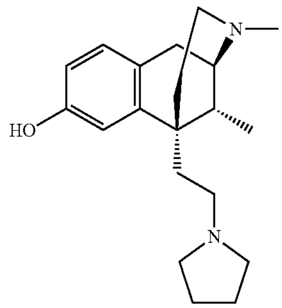 | (2R,6R,11R)-3,11-dimethyl-6-(2-(pyrrolidin-1-yl)ethyl)-1,2,3,4,5,6-hexahydro-2,6-methanobenzo[d]azocin-8-ol |
| 21 | 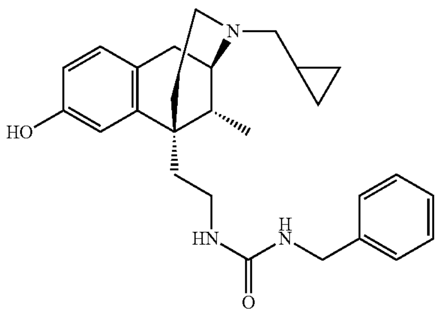 | 1-benzyl-3-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)urea |
| 22 | 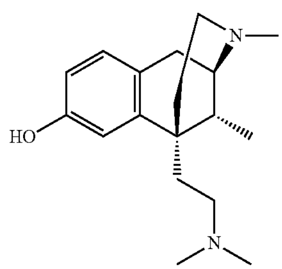 | (2R,6R,11R)-6-(2-(dimethyl-amino)-ethyl)-3,11-dimethyl-1,2,3,4,5,6-hexahydro-2,6-methanobenzo[d]azocin-8-ol |
| 23 | 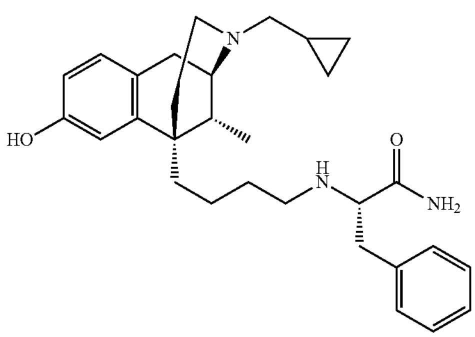 | (S)-2-((4-((2R,6R,11R)-3-(cyclopropyl-methyl)-8-hydroxy-11-methyl-2,3,4,5-tetrahydro-2,6-methanobenzo[d]azocin-6(1H)-yl)butyl)amino)-3-phenyl-propanamide |
| 24 | 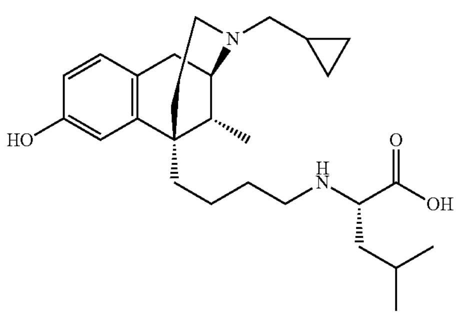 | (4-((2R,6R,11R)-3-(cyclopropyl-methyl)-8-hydroxy-11-methyl-2,3,4,5-tetrahydro-2,6-methanobenzo[d]azocin-6(1H)-yl)butyl)-L-leucine |

TABLE 2-continued

| Cpd # | Structure | Chemical name |
|---|---|---|
| 25 | 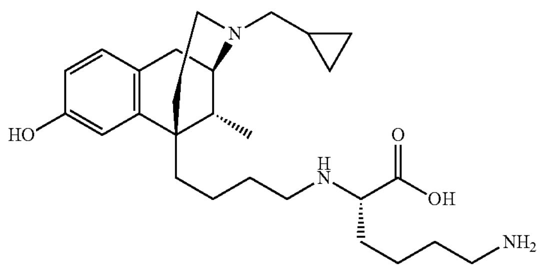 [SMILES: C[C@H]1[C@H]2Cc3ccc(O)cc3[C@]1(CCCCN[C@@H](CCCCN)C(=O)O)CCN2CC1CC1] | (4-((2R,6R,11R)-3-(cyclopropyl-methyl)-8-hydroxy-11-methyl-2,3,4,5-tetrahydro-2,6-methanobenzo[d]azocin-6(1H)-yl)butyl)-L-lysine |
| 26 | 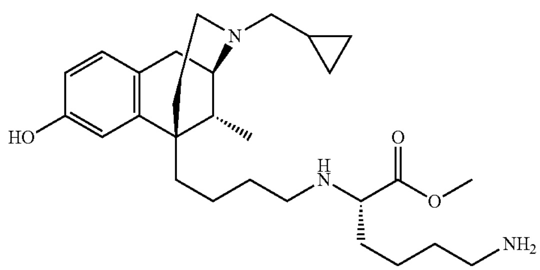 [SMILES: COC(=O)[C@H](CCCCN)NCCCC[C@]12CCN(CC3CC3)[C@H](Cc3ccc(O)cc31)[C@@H]2C] | methyl (4-((2R,6R,11R)-3-(cyclopropyl-methyl)-8-hydroxy-11-methyl-2,3,4,5-tetrahydro-2,6-methanobenzo[d]azocin-6(1H)-yl)butyl)-L-lysinate |
| 27 | 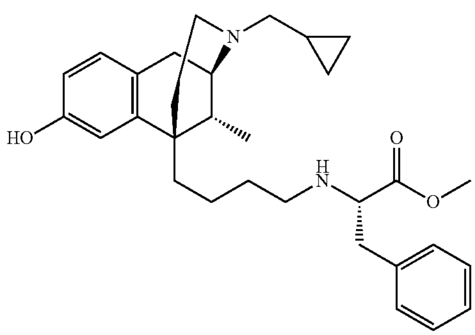 [SMILES: COC(=O)[C@H](Cc1ccccc1)NCCCC[C@]12CCN(CC3CC3)[C@H](Cc3ccc(O)cc31)[C@@H]2C] | methyl (4-((2R,6R,11R)-3-(cyclopropyl-methyl-8-hydroxy-11-methyl-2,3,4,5-tetrahydro-2,6-methanobenzo[d]azocin-6(1H)-yl)butyl)-L-phenylalaninate |
| 28 | 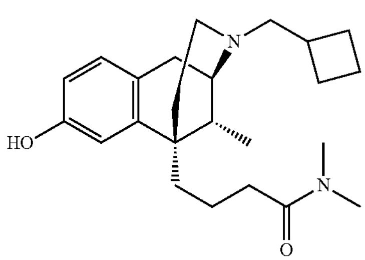 | 4-((2R,6R,11R)-3-(cyclobutylmethyl)-8-hydroxy-11-methyl-2,3,4,5-tetrahydro-2,6-methanobenzo[d]azocin-6(1H)-yl)-N,N-dimethylbutanamide |
| 29 | 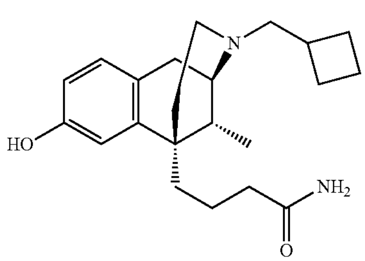 | 4-((2R,6R,11R)-3-(cyclobutylmethyl)-8-hydroxy-11-methyl-2,3,4,5-tetrahydro-2,6-methanobenzo[d]azocin-6(1H)-yl)butanamide |

TABLE 2-continued

| Cpd # | Structure | Chemical name |
|---|---|---|
| 30 | 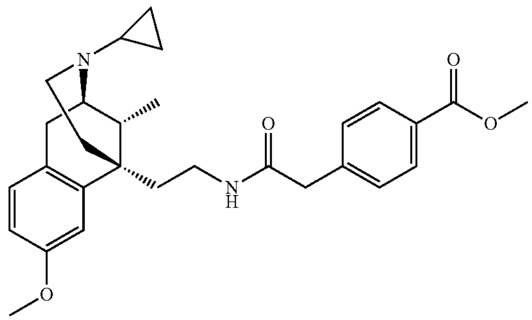 | methyl 4-(2-((2-((2R,6R,11R)-3-(cyclopropylmethyl)-8-methoxy-11-methyl-2,3,4,5-tetrahydro-2,6-methano-benzo[d]azocin-6(1H)-yl)ethyl)amino)-2-oxoethyl)benzoate |
| 31 | 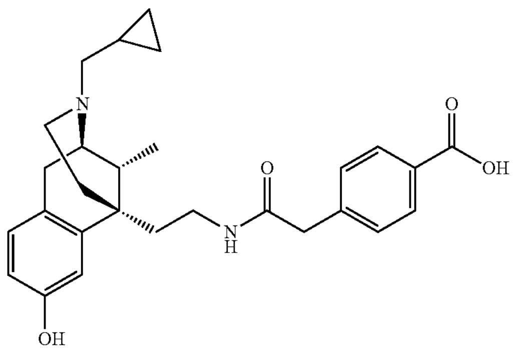 | 4-(2-((2-((2R,6R,11R)-3-(cyclopropyl-methyl)-8-hydroxy-11-methyl-2,3,4,5-tetrahydro-2,6-methanobenzo[d]azocin-6(1H)-yl)ethyl)amino)-2-oxoethyl)-benzoic acid |
| 32 | 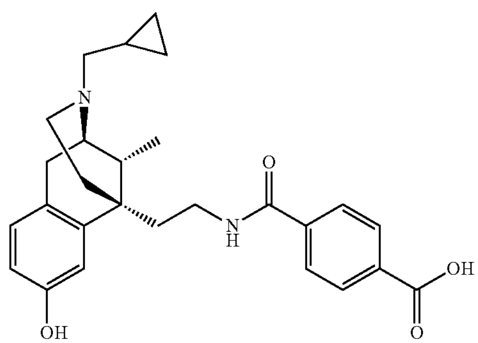 | 4-((2-((2R,6R,11R)-3-(cyclopropyl-methyl)-8-hydroxy-11-methyl-2,3,4,5-tetrahydro-2,6-methanobenzo[d]azocin-6(1H)-yl)ethyl)carbamoyl)benzoic acid |
| 33 | 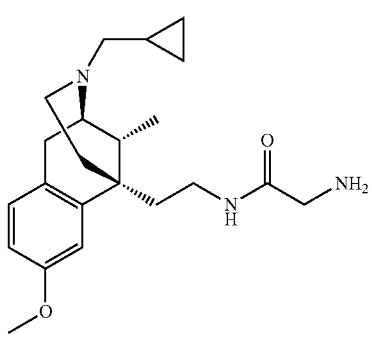 | 2-amino-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)acetamide |

TABLE 2-continued

| Cpd # | Structure | Chemical name |
|---|---|---|
| 34 | 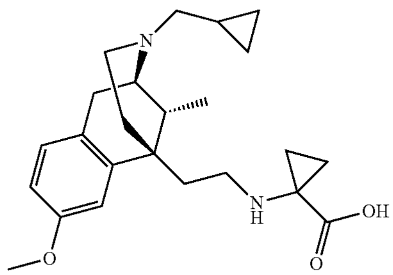 [SMILES: COc1ccc2c(c1)[C@]1(CCNC3(C(=O)O)CC3)CCN(CC3CC3)[C@H](C2)[C@@H]1C] | 1-((2-((2R,6R,11R)-3-(cyclopropyl-methyl)-8-methoxy-11-methyl-2,3,4,5-tetrahydro-2,6-methanobenzo[d]azocin-6(1H)-yl)ethyl)amino)cyclopropane-1-carboxylic acid |
| 35 | 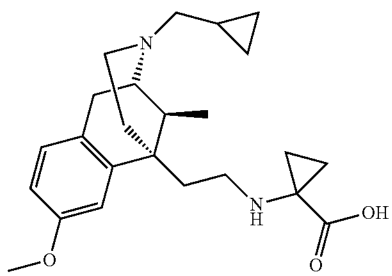 | 1-((2-((2S,6S,11S)-3-(cyclopropyl-methyl)-8-methoxy-11-methyl-2,3,4,5-tetrahydro-2,6-methanobenzo[d]azocin-6(1H)-yl)ethyl)amino)cyclopropane-1-carboxylic acid |
| 36 | 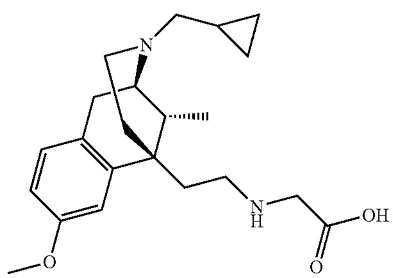 [SMILES: COc1ccc2c(c1)[C@]1(CCNCC(=O)O)CCN(CC3CC3)[C@H](C2)[C@@H]1C] | (2-((2R,6R,11R)-3-(cyclopropyl-methyl)-8-methoxy-11-methyl-2,3,4,5-tetrahydro-2,6-methanobenzo[d]azocin-6(1H)-yl)ethyl)glycine |
| 37 | 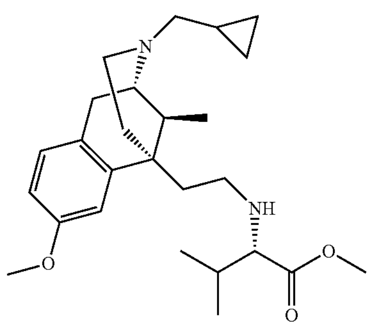 | methyl (2-((2S,6S,11S)-3-(cyclopropyl-methyl)-8-methoxy-11-methyl-2,3,4,5-tetrahydro-2,6-methanobenzo[d]azocin-6(1H)-yl)ethyl)-L-valinate |
| 38 | 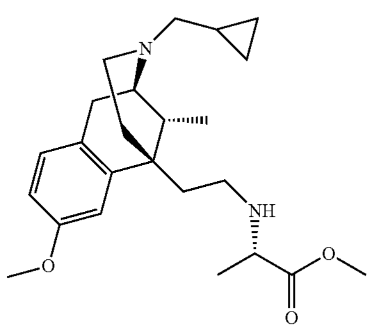 | methyl (2-((2R,6R,11R)-3-(cyclopropyl-methyl)-8-methoxy-11-methyl-2,3,4,5-tetrahydro-2,6-methanobenzo[d]azocin-6(1H)-yl)ethyl)-L-alaninate |

TABLE 2-continued

| Cpd # | Structure | Chemical name |
|---|---|---|
| 39 | 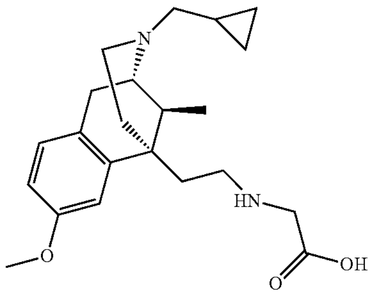 [SMILES: COc1ccc2c(c1)[C@@]1(CCNCC(=O)O)CCN(CC3CC3)[C@@H](C2)[C@H]1C] | (2-((2S,6S,11S)-3-(cyclopropylmethyl)-8-methoxy-11-methyl-2,3,4,5-tetrahydro-2,6-methanobenzo[d]azocin-6(1H)-yl)ethyl)glycine |
| 40 | 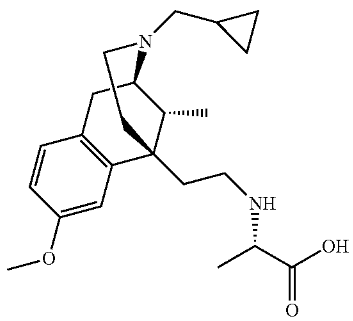 [SMILES: COc1ccc2c(c1)[C@]1(CCN[C@@H](C)C(=O)O)CCN(CC3CC3)[C@H](C2)[C@@H]1C] | (2-((2R,6R,11R)-3-(cyclopropyl-methyl)-8-methoxy-11-methyl-2,3,4,5-tetrahydro-2,6-methanobenzo[d]azocin-6(1H)-yl)ethyl)-L-ananine |
| 41 | 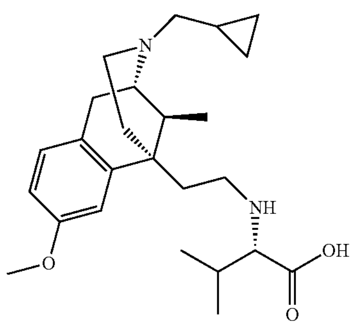 [SMILES: COc1ccc2c(c1)[C@@]1(CCN[C@H](C(=O)O)C(C)C)CCN(CC3CC3)[C@@H](C2)[C@H]1C] | (2-((2S,6S,11S)-3-(cyclopropylmethyl)-8-methoxy-11-methyl-2,3,4,5-tetrahydro-2,6-methanobenzo[d]azocin-6(1H)-yl)ethyl)-L-valine |
| 42 | 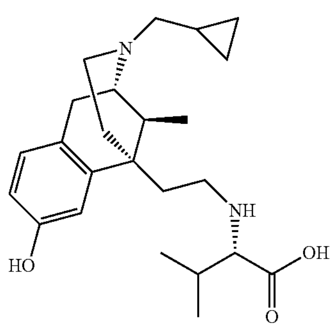 [SMILES: CC(C)[C@H](NCC[C@@]12CCN(CC3CC3)[C@@H](Cc3ccc(O)cc31)[C@H]2C)C(=O)O] | (2-((2S,6S,11S)-3-(cyclopropylmethyl)-8-hydroxy-11-methyl-2,3,4,5-tetrahydro-2,6-methanobenzo[d]azocin-6(1H)-yl)ethyl)-L-valine |
| 43 | 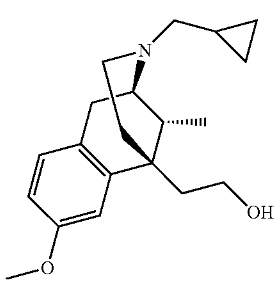 [SMILES: COc1ccc2c(c1)[C@]1(CCO)CCN(CC3CC3)[C@H](C2)[C@@H]1C] | 2-((2R,6S,11R)-3-(cyclopropylmethyl)-8-methoxy-11-methyl-2,3,4,5-tetrahydro-2,6-methanobenzo[d]azocin-6(1H)-yl)ethan-1-ol |

TABLE 2-continued

| Cpd # | Structure | Chemical name |
|---|---|---|
| 44 | 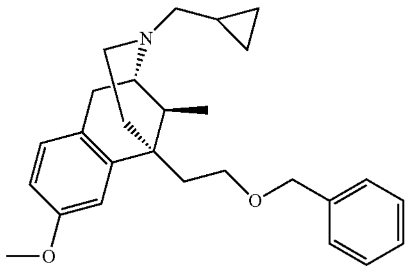 [SMILES: COc1ccc2c(c1)[C@@]1(CCOCc3ccccc3)CCN(CC3CC3)[C@@H](C2)[C@H]1C] | (2S,6R,11S)-6-(2-(benzyloxy)ethyl)-3-(cyclopropylmethyl)-8-methoxy-11-methyl-1,2,3,4,5,6-hexahydro-2,6-methanobenzo[d]azocine |
| 45 | 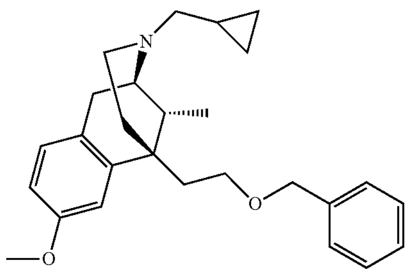 [SMILES: COc1ccc2c(c1)[C@]1(CCOCc3ccccc3)CCN(CC3CC3)[C@H](C2)[C@@H]1C] | (2R,6S,11R)-6-(2-(benzyloxy)ethyl)-3-(cyclopropylmethyl)-8-methoxy-11-methyl-1,2,3,4,5,6-hexahydro-2,6-methanobenzo[d]azocine |
| 46 | 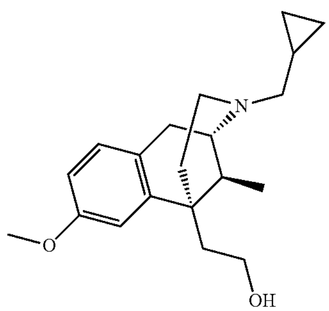 [SMILES: COc1ccc2c(c1)[C@@]1(CCO)CCN(CC3CC3)[C@@H](C2)[C@H]1C] | 2-((2S,6R,11S)-3-(cyclopropylmethyl)-8-methoxy-11-methyl-2,3,4,5-tetrahydro-2,6-methanobenzo[d]azocin-6(1H)-yl)ethan-1-ol |
| 47 | 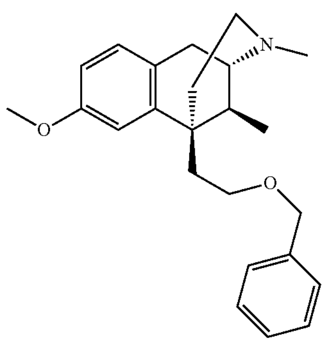 | (2S,6R,11S)-6-(2-(benzyloxy)ethyl)-8-methoxy-3,11-dimethyl-1,2,3,4,5,6-hexahydro-2,6-methanobenzo[d]azocine |
| 48 | 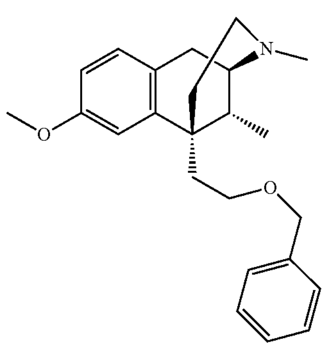 | (2R,6S,11R)-6-(2-(benzyloxy)ethyl)-8-methoxy-3,11-dimethyl-1,2,3,4,5,6-hexahydro-2,6-methanobenzo[d]azocine |

TABLE 2-continued

| Cpd # | Structure | Chemical name |
|---|---|---|
| 49 | 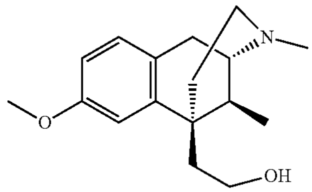 | 2-((2S,6R,11S)-8-methoxy-3,11-dimethyl-2,3,4,5-tetrahydro-2,6-methanobenzo[d]azocin-6(1H)-yl)ethan-1-ol |
| 50 | 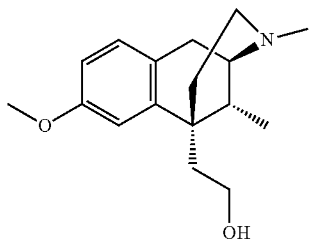 | 2-((2R,6S,11R)-8-methoxy-3,11-dimethyl-2,3,4,5-tetrahydro-2,6-methanobenzo[d]azocin-6(1H)-yl)ethan-1-ol |
| 51 | 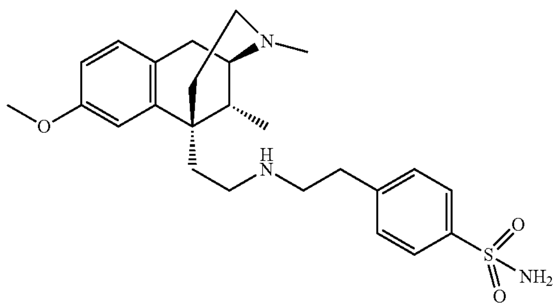 | 4-(2-((2-((2R,6R,11R)-8-methoxy-3,11-dimethyl-2,3,4,5-tetrahydro-2,6-methanobenzo[d]azocin-6(1H)-yl)ethyl)amino)ethyl)benzenesulfonamide |
| 52 | 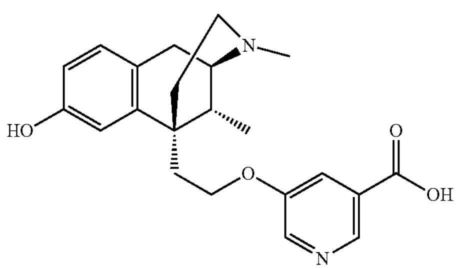 | 5-(2-((2R,6S,11R)-8-hydroxy-3,11-dimethyl-2,3,4,5-tetrahydro-2,6-methanobenzo[d]azocin-6(1H)-yl)ethoxy)nicotinic acid |
| 53 | 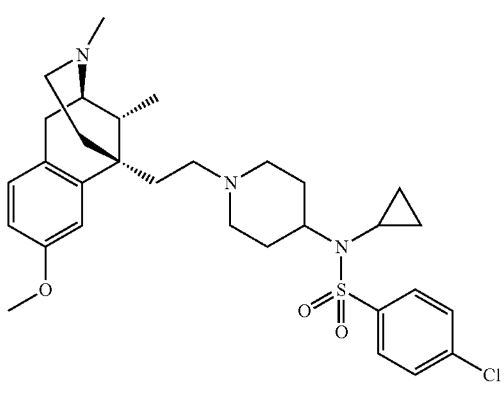 | 4-chloro-N-cyclopropyl-N-(1-(2-((2R,6R,11R)-8-methoxy-3,11-dimethyl-2,3,4,5-tetrahydro-2,6-methanobenzo[d]azocin-6(1H)-yl)ethyl)piperidin-4-yl)benzenesulfonamide |

TABLE 2-continued

| Cpd # | Structure | Chemical name |
|---|---|---|
| 54 | 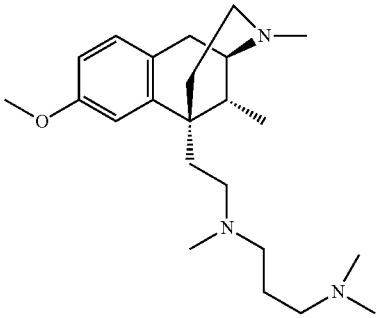 | $N^1$-2-((2R,6R,11R)-8-methoxy-3,11-dimethyl-2,3,4,5-tetrahydro-2,6-methano-benzo[d]azocin-6(1H)-yl)ethyl)-$N^1$,$N^3$,$N^3$-trimethylpropane-1,3-diamine |
| 55 | 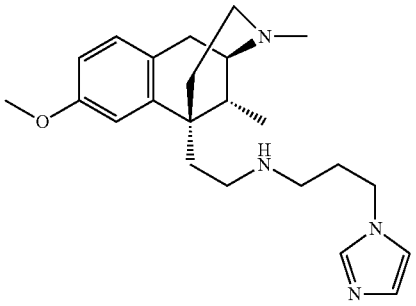 | 3-(1H-imidazol-1-yl)-N-(2-((2R,6R,11R)-8-methoxy-3,11-dimethyl-2,3,4,5-tetrahydro-2,6-methanobenzo[d]azocin-6(1H)-yl)ethyl)propan-1-amine |
| 56 | 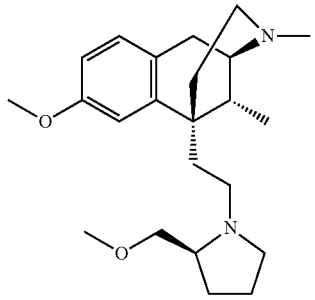 | (2R,6S,11R)-8-methoxy-6-(2-((S)-2-(methoxymethyl)pyrrolidin-1-yl)ethyl)-3,11-dimethyl-1,2,3,4,5,6-hexahydro-2,6-methanobenzo[d]azocine |
| 57 | 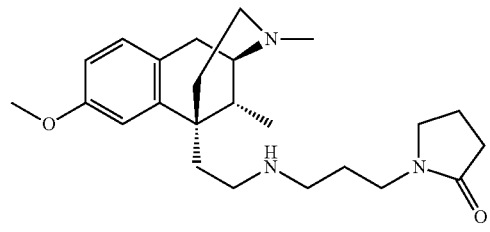 | 1-(3-((2-((2R,6R,11R)-8-methoxy-3,11-dimethyl-2,3,4,5-tetrahydro-2,6-methanobenzo-[d]azocin-6(1H)-yl)ethyl)amino)propyl)pyrrolidin-2-one |
| 58 | 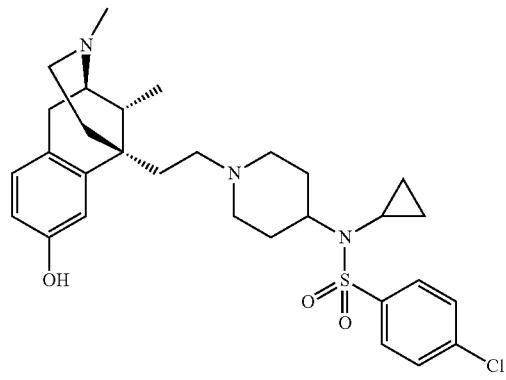 | 4-chloro-N-cyclopropyl-N-(1-(2-((2R,6R,11R)-8-hydroxy-3,11-dimethyl-2,3,4,5-tetrahydro-2,6-methanobenzo-[d]azocin-6(1H)-yl)ethyl)piperidin-4-yl)-benzenesulfonamide |

TABLE 2-continued

| Cpd # | Structure | Chemical name |
| --- | --- | --- |
| 59 | 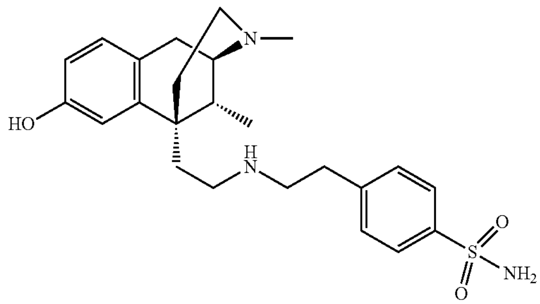 | 4-(2-((2-((2R,6R,11R)-8-hydroxy-3,11-dimethyl-2,3,4,5-tetrahydro-2,6-methanobenzo[d]azocin-6(1H)-yl)ethyl)amino)ethyl)benzenesulfonamide |
| 60 | 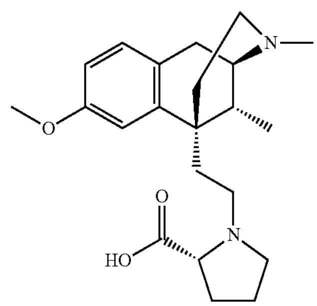 | (2-((2R,6S,11R)-8-methoxy-3,11-dimethyl-2,3,4,5-tetrahydro-2,6-methanobenzo[d]azocin-6(1H)-yl)ethyl)-D-proline |
| 61 | 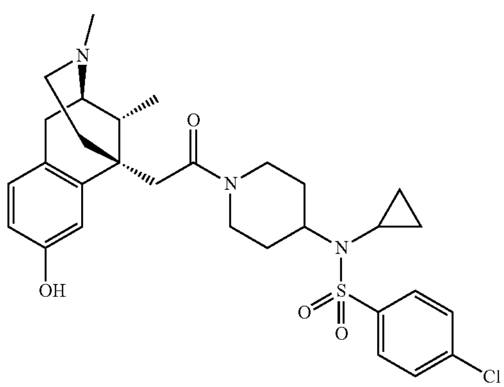 | 4-chloro-N-cyclopropyl-N-(1-(2-((2R,6S,11R)-8-hydroxy-3,11-dimethyl-2,3,4,5-tetrahydro-2,6-methano-benzo[d]azocin-6(1H)-yl)acetyl)-piperidin-4-yl)benzenesulfonamide |
| 62 | 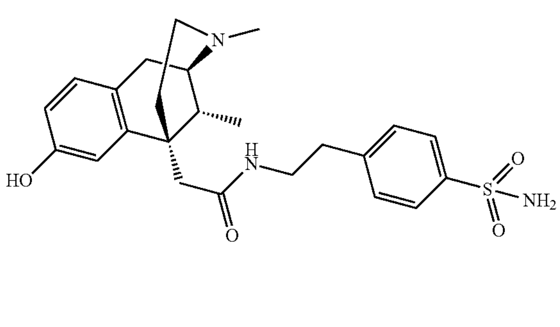 | 2-((2R,6S,11R)-8-hydroxy-3,11-dimethyl-2,3,4,5-tetrahydro-2,6-methanobenzo[d]azocin-6(1H)-yl)-N-(4-sulfamoylphenethyl)acetamide |

TABLE 2-continued

| Cpd # | Structure | Chemical name |
|---|---|---|
| 63 | 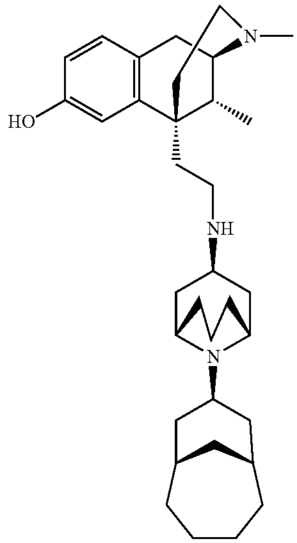 | (2R,6R,11R)-6-(2-(((1R,3R,5S)-9-((1R,6S,8r)-bicyclo[4.3.1]decan-8-yl)-9-azabicyclo[3.3.1]nonan-3-yl)amino)-ethyl)-3,11-dimethyl-1,2,3,4,5,6-hexahydro-2,6-methanobenzo[d]azocin-8-ol |
| 64 | 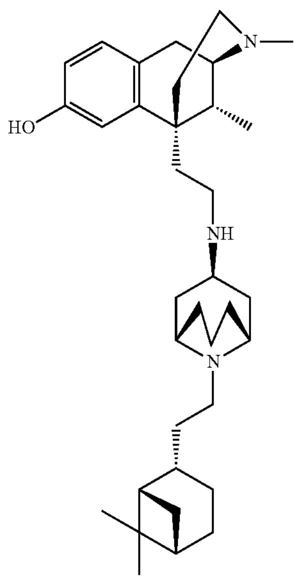 | (2R,6R,11R)-6-(2-(((1R,3S,5S)-9-(2-((1S,2S,5S)-6,6-dimethylbicyclo-[3.1.1]heptan-2-yl)ethyl)-9-azabicyclo-[3.3.1]nonan-3-yl)amino)ethyl)-3,11-dimethyl-1,2,3,4,5,6-hexahydro-2,6-methanobenzo[d]azocin-8-ol |
| 65 | 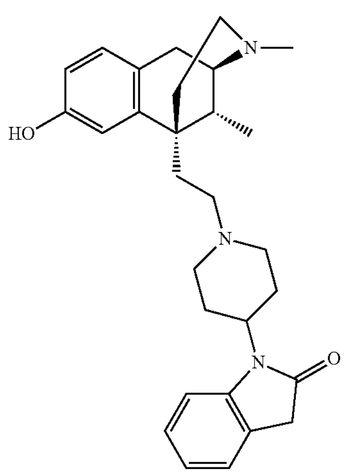 | 1-(1-(2-((2R,6R,11R)-8-hydroxy-3,11-dimethyl-2,3,4,5-tetrahydro-2,6-methanobenzo[d]azocin-6(1H)-yl)ethyl)piperidin-4-yl)indolin-2-one |

TABLE 2-continued

| Cpd # | Structure | Chemical name |
|---|---|---|
| 66 | 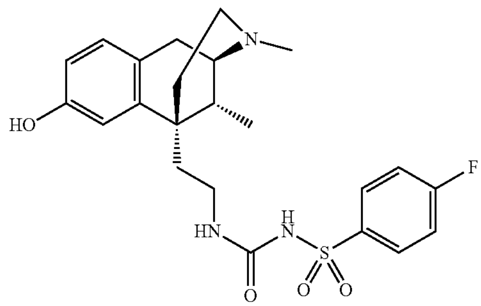 | 4-fluoro-N-((2-((2R,6R,11R)-8-hydroxy-3,11-dimethyl-2,3,4,5-tetrahydro-2,6-methanobenzo[d]azocin-6(1H)-yl)-ethyl)carbamoyl)benzenesul-fonamide |
| 67 | 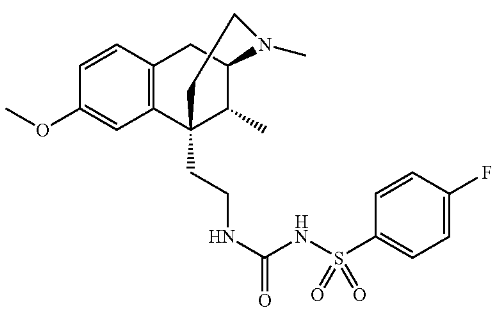 | 4-fluoro-N-((2-((2R,6R,11R)-8-methoxy-3,11-dimethyl-2,3,4,5-tetrahydro-2,6-methanobenzo[d]azocin-6(1H)-yl)ethyl)-carbamoyl)benzene-sulfonamide |
| 68 | 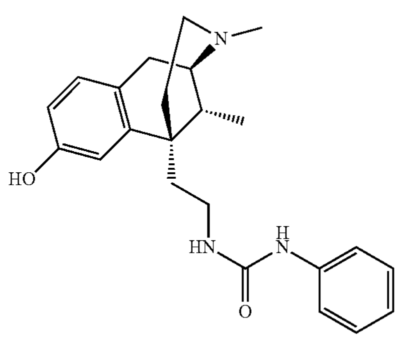 [SMILES: C[C@H]1[C@H]2Cc3ccc(O)cc3[C@@]1(CCNC(=O)Nc1ccccc1)CCN2C] | 1-(2-((2R,6R,11R)-8-hydroxy-3,11-dimethyl-2,3,4,5-tetrahydro-2,6-methano-benzo[d]azocin-6(1H)-yl)ethyl)-3-phenylurea |
| 69 | 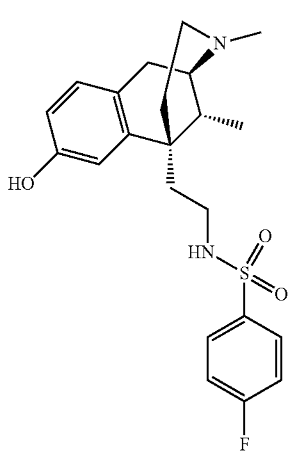 [SMILES: C[C@H]1[C@H]2Cc3ccc(O)cc3[C@@]1(CCNS(=O)(=O)c1ccc(F)cc1)CCN2C] | 4-fluoro-N-(2-((2R,6S,11R)-8-hydroxy-3,11-dimethyl-2,3,4,5-tetrahydro-2,6-methanobenzo[d]azocin-6(1H)-yl)ethyl)-benzenesulfonamide |

TABLE 2-continued

| Cpd # | Structure | Chemical name |
| --- | --- | --- |
| 70 | 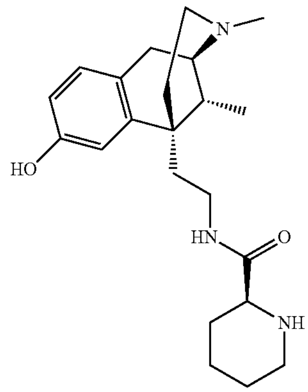 [SMILES: C[C@H]1[C@H]2Cc3ccc(O)cc3[C@@]1(CCNC(=O)[C@@H]1CCCCN1)CCN2C] | (S)-N-(2-((2R,6R,11R)-8-hydroxy-3,11-dimethyl-2,3,4,5-tetrahydro-2,6-methano-benzo[d]azocin-6(1H)-yl)ethyl)-piperidine-2-carboxamide |
| 71 | 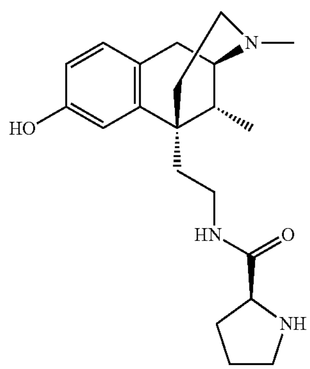 | (S)-N-(2-((2R,6R,11R)-8-hydroxy-3,11-dimethyl-2,3,4,5-tetrahydro-2,6-methano-benzo[d]azocin-6(1H)-yl)ethyl)-pyrrolidine-2-carboxamide |
| 72 | 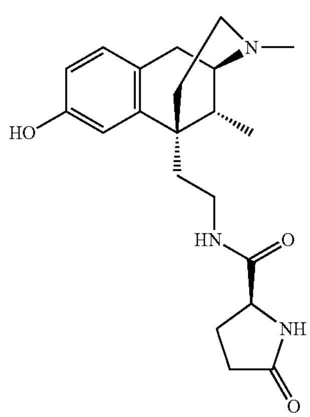 | (S)-N-(2-((2R,6R,11R)-8-hydroxy-3,11-dimethyl-2,3,4,5-tetrahydro-2,6-methano-benzo[d]azocin-6(1H)-yl)ethyl)-5-oxopyrrolidine-2-carboxamide |
| 73 | 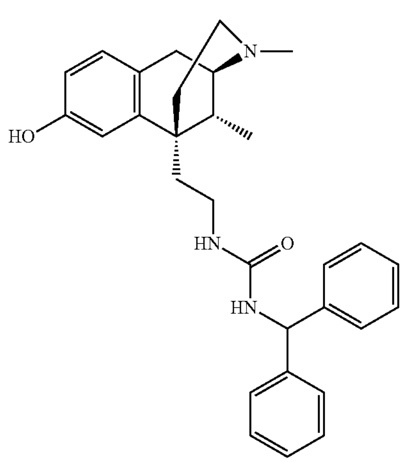 | 1-Benzhydryl-3-(2-((2R,6R,11R)-8-hydroxy-3,11-dimethyl-2,3,4,5-tetrahydro-2,6-methanobenzo[d]azocin-6(1H)-yl)ethyl)urea |

TABLE 2-continued
| Cpd # | Structure | Chemical name |
|---|---|---|
| 74 | 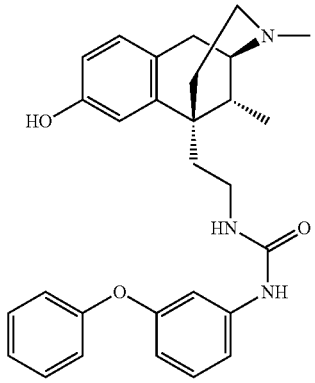 | 1-(2-((2R,6R,11R)-8-hydroxy-3,11-dimethyl-2,3,4,5-tetrahydro-2,6-methanobenzo[d]azocin-6(1H)-yl)ethyl)-3-(3-phenoxyphenyl)urea |
| 75 | 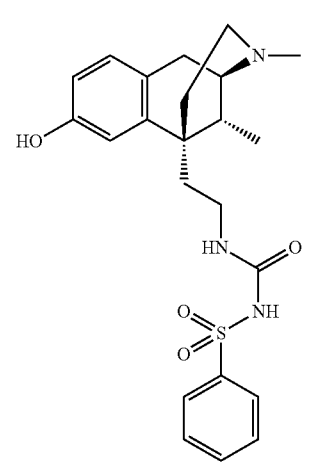 | N-((2-((2R,6R,11R)-8-hydroxy-3,11-dimethyl-2,3,4,5-tetrahydro-2,6-methanobenzo[d]azocin-6(1H)-yl)-ethyl)carbamoyl)benzenesulfonamide |
| 76 | 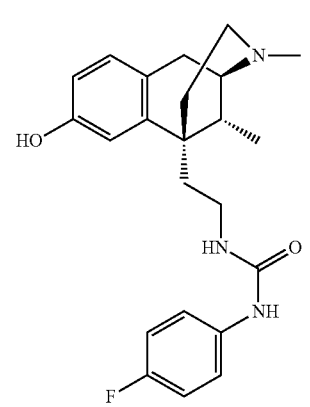 | 1-(4-fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea |

TABLE 2-continued

| Cpd # | Structure | Chemical name |
|---|---|---|
| 77 | 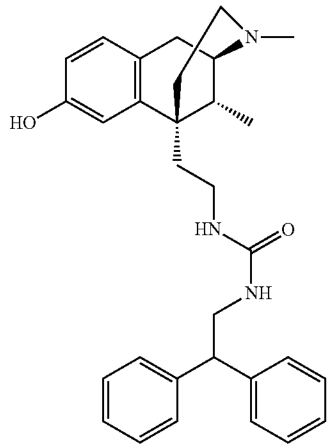 | 1-(2,2-diphenylethyl)-3-(2-((2R,6R,11R)-8-hydroxy-3,11-dimethyl-2,3,4,5-tetrahydro-2,6-methanobenzo[d]azocin-6(1H)-yl)ethyl)urea |
| 78 | 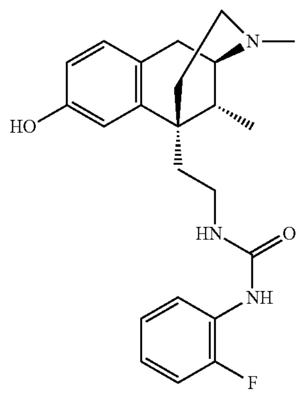 | 1-(2-fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea |
| 79 | 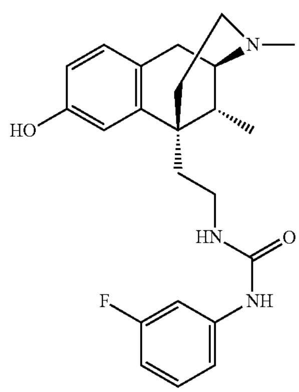 | 1-(3-fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea |
| 80 | 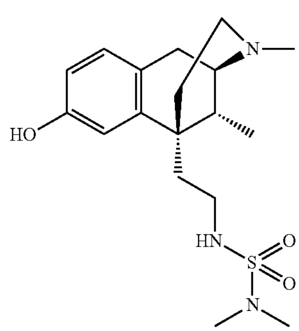 | |

TABLE 2-continued

| Cpd # | Structure | Chemical name |
| --- | --- | --- |
| 81 | 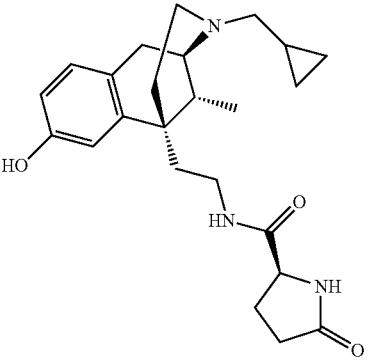 | (S)-N-(2-((2R,6R,11R)-3-(cyclopropyl-methyl)-8-hydroxy-11-methyl-2,3,4,5-tetrahydro-2,6-methanobenzo[d]azocin-6(1H)-yl)ethyl)-5-oxopyrrolidine-2-carboxamide |
| 82 | 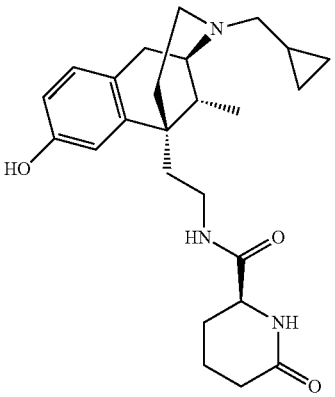 [SMILES: C[C@H]1[C@H]2Cc3ccc(O)cc3[C@]1(CCNC(=O)[C@@H]1CCCC(=O)N1)CCN2CC1CC1] | (S)-N-(2-((2R,6R,11R)-3-(cyclopropyl-methyl)-8-hydroxy-11-methyl-2,3,4,5-tetrahydro-2,6-methanobenzo[d]azocin-6(1H)-yl)ethyl)-6-oxopiperidine-2-carboxamide |
| 83 | 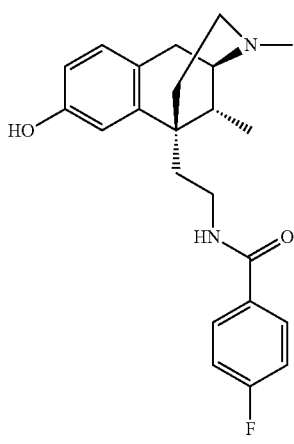 | 4-Fluoro-N-(2-((2R,6R,11R)-8-hydroxy-3,11-dimethyl-2,3,4,5-tetrahydro-2,6-methanobenzo[d]azocin-6(1H)-yl)ethyl)benzamide |
| 84 | 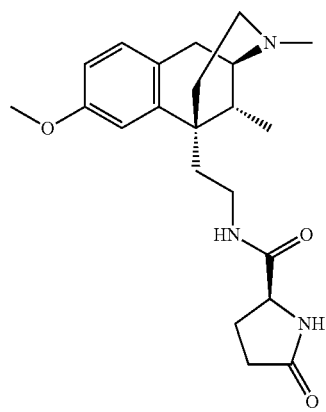 | (S)-N-(2-((2R,6R,11R)-8-methoxy-3,11-dimethyl-2,3,4,5-tetrahydro-2,6-methanobenzo[d]azocin-6(1H)-yl)ethyl)-5-oxopyrrolidine-2-carboxamide |

TABLE 2-continued

| Cpd # | Structure | Chemical name |
|---|---|---|
| 85 | 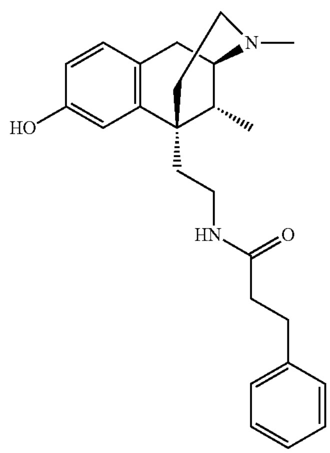 | N-(2-((2R,6R,11R)-8-hydroxy-3,11-dimethyl-2,3,4,5-tetrahydro-2,6-methanobenzo[d]azocin-6(1H)-yl)ethyl)-3-phenylpropanamide |
| 86 | 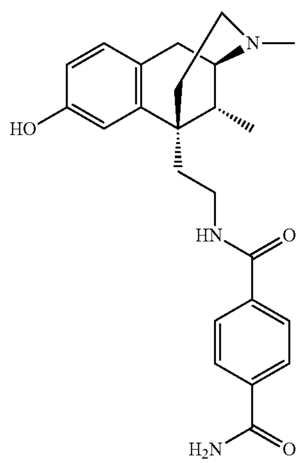 | N-(2-((2R,6R,11R)-8-hydroxy-3,11-dimethyl-2,3,4,5-tetrahydro-2,6-methanobenzo[d]azocin-6(1H)-yl)ethyl)terephthalamide |

The Compounds of the Invention can be in the form of prodrugs of the compounds of Formula I, Formula II, Formula A, or Formula B. Prodrugs are covalently bonded carrier molecules that release an active compound of Formula I, Formula II, Formula A, or Formula B in vivo. Non-limiting examples of prodrugs will typically include esters of the Compounds of the Invention that can be metabolized to the active compound by the action of enzymes in the body. Such prodrugs may be prepared by reacting a compound of Formula I, II, A, or B, with an anhydride, such as succinic anhydride.

The Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^{3}H$, $^{11}C$, and $^{14}C$. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

Isotopically labeled Compounds of the Invention, as well as pharmaceutically acceptable salts, prodrugs and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radiolabeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

The Compounds of the Invention also encompass all salts of the compounds of Formula I, II, A, or B. The invention includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of a particular Compound of the Invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, trifluoroacetic acid, and the like. Basic salts can be formed by mixing a solution of the particular Compound of the Invention and a pharmaceutically acceptable non-toxic base such as sodium hydroxide, potassium hydroxide, choline hydroxide, sodium carbonate and the like. The ratio between the particular Compound of the Invention and the pharmaceutically acceptable non-toxic acid/base in the resulting salt can be 1:1, 1:2, 1:3, or 1:4, respectively.

Compounds of the Invention also encompass solvates of the disclosed compounds of Formula I, II, A, or B. The term "solvate" as used herein is a combination, physical association and/or solvation of a compound of Formula I, II, A, or B with a solvent molecule such as, e.g. a disolvate, monosolvate or hemisolvate, where the ratio of solvent molecule to compound of Formula I, II, A, or B is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of Formula I, II, A, or B or may be present as a solvated form with a pharmaceutically acceptable solvent, such as water, methanol, ethanol, and the like, and it is intended that the invention include both solvated and unsolvated forms of Formula I, II, A, or B compounds.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3): 601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process of preparing a solvate would involve dissolving a compound of Formula I, II, A, or B in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

In certain embodiments, the Compounds of the Invention have activity as μ receptor antagonists. Certain Compounds of the Invention are expected to have dual activity as both μ receptor antagonists and κ receptor agonists. In other embodiments, Compounds of the Invention are expected to have an activity wherein they are μ receptor antagonists, κ receptor agonists, and δ receptor antagonists, and inactive at ORL-1 receptors. In other embodiments, certain Compounds of the Invention are expected to have an activity wherein they are μ receptor antagonists, κ receptor agonists, and δ receptor antagonists, and ORL-1 receptor antagonists. In other embodiments, certain Compounds of the Invention are expected to have an activity wherein they are μ receptor antagonists, κ receptor agonists, and δ receptor antagonists, and ORL-1 receptor partial agonists. Certain Compounds of the Invention are expected to be substantially restricted their activities to the GI tract.

It is expected that certain Compounds of the Invention that have μ antagonist activity and are substantially restricted to the GI tract will significantly reduce or prevent constipation that would otherwise occur in a patient as a result of treatment with a μ agonist. In one embodiment, the reduction or prevention of constipation is obtained without reducing the desired analgesic effect of the μ agonist. Further, certain Compounds of the Invention that also exhibit κ agonist activity should additionally stimulate GI motility via a non-μ receptor mediated mechanism.

In one embodiment, certain Compounds of the Invention are useful for modulating a pharmacodynamic response from ORL-1 receptors either centrally or peripherally, or both. The Compounds of the Invention may also be useful for modulating a pharmacodynamic response from one or more opioid receptors (μ, δ, κ) either centrally or peripherally, or both. The pharmacodynamic response may be attributed to the compound stimulating (agonizing) or inhibiting (antagonizing) the one or more receptors. Certain Compounds of the Invention may inhibit (or antagonize) the ORL-1 receptor, while also stimulating (or agonizing) one or more other receptors (e.g. as a μ, δ, and/or κ agonist). Compounds of the Invention having agonist activity may be either full or partial agonists.

In other embodiments, Compounds of the Invention can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

The invention also provides the use of a Compound of the Invention in the manufacture of a medicament for treating or preventing a Condition. In one embodiment, the Condition is pain, such as acute pain, chronic pain, or surgical pain. In certain instances, the chronic pain is neuropathic pain, postoperative pain, or inflammatory pain.

In another embodiment, a Compound of the Invention has agonist activity at the µ, δ and/or κ receptors. In another embodiment a Compound of the Invention has agonist activity at the µ receptor. In another embodiment, a Compound of the Invention has antagonist activity at the ORL-1 receptor. In another embodiment, certain Compounds of the invention can stimulate one receptor (e.g., a µ, δ and/or κ agonist) and inhibit a different receptor (e.g., an ORL-1 antagonist). In another embodiment, the Compound of the Invention is an agonist at the µ receptor, and an antagonist at the ORL-1 receptor. In another embodiment, the Compound of the Invention is an antagonist at the µ receptor, and an agonist at the κ receptor.

Various objects and advantages of the invention will become apparent from the following detailed description.

DEFINITIONS

In order that the invention may be more readily understood, certain terms used in the present disclosure are defined and collected herein for convenience.

As used herein, the term "alkyl" as used by itself or as part of another group refers to a straight- or branched-chain aliphatic hydrocarbon containing one or more carbon atoms. In certain embodiments, the "alkyl" group used herein is further designated by the number of carbon atoms of the aliphatic hydrocarbon chain. For example, "—($C_1$-$C_{10}$)alkyl refers to straight-chain and branched non-cyclic saturated hydrocarbons having 1, 2, 3, 4, 5, 6, 7, 8, 9, or 10 carbon atoms. Representative straight chain —($C_1$-$C_{10}$)alkyl groups include methyl, -ethyl, -n-propyl, -n-butyl, -n-pentyl, -n-hexyl, n-heptyl, n-octyl, n-nonyl and n-decyl. Representative branched —($C_1$-$C_{10}$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

Further, the term "—($C_1$-$C_6$)alkyl" refers to straight-chain and branched non-cyclic saturated hydrocarbons having from 1 to 6 carbon atoms. Representative straight chain —($C_1$-$C_6$)alkyl groups include methyl, -ethyl, -n-propyl, -n-butyl, -n-pentyl, and -n-hexyl. Representative branched-chain —($C_1$-$C_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-mehtylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "alkenyl" by itself or as part of another group refers to an alkyl group as defined above containing one, two or three carbon-to-carbon double bonds. For example, the term "—($C_2$-$C_{12}$)alkenyl" refers to straight chain and branched non-cyclic hydrocarbons having 2, 3, 4, 5, 6, 7, 8, 9, 10, 11, or 12 carbon atoms and including at least one carbon-carbon double bond. Representative straight chain and branched —($C_2$-$C_{12}$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

Also as used herein, the term "—($C_2$-$C_{10}$)alkenyl" refers to straight chain and branched non-cyclic hydrocarbons having 2, 3, 4, 5, 6, 7, 8, 9, or 10 carbon atoms and including at least one carbon-carbon double bond. Representative straight chain and branched —($C_2$-$C_{10}$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

Further, the term "—($C_2$-$C_6$)alkenyl" refers to straight chain and branched non-cyclic hydrocarbons having from 2 to 6 carbon atoms and including at least one carbon-carbon double bond. Representative straight chain and branched —($C_2$-$C_6$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, and the like.

As used herein, the term "alkynyl" by itself or as part of another group refers to an alkyl group as defined above containing one to three carbon-to-carbon triple bonds. For example, the term "—($C_2$-$C_{12}$)alkynyl" refers to straight chain and branched non-cyclic hydrocarbons having 2, 3, 4, 5, 6, 7, 8, 9, 10, 11, or 12 carbon atoms and including at least one carbon-carbon triple bond. Representative straight chain and branched —($C_2$-$C_{12}$)alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

Further, the term "—($C_2$-$C_{10}$)alkynyl" refers to straight chain and branched non-cyclic hydrocarbons having 2, 3, 4, 5, 6, 7, 8, 9, or 10 carbon atoms and including at least one carbon-carbon triple bond. Representative straight chain and branched —($C_2$-$C_{10}$)alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

Also as used herein, the term "—($C_2$-$C_6$)alkynyl" refers to straight chain and branched non-cyclic hydrocarbons having from 2 to 6 carbon atoms and including at least one carbon-carbon triple bond. Representative straight chain and branched —($C_2$-$C_6$)alkynyl groups include -acetylenyl, -propynyl, -1 butynyl, -2-butynyl, -1-pentynyl, -2-pentynyl, -3-methyl-1-butynyl, -4-pentynyl, and the like.

As used herein, the term "alkoxy" by itself or as part of another group refers to an optionally substituted alkyl, optionally substituted cycloalkyl, optionally substituted alkenyl, or optionally substituted alkynyl attached to a terminal oxygen atom. For example, "$C_1$-$C_{10}$ alkoxy" means a straight chain or branched non-cyclic hydrocarbon having one or more ether groups and 1, 2, 3, 4, 5, 6, 7, 8, 9, or 10 carbon atoms. Representative straight chain and branched —($C_1$-$C_{10}$)alkoxys include -methoxy, -ethoxy, -propoxy, -butyloxy, -pentyloxy, -hexyloxy, -heptyloxy, and the like.

As another example, "—($C_1$-$C_5$)alkoxy" means a straight chain or branched non-cyclic hydrocarbon having one or more ether groups and from 1 to 5 carbon atoms. Representative straight chain and branched ($C_1$-$C_5$)alkoxys include -methoxy, -ethoxy, -propoxy, -butyloxy, -pentyloxy, and the like.

As used herein, the term "alkoxyalkyl" or "(alkoxy)alkyl" by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

As used herein, As used herein, the term "cycloalkyl" by itself or as part of another group refers to saturated and partially unsaturated (containing one or two double bonds) cyclic aliphatic hydrocarbons containing one to three rings having from three or more carbon atoms (e.g., $C_{3-12}$ cycloalkyl) or the number of carbons designated. In one instance, the term "—$(C_3-C_{12})$cycloalkyl" refers to a cyclic saturated hydrocarbon having 3, 4, 5, 6, 7, 8, 9, 10, 11, or 12 carbon atoms. Representative $(C_3-C_{12})$cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As used herein, "—$(C_6-C_{14})$bicycloalkyl" means a bicyclic hydrocarbon ring system having 6, 7, 8, 9, 10, 11, 12, 13, or 14 carbon atoms and at least one saturated cyclic alkyl ring. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—$(C_8-C_{20})$tricycloalkyl" means a tricyclic hydrocarbon ring system having 8, 9, 10, 11, 12, 13, 14, 15, 16, 17, 18, 19, or 20 carbon atoms and at least one saturated cyclic alkyl ring. Representative —$(C_8-C_{20})$tricycloalkyls include -pyrenyl, -adamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta [e]azulenyl, hexadecahydrocycloocta[b]naphthalenyl, hexadecahydrocycloheptala[a]heptalenyl, tricyclo-pentadecanyl, tricyclo-octadecanyl, tricyclo-nonadecanyl, tricyclo-icosanyl, and the like.

As used herein, the term "cycloalkenyl" refers to cyclic aliphatic hydrocarbons that include at least one carbon-carbon double bond. For example, the term "—$(C_3-C_{12})$cycloalkenyl" refers to a cyclic hydrocarbon having 3, 4, 5, 6, 7, 8, 9, 10, 11, or 12 carbon atoms, and including at least one carbon-carbon double bond. Representative —$(C_3-C_{12})$cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As another example, the term "—$(C_4-C_{12})$cycloalkenyl" refers to a cyclic hydrocarbon having from 4 to 12 carbon atoms, and including at least one carbon-carbon double bond. Representative —$(C_4-C_{12})$cycloalkenyls include -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "bicycloalkenyl" means a bi-cyclic hydrocarbon ring system having at least one carbon-carbon double bond in at least one of the rings. In one embodiment, bicycloalkenyl used herein is a "—$(C_7-C_{14})$bicycloalkenyl" which has from 7 to 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—$(C_8-C_{20})$tricycloalkenyl" means a tri-cyclic hydrocarbon ring system having at least one carbon-carbon double bond in one of the rings and from 8 to 20 carbon atoms. Representative —$(C_8-C_{20})$tricycloalkenyls include -anthracenyl, -phenanthrenyl, -phenalenyl, -acenaphthalenyl, as-indacenyl, s-indacenyl, 2,3,6,7, 8,9,10,11-octahydro-1H-cycloocta[e]indenyl, 2,3, 4,7,8,9,10,11-octahydro-1H-cyclohepta-[a]naphthalenyl, 8, 9,10, 11-tetrahydro-7H-cyclohepta [a] naphthalenyl , 2,3,4,5,6,7, 8,9,10,11,12,13-dodecahydro-1H-cyclohepta[a]heptalenyl, 1,2,3,4,5,6,7,8,9,10,11, 12,13,14-tetradecahydro-dicyclohepta [a,c] cyclooctenyl, 2,3,4,5,6,7,8,9,10,11,12,13-dodecahydro-1H-dibenzo [a,d]cyclononenyl, and the like.

As used herein, the term "heterocyclo" or "heterocycle" by itself or as part of another group refers to saturated and partially unsaturated (e.g., containing one or two double bonds) cyclic groups containing one, two, or three rings having from three or more ring members (e.g., a 3- to 14-membered heterocyclo) and at least one heteroatom. For example, "-(3- to 12-membered)heterocycle" or "-(3- to 12-membered)heterocyclo" means a 3- to 12-membered monocyclic heterocyclic ring which is either saturated, or unsaturated, non-aromatic, or aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered)heterocycles include aziridinyl, thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(5- to 12-membered)heterocycle" or "-(5- to 12-membered)heterocyclo" means a 5- to 12-membered monocyclic heterocyclic ring which is either saturated, or unsaturated, non-aromatic, or aromatic. A 5-membered heterocycle can contain up to 4 heteroatoms; a 6-membered heterocycle can contain up to 4 heteroatoms; and a 7-membered heterocycle can contain up to 5 heteroatoms. Representative (5- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, oxepanyl, thiepinyl, 3,4,5,6-tetrahydro-2H-azepinyl, 1,4-thiazepinyl, azocinyl, thiocanyl, and the like.

As used herein, "-(4- to 8-membered)heterocycle" or "-(4- to 8-membered)heterocyclo" means a 4- to 8-membered monocyclic heterocyclic ring which is either saturated or unsaturated, non-aromatic, or aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like. -membered)bicycloheterocyclo" means a 7- to 12-membered bicyclic, heterocyclic ring which is either saturated, unsaturated, non-aromatic, or aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -benzo[d][1,3]dioxolyl, -indazolyl, -purinyl, -4H-quinolizinyl, -isoquinolyl, -quinolyl, -phthalazinyl, -naphthyridinyl, -carbazolyl, β-carbolinyl, -indolinyl, isoindolinyl, -1,2,3,4-tetrahydroquinolinyl, -1,2,3,4-tetrahydrois oquinolinyl, pyrrolopyrrolyl and the like.

As used herein, the term "aryl" by itself or as part of another group refers to a monocyclic or bicyclic aromatic ring system having from six or more carbon atoms (e.g., $C_6$-$C_{14}$ aryl). For example, a "-(6- to 14-membered)aryl" means an aromatic carbocyclic ring containing 6 to 14 carbon atoms, including both mono- and bicyclic ring systems. Representative -(5- to 14-membered)aryl groups include indenyl, -phenyl, -naphthyl, and the like.

As used herein a "-(7- to 12-membered)bicyclic aryl" means an bicyclic aromatic carbocyclic ring containing 7 to 12 carbon atoms. Representative -(7- to 12-membered) bicyclic aryl groups include -indenyl, -naphthyl, and the like.

As used herein, the term "aryloxy" by itself or as part of another group refers to an optionally substituted aryl attached to a terminal oxygen atom. For example, a "-(6- to 14-membered)aryloxy" means an oxygen substituted by an aromatic carbocyclic ring containing 6 to 14 carbon atoms, including both mono- and bicyclic ring systems, e.g. such as defined for the -(6- to 14-membered)aryl group above. Representative -(6- to 14-membered)aryloxy groups include phenoxy and 4-fluorophenoxy, and the like.

As used herein, the term "hydroxyalkyl" or "(hydroxy)alkyl" (also as "(hydroxyl)alkyl") by itself or as part of another group refers to an alkyl group substituted with one hydroxy group, i.e., the hydroxyalkyl group is a monohydroxyalkyl group, i.e., substituted with one hydroxy group. In one embodiment, the hydroxyalkyl group is a "hydroxy ($C_1$-$C_6$)alkyl", which means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein, a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a mono- or bicyclic hydrocarbon ring system having from 5 to 12 carbon atoms, which is either saturated, unsaturated, non-aromatic or aromatic. Representative -(5- to 12-membered)carbocyclic rings include cyclopentyl, cyclohexyl, cycloheptyl, cyclooctyl, cyclononyl, cyclodecyl, cycloundecyl, cyclododecyl, -indanyl, -norbornyl, -1,2,3,4-tetrahydronaphthalenyl, -5,6,7,8-tetrahydronaphthalenyl, -perhydronaphthalenyl, adamantyl, cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, heptalenyl, and the like.

As used herein a "(7- to 12-membered)bicyclic ring system" means a 7- to 12-membered carbocyclic or heterocyclic ring, which may be either unsaturated, saturated, non-aromatic or aromatic. Representative -(7- to 12-membered)bicyclic ring systems include azulenyl, norbornyl, 1,2,3,4-tetrahydronaphthalenyl, 5,6,7,8-tetrahydronaphthalenyl, perhydronaphthalenyl, bicyclo[3.2.0]hept-2-enyl, indenyl, naphthyl, pentalenyl, naphthalenyl, azulenyl, heptalenyl, 1,2,7,8-tetrahydro-naphthalenyl, quinolinyl, isoquinolinyl, chromonyl, coumarinyl, indolyl, indolizinyl, benzo[b]furanyl, benzo[b]thiophenyl, benzo[d][1,3]dioxolyl, indazolyl, purinyl, 4H-quinolizinyl, isoquinolyl, quinolyl, phthalazinyl, naphthyridinyl, carbazolyl, β-carbolinyl, indolinyl, isoindolinyl, 1,2,3,4-tetrahydroquinolinyl, 1,2,3,4-tetrahydro-isoquinolinyl, pyrrolopyrrolyl, and the like.

As used herein, the term "heteroaryl" or "heteroaromatic" refers to monocyclic and bicyclic aromatic ring systems having 5 or more ring atoms (e.g., 5- to 14-membered heteroaryl) and 1 or more heteroatoms independently chosen from oxygen, nitrogen and sulfur. For example, "(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —$CHBrCl$, —$CHClI$, and —$CHI_2$.

As used herein, "—C(halo)$_3$" means a methyl group where each of the hydrogens of the methyl group has been replaced with a halogen. Representative —C(halo)$_3$ groups include CF$_3$, —CCl$_3$, —CBr$_3$, and —CI$_3$.

As used herein, the term "sulfonyl" means —SO$_2$—.

As used herein, the term "—(C$_1$-C$_6$)alkylene" refers to bridging straight-chain and branched non-cyclic saturated hydrocarbons having 1, 2, 3, 4, 5, or 6 carbon atoms. Representative "—(C$_1$-C$_6$)alkylene" groups include methylene ( CH$_2$) ), ethylene ( CH$_2$CH$_2$—), propylene ( CH$_2$CH$_2$CH$_2$—), butylene ( CH$_2$CH$_2$CH$_2$CH$_2$—), pentylene ( CH$_2$CH$_2$CH$_2$CH$_2$CH$_2$—) and hexylene ( CH$_2$CH$_2$CH$_2$CH$_2$CH$_2$CH$_2$—), and the like.

As used herein, the term "optionally substituted" refers to a group that is either unsubstituted or substituted.

Optional substituents on optionally substituted groups, when not otherwise indicated, include 1, 2, or 3 groups each independently selected from the group consisting of —(C$_1$-C$_6$)alkyl, OH, halo, —C(halo)$_3$, —CH(halo)$_2$, —CH$_2$(halo), NH$_2$, —NH(C$_1$-C$_6$)alkyl, CN, SH, (5- to 12-membered) carbocyclic ring, (5- to 12-membered)-heterocycle, phenyl, benzyl, (=O), halo(C$_1$-C$_6$)alkyl-, —(C$_2$-C$_6$)alkenyl, —(C$_2$-C$_6$)alkynyl, hydroxy(C$_1$-C$_6$)alkyl-, OR$^{10}$ (such as OC(halo)$_3$ and —O(C$_1$-C$_6$)alkyl), —CONR$^{11}$R$^{12}$, and —COOR$^{13}$, where R$^{10}$ is selected from the group consisting of —(C$_1$-C$_6$)alkyl, —(C$_2$-C$_6$)alkenyl, —(C$_2$-C$_6$)alkynyl, —C(halo)$_3$, hydroxy(C$_1$-C$_6$)alkyl-, —(C$_3$-C$_{12}$)cycloalkyl, —(C$_6$-C$_{14}$)bicycloalkyl, —(C$_8$-C$_{20}$)tricycloalkyl, —(C$_4$-C$_{12}$)cycloalkenyl, —C$_7$-C$_{14}$)bicycloalkenyl, —(C$_8$-C$_{20}$)tricycloalkenyl, -(6- to 14-membered)aryl, -(5- to 12-membered)heteroaryl, -(3- to 12-membered)heterocycle, and -(7- to 12-membered) bicycloheterocycle; R$^{11}$ and R$^{12}$ are each independently —(C$_1$-C$_6$)alkyl, —(C$_3$-C$_8$)cycloalkyl, ((C$_3$-C$_8$)cycloalkyl)-(C$_1$-C$_6$)alkyl-, or together with the nitrogen atom to which they are attached form a (4- to 8-membered)heterocycle; and R$^{13}$ is selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, (C$_4$-C$_{12}$)cycloalkenyl, ((C$_3$-C$_{12}$)cycloalkyl)-(C$_1$-C$_6$)alkyl-, ((C$_4$-C$_{12}$)cycloalkenyl)-(C$_1$-C$_6$) alkyl-, —(C$_1$-C$_6$)alkoxy-COOR$^7$, —NH—C(=O)—NH—(C$_1$-C$_6$)alkyl, —NH—C(=O)-(6- to 14-membered)-aryl, —NH—C(=O) (C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-CO—OR$^7$, —NH—C(=O)—CH(NH$_2$)—(C$_1$-C$_6$) alkyl-CO—OR$^7$, —(C$_3$-C$_{12}$)cycloalkyl, (6- to 14-membered)aryl, (6- to 14-membered)aryloxy, —(C$_1$-C$_6$)alkoxyC (O)NR$^5$R$^6$, —NH—(C$_1$-C$_6$)alkylC(O)—NR$^5$R$^6$, —C(O) NH—(C$_1$-C$_6$)alkyl-COOR$^7$, —(C$_1$-C$_6$)alkyl-C(=O)—(C$_1$-C$_6$)alkoxy, —(C$_1$-C$_6$)alkoxy-C(=O)—(C$_1$-C$_6$)alkyl, —(C$_1$-C$_6$)alkyl-CN, —(C$_1$-C$_6$)alkyl-COOR$^7$, —(C$_1$-C$_6$)alkoxy-COOR$^7$, (C$_3$-C$_{12}$)cycloalkyl, ((C$_3$-C$_{12}$)cycloalkyl)-(C$_1$-C$_6$) alkyl-, ((C$_3$-C$_{12}$)cycloalkyl)-(C$_1$-C$_6$)alkoxy-, ((C$_3$-C$_{12}$) cycloalkyl)-(C$_1$-C$_6$)alkoxy-(C$_1$-C$_6$)alkyl-, (C$_4$-C$_{12}$) cycloalkenyl, ((C$_4$-C$_{12}$)-cycloalkenyl)-(C$_1$-C$_6$)alkyl-, ((C$_4$-C$_{12}$)cycloalkenyl)-(C$_1$-C$_6$)alkoxy-, ((C$_4$-C$_{12}$)cycloalkenyl)-(C$_1$-C$_6$)alkoxy-(C$_1$-C$_6$)alkyl-, -(6- to 14-membered)aryl, ((6- to14-membered)aryl)-(C$_1$-C$_6$)alkyl-, ((6- to 14-membered)aryl)-(C$_1$-C$_6$)alkoxy-, ((6- to 14-membered)aryl)-(C$_1$-C$_6$)alkoxy-(C$_1$-C$_6$)alkyl-, -(5- to 12-membered)heteroaryl, ((5- to 12-membered)heteroaryl)-(C$_1$-C$_6$)alkyl-, ((5- to 12-membered)heteroaryl)-(C$_1$-C$_6$)alkoxy-, ((5- to 12-membered)heteroaryl)-(C$_1$-C$_6$)alkoxy-(C$_1$-C$_6$)alkyl-, -(3- to 12-membered)heterocycle, ((3- to 12 membered)heterocycle)-(C$_1$-C$_6$)alkyl-, ((3- to 12 membered)heterocycle)-(C$_1$-C$_6$)alkoxy-, and ((3- to 12 membered)heterocycle)-(C$_1$-C$_6$)alkoxy (C$_1$-C$_6$)alkyl-.

As used herein, the term "stereoisomer" is a general term for all isomers of individual molecules that differ only in the orientation of their atoms in space. It includes enantiomers and isomers of compounds with more than one chiral center that are not minor images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its minor image compound rotates the plane of polarized light in the opposite direction.

The term "racemic" refers to a mixture of equal parts of enantiomers and which mixture is optically inactive. Racemic compounds can be separated into their enantiomers by chiral chromatography.

The term "resolution" refers to the separation or concentration or depletion of one of the two enantiomeric forms of a molecule.

The terms "a" and "an" refer to one or more.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001).

As used herein, prodrugs are considered to be compounds with moieties that can be metabolized in vivo. In general, such prodrugs will be functional derivatives of compounds of any of the formulae delineated herein, which will be readily convertible in vivo, e.g., by being metabolized, into the required compound of any of the formulae. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

Further, the following list provides an exemplified list of certain abbreviations used in the present disclosure:

LIST OF ABBREVIATIONS

Abbreviation Full name
ACN acetonitrile
AcOH acetic acid
Boc tert-butoxycarbonyl
° C degrees Celcius
Cbz benzyloxycarbonyl
d day(s)
DCM dichloromethane
DEAD diethyl azodicarboxylate
DIPEA diisopropylethylamine
DMF dimethylformamide
DMSO dimethylsulfoxide
EDCI 1-ethyl-3-(3-dimethylaminopropyl)carbodiimide)
EtOAc ethyl acetate
EtOH ethanol
h hour(s)

HATU 2-(7-aza-1H-benzotriazole -1-yl)-1,1,3,3-tetramethyluronium hexafluorophosphate
HPLC high pressure liquid chromatography
LAH lithium aluminum hydride
LDA lithium diisopropylamide
MeOH methanol
min minute(s)
MPLC medium pressure liquid chromatography
(Ph)$_3$P triphenylphosphine
PTSA p-toluenesulfonic acid
PyBOP benzotriazol-1-yl-oxytripyrrolidinophosphonium hexafluorophosphate
RT room temperature
s second(s)
TEA triethylamine
Tf trifluoromethanesulfonyl
TFA trifluoroacetic acid
THF tetrahydrofuran
TMEDA N,N,N',N'-tetramethylethylenediamine General Synthetic Schemes The compounds of Formula I or II can be prepared through organic synthetic procedures known in the art, including those disclosed in WO 2013/167963 A1. Further, certain illustrative preparation processes are also provided below.

Tetralone A can be converted to intermediate B with suitable amine (such as N,N-diethylenediamine) in a suitable solvent (such as toluene) at room temperature to 130° C. (Hatakeyama, et al., *J. Am. Chem. Soc.,* 2005, 127, 14192-14193). Compound C is prepared by alkylation of imine B with a suitable protected haloalcohol (such as, a benzyl bromoalkyl ether) in a suitable solvent (such as, tetrahydrofuran (THF)) in the presence of an Grignard reagent (such as, 2-mesityl magnesium bromide) at room temperature to 70° C. Compound C can be alkylated again with a haloacetonitrile in the presence of inorganic base (such as sodium hydride) in a suitable solvent (such as, toluene) at room temperature to 130° C. to provide nitrile D.

Olefin E can be provided by Wittig reaction on nitrile D with a yilde which can be prepared by reacting suitable phosphonium salt (such as methyltriphenyl-phosphonium bromide) with suitable organic base (such as potassium tert-butoxide) in suitable solvent (such as THF) at −78° C. to 80° C. Olefin E can be reduced to amine F with a suitable reducing agent (such as lithium aluminum hydride) in suitable solvent (such as, diethylether) at 0° C. to room temperature. Benzomorphan G is prepared by cyclizing amine F with suitable base (such as, lithium diisopropylamide) in the presence of tetramethylethylenediamine in suitable solvent such as THF at −78° C. to 80° C. (Trost et al., *J. Am. Chem. Soc.,* 2003, 125, 8744-8745).

Scheme A

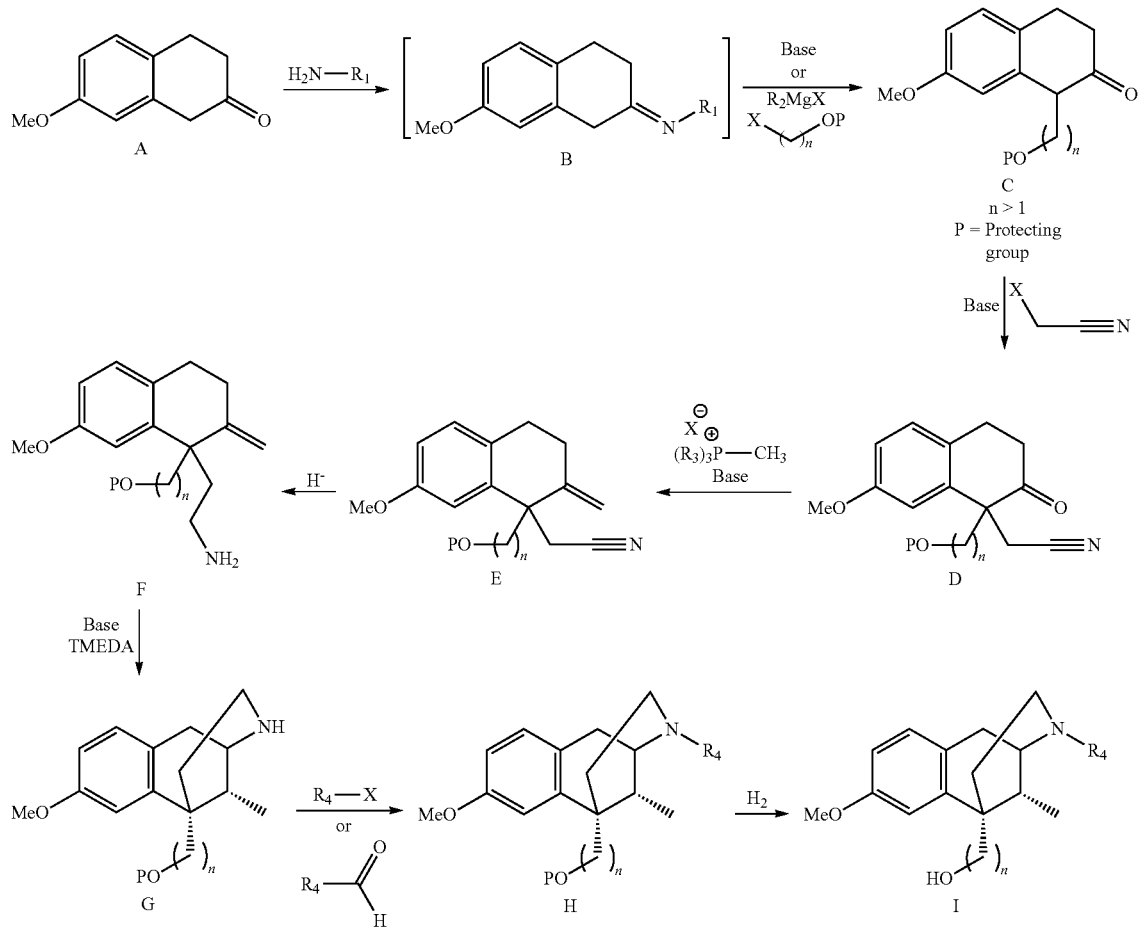

Benzomorphan G can be N-alkylated either by reaction with an alkyl halide in a suitable solvent (such as acetonitrile) with a suitable base (such as, potassium carbonate) or by reductive amination with an aldehyde in an suitable solvent (such as, isopropyl acetate) with a suitable reducing agent (such as, sodium triacetoxy-borohydride). Alcohol I is prepared by removing the benzyl protecting group with suitable catalyst (such as, palladium on carbon) in the presence of hydrogen gas in suitable solvent, such as 20% acetic acid in methanol.

Scheme B

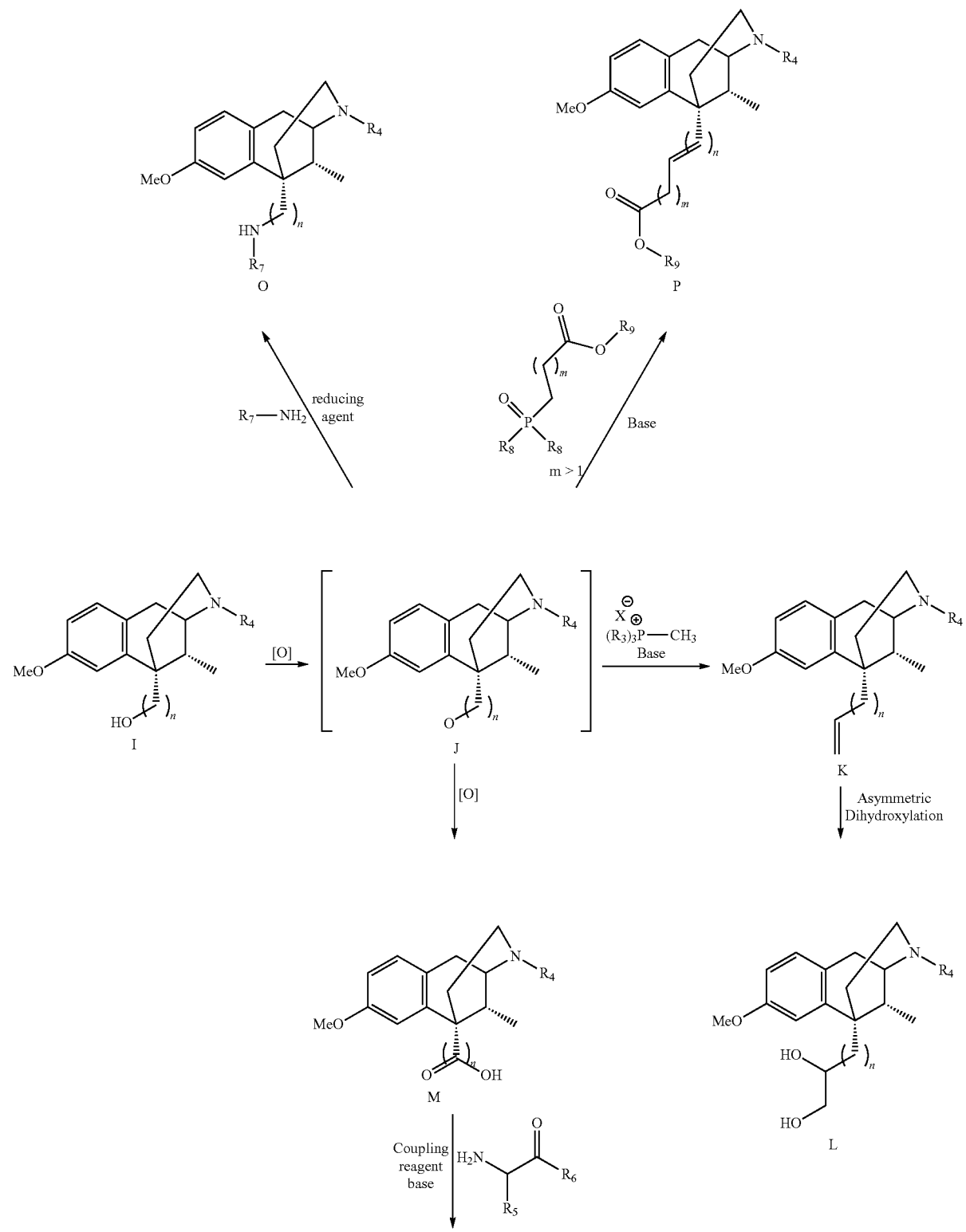

-continued

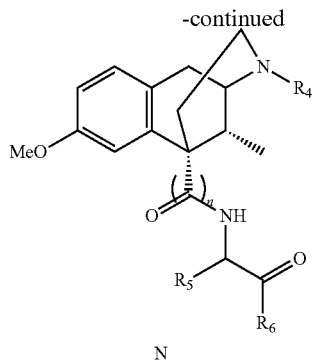

N

Alcohol I can be oxidized to aldehyde J with a suitable oxidizing agent, such as oxalyl chloride, dimethylsulfoxide (DMSO) and triethylamine, in a suitable solvent, such as dichloromethane (DCM), at −78° C. to room temperature.

Olefin K can be prepared by Wittig reaction of aldehyde J with a yilde which can be prepared by reacting a suitable phosphonium salt (such as, methyltriphenyl-phosphonium bromide) with a suitable organic base (such as potassium tert-butoxide) in a suitable solvent (such as, THF or toluene) at −78° C. to 130° C. Olefin K can then be converted to diol L with suitable asymmetric dihydroxylating reagents, such as AD-mix, in a suitable solvent, such as a mixture of isopropyl alcohol and water, at room temperature.

Acid M can be prepared by oxidizing aldehyde J with suitable oxidizing agent (such as, sodium chlorite and sodium bisulfate) in a suitable solvent (such as a mixture of water and acetonitrile) at room temperature. Amide N can be prepared by coupling acid M with suitable amino acid derivatives (such as amidated alanine) and suitable coupling reagent, such as 2-(1H-7-azabenzotriazol-1-yl)-1,1,3,3-tetramethyl uronium hexafluorophosphate methane-aminium (HATU), and suitable organic base, such as N,N-diisopropylethylamine (DIPEA) in a suitable solvent, such as N,N-dimethylformamide (DMF), at room temperature.

Amine O can be prepared from aldehyde J by reductive amination with an amine in a suitable solvent (such as, isopropyl acetate) with a suitable reducing agent (such as, sodium triacetoxyborohydride) at room temperature to 100° C.

C-6 substution chain can be extended to ester olefin P by Horner-Wadsworth-Emmons reaction of aldehyde J with suitable phosphonates (such as methyl diethylphosphonoacetate) in the presence of suitable organic base (such as potassium tert-butoxide) in a suitable solvent, such as THF, at −78° C. to 80° C.

Scheme C

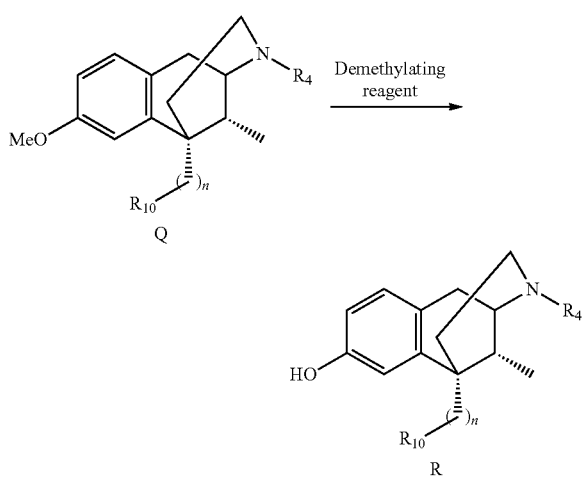

Phenol R can be prepared by demethylating methoxyphenol Q with a suitable demethylating reagent (such as, BBr$_3$) in suitable solvent (such as, dichloromethane) at −78° C. to room temperature.

Scheme D

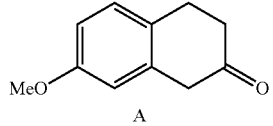 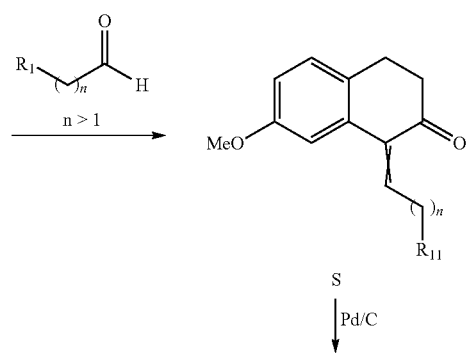

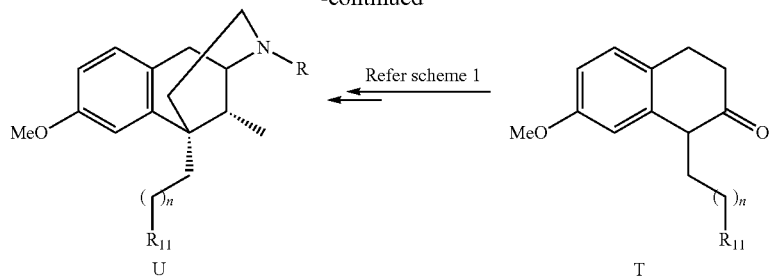

Tetralone A can be converted to intermediate S with a suitable aldehyde (such as, (E)-3-(furan-2-yl)acrylaldehyde) in a suitable solvent (such as, toluene) at room temperature to 130° C. Compound T is prepared by hydrogenation of olefin S with a suitable catalyst (such as, palladium on carbon) in the presence of hydrogen gas in a suitable solvent (such as, a mixture of EtOAc and EtOH).

In a similar manner as set forth in Scheme 1, compound T can be further carried on to prepare compound U.

The alpha substituted ketone in an opioid (such as Compound V-1) can be reduced to keto phenol W-1 with a suitable reducing agent (such as zinc metal) in a suitable solvent (such as aqueous acetone). The hydroxyl group in Compound W-1 can be converted to a suitable leaving group (such as a triflate) by the treatment with a suitable triflating reagent (such as N-phenyl triflimide) in the presence of a suitable base (such as cesium carbonate) in a suitable solvent (such as THF). The triflate in Compound X-1 can be reduced to Compound Y-1 by treatment with a suitable reagent (such as triethylsilane) in the presence of a suitable catalyst (such as palladium acetate) in a suitable solvent (such as, DMF).

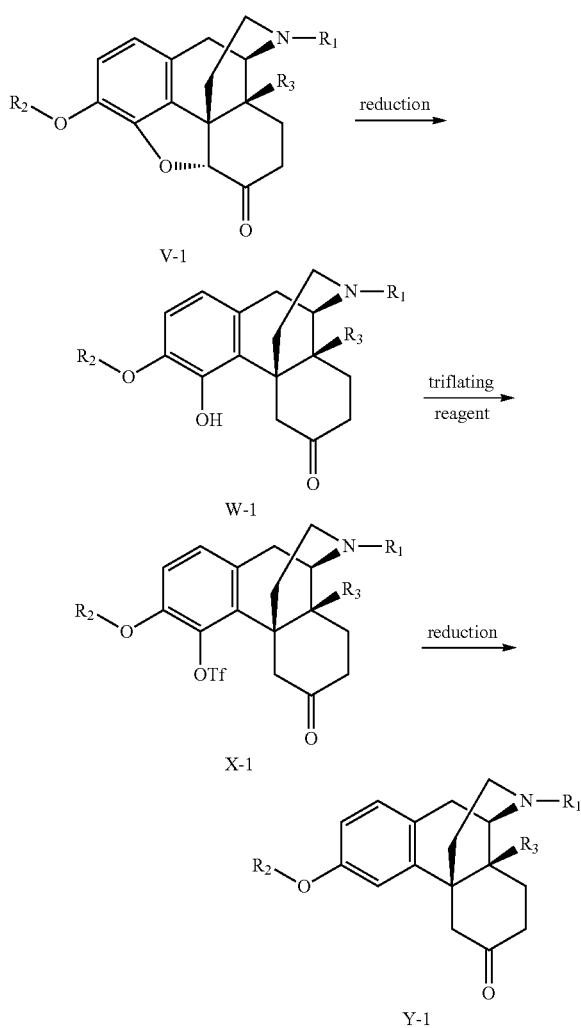

Scheme E

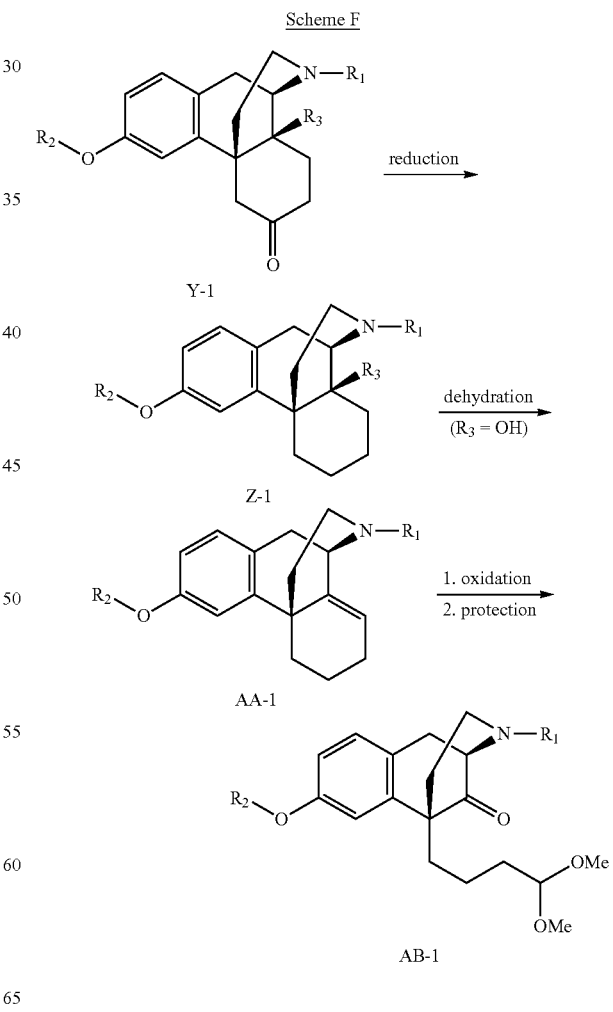

Scheme F

The ketone group in compound Y-1 can be reduced to a methylene group by a suitable reagent (such as tosylhydrazine) in a suitable solvent (such as EtOH), followed a reducing agent (such as catecholborane) in a suitable solvent (such as a mixture of THF and chloroform). Dehydration of the tertiary alcohol in Compound Z-1 ($R_3$=OH) to give alkene AA-1 can be accomplished by a treatment with a suitable dehydrating reagent (such as thionyl chloride) in a suitable base (such as pyridine). Oxidative cleavage of the double bond in Compound AA-1 can be accomplished by a suitable oxidizing reagent (such as ozone) in a suitable solvent (such as DCM) to give a keto aldehyde. The aldehyde can be protected by a treatment with an alcohol (such as MeOH) in the presence of a suitable acid catalyst (such as PTSA) to give Compound AB-1.

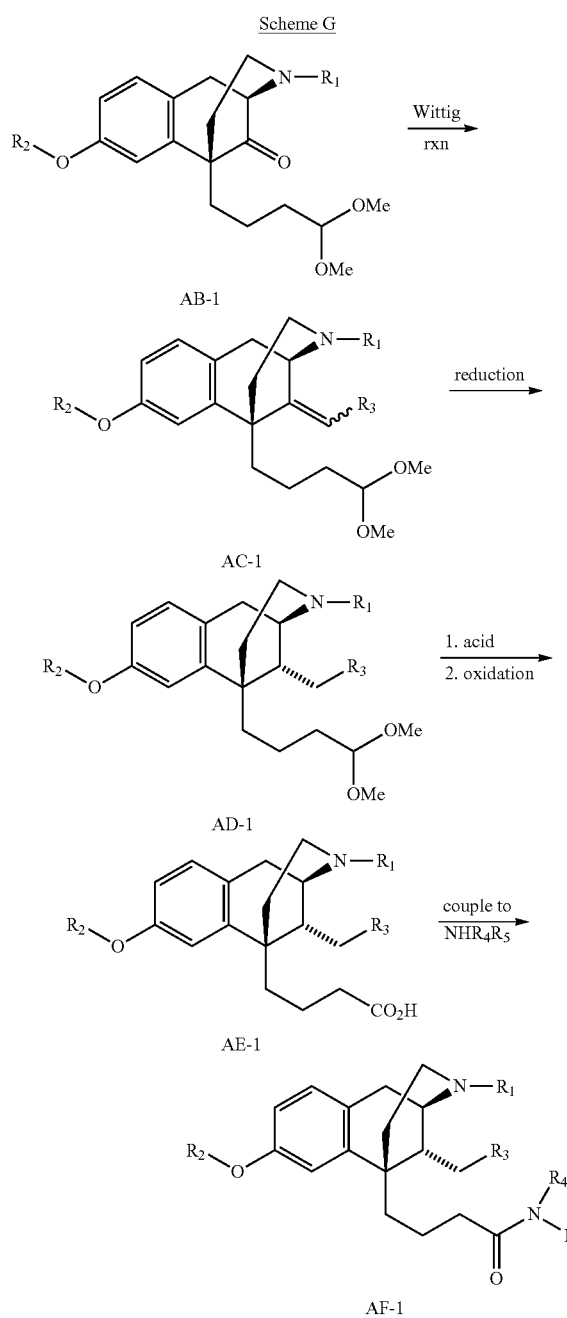

Scheme G

AB-1

AC-1

AD-1

AE-1

AF-1

The ketone in Compound AB-1 can be reacted with a suitable reagent (such as a Wittig reagent) in the presence of a suitable base (such as potassium tert-butoxide) in a suitable solvent (such as THF) to give olefin AC-1 which can be reduced to alkane AD-1 by reduction with a suitable reagent (such as hydrogen) in the presence of a suitable catalyst (such as palladium on carbon) in an appropriate solvent (such as MeOH). The protected aldehyde group in Compound AD-1 can be deprotected by a treatment with a suitable acid (such as TFA) in a suitable solvent or solvent mixture, such as DCM, acetone and water. The resulting aldehyde can be oxidized to carboxylic acid AE-1 by a treatment with a suitable oxidizing agent, such as a mixture of sodium chlorite and sodium dihydrogen phosphate, in a suitable solvent (such as aqueous CAN).

Compound AE-1 can then be converted to amide AF-1 by activation of the carboxylate group by a suitable reagent (such as, oxalyl chloride) in a suitable solvent (such as, DCM) followed by a treatment with an appropriate amine.

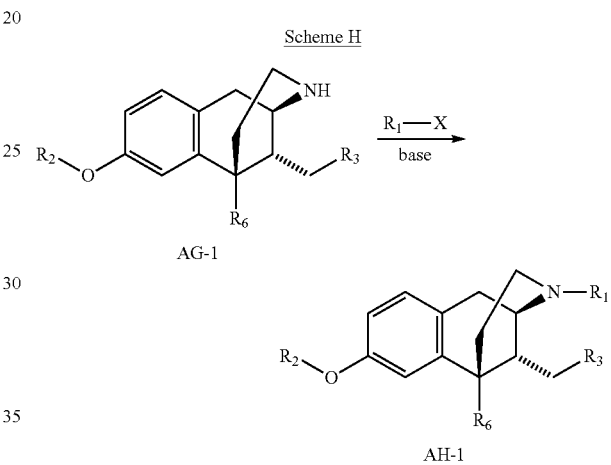

Scheme H

AG-1

AH-1

An opioid with a secondary amine (such as Compound AG-1) can be converted to a tertiary amine (such as Compound AH-1) by a treatment with a suitable alkyl halide in the presence of a suitable base (such as potassium carbonate) in a suitable solvent (such as CAN).

Testing Of Compounds

μ-opioid Receptor Binding Assay Procedures: Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-opioid Receptor Binding Data: Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures: [$^{35}$S] GTPγS functional assays were conducted using freshly thawed μ-receptor membranes (Perkin Elmer, Shelton, Conn.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S] GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 mM at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP $EC_{50}$ is the concentration of a compound providing 50% of the maximal response for the compound at a μ-opioid receptor. Compounds of the Invention will typically have a μ GTP $EC_{50}$ (nM) of about 5000 or less. In certain embodiments, Compounds of the Invention will have a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention will have a μ GTP $E_{max}$ (%) of greater than about 10%; or greater than about 20%. In certain embodiments, Compounds of the Invention will have a μ GTP $E_{max}$ (%) of greater than about 50%; or greater than about 65%; or greater than about 75%; or greater than about 85%; or greater than about 100%.

κ-opioid Receptor Binding Assay Procedures: Membranes from recombinant HEK-293 cells expressing the human κ opioid receptor (κ) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-opioid Receptor Binding Data: In certain embodiments, the Compounds of the Invention will have a Ki (nM) for K receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures: Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data: κ GTP $EC_{50}$ is the concentration of a compound providing 50% of the maximal response for the compound at a κ receptor. Certain Compounds of the Invention will have a κ GTP $EC_{50}$ (nM) of about 20,000 or less to stimulate κ opioid receptor function. In certain embodiments, Compounds of the Invention will have a κ GTP $EC_{50}$ (nM) of about 10,000 or less; or about 5000 or less; or about 2000 or less; or about 1500 or less; or about 1000 or less; or about 600 or less; or about 100 or less;

or about 50 or less; or about 25 or less; or about 10 or less; or about 1 or less; or about 0.1 or less.

κ GTP $E_{max}$ (%) is the maximal effect elicited by a compound relative to the effect elicited by U69,593. Certain Compounds of the Invention will have a κ GTP $E_{max}$ (%) of greater than about 1%; or greater than about 5%; or greater than about 10%; or greater than about 20%. In certain embodiments, Compounds of the Invention will have a κ GTP $E_{max}$ (%) of greater than about 50%; or greater than about 75%; or greater than about 90%; or greater than about 100%.

δ-opioid Receptor Binding Assay Procedures: δ-opioid Receptor Binding Assay Procedures were conducted as follows. Radioligand dose-displacement assays used 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM MgCl$_2$, 5% DMSO, 50 mM Trizma base, pH 7.4). Non-specific binding was determined in the presence of 25 μM unlabeled naloxone. All reactions were performed in 96-deep well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 500 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

δ-opioid Receptor Binding Data: In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures: Functional [$^{35}$S]GTPγS binding assays were conducted as follows. δ opioid receptor membrane solution was prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 1-2 hours. Fifty μl/well scintillation cocktail (Perkin Elmer, Shelton, Conn.) was added and plates were counted in a Packard Top-count for 1 min/well.

δ-Opioid Receptor Functional Data: δ GTP $EC_{50}$ is the concentration of a compound providing 50% of the maximal response for the compound at a δ receptor. Certain Compounds of the Invention will have a δ GTP $EC_{50}$ (nM) of about 20,000 or less; or about 10,000 or less. In certain embodiments, the Compounds of the Invention will have a δ GTP $EC_{50}$ (nM) of about 3500 or less; or of about 1000 or less; or of about 500 or less; or of about 100 or less; or of about 90 or less; or of about 50 or less; or of about 25 or less; or of about 10 or less.

δ GTP $E_{max}$ (%) is the maximal effect elicited by a compound relative to the effect elicited by met-enkephalin. Certain Compounds of the Invention of the invention will have a δ GTP $E_{max}$ (%) of greater than about 1%; or of greater than about 5%; or of greater than about 10%. In one embodiment, the Compounds of the Invention will have a δ GTP $E_{max}$ (%) of greater than about 30%. In other embodiments, the Compounds of the Invention will have a δ GTP $E_{max}$ (%) of greater than about 50%; or of greater than about 75%; or of greater than about 90%. In another embodiment, the Compounds of the Invention will have a δ GTP $E_{max}$ (%) of about 100% or greater.

ORL-1 Receptor Binding Assay Procedure: Membranes from recombinant HEK-293 cells expressing the human opioid receptor-like receptor (ORL-1) (Perkin Elmer, Shelton, Conn.) were prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Radioligand binding assays (screening and dose-displacement) used 0.1 nM [$^3$H]-nociceptin (Perkin Elmer, Shelton, Conn.; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at room temperature. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by three filtration washes with 500 μl ice-cold binding buffer. Filter plates were subsequently dried at 50° C. for 2-3 hours. Fifty μl/well scintillation cocktail (Perkin Elmer, Shelton, Conn.) was added and plates were counted in a Packard Top-Count for 1 min/well. The data from screening and dose-displacement experiments were analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure: Membranes from recombinant HEK-293 cells expressing the human opioid receptor-like (ORL-1) (Perkin Elmer, Shelton, Conn.) were prepared by lysing cells in ice-cold hypotonic buffer (2.5 mM Mg $Cl_2$, 50 mM HEPES, pH 7.4) (10 ml/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/ml. Protein concentrations were determined using the BioRad protein assay reagent with bovine serum albumen as standard. Aliquots of the ORL-1 receptor membranes were stored at −80° C.

Functional [$^{35}$S]GTPγS binding assays were conducted as follows. ORL-1 membrane solution was prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 μl of 20× concentrated stock solutions of agonist/nociceptin prepared in DMSO. Plates were incubated for 30 min at room temperature with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well. Data were analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) will have an ORL-1 GTP $EC_{50}$ (nM) of greater than about 10,000 (i.e. will not stimulate at therapeutic concentrations) In certain embodiments Compounds of the Invention will have an ORL-1 GTP $EC_{50}$ (nM) of about 20,000 or less. In one embodiment, the Compounds of the Invention will have an ORL-1 GTP $EC_{50}$ (nM) of about 10,000 or less; or of about 5000 or less; or of about 1000 or less. In still other embodiments, the Compounds of the Invention will have an ORL-1 GTP $EC_{50}$ (nM) of about 100 or less; or of about 10 or less; or of about 1 or less; or of about 0.1 or less.

ORL-1 GTP $E_{max}$ % is the maximal effect elicited by a compound relative to the effect elicited by nociceptin, a standard ORL-1 agonist. In certain embodiments, Compounds of the Invention will have an ORL-1 GTP $E_{max}$ of less than 10% (which, for the purposes of this invention, is interpreted as having antagonist activity at ORL-1 receptors). Certain Compounds of the Invention will have an ORL-1 GTP $E_{max}$ (%) of greater than 1%; or of greater than 5%; or of greater than 10%. In other embodiments the Compounds of the Invention will have an ORL-1 GTP $E_{max}$ of greater than 20%; or of greater than 50%; or of greater than 75%; or of greater than 88%; or of greater than 100%.

In Vivo Assays for Prevention or Treatment of Pain

Test Animals: Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain: To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail.

Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ s - \text{pre-administration latency})} \times 100$$

The rat tail flick test is described in F. E. D+Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). Rats are placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) excape or attempted escapre from the testing device; or 4) vocalization. Data are expressed as response latency(s) and the percentage of the maximal possible effect is calculated as described above for the tail flick test. The hot plate test is described in G. Woolfe and A. D. Macdonald, *J. Pharmacol. Exp. Ther.* 80: 300-307 (1944).

Inflammatory Pain: To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342: 666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," Pain 43: 205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3): 355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31: 451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1): 77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paws are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw is considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in an animal in need thereof. The Compounds of the Invention can be administered to any animal requiring modulation of the opioid and/or ORL-1 receptors.

When administered to an animal, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, suppositories, aerosols, sprays, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., $16^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249: 1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol.* 2, *Applications and Evaluation*, R. S. Langer and D. L. Wise eds., CRC Press (1984). Other controlled- or sustained-release systems that are discussed in the review by Langer, *Science* 249: 1527-1533 (1990) can be selected for use according to the present invention. In one embodiment, a pump can be used (Langer, *Science* 249:1527-1533 (1990); Sefton, *CRC Crit. Ref. Biomed. Eng.* 14: 201 (1987); Buchwald et al., *Surgery* 88: 507 (1980); and Saudek et al., *N. Engl. J. Med.* 321: 574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23: 61 (1983); Levy et al., *Science* 228: 190 (1985); During et al., *Ann. Neurol.* 25: 351 (1989); and Howard et al., *J. Neurosurg.* 71: 105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing the μ-opioid receptors is contacted with a Compound of the Invention in vitro, the amount effective for inhibiting or activating the μ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 μL to about 1 mL. In another embodiment, the volume of solution or suspension will be about 200 μL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined herein-above. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Inset, *Analgesic-Antipyretic and Anti-inflammatory Agents and Drugs Employed in the Treatment of Gout*, in Goodman & Gilman's The Pharmacological Basis of Therapeutics 617-57 (Perry B. Molinhoff and Raymond W. Ruddon eds., $9^{th}$ ed 1996); and Glen R. Hanson, *Analgesic, Antipyretic and Anti-Inflammatory Drugs in Remington: The Science and Practice of Pharmacy Vol IA* 1196-1221 (A. R. Gennaro ed. $19^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5- (3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethyl-barbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a

Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

Synthesis of Methyl 4-(2-((2-((2R,6R,11R)-3-(cyclopropylmethyl)-8-methoxy-11-methyl-2,3,4,5-tetrahydro-2,6-methanobenzo[d]azocin-6(1H)-yl)ethyl)amino)-2-oxoethyl)benzoate (Compound 30) and 4-(2-((2-((2R,6R,11R)-3-(cyclopropylmethyl)-8-hydroxy-11-methyl-2,3,4,5-tetrahydro-2,6-methanobenzo[d]azocin-6(1H)-yl)ethyl)amino)-2-oxoethyl)benzoic acid (Compound 31)

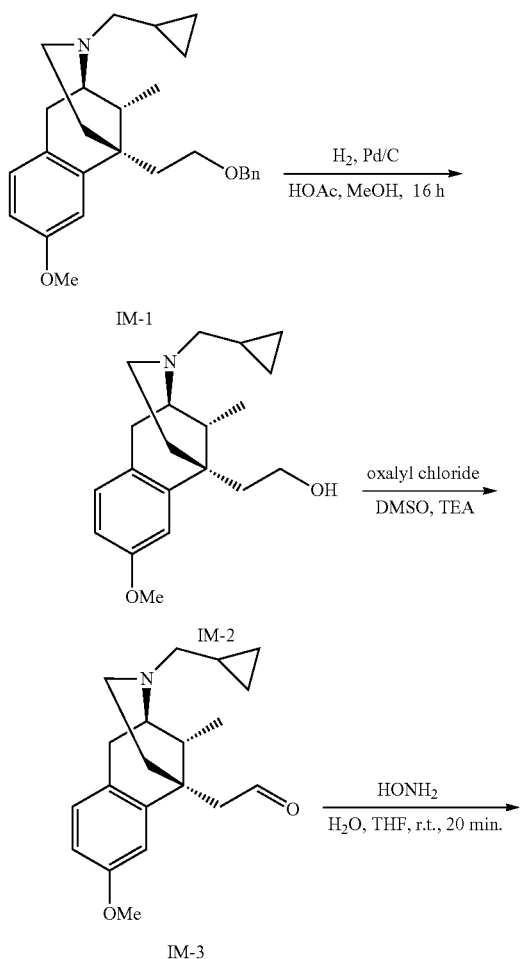

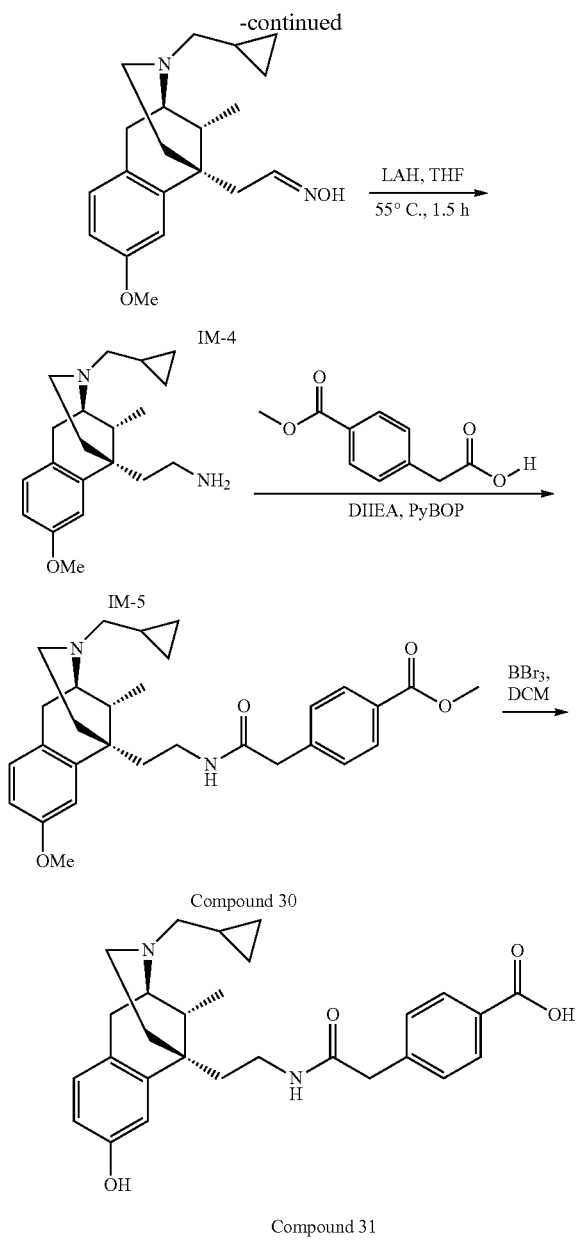

Compound IM-1 was prepared through the synthetic procedures similar to those delineated in WO 2013/167963A1. To a solution of Compound IM-1(2.00 g, 4.93 mmol) in MeOH (35 ml) was added HOAc (3.5 ml) and 10% Pd/C (0.70 g). The mixture was hydrogenated at 60 psi for 16 h. The reaction was 75% complete by LC/MS. The mixture was then filtered through celite, concentrated to dryness, dissolved in DCM, washed with aqueous 10% $Na_2CO_3$, dried over $Na_2SO_4$, and concentrated to dryness. Purification on silica gel with 0 to 15% MeOH in DCM followed by 5 to 20% (1N NH3 in MeOH) in DCM afforded 1.00 g of Compound IM-2 as a white solid. L LCMS: m/z=316 [M+H]$^+$ (Calc: 315).

To a flask containing a solution of oxalyl chloride (0.25 ml, 2.90 mmol) in DCM (7.0 ml) at −78° C. was added DMSO (0.41 ml) and the mixture was stirred for 10 minutes at −78° C. A solution of Compound IM-2 (0.46 g, 1.45 mmol) in DCM (6.0 ml) was added via cannula and the mixture was stirred at −78° C. for 15 minutes. Triethylamine (0.81 ml) was added and the reaction was stirred for 10 minutes at −78° C. and then warmed to 0° C. It was complete after 10 minutes by LC/MS. The DCM was removed and the solid residue was purified on silica gel with 0 to 7.7% MeOH in DCM to afford 0.45 g (98%) of Compound IM-3. LC/MS, m/z=314 [M+H]+ (Calc: 313).

To a solution of Compound IM-3 (0.49 g, 1.56 mmol) in THF (3.3 ml) at room temperature was added 50% hydroxylamine in water (0.16 ml, 2.34 mmol). The reaction was complete in 20 minutes. Evaporation of the THF and water afforded a quantitative yield of Compound IM-4. LC/MS, m/z=329 [M+H]+ (Calc: 328)

To a solution of Compound IM-4 (0.43 g, 1.31 mmol) in THF (6.0 ml) at room temperature was added a 2 M solution of lithium aluminum hydride (1.96 ml, 3.92 mmol). The solution was heated to 55° C. for 1.2 h. Then it was cooled down to room temperature and slowly added to hydrated $Na_2SO_4$ and the solid was filtered and washed several times with THF. The filtrate was concentrated to afford Compound IM-5 as a resinous solid which was used as is in the next step. LC/MS, m/z=315 [M+H]+ (Calc: 314)

To a solution of Compound IM-5 (0.100 g, 0.318 mmol) in DCM (1.6 ml) were added 2-(4-(methoxycarbonyl)phenyl)acetic acid (0.074 g, 0.382 mmol), diisopropylethylamine (DIIEA; 0.123 g, 0.954 mmol) and PyBOP (0.20 g, 0.382 mmol). The reaction mixture was stirred at room temperature for 10 minutes, concentrated to dryness, re-dissolved in DCM and purified on silica gel with 15 to 30% EtOAc in Hexanes followed by 0 to 30% MeOH in EtOAc and finally by prep HPLC to afford 0.030 g of the TFA salt of Compound 30 as a white solid.

The TFA salt of Compound 30: $^1$H NMR (400 MHz, DMSO-$d_6$) δ 9.14 (br. s., 1H), 8.09 (t, J=5.26 Hz, 1H), 7.75 (d, J=8.33 Hz, 2H), 7.26 (d, J=8.33 Hz, 2H), 6.92 (d, J=8.33 Hz, 1H), 6.59-6.71 (m, 2H), 3.68 (s, 4H), 3.56 (s, 3H), 3.38 (s, 2H), 3.01-3.17 (m, 4H), 2.91-2.98 (m, 1H), 2.85 (d, J=5.70 Hz, 2H), 2.26 (d, J=13.81 Hz, 1H), 2.08-2.18 (m, 1H), 2.04 (dd, J=4.38, 14.25 Hz, 1H), 1.89-2.00 (m, 1H), 1.59-1.73 (m, 1H), 1.25 (d, J=13.15 Hz, 1H), 0.88 (br. s., 1H), 0.67 (d, J=6.80 Hz, 3H), 0.42-0.52 (m, 2H), 0.20 (d, J=3.29 Hz, 2H). LC/MS m/z=491 [M+H]$^+$ (Calc: 490).

Compound 30 (0.050 g, 0.102 mmol) was dissolved in DCM (0.60 ml) at 0° C. and was treated with a 1 molar solution of $BBr_3$ in DCM (0.408 mmol, 0.41 ml). The resulting mixture was stirred for 1 h at 0 degree. The reaction was then maintained at 0° C. and treated with 4N aqueous sodium hydroxide (1.53 mmol, 0.4 ml). DCM was removed under reduced pressure. MeOH and THF were added until the mixture was homogeneous and then it was stirred for 16 h at room temperature.

MeOH and THF were thereafter removed under reduced pressure and the aqueous portion was neutralized with aq HCl, concentrated to dryness, absorbed onto silica gel and purified on silica gel with 0 to 30% MeOH in EtOAc, and then with 0 to 30% MeOH in DCM to afford 0.022 g of Compound 31 as a white solid.

Compound 31: $^1$H NMR (400 MHz, D2O) δ 7.49 (d, J=8.33 Hz, 2H), 7.04 (d, J=8.11 Hz, 2H), 6.75 (d, J=8.55 Hz, 1H), 6.48 (d, J=2.19 Hz, 1H), 6.43 (dd, J=2.41, 8.33 Hz, 1H), 3.52 (br. s., 1H), 3.31 (s, 2H), 2.99-3.19 (m, 2H), 2.81 (br. s., 3H), 2.64-2.72 (m, 1H), 2.60 (dd, J=7.67, 13.37 Hz, 1H), 2.31 (br. s., 1H), 1.80-1.90 (m, 2H), 1.71 (dd, J=9.21, 13.37 Hz, 1H), 1.55-1.65 (m, 1H), 1.09 (d, J=13.59 Hz, 1H), 0.66 (br. s., 1H), 0.53 (d, J=6.80 Hz, 3H), 0.36 (d, J=7.89 Hz, 2H), 0.00 (br. s., 2H); LCMS: m/z=463 [M+H]$^+$ (Calc: 462).

In a similar manner, the following compounds were prepared:

(S)-2-acetamido-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)propanamide (Compound 4): $^1$H NMR (400 MHz, METHANOL-d$_4$) δ ppm 7.10-7.18 (m, 1 H), 6.81-6.93 (m, 2 H), 4.22-4.32 (m, 1 H), 3.85-3.96 (m, 1 H), 3.74-3.81 (m, 3 H), 3.39-3.57 (m, 2 H), 3.33-3.39 (m, 3 H), 2.98-3.29 (m, 4 H), 2.59-2.77 (m, 1 H), 2.15-2.44 (m, 3 H), 1.93-2.08 (m, 4 H), 1.45-1.60 (m, 1 H), 1.29-1.40 (m, 3 H), 1.06-1.20 (m, 1 H), 0.96-1.06 (m, 3 H), 0.72-0.83 (m, 2 H), 0.41-0.52 (m, 2 H). LCMS: m/z 428.3 [M+H]$^+$ (Calc: 428.58).

(S)-1-acetyl-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)pyrrolidine-2-carboxamide (Compound 5): $^1$H NMR (400 MHz, METHANOL-d$_4$) δ ppm 7.09-7.19 (m, 1 H), 6.80-6.95 (m, 2 H), 4.29-4.59 (m, 1 H), 3.83-3.96 (m, 1 H), 3.75-3.82 (m, 3 H), 3.66-3.75 (m, 1 H), 3.55-3.65 (m, 1 H), 3.34-3.54 (m, 4 H), 3.11-3.29 (m, 3 H), 2.58-2.77 (m, 1 H), 2.17-2.41 (m, 4 H), 1.90-2.15 (m, 7 H), 1.45-1.62 (m, 1 H), 1.28-1.41 (m, 2 H), 1.07-1.17 (m, 1 H), 0.97-1.06 (m, 3 H), 0.72-0.83 (m, 2 H), 0.40-0.51 (m, 2 H). LCMS: m/z 454.2 [M+H]$^+$ (Calc: 454.62).

(S)-(9H-fluoren-9-yl)methyl 2-((2-((2R, 6R, 11R)-3-(cyclopropylmethyl)-8-methoxy-11-methyl-1,2,3,4,5,6-hexahydro-2,6-methanobenzo[d]azocin-6-yl)ethyl)carbamoyl)-piperidine-1-carboxylate (Compound IM-14):

IM-14

LCMS: m/z 647.3 [M+H]$^+$.

Example 2

Synthesis of 4-((2-((2R,6R,11R)-3-(cyclopropylmethyl)-8-hydroxy-11-methyl-2,3,4,5-tetrahydro-2,6-methanobenzo[d]azocin-6(1H)-yl)ethyl)carbamoyl)benzoic acid (Compound 32)

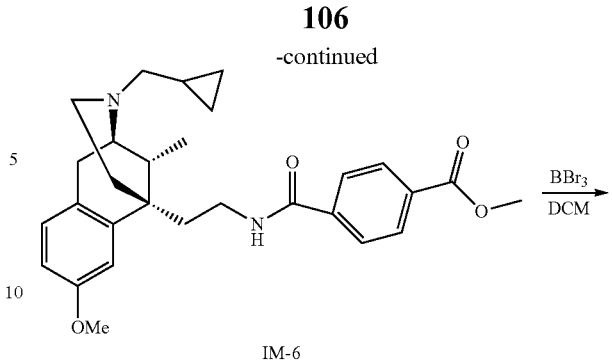

To a solution of Compound IM-5 (0.100 g, 0.318 mmol) in DCM (1.6 ml) were added 4-(methoxycarbonyl)benzoic acid (0.069 g, 0.382 mmol), diisopropylethylamine (0.123 g, 0.954 mmol) and PyBOP (0.20 g, 0.382 mmol). The reaction mixture was stirred at room temperature for 10 minutes, concentrated to dryness, re-dissolved in DCM and purified on silica gel with 15 to 30% EtOAc in Hexanes followed by 0 to 10% MeOH in DCM to afford 0.083 g of Compound IM-6. LC/MS, m/z=477 [M+H]$^+$ (Calc: 476)

A solution of Compound IM-6 (0.0833 g, 0.175 mmol) in DCM (0.7 ml) was cooled to 0° C. It was then treated with a 1 molar solution of BBr$_3$ in DCM (0.700 mmol, 0.700 ml) and stirred at room temperature for 16 h. The reaction was treated with H$_2$O, the DCM layer was discarded and the aqueous portion was adjusted to pH 6.0 and was dried under reduced pressure and purified on silica gel eluting first with 15 to 60% EtOAc in Hexanes then with 0 to 30% MeOH in DCM. It was then purified a second time by prep HPLC to afford 0.026 g of the TFA salt of Compound 32 as a white solid.

Compound 32: $^1$H NMR (400 MHz, MeOH) δ 8.70 (t, J=5.59 Hz, 1H), 8.14 (d, J=8.55 Hz, 2H), 7.93 (d, J=8.77 Hz, 2H), 7.02 (d, J=8.33 Hz, 1H), 6.83 (d, J=2.63 Hz, 1H), 6.73 (dd, J=2.41, 8.33 Hz, 1H), 3.89 (br. s., 1H), 3.58-3.67 (m, 2H), 3.35-3.41 (m, 2H), 3.14-3.25 (m, 2H), 3.03 (d, J=18.63 Hz, 1H), 2.94-3.00 (m, 1H), 2.65-2.75 (m, 1H), 2.36-2.48 (m, 2H), 2.26-2.34 (m, 1H), 2.09-2.20 (m, 1H), 1.58 (d, J=12.50 Hz, 1H), 1.10 (d, J=7.02 Hz, 3H), 0.82 (d, J=8.33 Hz, 2H), 0.47 (d, J=5.48 Hz, 2H). LCMS: m/z=449 [M+H]$^+$ (Calc: 448).

Example 3

Synthesis of 2-amino-N-(2-(2R,6R,11R)-3-(cyclopropylmethyl)-8-methoxy-11-methyl-2,3,4,5-tetrahydro-2, 6-methanobenzo[d] azocin-6(1H)-yl)ethyl) acetamide (Compound 33)

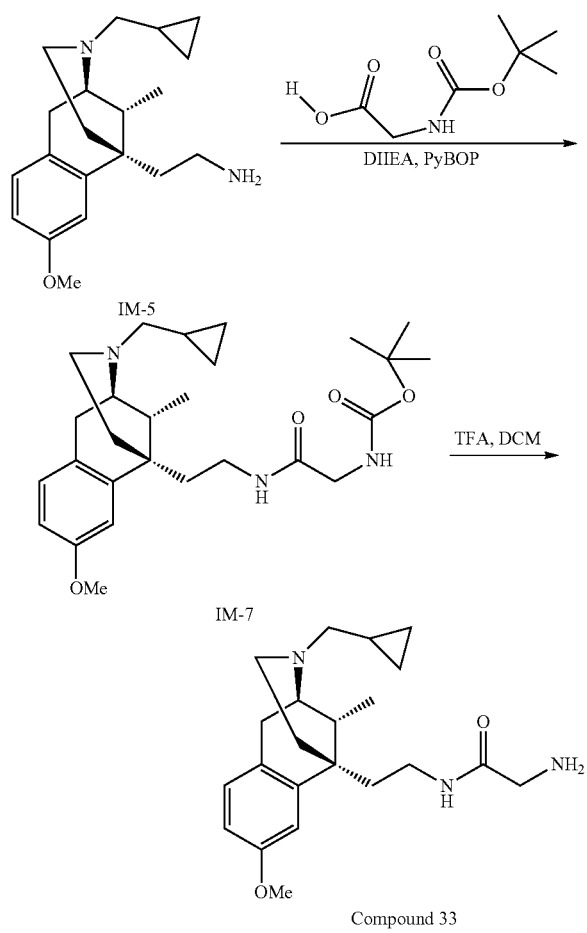

A solution of Compound IM-5 (0.100 g, 0.318 mmol) in DCM (1.6 ml) was treated with 2-((tertbutoxycarbonyl)amino)acetic acid (0.067 g, 0.382 mmol), DIIEA (0.123 g, 0.954 mmol) and PyBOP (0.199 g, 0.382 mmol). The mixture was stirred at room temperature for 10 minutes and concentrated to dryness. It was then re-dissolved in DCM and purified on silica gel with 15 to 30% EtOAc in Hexanes followed by 0 to 30% MeOH in EtOAc to afford 0.14 g of Compound IM-7 which had an unknown quantity of a polar impurity and was carried on as is to the next step. LC/MS, m/z=472 [M+H]+ (Calc: 471)

Compound IM-7 (0.065 g, 0.138 mmol) was dissolved in DCM (0.70 ml) and treated with trifluoroacetic acid (0.10 ml, 1.38 mmol) at room temperature. The mixture was stirred for 16 h, concentrated to dryness and purified by prep HPLC to afford 0.044 g of TFA salt of Compound 33 as a white solid.

Compound 33: $^1$H NMR (400 MHz, MeOH) δ 7.13 (d, J=8.77 Hz, 1H), 6.80-6.87 (m, 2H), 3.90 (br. s., 1H), 3.80 (s, 3H), 3.65 (s, 2H), 3.47 (dt, J=5.92, 10.08 Hz, 2H), 3.36-3.41 (m, 1H), 3.20 (td, J=6.82, 13.76 Hz, 2H), 3.04-3.12 (m, 1H), 2.99 (dd, J=7.67, 13.37 Hz, 1H), 2.59-2.70 (m, 1H), 2.40 (dd, J=4.17, 13.37 Hz, 2H), 2.17-2.28 (m, 1H), 1.97-2.09 (m, 1H), 1.53 (d, J=12.93 Hz, 1H), 1.07-1.17 (m, 1H), 1.03 (d, J=7.02 Hz, 3H), 0.80 (d, J=8.33 Hz, 2H), 0.46 (d, J=5.04 Hz, 2H). LCMS: m/z=372 [M+H]+ (Calc: 371).

Example 4

Synthesis of ethyl 4-(3-(2-((2R,6R,11R)-3-(cyclopropylmethyl)-8-methoxy-11-methyl-2,3,4,5-tetrahydro-2,6-methanobenzo[d]azocin-6(1H)-yl)ethyl)ureido)benzoate (Compound 1)

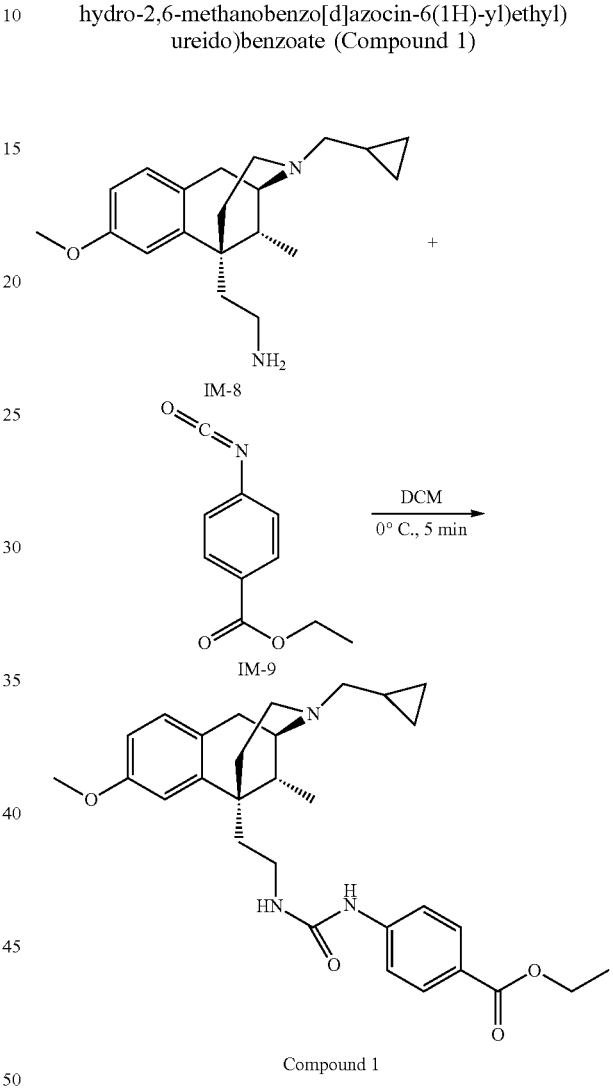

Compound IM-8 was prepared according to the synthetic procedures delioneated in WO 2013/167963A1 (See, e.g., Example 7). Dissolve Compound IM-8 (43 mgs, 0.137 mmol) in dichloromethane (2 ml) and cool in an ice bath. To the solution slowly add JJE2 (26.1 mgs, 0.137 mmol) dissolved in 1 ml DCM. Stir for five minutes. Chromatograph reaction mixture directly using a 24-gram silica column and a gradient of methanol in dichloromethane as the eluent to provide the title compound as a clear oil. Purified further by prep HPLC to provide ethyl 4-(3-(2-((2R,6R, 11R)-3-(cyclopropylmethyl)-8-methoxy-11-methyl-2,3,4,5-tetrahydro-2,6-methanobenzo-[d]azocin-6(1H)-yl)ureido)benzoate (Compound 1) as a white solid.

Compound 1: $^1$H NMR (METHANOL-d$_4$) δ 7.86-7.97 (m, 2H), 7.49 (d, J=8.8 Hz, 2H), 7.03 (d, J=8.6 Hz, 1H), 6.83 (d, J=2.6 Hz, 1H), 6.73 (dd, J=8.5, 2.5 Hz, 1H), 4.32 (q, J=7.0 Hz, 2H), 3.75 (s, 3H), 3.46 (t, J=8.3 Hz, 2H), 3.38 (br. s., 1H), 2.92-3.01 (m, 1H), 2.75-2.92 (m, 2H), 2.68 (br. s., 1H), 2.54 (br. s., 1H), 2.11-2.30 (m, 4H), 1.93-2.06 (m, 1H), 1.25-1.42 (m, 4H), 0.96 (d, J=7.0 Hz, 4H), 0.60 (d, J=8.1 Hz, 2H), 0.17-0.32 (m, 2H). LCMS: m/z 506.2 [M+H]$^+$ (Calc: 506.65).

In a similar manner, the following compounds were prepared:

1-(2-((2R,6R,11R)-3-(cyclopropylmethyl)-8-hydroxy-11-methyl-2,3,4,5-tetrahydro-2,6-methanobenzo[d]azocin-6 (1H)-yl)ethyl)-3-(4-fluorophenyl)urea (Compound 18): $^1$H NMR (400 MHz, METHANOL-d$_4$) δ ppm 7.32-7.41 (m, 2 H), 6.96-7.09 (m, 3 H), 6.77-6.84 (m, 1 H), 6.65-6.74 (m, 1 H), 3.79-3.97 (m, 1 H), 3.34-3.53 (m, 3 H), 3.21-3.29 (m, 1 H), 2.95-3.20 (m, 3 H), 2.63-2.76 (m, 1 H), 2.28-2.49 (m, 2 H), 2.16-2.27 (m, 1 H), 1.96-2.07 (m, 1 H), 1.34-1.60 (m, 1 H), 1.08-1.33 (m, 1 H), 0.95-1.08 (m, 3 H), 0.72-0.84 (m, 2 H), 0.41-0.53 (m, 2 H). LCMS: m/z 438.3 [M+H]+ (Calc: 438.55).

Further, using 4-fluorobenzenesulfonyl isocyanate as a starting material, N-((2-((2R,6R,11R)-3-(cyclopropylmethyl)-8-hydroxy-11-methyl-2,3,4,5-tetrahydro-2,6-methano-benzo[d]azocin-6(1H)-yl)ethyl)carbamoyl)-4-fluorobenzenesulfonamide (Compound 19) was prepared: $^1$H NMR (400 MHz, METHANOL-d$_4$) δ ppm 8.02-8.12 (m, 2 H), 7.28-7.41 (m, 2 H), 6.97-7.07 (m, 1 H), 6.65-6.77 (m, 2 H), 3.76-3.91 (m, 1 H), 3.33-3.45 (m, 2 H), 3.19-3.29 (m, 1 H), 2.92-3.17 (m, 3 H), 2.59-2.74 (m, 1 H), 2.04-2.38 (m, 3 H), 1.84-1.99 (m, 1 H), 1.27-1.55 (m, 1 H), 1.04-1.17 (m, 1 H), 0.88-1.02 (m, 3 H), 0.70-0.85 (m, 2 H), 0.40-0.53 (m, 2 H). LCMS: m/z 502.2 [M+H]$^+$ (Calc: 502.61).

1-Benzyl-3-(2-((2R,6R,11R)-3-(cyclopropylmethyl)-8-hydroxy-11-methyl-2,3,4,5-tetrahydro-2,6-methanobenzo [d]azocin-6(1H)-yl)ethyl)urea (Compound 21): $^1$H NMR (400 MHz, METHANOL-d$_4$) δ ppm 7.27-7.40 (m, 4 H), 7.19-7.27 (m, 1 H), 7.00-7.07 (m, 1 H), 6.77-6.83 (m, 1 H), 6.66-6.73 (m, 1 H), 4.32-4.39 (m, 2 H), 3.76-3.95 (m, 1 H), 3.33-3.54 (m, 3 H), 2.97-3.28 (m, 4 H), 2.62-2.75 (m, 1 H), 2.26-2.47 (m, 2 H), 2.12-2.23 (m, 1 H), 1.91-2.02 (m, 1 H), 1.29-1.58 (m, 1 H), 1.05-1.20 (m, 1 H), 0.93-1.05 (m, 3 H), 0.73-0.83 (m, 2 H), 0.42-0.52 (m, 2 H). LCMS: m/z 434.2 [M+H]$^+$ (Calc: 434.59).

1-(2-((2R,6R,11R)-8-hydroxy-3,11-dimethyl-2,3,4,5-tetrahydro-2,6-methano-benzo[d]azocin-6(1H)-yl)ethyl)-3-phenylurea (Compound 68): $^1$H NMR (METHANOL-d$_4$) δ7.26-7.32 (m, 2H), 7.17 (t, J=8.0 Hz, 2H), 6.87-6.99 (m, 2H), 6.70-6.75 (m, 1H), 6.57-6.63 (m, 1H), 3.53-3.63 (m, 1H), 3.31-3.39 (m, 2H), 3.02-3.15 (m, 3H), 2.82 (s, 3H), 2.63 (td, J=13.0, 3.4 Hz, 1H), 2.26-2.36 (m, 2H), 2.09-2.20 (m, 1H), 1.88-1.98 (m, 1H), 1.31-1.46 (m, 1H), 0.93 (d, J=6.9 Hz, 3H); LC/MS, m/z=380.2 [M+H]$^+$ (Calc: 380.23).

1-Benzhydryl-3-(2-((2R,6R,11R)-8-hydroxy-3,11-dimethyl-2,3,4,5-tetrahydro-2,6-methanobenzo[d]azocin-6 (1H)-yl)ethyl)urea (Compound 73): $^1$H NMR (METHANOL-d$_4$) δ: 7.26-7.37 (m, 10H), 7.06 (d, J=8.3 Hz, 1H), 6.79 (d, J=2.4 Hz, 1H), 6.70 (dd, J=8.3, 2.4 Hz, 1H), 6.03 (s, 1H), 3.68 (d, J=2.6 Hz, 1H), 3.42 (t, J=8.0 Hz, 2H), 3.12-3.21 (m, 3H), 2.91 (s, 3H), 2.71 (td, J=13.1, 3.5 Hz, 1H), 2.32-2.42 (m, 2H), 2.15-2.24 (m, 1H), 1.93-2.02 (m, 1H), 1.48 (d, J=12.5 Hz, 1H), 0.99 (d, J=6.9 Hz, 3H); LC/MS, m/z=470.2 [M+H]$^+$ (Calc: 470.28).

1-(2-((2R,6R,11R)-8-hydroxy-3,11-dimethyl-2,3,4,5-tetrahydro-2,6-methanobenzo[d]azocin-6(1H)-yl)ethyl)-3-(3-phenoxyphenyl)urea (Compound 74): $^1$H NMR (METHANOL-d$_4$) δ 7.32-7.41 (m, 2H), 7.20-7.29 (m, 2H), 7.04-7.14 (m, 3H), 6.96-7.02 (m, 2H), 6.82 (d, J=2.4 Hz, 1H), 6.70 (dd, J=8.3, 2.5 Hz, 1H), 6.60 (dd, J=8.0, 1.7 Hz, 1H), 3.62-3.74 (m, 1H), 3.43 (t, J=8.1 Hz, 2H), 3.13-3.25 (m, 3H), 2.92 (s, 3H), 2.72 (td, J=12.9, 3.3 Hz, 1H), 2.35-2.46 (m, 2H), 2.16-2.29 (m, 1H), 1.94-2.07 (m, 1H), 1.37-1.58 (m, 1H), 1.02 (d, J=6.9 Hz, 3H); LC/MS, m/z=472.2 [M+H]$^+$ (Calc: 472.26).

1-(4-Fluorophenyl)-3-(2-((2R,6R,11R)-8-hydroxy-3,11-dimethyl-2,3,4,5-tetrahydro-2,6-methanobenzo [d]azocin-6 (1H)-yl)ethyl)urea (Compound 76): $^1$H NMR (METHANOL-d$_4$) δ7.24-7.32 (m, 2H), 6.87-6.99 (m, 3H), 6.69-6.75 (m, 1H), 6.56-6.64 (m, 1H), 3.52-3.64 (m, 1H), 3.30-3.38 (m, 2H), 3.01-3.14 (m, 3H), 2.82 (s, 3H), 2.63 (td, J=13.0, 3.3 Hz, 1H), 2.24-2.36 (m, 2H), 2.08-2.20 (m, 1H), 1.86-1.99 (m, 1H), 1.27-1.46 (m, 1H), 0.92 (d, J=6.9 Hz, 3H); LC/MS, m/z=398.3 [M+H]$^+$ (Calc: 398.22).

1-(2,2-Diphenylethyl)-3-(2-((2R,6R,11R)-8-hydroxy-3,11-dimethyl-2,3,4,5-tetrahydro-2,6-methanobenzo[d]azocin-6(1H)-yl)ethyl)urea (Compound 77): $^1$H NMR (METHANOL-d$_4$) δ 7.19-7.27 (m, 8H), 7.09-7.15 (m, 2H), 6.89-6.98 (m, 1H), 6.59-6.66 (m, 2H), 4.22 (t, J=8.2 Hz, 1H), 3.82 (d, J=8.1 Hz, 2H), 3.51-3.61 (m, 1H), 3.00-3.14 (m, 3H), 2.80 (s, 3H), 2.59 (td, J=13.0, 3.4 Hz, 1H), 2.17-2.32 (m, 2H), 1.91-2.03 (m, 1H), 1.67-1.79 (m, 1H), 1.18-1.36 (m, 1H), 0.83 (d, J=6.9 Hz, 3H); LC/MS, m/z=484.2 [M+H]$^+$ (Calc: 484.30).

1-(2-Fluorophenyl)-3-(2-((2R,6R,11R)-8-hydroxy-3,11-dimethyl-2,3,4,5-tetrahydro-2,6-methanobenzo[d]azocin-6 (1H)-yl)ethyl)urea (Compound 78): $^1$H NMR (METHANOL-d$_4$) δ 7.81 (td, J=8.2, 1.8 Hz, 1H), 6.88-7.05 (m, 4H), 6.69-6.76 (m, 1H), 6.57-6.64 (m, 1H), 3.52-3.68 (m, 1H), 3.31-3.42 (m, 2H), 3.02-3.16 (m, 3H), 2.82 (s, 3H), 2.63 (td, J=13.0, 3.5 Hz, 1H), 2.23-2.36 (m, 2H), 2.06-2.20 (m, 1H), 1.92 (dq, J=10.0, 6.7 Hz, 1H), 1.33-1.47 (m, 1H), 0.93 (d, J=6.9 Hz, 3H); LC/MS, m/z=398.3 [M+H]$^+$ (Calc: 398.22).

1-(3-Fluorophenyl)-3-(2-((2R,6R,11R)-8-hydroxy-3,11-dimethyl-2,3,4,5-tetrahydro-2,6-methanobenzo[d]azocin-6 (1H)-yl)ethyl)urea (Compound 79): $^1$H NMR (METHANOL-d$_4$) δ 7.35-7.44 (m, 1H), 7.20-7.28 (m, 1H), 7.02-7.11 (m, 2H), 6.79-6.85 (m, 1H), 6.65-6.74 (m, 2H), 3.65-3.74 (m, 1H), 3.40-3.52 (m, 2H), 3.12-3.26 (m, 3H), 2.93 (s, 3H), 2.73 (t, J=11.8 Hz, 1H), 2.36-2.47 (m, 2H), 2.19-2.31 (m, 1H), 1.97-2.08 (m, 1H), 1.38-1.58 (m, 1H), 1.04 (d, J=6.7 Hz, 3H); LC/MS, m/z=398.3 [M+H]$^+$ (Calc: 398.22).

Example 5

Synthesis of 4-(3-(2-((2R,6R,11R)-3-(cyclopropylmethyl)-8-hydroxy-11-methyl-2, 3,4,5-tetrahydro-2, 6-methanobenzo[d]azocin-6(1H)-yl)ethyl)ureido) benzoic acid (Compound 2)

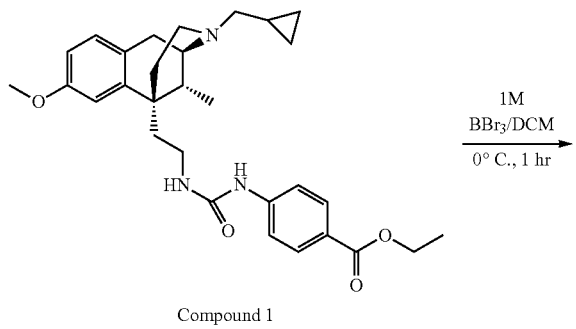

Compound 1

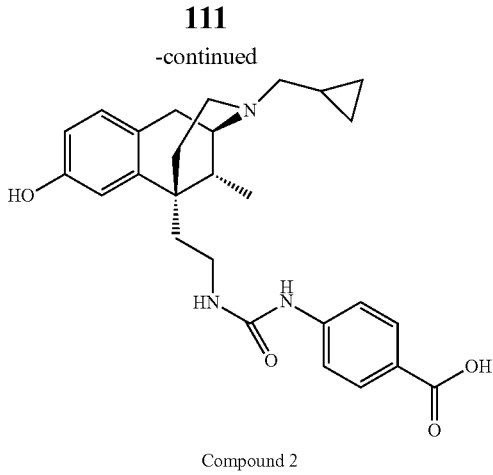

Compound 2

Compound 2 was prepared from Compound 1 in a similar way as Compound 31 (see Example 1): $^1$H NMR (METHANOL-$d_4$) δ 7.93 (d, J=8.8 Hz, 2H), 7.47-7.55 (m, 2H), 6.99-7.09 (m, 1H), 6.80 (d, J=2.4 Hz, 1H), 6.66-6.74 (m, 1H), 3.81-3.98 (m, 1H), 3.34-3.52 (m, 3H), 2.98-3.26 (m, 3H), 2.97-3.28 (m, 4H), 2.64-2.77 (m, 1H), 2.17-2.43 (m, 3H), 1.97-2.09 (m, 1H), 1.34-1.61 (m, 1H), 0.96-1.19 (m, 4H), 0.72-0.84 (m, 2H), 0.40-0.55 (m, 2H). LCMS: m/z 464.2 [M+H]$^+$ (Calc: 464.57).

Example 6

Synthesis of N-(2-((2R,6S,11R)-3-(cyclopropylmethyl)-8-hydroxy-11-methyl-2,3,4,5-tetrahydro-2,6-methanobenzo[d]azocin-6(1H)-yl)ethyl)methanesulfonamide (Compound 3)

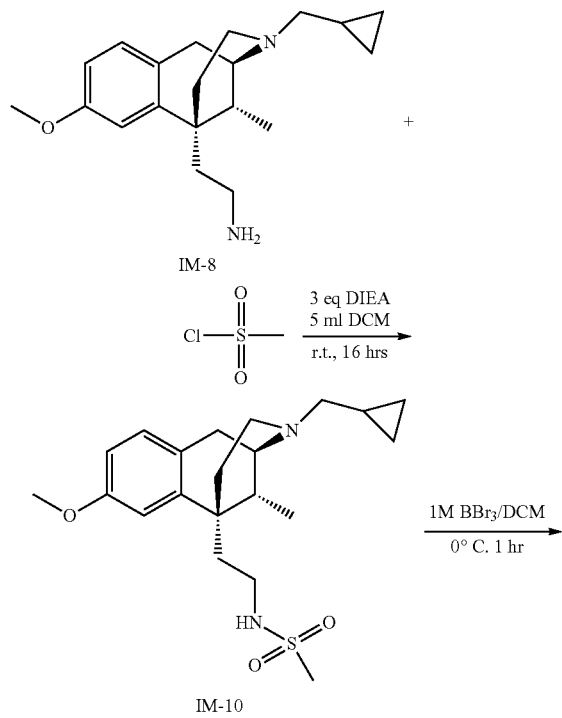

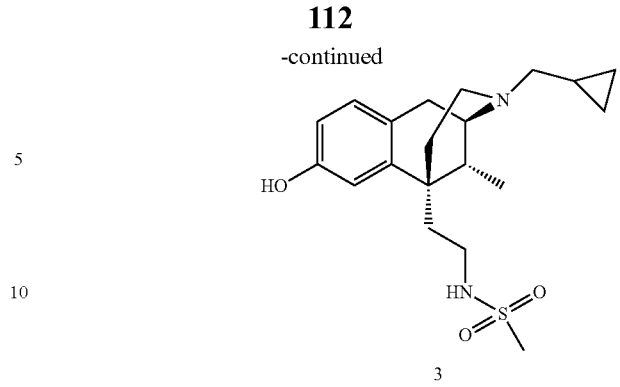

Compound IM-8 was dissolved into dichloromethane (2 ml). To the solution was added DIEA (0.065 gr, 0.504 mmol, 0.09 ml). The resulting solution was cooled in an ice bath for 15 minutes. Then, methanesulfonyl chloride (0.023 gr, 0.202 mmol) was dissolved into 3 ml DCM and carefully added under nitrogen to the above mixture, then stirred at room temperature over 16 hours. The reaction mixture was concentrated under reduced pressure and chromatographed using a 12-gram silica column using a gradient of ammoniacal methanol (40% max.) in dichloromethane as the eluent to provide Compound IM-10 in a good purity. LCMS: m/z 393.2 [M+H]$^+$ Compound 3 was then prepared from Compound IM-10 in a similar way as that for the preparation of Compound 31 (see Example 1). Compound 3: $^1$H NMR (400 MHz, METHANOL-$d_4$) δ ppm 7.01-7.09 (m, 1 H), 6.76-6.82 (m, 1 H), 6.67-6.74 (m, 1 H), 3.80-3.94 (m, 1 H), 3.34-3.49 (m, 2 H), 3.22-3.30 (m, 3 H), 3.10-3.16 (m, 1 H), 3.01-3.08 (m, 1 H), 2.96-3.00 (m, 3 H), 2.21-2.74 (m, 4 H), 1.97-2.13 (m, 1 H), 1.31-1.60 (m, 1 H), 1.05-1.18 (m, 1 H), 0.90-1.05 (m, 3 H), 0.72-0.87 (m, 2 H), 0.41-0.54 (m, 2 H). LCMS: m/z 379.2 [M+H]$^+$ (Calc: 379.53).

In a similar method, the following compounds were prepared:

N-(2-((2R,6S,11R)-3-(cyclopropylmethyl)-8-hydroxy-11-methyl-2,3,4,5-tetrahydro-2,6-methanobenzo[d]azocin-6(1H)-yl)ethyl)cyclopropanesulfonamide (Compound 6): $^1$H NMR (400 MHz, METHANOL-$d_4$) δ ppm 7.01-7.09 (m, 1 H), 6.76-6.82 (m, 1 H), 6.65-6.73 (m, 1 H), 3.90 (t, J=4.27 Hz, 1 H), 3.33-3.49 (m, 3 H), 2.92-3.29 (m, 4 H), 2.64-2.81 (m, 1 H), 2.54-2.63 (m, 1 H), 2.24-2.46 (m, 3 H), 2.01-2.12 (m, 1 H), 1.43-1.60 (m, 1 H), 1.03-1.20 (m, 5 H), 0.96-1.02 (m, 3 H), 0.73-0.84 (m, 2 H), 0.43-0.53 (m, 2 H). LCMS: m/z 379.2 [M+H]$^+$ (Calc: 379.53);

Compound 9: $^1$H NMR (400 MHz, METHANOL-$d_4$) δ ppm 7.00-7.09 (m, 1 H), 6.76-6.83 (m, 1 H), 6.65-6.74 (m, 1 H), 3.79-3.94 (m, 1 H), 3.34-3.41 (m, 1 H), 3.10-3.29 (m, 4 H), 2.84-3.09 (m, 2 H), 2.77-2.84 (m, 6 H), 2.61-2.76 (m, 1 H), 2.21-2.53 (m, 3 H), 1.98-2.14 (m, 1 H), 1.31-1.58 (m, 1 H), 1.05-1.19 (m, 1 H), 0.91-1.05 (m, 3 H), 0.72-0.85 (m, 2 H), 0.42-0.54 (m, 2 H). LCMS: m/z 408.1 [M+H]$^+$ (Calc: 408.57).

N-(2-((2R,6S,11R-8-hydroxy-3,11-dimethyl-2,3,4,5-tetrahydro-2,6-methano-benzo[d]azocin-6(1H)-yl)ethyl)methanesulfonamide (Compound 13): $^1$H NMR (400 MHz, METHANOL-$d_4$) δ ppm 6.99-7.10 (m, 1 H), 6.75-6.82 (m, 1 H), 6.67-6.74 (m, 1 H), 3.59-3.73 (m, 1 H), 3.25-3.30 (m, 1 H), 3.11-3.24 (m, 3 H), 2.47-3.10 (m, 8 H), 2.17-2.36 (m, 3 H), 1.98-2.12 (m, 1 H), 1.27-1.59 (m, 1 H), 0.89-1.08 (m, 3 H). LCMS: m/z 339.1 [M+H]$^+$ (Calc: 339.47).

4-Chloro-N-cyclopropyl-N-(1-(2-((2R,6R,11R)-8-methoxy-3,11-dimethyl-2,3,4,5-tetrahydro-2,6-methanobenzo[d]azocin-6(1H)-yl)ethyl)piperidin-4-yl)-benzene-sulfonamide (Compound 53): ¹H NMR (METHANOL-d₄) δ 7.81 (d, J=8.6 Hz, 2H), 7.55 (d, J=8.8 Hz, 2H), 7.01-7.12 (m, 1H), 6.74-6.85 (m, 2H), 4.01-4.14 (m, 1H), 3.69 (s, 3H), 3.64 (d, J=17.4 Hz, 2H), 3.03-3.16 (m, 2H), 2.83 (s, 3H), 2.56-2.66 (m, 1H), 2.39 (td, J=12.6, 4.3 Hz, 1H), 2.07-2.28 (m, 4H), 2.00 (dt, J=6.7, 3.2 Hz, 1H), 1.77-1.88 (m, 2H), 1.46 (d, J=13.4 Hz, 1H), 0.88 (d, J=6.8 Hz, 3H), 0.83 (d, J=3.3 Hz, 2H), 0.69-0.76 (m, 2H); LC/MS, m/z=572.3 [M+H]⁺ (Calc: 572.27).

4-Chloro-N-cyclopropyl-N-(1-(2-((2R,6R,11R)-8-hydroxy-3,11-dimethyl-2,3,4,5-tetrahydro-2,6-methanobenzo[d]azocin-6(1H)-yl)ethyl)piperidin-4-yl)-benzenesulfonamide (Compound 58): ¹H NMR (METHANOL-d₄) δ: 7.79 (d, J=8.6 Hz, 2H), 7.54 (d, J=8.6 Hz, 2H), 6.82 (d, J=8.4 Hz, 1H), 6.61 (d, J=2.4 Hz, 1H), 6.48 (dd, J=8.1, 2.4 Hz, 1H), 3.69-3.82 (m, 1H), 2.95-3.05 (m, 2H), 2.75-2.91 (m, 2H), 2.34-2.64 (m, 4H), 2.29 (s, 3H), 1.77-2.11 (m, 10H), 1.41-1.54 (m, 2H), 1.07 (d, J=12.3 Hz, 1H), 0.84-0.90 (m, 2H), 0.77 (d, J=6.8 Hz, 3H), 0.72 (m, 2H); LC/MS, m/z=558.2 [M+H]⁺ (Calc: 558.26).

4-Chloro-N-cyclopropyl-N-(1-(2-((2R,6S,11R)-8-hydroxy-3,11-dimethyl-2,3,4,5-tetrahydro-2,6-methanobenzo[d]azocin-6(1H)-yl)acetyl)-piperidin-4-yl)benzenesulfonamide (Compound 61): ¹H NMR (METHANOL-d₄) δ: 7.80 (dd, J=8.5, 3.2 Hz, 2H), 7.53 (d, J=7.7 Hz, 2H), 6.87-7.00 (m, 1H), 6.71 (br. s., 1H), 6.56-6.65 (m, 1H), 4.58 (br. s., 1H), 3.89-4.13 (m, 2H), 3.54 (br. s., 1H), 2.94-3.12 (m, 5H), 2.79 (s, 3H), 2.44-2.65 (m, 2H), 1.97 (dd, J=6.3, 3.4 Hz, 1H), 1.67-1.92 (m, 2H), 1.43-1.66 (m, 3H), 0.76-0.91 (m, 5H), 0.62-0.75 (m, 2H); LC/MS, m/z=572.3 [M+H]⁺ (Calc: 572.23).

4-Fluoro-N-(2-((2R,6S,11R)-8-hydroxy-3,11-dimethyl-2,3,4,5-tetrahydro-2,6-methanobenzo[d]azocin-6(1H)-yl)ethyl)benzenesulfonamide (Compound 69): ¹H NMR (METHANOL-d₄) δ: 7.81-7.95 (m, 2H), 7.19-7.31 (m, 2H), 6.88-6.98 (m, 1H), 6.56-6.65 (m, 2H), 3.49-3.58 (m, 1H), 2.89-3.11 (m, 4H), 2.78 (s, 3H), 2.58 (td, J=13.0, 3.4 Hz, 1H), 2.01-2.24 (m, 3H), 1.85 (ddd, J=13.6, 11.6, 5.6 Hz, 1H), 1.25-1.37 (m, 2H), 0.78 (d, J=6.9 Hz, 3H); LC/MS, m/z=419.1 [M+H]⁺ (Calc: 419.18).

Example 7

Synthesis of N-cyclopropyl-N-(1-(2((2R,6R,11R)-8-hydroxy-3,11-dimethyl-2,3,4,5-tetrahydro-2,6-methanobenzo[d]azocin-6(1H)-yl)ethyl)piperidin-4-yl)benzenesulfonamide (Compound 7)

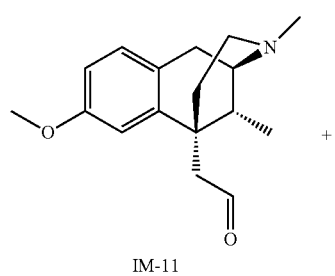

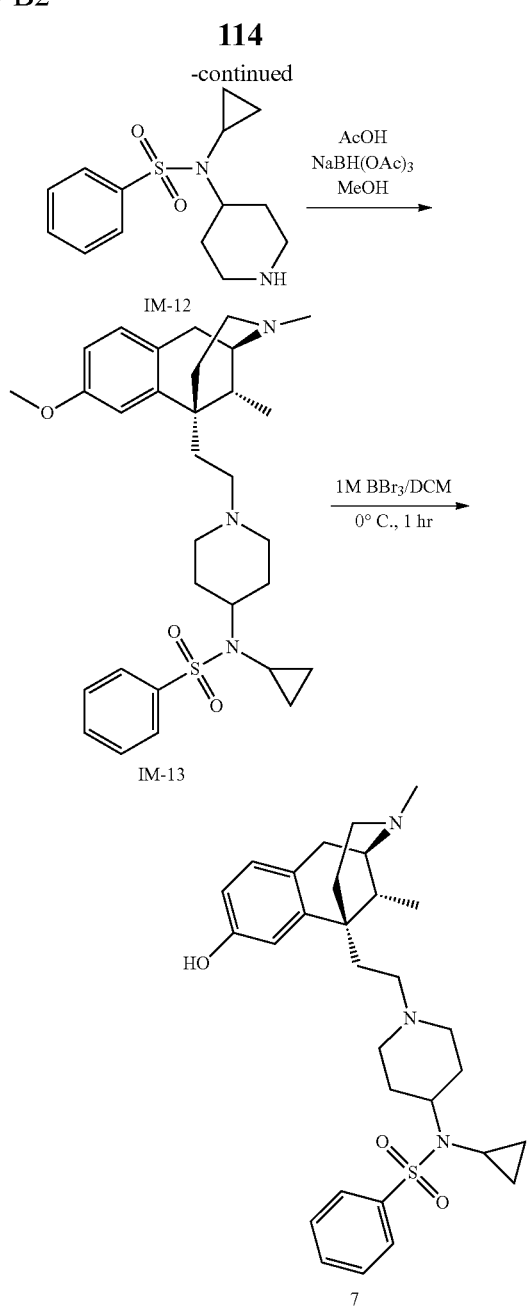

Compound IM-11 was prepared through the procedure for Compound J. Compound IM-11 (88 mgs, 0.322 mmol) was dissolved in methanol (2 ml). To the solution was added Compound IM-12 (199 mgs, 0.708 mmol) dissolved in methanol (1 ml) and acetic acid (0.1 ml). The resulting mixture was stirred at room temperature for 1 hr. Then, the reaction mixture was cooled in an ice bath, and NaBH(OAc)₃ (375 mgs, 1.77 mmol) was added portion-wise. The reaction mixture was removed from the bath, stirred for 1 hour at room temperature, and concentrated under reduced pressure. The residue was chromatographed by combiflash without workup using a 4-gram silica column and a gradient of MeOH (40% max) in DCM as the eluent to provide N-cyclopropyl-N-(1-(2-((2R,6R,11R)-8-methoxy-3,11-dimethyl-1,2,3,4,5,6-hexahydro-2,6-methanobenzo[d]azocin-6-yl)ethyl)piperidin-4-yl)benzenesulfonamide (Compound IM-13). LCMS: m/z 538.3 [M+H]⁺

Deprotection of Compound IM-13 by using the procedures delineated above affords Compound 7: ¹H NMR (400

MHz, METHANOL-d$_4$) δ ppm 7.88-7.98 (m, 2 H), 7.67-7.77 (m, 1 H), 7.57-7.67 (m, 1 H), 7.01-7.12 (m, 1 H), 6.70-6.83 (m, 2 H), 4.18 (tt, J=12.13, 3.72 Hz, 1 H), 3.46-3.96 (m, 4 H), 3.00-3.28 (m, 6 H), 2.86-2.97 (m, 3 H), 2.66-2.82 (m, 1 H), 2.06-2.50 (m, 7 H), 1.86-1.99 (m, 2 H), 1.38-1.61 (m, 1 H), 0.89-1.05 (m, 5 H), 0.77-0.89 (m, 2 H). LCMS: m/z 524.3 [M+H]$^+$ (Calc: 524.73).

(2R,6R,11R)-6-(2-(4-(bis(4-fluorophenyl)methyl)piperazin-1-yl)ethyl)-3,11-dimethyl-1,2,3,4,5,6-hexahydro-2,6-methanobenzo[d]azocin-8-ol (Compound 8) was prepared when using 1-(bis(4-fluorophenyl)-methyl)piperazine (rather than Compound IM-12) as a starting material in the above procedure.

Compound 8: $^1$H NMR (400 MHz, METHANOL-d$_4$) δ ppm 7.43-7.53 (m, 3 H), 7.01-7.12 (m, 4 H), 6.76-6.80 (m, 1 H), 6.70-6.76 (m, 1 H), 4.47-4.53 (m, 1 H), 3.59-3.75 (m, 3 H), 3.33-3.54 (m, 3 H), 3.19-3.29 (m, 2 H), 3.12-3.18 (m, 2 H), 2.99-3.12 (m, 3 H), 2.88-2.98 (m, 3 H), 2.69-2.80 (m, 1 H), 2.31-2.47 (m, 3 H), 2.17-2.25 (m, 2 H), 1.39-1.59 (m, 1 H), 0.92-1.03 (m, 3 H). LCMS: m/z 532.2 [M+H]$^+$ (Calc: 532.68).

Likewise, using pyrrolidine (rather than Compound IM-12) as a starting material, (2R,6R,11R)-3,11-dimethyl-6-(2-(pyrrolidin-1-yl)ethyl)-1,2,3,4,5,6-hexahydro-2,6-methanobenzo[d]azocin-8-ol (Compound 20) was prepared: $^1$H NMR (400 MHz, METHANOL-d$_4$) δ ppm 7.01-7.13 (m, 1 H), 6.77-6.83 (m, 1 H), 6.71-6.77 (m, 1 H), 3.74-3.87 (m, 2 H), 3.53-3.74 (m, 1 H), 3.34-3.52 (m, 2 H), 3.03-3.28 (m, 5 H), 2.89-3.00 (m, 3 H), 2.74 (td, J=13.02, 3.56 Hz, 1 H), 2.38-2.48 (m, 1 H), 2.14-2.37 (m, 5 H), 1.99-2.13 (m, 2 H), 1.40-1.61 (m, 1 H), 0.93-1.06 (m, 3 H). LCMS: m/z 315.1 [M+H]$^+$ (Calc: 315.47).

Further, replacing Compound IM-12 in the above procedure with thiomorpholine 1,1-dioxide, 4-(2-((2R,6R,11R)-8-hydroxy-3,11-dimethyl-2,3,4,5-tetrahydro-2,6-methanobenzo-[d]azocin-6(1H)-yl)ethyl)thiomorpholine 1,1-dioxide (Compound 10) was prepared: $^1$H NMR (400 MHz, METHANOL-d$_4$) δ ppm 6.98-7.10 (m, 1 H), 6.78-6.85 (m, 1 H), 6.66-6.74 (m, 1 H), 3.57-3.73 (m, 1 H), 3.35-3.45 (m, 1 H), 3.25 (d, J=8.30 Hz, 5 H), 3.11-3.18 (m, 3 H), 3.01-3.10 (m, 1 H), 2.81-2.99 (m, 5 H), 2.73 (td, J=13.07, 3.59 Hz, 1 H), 1.91-2.48 (m, 5 H), 1.34-1.59 (m, 1 H), 0.90-1.03 (m, 3 H). LCMS: m/z 379.2 [M+H]$^+$ (Calc: 379.53).

The following compounds were similarly prepared:

(2S,6S,11S)-6-(2-(4-(bis(4-fluoro-phenyl)methyl)piperazin-1-yl)ethyl)-3,11-dimethyl-1,2,3,4,5,6-hexahydro-2,6-methanobenzo[d]azocin-8-ol (Compound 15). The desired enantiomer was obtained through a chiral separation during the synthesis of intermediates. Compound 15: $^1$H NMR (400 MHz, METHANOL-d$_4$) δ ppm 7.48 (ddquin, J=7.04, 5.34, 1.84, 1.84, 1.84, 1.84 Hz, 4 H), 6.99-7.13 (m, 5 H), 6.69-6.80 (m, 2 H), 4.50 (quin, J=0.95 Hz, 1 H), 3.59-3.79 (m, 3 H), 3.33-3.55 (m, 3 H), 2.88-3.25 (m, 8 H), 2.74 (td, J=13.04, 3.56 Hz, 1 H), 2.29-2.54 (m, 3 H), 2.12-2.28 (m, 3 H), 1.36-1.61 (m, 1 H), 0.90-1.09 (m, 3 H). LCMS: m/z 532.2 [M+H]$^+$ (Calc: 532.68).

N-cyclopropyl-N-(1-(2-((2S,6S,11S)-8-hydroxy-3,11-dimethyl-2,3,4,5-tetrahydro-2,6-methanobenzo[d]azocin-6(1H)-yl)ethyl)piperidin-4-yl)benzenesulfonamide (Compound 14). The desired enantiomer was obtained through a chiral separation during the synthesis of intermediates. Compound 14: $^1$H NMR (400 MHz, METHANOL-d$_4$) δ ppm 7.85-7.97 (m, 1H), 7.65-7.71 (m, 1H), 7.58-7.65 (m, 1 H), 6.94-7.03 (m, 1 H), 6.72-6.78 (m, 1 H), 6.60-6.68 (m, 1 H), 3.88 (tt, J=11.98, 3.84 Hz, 1 H), 2.78-3.21 (m, 5 H), 2.42-2.77 (m, 6 H), 1.88-2.21 (m, 9 H), 1.59 (ddt, J=12.43, 6.31, 3.06, 3.06 Hz, 2 H), 1.26-1.39 (m, 1 H), 0.85-1.01 (m, 5 H), 0.74-0.84 (m, 2 H). LCMS: m/z 324.3 [M+H]$^+$ (Calc: 324.73).

(2R,6R,11R)-3-(cyclopropylmethyl)-6-(2-((4-fluorobenzyl)amino)ethyl)-11-methyl-1,2,3,4,5,6-hexahydro-2,6-methanobenzo[d]azocin-8-ol (Compound 16): $^1$H NMR (400 MHz, METHANOL-d$_4$) δ ppm 7.41-7.56 (m, 2 H), 7.08-7.22 (m, 2 H), 6.92-7.01 (m, 1 H), 6.58-6.70 (m, 2 H), 4.16-4.28 (m, 2 H), 3.72-3.90 (m, 1 H), 3.24-3.40 (m, 3 H), 3.12-3.18 (m, 1 H), 3.01-3.08 (m, 2 H), 2.89-2.99 (m, 1 H), 2.53-2.69 (m, 1 H), 2.22-2.37 (m, 1 H), 2.00-2.21 (m, 3 H), 1.29-1.51 (m, 1 H), 1.03 (quin, J=6.47 Hz, 1 H), 0.83-0.96 (m, 3 H), 0.62-0.78 (m, 2 H), 0.30-0.48 (m, 2 H). LCMS: m/z 409.2 [M+H]$^+$ (Calc: 409.55).

(2R,6R,11R)-3-(cyclopropylmethyl)-6-(2-((furan-2-ylmethyl)amino)ethyl)-11-methyl-1,2,3,4,5,6-hexahydro-2,6-methanobenzo[d]azocin-8-ol (Compound 17): $^1$H NMR (400 MHz, METHANOL-d$_4$) δ ppm 7.61-7.70 (m, 1 H), 7.00-7.12 (m, 1 H), 6.64-6.81 (m, 3 H), 6.47-6.57 (m, 1 H), 4.32-4.49 (m, 2 H), 3.80-4.01 (m, 1 H), 3.35-3.49 (m, 1 H), 3.17-3.29 (m, 3 H), 3.10-3.17 (m, 2 H), 2.94-3.09 (m, 1 H), 2.61-2.76 (m, 1 H), 2.21-2.45 (m, 3 H), 2.09-2.20 (m, 1 H), 1.37-1.59 (m, 1 H), 1.06-1.20 (m, 1 H), 0.88-1.05 (m, 3 H), 0.68-0.87 (m, 2 H), 0.38-0.56 (m, 2 H). LCMS: m/z 381.3 [M+H]$^+$ (Calc: 381.52).

Example 8

Synthesis of (S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)piperidine-2-carboxamide (Compound 11)

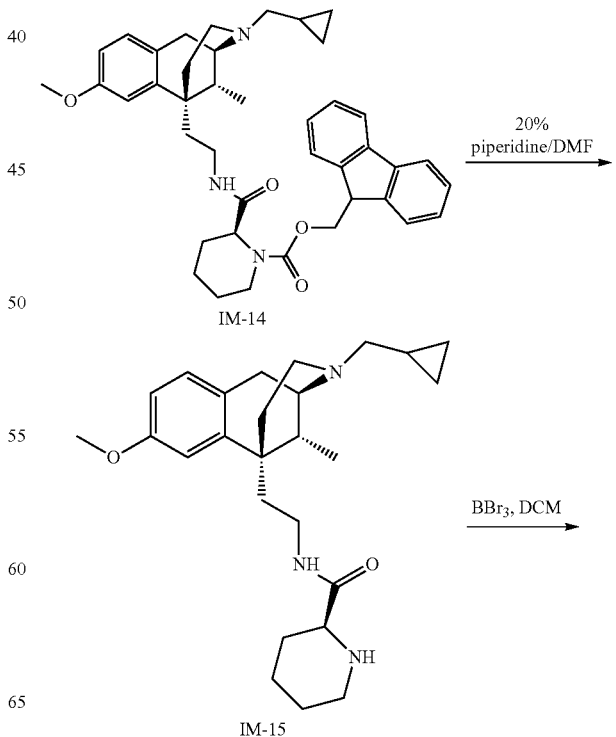

-continued

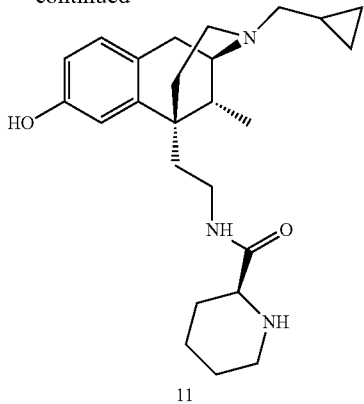

11

Compound IM-14 was dissolved in 2 ml DMF. To the resulting solution was added about 1 ml 20% piperidine/DMF. The mixture was stirred for 5 minutes, and then concentrated under reduced pressure and chromatographed using a 4-gram silica column and a gradient of ammoniacal methanol (10% conc. ammonia in methanol) in DCM as the eluent to provide Compound IM-15: LCMS: m/z 647.3 [M+H]$^+$.

Compound 11 was obtained from Compound IM-15 through the procedure delineated in Example 1 in converting Compound 30 to Compound 31. Compound 11: $^1$H NMR (400 MHz, METHANOL-d$_4$) δ ppm 6.99-7.11 (m, 1 H), 6.72-6.78 (m, 1 H), 6.65-6.72 (m, 1 H), 3.87-4.00 (m, 1 H), 3.73-3.87 (m, 1 H), 3.35-3.54 (m, 4 H), 2.98-3.29 (m, 5 H), 2.62-2.74 (m, 1 H), 1.84-2.39 (m, 8 H), 1.67-1.76 (m, 2 H), 1.35-1.59 (m, 1 H), 1.08-1.21 (m, 1 H), 0.95-1.07 (m, 3 H), 0.73-0.84 (m, 2 H), 0.41-0.55 (m, 2 H). LCMS: m/z 412.2 [M+H]$^+$ (Calc: 412.58).

In a similar manner, the following compounds were prepared:

(S)-N-(2-((2R,6R,11R)-8-hydroxy-3,11-dimethyl-2,3,4,5-tetrahydro-2,6-methano-benzo[d]azocin-6(1H)-yl)ethyl) piperidine-2-carboxamide (Compound 70): $^1$H NMR (METHANOL-d$_4$) δ7.07 (d, J=8.3 Hz, 1H), 6.79 (d, J=2.4 Hz, 1H), 6.71 (dd, J=8.3, 2.5 Hz, 1H), 3.87-3.94 (m, 1H), 3.71 (br. s., 1H), 3.39-3.56 (m, 3H), 3.10-3.26 (m, 3H), 2.92 (s, 3H), 2.65-2.77 (m, 1H), 2.34-2.48 (m, 2H), 2.19-2.32 (m, 2H), 1.85-2.06 (m, 3H), 1.67-1.82 (m, 3H), 1.52 (d, J=13.0 Hz, 1H), 1.01 (d, J=6.9 Hz, 3H); LC/MS, m/z=372.3 [M+H]$^+$ (Calc: 372.27).

(S)-N-(2-((2R,6R,11R)-8-hydroxy-3,11-dimethyl-2,3,4,5-tetrahydro-2,6-methano-benzo[d]azocin-6(1H)-yl)ethyl) pyrrolidine-2-carboxamide (Compound 71): $^1$H NMR (METHANOL-d$_4$) δ 6.96 (d, J=8.4 Hz, 1H), 6.69 (d, J=2.4 Hz, 1H), 6.60 (dd, J=8.3, 2.4 Hz, 1H), 4.16-4.31 (m, 1H), 3.51-3.64 (m, 1H), 3.24-3.45 (m, 3H), 3.11 (dd, J=12.7, 3.7 Hz, 1H), 3.06 (br. s., 2H), 2.81 (s, 3H), 2.55-2.68 (m, 1H), 2.23-2.45 (m, 3H), 2.07-2.20 (m, 1H), 1.88-2.04 (m, 4H), 1.25-1.44 (m, 1H), 0.91 (d, J=6.9 Hz, 3H); LC/MS, m/z=358.2 [M+H]$^+$ (Calc: 358.25).

(S)-N-(2-((2R,6R,11R)-8-hydroxy-3,11-dimethyl-2,3,4,5-tetrahydro-2,6-methano-benzo[d]azocin-6(1H)-yl)ethyl)-5-oxopyrrolidine-2-carboxamide (Compound 72): $^1$H NMR (METHANOL-d$_4$) δ 7.07 (d, J=8.4 Hz, 1H), 6.80 (d, J=2.4 Hz, 1H), 6.70-6.73 (m, 1H), 4.34-4.40 (m, 1H), 3.71 (br. s., 1H), 3.41-3.54 (m, 2H), 3.13-3.25 (m, 3H), 2.92 (s, 3H), 2.68-2.78 (m, 1H), 2.38-2.60 (m, 4H), 2.12-2.27 (m, 2H), 1.96-2.06 (m, 1H), 1.51 (d, J=12.5 Hz, 1H), 1.02 (d, J=6.9 Hz, 3H); LC/MS, m/z=372.1 [M+H]$^+$ (Calc: 372.23).

(S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-5-oxopyrrolidine-2-carboxamide (Compound 81): $^1$H NMR (METHANOL-d$_4$) δ 6.91-6.98 (m, 1H), 6.68-6.73 (m, 1H), 6.57-6.64 (m, 1H), 4.23 (dd, J=8.2, 4.9 Hz, 1H), 3.76-3.88 (m, 1H), 3.32-3.44 (m, 2H), 3.25-3.32 (m, 1H), 3.13-3.19 (m, 1H), 3.01-3.07 (m, 1H), 2.92 (dd, J=13.4, 7.8 Hz, 1H), 2.57 (td, J=12.9, 3.3 Hz, 1H), 2.31-2.48 (m, 5H), 1.99-2.16 (m, 2H), 1.84-1.94 (m, 1H), 1.29-1.44 (m, 1H), 1.06-1.16 (m, 1H), 0.93 (d, J=6.9 Hz, 3H), 0.61-0.70 (m, 2H), 0.35-0.48 (m, 2H); LC/MS, m/z=412.2 [M+H]$^+$ (Calc: 412.26).

(S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-6-oxopiperidine-2-carboxamide (Compound 82): $^1$H NMR (METHANOL-d$_4$) δ6.90-6.98 (m, 1H), 6.66-6.73 (m, 1H), 6.57-6.64 (m, 1H), 4.21 (br. s., 1H), 3.76-3.88 (m, 1H), 3.25-3.47 (m, 3H), 3.13-3.19 (m, 1H), 3.01-3.07 (m, 1H), 2.92 (dd, J=13.4, 7.8 Hz, 1H), 2.52-2.64 (m, 3H), 2.32-2.47 (m, 2H), 2.04-2.18 (m, 2H), 1.78-1.96 (m, 4H), 1.29-1.46 (m, 1H), 1.07-1.16 (m, 1H), 0.93 (d, J=6.9 Hz, 3H), 0.64-0.71 (m, 2H), 0.34-0.48 (m, 2H); LC/MS, m/z=426.1 [M+H]$^+$ (Calc: 426.28).

4-Fluoro-N-(2-((2R,6R,11R)-8-hydroxy-3,11-dimethyl-2,3,4,5-tetrahydro-2,6-methanobenzo[d]azocin-6(1H)-yl) ethyl)benzamide (Compound 83): $^1$H NMR (METHANOL-d$_4$) δ 7.80-7.88 (m, 2H), 7.03-7.18 (m, 2H), 6.89-7.02 (m, 1H), 6.69-6.76 (m, 1H), 6.60 (dd, J=8.3, 2.4 Hz, 1H), 3.45-3.65 (m, 3H), 2.95-3.17 (m, 2H), 2.83 (s, 3H), 2.65 (td, J=13.1, 3.5 Hz, 1H), 2.29-2.44 (m, 2H), 2.14-2.27 (m, 1H), 1.93-2.07 (m, 1H), 1.34-1.48 (m, 1H), 0.97 (d, J=6.9 Hz, 3H); LC/MS, m/z=383.1 [M+H]$^+$ (Calc: 383.21).

(S)-N-(2-((2R,6R,11HR)-8-methoxy-3,11-dimethyl-2,3,4,5-tetrahydro-2,6-methano-benzo[d]azocin-6(1H)-yl) ethyl)-5-oxopyrrolidine-2-carboxamide (Compound 84): $^1$H NMR (METHANOL-d$_4$) δ 7.10-7.21 (m, 1H), 6.81-6.95 (m, 2H), 4.28 (dd, J=8.5, 4.9 Hz, 1H), 3.79 (s, 3H), 3.65-3.75 (m, 1H), 3.40-3.53 (m, 2H), 3.29 (t, J=6.6 Hz, 1H), 3.14-3.25 (m, 2H), 2.92 (m, 3H), 2.71 (td, J=13.0, 3.4 Hz, 1H), 2.34-2.59 (m, 4H), 2.22-2.32 (m, 1H), 2.07-2.17 (m, 1H), 1.92-2.06 (m, 1H), 1.44-1.59 (m, 1H), 1.15 (t, J=7.2 Hz, 1H), 1.02 (d, J=6.9 Hz, 3H); LC/MS, m/z=386.2 [M+H]$^+$ (Calc: 386.24).

N-(2-((2R,6R,11R)-8-hydroxy-3,11-dimethyl-2,3,4,5-tetrahydro-2,6-methano-benzo[d]azocin-6(1H)-yl)ethyl)terephthalamide (Compound 86): $^1$H NMR (METHANOL-d$_4$) δ 7.95-8.06 (m, 4H), 7.00-7.14 (m, 1H), 6.81-6.89 (m, 1H), 6.68-6.76 (m, 1H), 3.58-3.76 (m, 3H), 3.14-3.29 (m, 3H), 2.94 (s, 3H), 2.69-2.80 (m, 1H), 2.42-2.56 (m, 2H), 2.28-2.39 (m, 1H), 2.05-2.19 (m, 1H), 1.44-1.62 (m, 1H), 1.08 (d, J=6.9 Hz, 3H); LC/MS, m/z=408.1 [M+H]$^+$ (Calc: 408.23).

Example 9

Synthesis of (S)-2-((4-((2R,6R,11R)-3-(cyclopropyl-methyl)-8-hydroxy-11-methyl-2,3,4,5-tetrahydro-2,6-methanobenzo[d]azocin-6(1H)-yl)butyl)amino)-3-phenyl-propanamide (Compound 23), methyl (4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-lysinate (Compound 26), and methyl (4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-phenylalaninate (Compound 27)

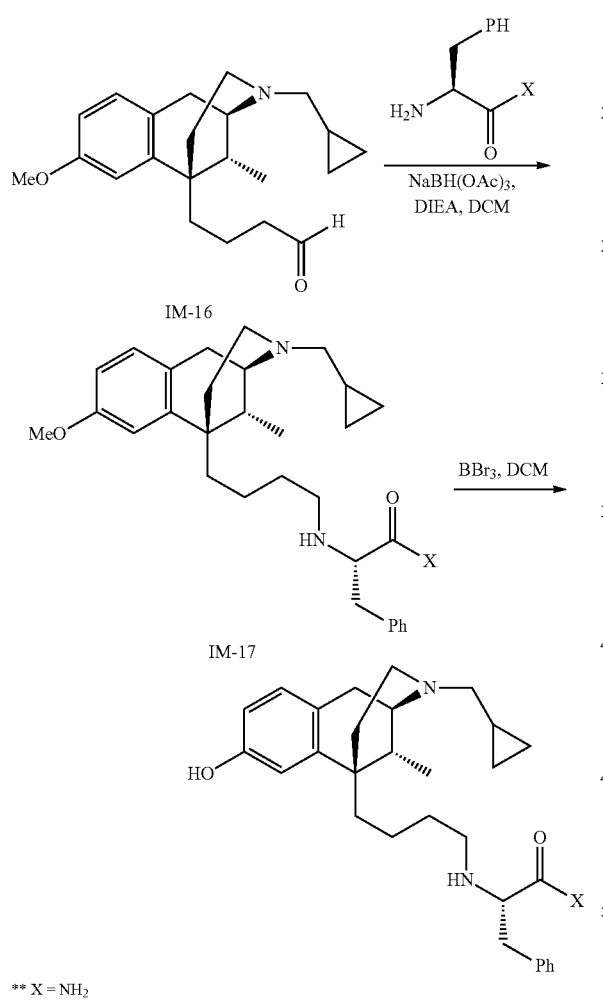

** X = NH$_2$

Compound IM-16 was prepared in a way similar as Compound IM-3 (see above). A solution of Compound IM-16 (50 mg, 0.15 mmol) in 1 mL DCM was added to the appropriate amino acid t-butyl ester or amide (0.18 mmol, 1.2 equiv) and NaBH(OAc)$_3$ (47 mg, 0.22 mmol, 1.5 equiv). DIEA (0.08 mL, 3 equiv) was added and the solution was stirred at RT for 19 h. MeOH was added and the solution concentrated to yield Compound IM-17 (when X=NH$_2$). DCM (1 mL) was added followed by the slow addition of a DCM solution of BBr$_3$ (1M, 0.44 mL, 3 equiv) at 0° C. The solution was allowed to warm to RT over 2 h, quenched with MeOH, and concentrated to give a crude product.

The crude product was purified by preparatory HPLC [0-40% MeCN/H$_2$O (0.01% TFA)] to yield the TFA salt of Compound 23: $^1$H NMR (MeOH) δ: 7.43-7.30 (m, 5H), 7.05 (d, J=8.1 Hz, 1H), 6.79 (d, J=2.2 Hz, 1H), 6.71 (dd, J=8.3, 2.4 Hz, 1H), 4.09 (t, J=7.2 Hz, 1H), 3.93-3.88 (m, 1H), 3.46-2.97 (m, 8H, overlapped with MeOH), 2.76-2.64 (m, 1H), 2.34-2.20 (m, 2H), 2.09-1.94 (m, 1H), 1.89-1.73 (m, 3H), 1.63-1.50 (m, 2H), 1.46 (d, J=14.7 Hz, 1H), 1.17-1.07 (m, 1H), 0.96 (d, J=6.8 Hz, 3H), 0.84-0.74 (m, 2H), 0.84-0.74 (m, 2H), 0.52-0.42 (m, 2H).

Likewise, the following compounds were prepared:

Compound 26.3TFA salts: $^1$H NMR (MeOH) δ: 6.94 (d, J=8.1 Hz, 1H), 6.75 (d, J=2.4 Hz, 1H), 6.60 (dd, J=8.2, 2.5 Hz, 1H), 3.76 (s, 3H), 3.02-2.72 (m, 6H), 2.72-2.62 (m, 2H), 2.63-2.49 (m, 2H), 2.37-2.11 (m, 3H), 1.99-1.88 (m, 1H), 1.80-1.36 (m, 12H), 1.19 (d, J=12.3 Hz, 1H), 1.02-0.92 (m, 1H), 0.87 (d, J=6.8 Hz, 3H), 0.67-0.56 (m, 2H), 0.32-0.18 (m, 2H).

Compound 27.2TFA salts: $^1$H NMR (MeOH) δ: 7.19-7.08 (m, 3H), 7.08-7.00 (m, 2H), 6.82 (d, J=8.6 Hz, 1H), 6.57 (d, J=2.2 Hz, 1H), 6.48 (dd, J=8.3, 2.4 Hz, 1H), 4.23-3.95 (m, 1H), 3.68 (br. s., 1H), 3.52 (s, 3H), 3.22-2.75 (m, 8H, overlapped with MeOH), 2.47 (t, J=13.0 Hz, 1H), 2.10-1.96 (m, 2H), 1.87-1.74 (m, 1H), 1.64-1.50 (m, 3H), 1.42-1.27 (m, 2H), 1.23 (d, J=12.9 Hz, 1H), 0.95-0.83 (m, 1H), 0.73 (d, J=6.8 Hz, 3H), 0.61-0.52 (m, 2H), 0.29-0.17 (m, 2H).

TFA salt of 4-((2R,6R,11R)-3-(cyclobutylmethyl)-8-hydroxy-11-methyl-2,3,4,5-tetrahydro-2,6-methanobenzo[d]azocin-6(1H)-yl)butanamide (Compound 29): $^1$H NMR (MeOH) δ: 6.94 (d, J=8.6 Hz, 1H), 6.67 (d, J=2.4 Hz, 1H), 6.58 (dd, J=8.3, 2.4 Hz, 1H), 3.56-3.48 (m, 1H), 3.40-2.98 (m, 4H, overlapped with MeOH), 2.74-2.52 (m, 2H), 2.31-2.20 (m, 3H), 2.20-2.03 (m, 5H), 2.01-1.74 (m, 7H), 1.73-1.58 (m, 4H), 1.30 (d, J=14.0 Hz, 1H), 0.83 (d, J=7.0 Hz, 3H).

TFA salt of 4-((2R,6R,11R)-3-(cyclobutylmethyl)-8-hydroxy-11-methyl-2,3,4,5-tetrahydro-2,6-methanobenzo[d]azocin-6(1H)-yl)-N,N-dimethylbutanamide (Compound 28): $^1$H NMR (MeOH) δ: 6.94 (d, J=8.3 Hz, 1H), 6.67 (d, J=2.4 Hz, 1H), 6.58 (dd, J=8.3, 2.4 Hz, 1H), 3.57-3.51 (m, 1H), 3.17-3.05 (m, 2H, overlapped with MeOH), 3.04-3.02 (m, 2H), 3.01 (s, 3H), 2.87 (s, 3H), 2.73-2.54 (m, 3H), 2.47-2.39 (m, 3H), 2.22-2.03 (m, 6H), 1.98-1.75 (m, 8H), 1.74-1.61 (m, 4H), 1.31 (d, J=14.3 Hz, 1H), 0.85 (d, J=7.0 Hz, 3H). LC/MS, m/z=385 [M +H]$^+$ (Calc: 384).

Example 10

Synthesis of TFA salt of (4-((2R,6R,11R)-3-(cyclopropyl-methyl)-8-hydroxy-11-methyl-2,3,4,5-tetrahydro-2,6-methanobenzo[d] azocin-6(1H)-yl)butyl)-L-lysine (Compound 25)

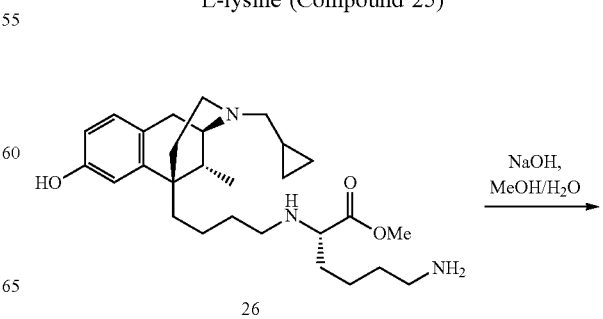

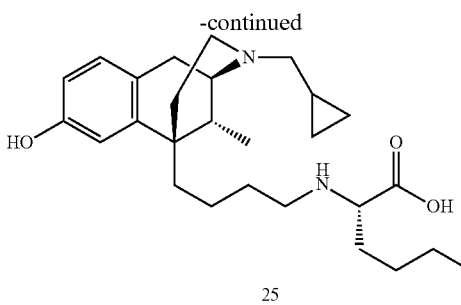

25

To Compound 26 was added 0.2 mL MeOH and 0.2 mL 1M NaOH. The resulting solution was stirred at RT for 20 h., and was then acidified with TFA, concentrated, and purified by preparatory HPLC [0-40% MeCN/H₂O (0.01% TFA)] to yield the TFA salts of Compound 25.

Compound 25.3TFA salts: ¹H NMR (MeOH) δ: 6.72 (d, J=8.3 Hz, 1H), 6.56 (d, J=2.6 Hz, 1H), 6.38 (dd, J=8.3, 2.4 Hz, 1H), 3.32-3.29 (m, 1H), 3.25-3.21 (m, 1H), 3.00-2.97 (m, 1H), 2.97-2.93 (m, 2H), 2.74-2.61 (m, 4H), 2.59-2.45 (m, 3H), 2.40-2.32 (m, 1H), 2.26-2.18 (m, 1H), 1.97-1.89 (m, 3H), 1.79-1.70 (m, 1H), 1.60-1.23 (m, 11H), 0.95 (d, J=9.4 Hz, 1H), 0.78-0.69 (m, 1H), 0.66 (d, J=7.0 Hz, 3H), 0.42-0.32 (m, 2H), 0.07-0.08 (m, 1H).

In a similar manner, TFA salts of (4-((2R,6R,11R)-3-(cyclopropyl-methyl)-8-hydroxy-11-methyl-2,3,4,5-tetrahydro-2,6-methanobenzo[d]azocin-6(1H)-yl)butyl)-L-leucine (Compound 24) were obtained.

Compound 24.2TFA salts: ¹H NMR (MeOH) δ: 7.05 (d, J=8.3 Hz, 1H), 6.82 (d, J=2.2 Hz, 1H), 6.71 (dd, J=8.3, 2.6 Hz, 1H), 3.91 (br. s., 1H), 3.86-3.74 (m, 1H), 3.45-2.99 (m, 8H, overlapped with MeOH), 2.76-2.63 (m, 1H), 2.38-2.22 (m, 2H), 2.15-1.99 (m, 1H), 1.93-1.76 (m, 4H), 1.74-1.53 (m, 3H), 1.48 (d, J=14.5 Hz, 1H), 1.18-1.09 (m, 1H), 1.08-1.00 (m, 6H), 0.97 (d, J=6.8 Hz, 3H), 0.84-0.74 (m, 2H), 0.53-0.43 (m, 2H).

Example 11

In similar manners as those set forth in Examples 1-10, the following compounds were prepared:

(2R,6S,11R)-6-(2-hydroxyethyl)-3,11-dimethyl-1,2,3,4,5,6-hexahydro-2,6-methanobenzo[d]azocin-8-ol (Compound 12): ¹H NMR (400 MHz, METHANOL-d₄) δ ppm 7.38-7.52 (m, 1 H), 7.16-7.26 (m, 1 H), 7.06-7.16 (m, 1 H), 4.19-5.18 (m, 2 H), 3.97-4.14 (m, 1 H), 3.37-3.83 (m, 4 H), 3.32-3.35 (m, 1 H), 3.06-3.20 (m, 1 H), 2.60-2.98 (m, 3 H), 2.38-2.49 (m, 1 H), 1.73-2.02 (m, 1 H), 1.32-1.46 (m, 3 H). LCMS: m/z 262.2 [M+H]⁺ (Calc: 262.36).

1-((2-((2R,6R,11R)-3-(cyclopropylmethyl)-8-methoxy-11-methyl-2,3,4,5-tetrahydro-2,6-methanobenzo[d]azocin-6(1H)-yl)ethyl)amino)cyclopropane-1-carboxylic acid (Compound 34): ¹H NMR (400 MHz, MeOD) δ ppm 0.34-0.43 (m, 2 H), 0.70 (d, J=8.11 Hz, 2 H), 0.97 (d, J=7.02 Hz, 3 H), 1.03-1.19 (m, 3 H), 1.25-1.45 (m, 3 H), 2.07 (m, 1 H), 2.20-2.45 (m, 3 H), 2.46-2.58 (m, 1 H), 2.86-3.12 (m, 5 H), 3.14-3.30 (m, 2 H), 3.79 (s, 4H), 6.83 (dd, J=8.33, 2.41 Hz, 1 H), 6.86-6.90 (m, 1 H), 7.13 (d, J=8.33 Hz, 1 H). LC/MS, m/z=399, [M+H]⁺ (Calc: 398).

1-((2-((2S,6S,11S)-3-(cyclopropylmethyl)-8-methoxy-11-methyl-2,3,4,5-tetrahydro-2,6-methanobenzo[d]azocin-6(1H)-yl)ethyl)amino)cyclopropane-1-carboxylic acid (Compound 35): ¹H NMR (400 MHz, MeOD) δ ppm 0.31-0.38 (m, 2 H), 0.68 (dd, J=8.00, 1.21 Hz, 2 H), 0.96 (d, J=7.02 Hz, 3 H), 0.99-1.03 (m, 2 H), 1.07-1.15 (m, 1 H), 1.22-1.41 (m, 3 H), 2.04 (td, J=12.77, 5.37 Hz, 1 H), 2.21 (td, J=12.61, 3.95 Hz, 1 H), 2.28-2.52 (m, 3 H), 2.80-2.88 (m, 1 H), 2.91-3.07 (m, 4 H), 3.07-3.16 (m, 1 H), 3.20 (d, J=12.28 Hz, 1 H), 3.70 (s, 1 H), 3.79 (s, 3 H), 6.81 (dd, J=8.33, 2.63 Hz, 1 H), 6.87 (d, J=2.41 Hz, 1 H), 7.11 (d, J=8.55 Hz, 1 H). LC/MS, m/z=399, [M+H]⁺ (Calc: 398).

(2-((2R,6R,11R)-3-(cyclopropylmethyl)-8-methoxy-11-methyl-2,3,4,5-tetrahydro-2,6-methanobenzo[d]azocin-6(1H)-yl)ethyl)glycine (Compound 36): ¹H NMR (400 MHz, MeOD) δ ppm 0.31-0.44 (m, 2 H), 0.63-0.72 (m, 2 H), 0.83-0.94 (m, 3 H), 0.98-1.09 (m, 1 H), 1.21 (t, J=7.34 Hz, 1 H), 1.24-1.30 (m, 1 H), 1.48 (d, J=13.59 Hz, 1 H), 2.03-2.26 (m, 3 H), 2.28-2.42 (m, 1 H), 2.51-2.64 (m, 1 H), 2.95 (dd, J=13.37, 7.89 Hz, 1 H), 2.99-3.17 (m, 4 H), 3.31 (d, J=8.77 Hz, 1 H), 3.70 (s, 3 H), 3.78-3.89 (m, 3 H), 6.75-6.81 (m, 2 H), 7.08 (d, J=8.99 Hz, 1 H). LC/MS, m/z=373, [M+H]⁺ (Calc: 372).

Methyl (2-((2S,6S,11S)-3-(cyclopropylmethyl)-8-methoxy-11-methyl-2,3,4,5-tetrahydro-2,6-methanobenzo[d]azocin-6(1H)-yl)ethyl)-L-valinate (Compound 37): ¹H NMR (400 MHz, MeOD) δ ppm −0.10-0.07 (m, 2 H), 0.37 (m, 2 H), 0.65-0.75 (m, 4 H), 0.76-0.81 (m, 3 H), 0.84 (d, J=7.02 Hz, 3 H), 1.02 (d, J=9.43 Hz, 1 H), 1.76-2.01 (m, 6 H), 2.18 (dd, J=12.61, 6.69 Hz, 1 H), 2.27-2.37 (m, 1 H), 2.40-2.57 (m, 3 H), 2.59-2.68 (m, 1 H), 2.69-2.77 (m, 1 H), 2.93-3.05 (m, 2 H), 3.58 (d, J=4.17 Hz, 6 H), 6.53 (dd, J=8.33, 2.63 Hz, 1 H), 6.65 (d, J=2.63 Hz, 1 H), 6.82 (d, J=8.33 Hz, 1 H). LC/MS, m/z=429, [M+H]⁺ (Calc: 428).

Methyl (2-((2R,6R,11R)-3-(cyclopropylmethyl)-8-methoxy-11-methyl-2,3,4,5-tetrahydro-2,6-methanobenzo[d]azocin-6(1H)-yl)ethyl)-L-alaninate (Compound 38): ¹H NMR (400 MHz, MeOD) δ ppm −0.08-0.05 (m, 2 H), 0.30-0.42 (m, 2 H), 0.68 (d, J=7.02 Hz, 4 H), 0.98-1.05 (m, 1 H), 1.17 (d, J=7.02 Hz, 3 H), 1.69-1.79 (m, 1 H), 1.80-2.01 (m, 4 H), 2.17 (dd, J=12.83, 6.69 Hz, 1 H), 2.27-2.35 (m, 1 H), 2.45-2.64 (m, 4 H), 2.68-2.76 (m, 1 H), 3.01 (dd, J=5.48, 3.29 Hz, 1 H), 3.13 (dt, J=3.29, 1.64 Hz, 2 H), 3.25-3.33 (m, 1H), 3.53-3.59 (m, 6 H), 6.52 (dd, J=8.33, 2.63 Hz, 1 H), 6.64 (d, J=2.41 Hz, 1 H), 6.81 (d, J=8.55 Hz, 1 H). LC/MS, m/z=401, [M+H]⁺ (Calc: 400).

(2-((2S,6S,11S)-3-(cyclopropylmethyl)-8-methoxy-11-methyl-2,3,4,5-tetrahydro-2,6-methanobenzo[d]azocin-6(1H)-yl)ethyl)glycine (Compound 39): ¹H NMR (400 MHz, MeOD) δ ppm 0.44-0.52 (m, 2 H), 0.79 (m, 2 H), 1.01 (d, J=6.80 Hz, 3 H), 1.10-1.19 (m, 1H), 1.56 (d, J=14.69 Hz, 1 H), 2.17-2.35 (m, 3 H), 2.40-2.52 (m, 1 H), 2.71 (m, 1 H), 3.03-3.30 (m, 6 H), 3.36-3.43 (m, 1 H), 3.64 (s, 2 H), 3.81 (s, 3 H), 3.93 (m, 1 H), 6.86-6.92 (m, 2 H), 7.15-7.22 (m, 1 H). LC/MS, m/z=373, [M+H]⁺ (Calc: 372).

(2-((2R,6R,11R)-3-(cyclopropylmethyl)-8-methoxy-11-methyl-2,3,4,5-tetrahydro-2,6-methanobenzo[d]azocin-6(1H)-yl)ethyl)-L-alanine (Compound 40): ¹H NMR (400 MHz, MeOD) δ ppm 0.37 (m, 2 H), 0.67 (m, 2 H), 0.90 (d, J=6.58 Hz, 3 H), 0.99-1.12 (m, 7 H), 1.45 (d, J=13.37 Hz, 1 H), 2.08-2.31 (m, 4 H), 2.36-2.48 (m, 1 H), 2.51-2.61 (m, 1 H), 2.93 (dd, J=12.93, 7.67 Hz, 1 H), 3.00-3.18 (m, 5 H), 3.30 (d, J=12.93 Hz, 1 H), 3.44 (d, J=3.95 Hz, 1 H), 3.70 (s, 3 H), 3.87 (m, 1 H), 6.72-6.82 (m, 2 H), 7.07 (d, J=8.55 Hz, 1 H). LC/MS, m/z=387, [M+H]⁺ (Calc: 386).

(2-((2S,6S,11S)-3-(cyclopropylmethyl)-8-methoxy-11-methyl-2,3,4,5-tetrahydro-2,6-methanobenzo[d]azocin-6(1H)-yl)ethyl)-L-valine (Compound 41): ¹H NMR (400 MHz, MeOD) δ ppm 0.48 (m, 2 H), 0.76 (m, 2 H), 1.00 (d, J=6.80 Hz, 3 H), 1.19 (d, J=7.45, 4.60 Hz, 2 H), 1.50-1.63 (m, 4 H), 2.22 (td, J=12.39, 5.70 Hz, 1 H), 2.32-2.55 (m, 3 H), 2.67 (m, 1 H), 3.07 (br. s., 1 H), 3.13-3.31 (m, 5 H), 3.42 (d, J=11.40 Hz, 1 H), 3.69-3.77 (m, 1 H), 3.79-3.83 (m, 3 H), 3.96 (br. s., 1 H), 6.83-6.93 (m, 2 H), 7.19 (d, J=8.11 Hz, 1 H). LC/MS, m/z=415 , [M+H]⁺ (Calc: 414).

(2-((2S,6S,11S)-3-(cyclopropylmethyl)-8-hydroxy-11-methyl-2,3,4,5-tetrahydro-2,6-methanobenzo[d]azocin-6(1H)-yl)ethyl)-L-valine (Compound 42): ¹H NMR (400 MHz, MeOD) δ ppm 0.31-0.42 (m, 2 H), 0.61-0.73 (m, 2 H), 0.83-0.93 (m, 3 H), 1.02 (d, J=7.02 Hz, 4 H), 1.11 (d, J=7.02 Hz, 3 H), 1.46 (d, J=14.03 Hz, 1 H), 2.05-2.28 (m, 4 H), 2.29-2.41 (m, 1 H), 2.60 (td, J=12.93, 3.51 Hz, 1 H), 2.95 (dd, J=13.48, 7.78 Hz, 1 H), 3.01-3.19 (m, 5H), 3.30 (d, J=12.93 Hz, 1 H), 3.71-3.88 (m, 2 H), 6.58-6.71 (m, 2 H), 6.96 (d, J=8.33 Hz, 1H). LC/MS, m/z=401 , [M+H]⁺ (Calc: 400).

2-((2R,6S,11R)-3-(cyclopropylmethyl)-8-methoxy-11-methyl-2,3,4,5-tetrahydro-2,6-methanobenzo[d]azocin-6(1H)-yl)ethan-1-ol (Compound 43): ¹H NMR (600 MHz, MeOD) δ ppm −0.07-0.03 (m, 2 H), 0.31-0.38 (m, 2 H), 0.70 (d, J=7.10 Hz, 4 H), 1.05 (d, J=12.55 Hz, 1 H), 1.79-1.92 (m, 3 H), 1.93-2.05 (m, 2 H), 2.17 (dd, J=12.72, 6.61 Hz, 1 H), 2.31 (dd, J=12.72, 6.61 Hz, 1 H), 2.44-2.56 (m, 2 H), 2.72 (d, J=18.33 Hz, 1 H), 3.01 (m, 1 H), 3.57 (s, 3 H), 3.66 (m, 2 H), 6.52 (dd, J=8.42, 2.31 Hz, 1 H), 6.63 (d, J=2.31 Hz, 1 H), 6.81 (d, J=8.42 Hz, 1 H). LC/MS, m/z=316 , [M+H]⁺ (Calc: 315).

(2S,6R,11S)-6-(2-(benzyloxy)ethyl)-3-(cyclopropylmethyl)-8-methoxy-11-methyl-1,2,3,4,5,6-hexahydro-2,6-methanobenzo[d]azocine (Compound 44): ¹H NMR (600 MHz, MeOD) δ ppm −0.06-0.03 (m, 2 H), 0.31-0.40 (m, 2 H), 0.65-0.76 (m, 4 H), 1.04 (d, J=12.72 Hz, 1 H), 1.85-1.93 (m, 3 H), 1.94-2.03 (m, 1 H), 2.10 (m, 1 H), 2.18 (dd, J=12.72, 6.61 Hz, 1 H), 2.31 (dd, J=12.72, 6.44 Hz, 1 H), 2.48-2.55 (m, 2 H), 2.72 (d, J=18.33 Hz, 1 H), 3.01 (m, 1 H), 3.56 (s, 3 H), 3.57-3.64 (m, 2 H), 4.40 (s, 2 H), 6.52 (dd, J=8.34, 2.23 Hz, 1 H), 6.64 (d, J=2.15 Hz, 1 H), 6.81 (d, J=8.42 Hz, 1 H), 7.08-7.13 (m, 1 H), 7.15-7.19 (m, 2 H), 7.19-7.24 (m, 2 H). LC/MS, m/z=406 , [M+H]⁺ (Calc: 405).

(2R,6S,11R)-6-(2-(benzyloxy)ethyl)-3-(cyclopropylmethyl)-8-methoxy-11-methyl-1,2,3,4,5,6-hexahydro-2,6-methanobenzo[d]azocine (Compound 45): ¹H NMR (600 MHz, CDCl₃) δ ppm 0.04-0.14 (m, 2 H), 0.46-0.54 (m, 2 H), 0.79-0.88 (m, 4 H), 1.23 (d, J=12.65 Hz, 1 H), 1.93-2.03 (m, 2 H), 2.06-2.18 (m, 2 H), 2.22-2.32 (m, 2 H), 2.44 (dd, J=12.65, 6.24 Hz, 1 H), 2.60 (dd, J=18.16, 5.87 Hz, 1 H), 2.68 (dd, J=11.55, 3.30 Hz, 1 H), 2.84 (d, J=18.16 Hz, 1 H), 3.08-3.12 (m, 1 H), 3.71 (td, J=9.45, 5.69 Hz, 1 H), 3.76 (s, 3 H), 3.77-3.83 (m, 1 H), 6.68 (dd, J=8.34, 2.29 Hz, 1 H), 6.83 (d, J=2.20 Hz, 1 H), 6.96 (d, J=8.44 Hz, 1 H), 7.25-7.31 (m, 1 H), 7.34-7.40 (m, 3 H). LC/MS, m/z=406 , [M+H]⁺ (Calc: 405).

2-((2S,6R,11S)-3-(cyclopropylmethyl)-8-methoxy-11-methyl-2,3,4,5-tetrahydro-2,6-methanobenzo[d]azocin-6(1H)-yl)ethan-1-ol (Compound 46): ¹H NMR (600 MHz, MeOD) δ ppm 0.36-0.44 (m, 2 H), 0.69-0.77 (m, 2 H), 0.96 (d, J=6.97 Hz, 1 H), 1.07 (m, 1 H), 1.46 (m, 1 H), 2.01-2.09 (m, 1 H), 2.25-2.31 (m, 2 H), 2.36 (t, J=13.66 Hz, 1 H), 2.56 (t, J=12.93 Hz, 1 H), 2.90-2.97 (m, 1 H), 3.05-3.12 (m, 3 H), 3.22 (d, J=12.10 Hz, 1 H), 3.75 (m, 1 H), 3.78 (s, 3 H), 3.82-3.90 (m, 2 H), 6.81 (dd, J=8.44, 1.28 Hz, 1 H), 6.89 (s, 1 H), 7.10 (d, J=8.44 Hz, 1 H). LC/MS, m/z=316 , [M+H]⁺ (Calc: 315).

(2S,6R,11S)-6-(2-(benzyloxy)ethyl)-8-methoxy-3,11-dimethyl-1,2,3,4,5,6-hexahydro-2,6-methanobenzo[d]azocine (Compound 47): ¹H NMR (METHANOL-d₄) δ: 7.25-7.45 (m, 5H), 7.02 (d, J=8.6 Hz, 1H), 6.83 (d, J=2.6 Hz, 1H), 6.72 (dd, J=8.5, 2.5 Hz, 1H), 4.59 (s, 2H), 3.78 (m, 1H), 3.75 (s, 3H), 2.99 (d, J=18.3 Hz, 1H), 2.86 (dd, J=5.6, 3.4 Hz, 1H), 2.64-2.76 (m, 1H), 2.40-2.47 (m, 1H), 2.37 (s, 3H), 2.29 (ddd, J=14.0, 8.3, 6.2 Hz, 1H), 2.00-2.17 (m, 4H), 1.19-1.27 (m, 1H), 0.86 (d, J=6.8 Hz, 3H); LC/MS, m/z=366.3 [M+H]⁺ (Calc: 366.24).

(2R,6S,11R)-6-(2-(benzyloxy)ethyl)-8-methoxy-3,11-dimethyl-1,2,3,4,5,6-hexahydro-2,6-methanobenzo[d]azocine (Compound 48): ¹H NMR (METHANOL-d₄) δ: 7.25-7.45 (m, 5H), 7.02 (d, J=8.6 Hz, 1H), 6.83 (d, J=2.6 Hz, 1H), 6.72 (dd, J=8.5, 2.5 Hz, 1H), 4.59 (s, 2H), 3.78 (m, 1H), 3.75 (s, 3H), 2.99 (d, J=18.3 Hz, 1H), 2.86 (dd, J=5.6, 3.4 Hz, 1H), 2.64-2.76 (m, 1H), 2.40-2.47 (m, 1H), 2.37 (s, 3H), 2.29 (ddd, J=14.0, 8.3, 6.2 Hz, 1H), 2.00-2.17 (m, 4H), 1.19-1.27 (m, 1H), 0.86 (d, J=6.8 Hz, 3H); LC/MS, m/z=366.3 [M+H]⁺ (Calc: 366.24).

5-(2-((2R,6S,11HR)-8-hydroxy-3,11-dimethyl-2,3,4,5-tetrahydro-2,6-methanobenzo[d]azocin-6(1H)-yl)ethoxy) nicotinic acid (Compound 52): ¹H NMR (METHANOL-d₄) δ: 8.71 (s, 1H), 8.39 (d, J=2.6 Hz, 1H), 7.94 (br. s., 1H), 7.07 (d, J=8.4 Hz, 1H), 6.86 (d, J=2.4 Hz, 1H), 6.73 (dd, J=8.3, 2.3 Hz, 1H), 4.36-4.48 (m, 2H), 3.64-3.74 (m, 1H), 3.11-3.24 (m, 2H), 2.94 (s, 3H), 2.80 (br. s., 1H), 2.44-2.67 (m, 3H), 2.30-2.40 (m, 1H), 1.60 (d, J=14.1 Hz, 1H), 1.06 (d, J=6.8 Hz, 3H); LC/MS, m/z=383.3 [M+H]⁺ (Calc: 383.20).

2-((2S,6R,11S)-8-methoxy-3,11-dimethyl-2,3,4,5-tetrahydro-2,6-methano-benzo[d]azocin-6(1H)-yl)ethan-1-ol (Compound 49): ¹H NMR (METHANOL-d₄) δ: 7.03 (d, J=8.4 Hz, 1H), 6.83 (d, J=2.4 Hz, 1H), 6.73 (dd, J=8.4, 2.6 Hz, 1H), 3.84 (dt, J=9.7, 5.5 Hz, 2H), 3.77 (s, 3H), 3.00 (d, J=18.3 Hz, 1H), 2.88 (dd, J=5.5, 3.3 Hz, 1H), 2.66-2.76 (m, 1H), 2.46 (d, J=7.0 Hz, 1H), 2.39 (s, 3H), 2.15-2.25 (m, 1H), 2.13 (d, J=8.4 Hz, 2H), 1.98-2.07 (m, 2H), 1.21-1.28 (m, 1H), 0.90 (d, J=7.0 Hz, 3H); LC/MS, m/z=276.3 [M+H]⁺ (Calc: 276.20).

2-((2R,6S,11HR)-8-methoxy-3,11-dimethyl-2,3,4,5-tetrahydro-2,6-methanobenzo-[d]azocin-6(1H)-yl)ethan-1-ol (Compound 50): ¹H NMR (METHANOL-d₄) δ: 7.03 (d, J=8.4 Hz, 1H), 6.83 (d, J=2.4 Hz, 1H), 6.73 (dd, J=8.4, 2.6 Hz, 1H), 3.84 (dt, J=9.7, 5.5 Hz, 2H), 3.77 (s, 3H), 3.00 (d, J=18.3 Hz, 1H), 2.88 (dd, J=5.5, 3.3 Hz, 1H), 2.66-2.76 (m, 1H), 2.46 (d, J=7.0 Hz, 1H), 2.39 (s, 3H), 2.15-2.25 (m, 1H), 2.13 (d, J=8.4 Hz, 2H), 1.98-2.07 (m, 2H), 1.21-1.28 (m, 1H), 0.90 (d, J=7.0 Hz, 3H); LC/MS, m/z=276.3 [M+H]⁺ (Calc: 276.20).

4-(2-((2R,6R,11HR)-8-methoxy-3,11-dimethyl-2,3,4,5-tetrahydro-2,6-methanobenzo-[d]azocin-6(1H)-yl)ethyl)amino)ethyl)benzenesulfonamide (Compound 51): ¹H NMR (METHANOL-d₄) δ: 7.86 (d, J=8.4 Hz, 2H), 7.46 (d, J=8.4 Hz, 2H), 7.03 (d, J=8.4 Hz, 1H), 6.82 (d, J=2.6 Hz, 1H), 6.69-6.76 (m, 1H), 3.76 (s, 3H), 2.96 (s, 3H), 2.78-2.92 (m, 3H), 2.71 (dd, J=18.4, 5.8 Hz, 1H), 2.46 (d, J=8.4 Hz, 1H), 2.39 (s, 3H), 2.05-2.18 (m, 3H), 1.94-2.05 (m, 2H), 1.16-1.23 (m, 1H), 0.88 (d, J=7.0 Hz, 3H); LC/MS, m/z=458.3 [M+H]⁺ (Calc: 458.25).

N¹-(2-((2R,6R,11HR)-8-methoxy-3,11-dimethyl-2,3,4,5-tetrahydro-2,6-methanobenzo[d]azocin-6(1H)-yl)ethyl)-N¹,N³,N³-trimethylpropane-1,3-diamine (Compound 54): ¹H NMR (METHANOL-d₄) δ: 7.20 (d, J=8.6 Hz, 1H), 6.84-6.96 (m, 2H), 3.81 (s, 3H), 3.73 (br. s., 1H), 3.39 (br. s., 1H), 3.19-3.30 (m, 3H), 3.05 (s, 3H), 2.91-2.99 (m, 9H), 2.69-2.81 (m, 1H), 2.49-2.62 (m, 1H), 2.24-2.39 (m, 5H), 1.58 (d, J=13.0 Hz, 1H), 1.00 (d, J=6.8 Hz, 3H); LC/MS, m/z=374.2 [M+H]⁺ (Calc: 374.32).

3-(1H-imidazol-1-yl)-N-(2-((2R,6R,11R)-8-methoxy-3,11-dimethyl-2,3,4,5-tetrahydro-2,6-methanobenzo[c]azocin-6(1H)-yl)ethyl)propan-1-amine (Compound 55): ¹H NMR (METHANOL-d₄) δ: 7.65-7.73 (m, 1H), 7.14-7.21 (m, 1H), 6.96-7.07 (m, 2H), 6.82 (d, J=2.6 Hz, 1H), 6.74 (dd, J=8.4, 2.6 Hz, 1H), 4.09-4.18 (m, 2H), 3.77 (s, 3H), 3.01 (d, J=18.5 Hz, 1H), 2.86-2.93 (m, 1H), 2.73-2.84 (m, 2H), 2.62-2.70 (m, 2H), 2.47 (d, J=8.6 Hz, 1H), 2.40 (s, 3H), 1.93-2.15 (m, 7H), 1.18-1.23 (m, 1H), 0.88 (d, J=7.0 Hz, 3H); LC/MS, m/z=383.3 [M+H]$^+$ (Calc: 383.28).

(2R,6S,11R)-8-methoxy-6-(2-((S)-2-(methoxymethyl) pyrrolidin-1-yl)ethyl)-3,11-dimethyl-1,2,3,4,5,6-hexahydro-2,6-methanobenzo[d]azocine (Compound 56): $^1$H NMR (METHANOL-d$_4$) δ: 6.93 (d, J=8.4 Hz, 1H), 6.73 (d, J=2.4 Hz, 1H), 6.63 (dd, J=8.4, 2.6 Hz, 1H), 3.66 (s, 3H), 3.26-3.40 (m, 2H), 3.24 (s, 3H), 3.12 (td, J=12.2, 4.5 Hz, 1H), 2.90 (d, J=18.5 Hz, 1H), 2.79 (dd, J=5.4, 3.4 Hz, 1H), 2.55-2.72 (m, 2H), 2.32-2.47 (m, 2H), 2.28 (s, 3H), 2.04-2.15 (m, 1H), 1.97-2.03 (m, 2H), 1.79-1.96 (m, 2H), 1.67-1.77 (m, 2H), 1.40-1.54 (m, 1H), 1.04-1.12 (m, 1H), 0.78 (d, J=7.0 Hz, 3H); LC/MS, m/z=373.4 [M+H]$^+$ (Calc: 373.29).

1-(3-((2-((2R,6R,11R)-8-methoxy-3,11-dimethyl-2,3,4,5-tetrahydro-2,6-methanobenzo-[d]azocin-6(1H)-yl)ethyl) amino)propyl)pyrrolidin-2-one (Compound 57): $^1$H NMR (METHANOL-d$_4$) δ: 6.93 (d, J=8.4 Hz, 1H), 6.73 (d, J=2.4 Hz, 1H), 6.63 (dd, J=8.4, 2.6 Hz, 1H), 3.66 (s, 3H), 3.38 (dt, J=10.3, 7.2 Hz, 4H), 3.23-3.31 (m, 2H), 2.85-2.94 (m, 1H), 2.61-2.82 (m, 4H), 2.51-2.61 (m, 2H), 2.27-2.39 (m, 4H), 1.87-2.06 (m, 4H), 1.57-1.77 (m, 4H), 1.06-1.14 (m, 1H), 0.78 (d, J=6.8 Hz, 3H); LC/MS, m/z=400.4 [M+H]$^+$ (Calc: 400.30).

4-(2-((2R,6R,11R)-8-hydroxy-3,11-dimethyl-2,3,4,5-tetrahydro-2,6-methanobenzo[d]azocin-6(1H)-yl)ethyl)amino) ethyl)benzenesulfonamide (Compound 59): $^1$H NMR (METHANOL-d$_4$) δ: 7.81 (d, J=8.1 Hz, 2H), 7.41 (d, J=8.1 Hz, 2H), 6.92-7.00 (m, 1H), 6.60-6.68 (m, 2H), 3.51-3.64 (m, 1H), 3.26-3.37 (m, 2H), 3.08-3.18 (m, 3H), 2.99-3.08 (m, 1H), 2.82 (s, 3H), 2.59-2.70 (m, 1H), 2.20-2.32 (m, 1H), 2.00-2.16 (m, 3H), 1.27-1.48 (m, 1H), 0.88 (d, J=6.8 Hz, 3H); LC/MS, m/z=444.1 [M+H]$^+$ (Calc: 444.23).

(2-((2R,6S,11R)-8-methoxy-3,11-dimethyl-2,3,4,5-tetrahydro-2,6-methanobenzo-[d]azocin-6(1H)-yl)ethyl)-D-proline (Compound 60): $^1$H NMR (METHANOL-d$_4$) δ: 7.02-7.14 (m, 1H), 6.71-6.87 (m, 2H), 4.32 (t, J=8.5 Hz, 1H), 3.75-3.86 (m, 1H), 3.71 (s, 3H), 3.50-3.65 (m, 2H), 3.32 (td, J=12.3, 5.1 Hz, 1H), 3.08-3.18 (m, 2H), 2.84 (s, 3H), 2.63 (td, J=13.0, 3.3 Hz, 1H), 2.53 (dd, J=12.4, 9.6 Hz, 1H), 2.37 (td, J=12.7, 3.2 Hz, 1H), 2.06-2.24 (m, 5H), 1.93-2.04 (m, 1H), 1.40-1.56 (m, 1H), 0.91 (d, J=6.8 Hz, 3H); LC/MS, m/z=373.2 [M+H]$^+$ (Calc: 373.25).

2-((2R,6S,11R)-8-hydroxy-3,11-dimethyl-2,3,4,5-tetrahydro-2,6-methano-benzo[d]azocin-6(1H)-yl)-N-(4-sulfamoylphenethyl)acetamide (Compound 62): $^1$H NMR (METHANOL-d$_4$) δ: 7.86 (d, J=8.1 Hz, 2H), 7.47 (d, J=8.4 Hz, 2H), 7.00 (d, J=8.1 Hz, 1H), 6.72 (d, J=2.4 Hz, 2H), 4.60 (br. s., 2H), 3.63 (dt, J=13.6, 7.0 Hz, 1H), 3.51 (dt, J=13.5, 6.9 Hz, 1H), 3.18-3.29 (m, 1H), 2.90-3.05 (m, 4H), 2.80-2.89 (m, 2H), 2.68 (s, 3H), 2.45-2.61 (m, 3H), 2.27-2.36 (m, 1H), 1.29-1.41 (m, 1H), 0.88 (d, J=6.8 Hz, 3H); LC/MS, m/z=458.1 [M+H]$^+$ (Calc: 458.21).

(2R,6R,11R)-6-(2-(((1R,3R,5S)-9-((1R,6S,8r)-bicyclo [4.3.1]decan-8-yl)-9-azabicyclo[3.3.1]nonan-3-yl)amino) ethyl)-3,11-dimethyl-1,2,3,4,5, 6-hexahydro-2,6-methanobenzo[d]azocin-8-ol (Compound 63): $^1$H NMR (METHANOL-d$_4$) δ: 6.83 (d, J=8.4 Hz, 1H), 6.61 (d, J=2.2 Hz, 1H), 6.49 (dd, J=8.3, 2.3 Hz, 1H), 3.45 (d, J=9.7 Hz, 2H), 2.96-3.11 (m, 2H), 2.73-2.86 (m, 4H), 2.58 (dd, J=18.4, 5.8 Hz, 1H), 2.26-2.40 (m, 6H), 2.16 (br. s., 2H), 1.92-2.09 (m, 5H), 1.83-1.91 (m, 2H), 1.62-1.79 (m, 8H), 1.32-1.58 (m, 6H), 1.09-1.25 (m, 4H), 0.79 (d, J=6.8 Hz, 3H); LC/MS, m/z=520.3 [M+H]$^+$ (Calc: 520.43).

(2R,6R,11R)-6-(2-(((1R,3S, 5S)-9-(2-((1S,2S,5S)-6,6-dimethylbicyclo-[3.1.1]heptan-2-yl)ethyl)-9-azabicyclo [3.3.1]nonan-3-yl)amino)ethyl)-3,11-dimethyl-1,2,3,4,5,6-hexahydro-2,6-methanobenzo[d]azocin-8-ol (Compound 64): $^1$H NMR (METHANOL-d$_4$) δ: 6.82 (d, J=8.1 Hz, 1H), 6.63 (d, J=2.4 Hz, 1H), 6.48 (dd, J=8.1, 2.4 Hz, 1H), 3.05 (d, J=9.7 Hz, 2H), 2.87 (d, J=18.3 Hz, 1H), 2.71-2.81 (m, 3H), 2.49-2.62 (m, 4H), 2.31-2.39 (m, 2H), 2.27 (s, 3H), 1.76-2.06 (m, 10H), 1.34-1.47 (m, 6H), 1.12-1.21 (m, 3H), 1.10 (s, 3H), 0.90-0.98 (m, 5H), 0.77-0.83 (m, 4H); LC/MS, m/z=534.5 [M+H]$^+$ (Calc: 534.44).

1-(1-(2-((2R,6R,11R)-8-hydroxy-3,11-dimethyl-2,3,4,5-tetrahydro-2,6-methanobenzo[d]azocin-6(1H)-yl)ethyl)piperidin-4-yl)indolin-2-one (Compound 65): $^1$H NMR (METHANOL-d$_4$) δ: 7.17-7.24 (m, 2H), 7.08 (d, J=7.9 Hz, 1H), 6.93-7.02 (m, 2H), 6.73 (d, J=2.4 Hz, 1H), 6.65 (dd, J=8.4, 2.2 Hz, 1H), 4.28-4.45 (m, 1H), 3.79 (d, J=10.8 Hz, 2H), 3.54-3.67 (m, 1H), 3.48 (s, 2H), 3.25-3.35 (m, 2H), 3.05-3.18 (m, 4H), 2.76-2.88 (m, 4H), 2.62-2.71 (m, 1H), 2.34-2.47 (m, 1H), 2.10-2.22 (m, 3H), 1.91-2.06 (m, 2H), 1.37-1.52 (m, 1H), 0.92 (d, J=6.8 Hz, 3H); LC/MS, m/z=460.4 [M+H]$^+$ (Calc: 460.30).

4-Fluoro-N-((2-((2R,6R,11R)-8-hydroxy-3,11-dimethyl-2,3,4,5-tetrahydro-2,6-methanobenzo[d]azocin-6(1H)-yl) ethyl)carbamoyl)benzenesul-fonamide (Compound 66): $^1$H NMR (METHANOL-d$_4$) δ: 7.93-8.02 (m, 2H), 7.24 (t, J=8.7 Hz, 2H), 6.88-6.97 (m, 1H), 6.55-6.66 (m, 2H), 3.47-3.59 (m, 1H), 2.98-3.10 (m, 3H), 2.79 (s, 3H), 2.54-2.64 (m, 1H), 2.15-2.28 (m, 2H), 1.95-2.10 (m, 1H), 1.71-1.84 (m, 1H), 1.26-1.41 (m, 2H), 0.85 (d, J=6.8 Hz, 3H); LC/MS, m/z=462.1 [M+H]$^+$ (Calc: 462.19).

4-Fluoro-N-((2-((2R,6R,11R)-8-methoxy-3, 11-dimethyl-2,3,4,5-tetrahydro-2,6-methanobenzo[d]azocin-6(1H)-yl) ethyl)carbamoyl)benzene-sulfonamide (Compound 67): $^1$H NMR (METHANOL-d$_4$) δ: 8.04-8.11 (m, 2H), 7.35 (t, J=8.8 Hz, 2H), 7.08-7.18 (m, 1H), 6.79-6.90 (m, 2H), 3.78 (s, 3H), 3.60-3.71 (m, 1H), 3.12-3.22 (m, 3H), 2.91 (s, 3H), 2.68 (td, J=13.2, 3.5 Hz, 1H), 2.26-2.39 (m, 2H), 2.08-2.21 (m, 1H), 1.84-1.97 (m, 1H), 1.37-1.53 (m, 3H), 0.96 (d, J=6.9 Hz, 3H); LC/MS, m/z=476.2 [M+H]$^+$ (Calc: 476.20).

N-((2-((2R,6R,11R)-8-hydroxy-3,11-dimethyl-2,3,4,5-tetrahydro-2,6-methanobenzo[d]azocin-6(1H)-yl)-ethyl)carbamoyl)benzenesulfonamide (Compound 75): $^1$H NMR (METHANOL-d$_4$) δ: 7.87-7.95 (m, 2H), 7.58 (d, J=7.4 Hz, 1H), 7.48-7.55 (m, 2H), 6.87-6.97 (m, 1H), 6.57-6.64 (m, 2H), 3.46-3.58 (m, 1H), 2.99-3.10 (m, 3H), 2.79 (s, 3H), 2.58 (td, J=13.0, 3.4 Hz, 1H), 2.12-2.30 (m, 2H), 1.89-2.05 (m, 1H), 1.67-1.82 (m, 1H), 1.33 (d, J=12.7 Hz, 1H), 0.83 (d, J=6.9 Hz, 3H); LC/MS, m/z=444.1 [M+H]$^+$ (Calc: 444.20).

Compound 80:

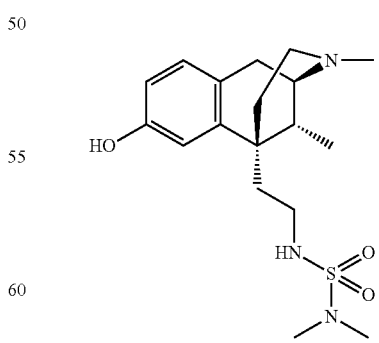

$^1$H NMR (METHANOL-d$_4$) δ: 7.01-7.09 (m, 1H), 6.79-6.83 (m, 1H), 6.70-6.75 (m, 1H), 3.64-3.73 (m, 1H), 3.18-3.28 (m, 3H), 3.16 (br. s., 2H), 2.91 (s, 3H), 2.79-2.84 (m, 6H), 2.72 (td, J=13.0, 3.3 Hz, 1H), 2.41 (br. s., 1H), 2.39-2.41 (m,

1H), 2.35-2.39 (m, 1H), 2.23-2.32 (m, 1H), 2.05 (ddd, J=13.6, 11.0, 6.2 Hz, 1H), 1.39-1.53 (m, 1H), 0.98 (d, J=6.9 Hz, 3H); LC/MS, m/z=368.3 [M+H]+ (Calc: 368.20).

N-(2-((2R,6R,11R)-8-hydroxy-3,11-dimethyl-2,3,4,5-tetrahydro-2,6-methanobenzo[d]azocin-6(1H)-y)ethyl)-3-phenylpropanamide (Compound 85): $^1$H NMR (METHANOL-$d_4$) δ: 7.09-7.24 (m, 5H), 6.88-6.99 (m, 1H), 6.59-6.65 (m, 2H), 3.51-3.61 (m, 1H), 3.26-3.41 (m, 2H), 3.01-3.12 (m, 3H), 2.86-2.93 (m, 1H), 2.80 (s, 3H), 2.54-2.65 (m, 2H), 2.16-2.33 (m, 2H), 1.88-1.97 (m, 1H), 1.62-1.75 (m, 1H), 1.27-1.37 (m, 2H), 0.86 (d, J=6.9 Hz, 2H); LC/MS, m/z=393.1 [M+H]+ (Calc: 393.25).

Example 12

The following Tables provide results on the efficacy of binding and activity response of exemplified Compounds of the Invention at the ORL1, μ-, δ- and κ-opioid receptors.

In TABLE 3, binding affinity of certain Compounds of the Invention to the ORL-1, μ-, and κ-opioid receptors was determined as described above in HEK-293 or CHO cells.

In TABLE 4, activity response of certain Compounds of the Invention to the μ- and κ-opioid receptors was determined as described above for functional assays using HEK-293 or CHO cells.

TABLE 5 and TABLE 6 present activity response of certain Compounds of the

Invention to the μ- and κ-opioid receptors as determined by the functional assays above described by using U-2 OS cells.

TABLE 3

Binding Affinity of Exemplified Compounds of the Invention in HEK-293 or CHO Cells

| Compd No. | $K_i$ (nM) Opioid Receptor | | | |
|---|---|---|---|---|
| | ORL-1 | μ | κ | δ |
| 2 | | | 7.08 ± 0.71 | |
| 10 | | | 77.0 ± 2.02 | |
| 11 | | | 0.17 ± 0.044 | |
| 12 | | | 22.4 ± 3.57 | |
| 13 | | | 20.5 ± 3.21 | |
| 23 | | 0.20 ± 0.012 | 0.048 ± 0.01 | |
| 24 | | 2.89 ± 0.63 | 0.55 ± 0.11 | |
| 25 | | 3.58 ± 1.45 | 0.077 ± 0.014 | |
| 26 | | 0.73 ± 0.10 | 0.053 ± 0.00 | |
| 27 | | 0.071 ± 0.021 | 0.054 ± 0.01 | |
| 28 | | 1.45 ± 0.013 | 0.22 ± 0.056 | |
| 29 | | 1.82 ± 0.57 | 0.12 ± 0.019 | |
| 30 | | 389.0 ± 123.6 | 6.18 ± 1.72 | |
| 31 | | 25.1 ± 7.56 | 18.4 ± 3.60 | |
| 32 | | 5.62 ± 1.41 | 35.0 ± 5.97 | |
| 33 | | 936.5 ± 189.2 | 1.04 ± 0.071 | |
| 34 | | 1470 ± 177.5 | 285.6 ± 2.93 | |
| 35 | | >20 | >20 | |
| 36 | | 1015 ± 51.3 | 133.3 ± 22.9 | |
| 37 | | 13866 | 8992 ± 2057 | |
| 38 | | 94.7 ± 18.6 | 0.78 ± 0.14 | |
| 39 | | >20 | >20 | |
| 40 | | 871.1 ± 211.1 | 248.3 ± 95.7 | |
| 41 | | >20 | >20 | |
| 42 | | 4611 ± 550.9 | 2619 ± 729.2 | |
| 43 | | 233.2 ± 46.9 | 3.63 ± 0.70 | |
| 44 | | 1843 ± 221.9 | 118.1 ± 8.52 | |
| 45 | | 543.4 ± 116.1 | 0.16 ± 0.030 | |
| 46 | | | >20 | 3583 ± 457.5 |
| 63 | 125.3 ± 24.2 | | | |
| 64 | 563.3 ± 97.5 | | | |

TABLE 4

Activity Response of Exemplified Compounds of the Invention in HEK-293 or CHO Cells

| | GTPγS ($EC_{50}$: nM, $E_{max}$: %) | | | |
|---|---|---|---|---|
| Cpd | μ | | κ | |
| No. | $EC_{50}$ | $E_{max}$ | $EC_{50}$ | $E_{max}$ |
| 1 | 4.21 ± 0.67 | 27.8 ± 0.85 | 33.4 ± 2.26 | 78.3 ± 0.91 |
| 4 | >20 | 0.00 | | |
| 5 | 468.3 ± 122.4 | 16.3 ± 1.44 | | |
| 6 | >20 | −0.33 ± 0.67 | | |
| 7 | 623.5 ± 65.9 | 54.5 ± 4.33 | | |
| 8 | 796.1 ± 72.2 | 47.0 ± 1.53 | | |
| 10 | 133.0 ± 16.1 | 51.0 ± 1.08 | 515.8 ± 33.9 | 26.6 ± 1.52 |
| 11 | 18.3 ± 5.58 | 23.0 ± 1.38 | 1.04 ± 0.059 | 84.0 ± 3.63 |
| 12 | 237.4 ± 36.2 | 58.2 ± 1.65 | 343.6 ± 32.6 | 37.1 ± 1.43 |
| 13 | 284.7 ± 72.0 | 25.0 ± 1.53 | 166.0 ± 1.48 | 30.8 ± 0.19 |
| 14 | 11929 ± 1225 | 69.0 ± 0.58 | | |
| 15 | 3455 ± 314.0 | 97.7 ± 1.76 | | |
| 16 | 3.04 ± 0.26 | 10.8 ± 1.25 | | |
| 17 | >20 | −0.88 ± 0.94 | | |
| 18 | 0.12 ± 0.00 | 22.4 ± 1.04 | | |
| 19 | 17.3 ± 6.99 | 10.1 ± 0.98 | | |
| 20 | >20 | 108.3 ± 10.1 | | |
| 21 | 0.28 ± 0.027 | 54.7 ± 2.63 | | |
| 22 | 1069 ± 142.9 | 37.3 ± 1.00 | | |
| 23 | >20 | 1.00 | 1.49 ± 0.58 | 99.0 ± 6.35 |
| 24 | 5.46 ± 0.51 | 19.5 ± 2.26 | 9.32 ± 2.97 | 102.0 ± 5.57 |
| 25 | >20 | 1.00 | 2.33 ± 0.51 | 103.8 ± 5.03 |
| 26 | >20 | 0.33 ± 0.67 | 0.19 ± 0.058 | 51.0 ± 2.04 |
| 27 | >20 | 1.00 | 0.60 ± 0.12 | 61.7 ± 4.33 |
| 28 | >20 | 1.00 ± 0.00 | 4.58 ± 0.38 | 95.3 ± 1.45 |
| 29 | >20 | 1.00 | 7.60 ± 1.67 | 87.7 ± 3.18 |
| 30 | >20 | 0.00 ± 0.58 | 259.4 ± 33.1 | 83.0 ± 7.77 |
| 31 | >20 | 0.00 | 94.2 ± 33.8 | 88.7 ± 6.89 |
| 32 | >20 | −1.00 | 144.3 ± 25.4 | 91.3 ± 9.94 |
| 33 | 356.1 ± 111.0 | 92.7 ± 6.57 | 61.2 ± 20.1 | 113.0 ± 1.00 |
| 34 | 2880 ± 309.5 | 70.3 ± 3.71 | 7900 ± 2009 | 81.3 ± 10.2 |
| 35 | 17497 ± 6779 | 13.0 ± 1.53 | | |
| 36 | 797.9 ± 24.1 | 39.0 ± 1.53 | 1984 ± 216.2 | 69.0 ± 6.24 |
| 37 | 9394 ± 819.9 | 19.3 ± 2.33 | | |
| 38 | 551.1 ± 172.5 | 15.8 ± 1.03 | 286.6 ± 30.0 | 109.3 ± 5.46 |
| 39 | >20 | 19.7 ± 3.18 | | |
| 40 | 1660 ± 244.9 | 77.7 ± 6.12 | 7890 ± 1340 | 86.3 ± 7.54 |
| 41 | >20 | 0.00 | | |
| 42 | 2387 ± 230.1 | 56.0 ± 2.52 | | |
| 43 | 1150 ± 199.1 | 22.0 ± 1.58 | 355.1 ± 63.6 | 97.7 ± 5.36 |
| 44 | | | 853.9 ± 240.5 | 32.0 ± 0.58 |
| 45 | 266.7 ± 20.1 | 16.3 ± 0.88 | 16.3 ± 0.74 | 104.0 ± 5.03 |
| 48 | 2238 ± 190.2 | 53.1 ± 4.36 | | |
| 52 | 320.4 ± 46.9 | 35.0 ± 1.53 | | |
| 58 | 178.6 ± 12.7 | 53.3 ± 2.96 | | |
| 59 | 369.1 ± 50.2 | 38.0 ± 4.18 | | |
| 61 | 282.5 ± 28.8 | 35.7 ± 1.20 | | |
| 62 | 537.9 ± 22.9 | 17.0 ± 1.53 | | |
| 63 | 2.43 ± 0.67 | 74.7 ± 2.40 | | |
| 64 | 19.6 ± 5.19 | 43.5 ± 2.96 | | |
| 65 | 12.1 ± 1.25 | 108.7 ± 2.30 | | |
| 66 | 174.2 ± 13.1 | 37.3 ± 0.88 | | |
| 67 | 2448 ± 692.0 | 26.3 ± 3.38 | | |
| 68 | 28.5 ± 2.07 | 75.8 ± 2.39 | | |
| 69 | 5.42 ± 1.11 | 59.3 ± 1.20 | | |
| 70 | 782.8 ± 207.9 | 27.7 ± 0.88 | | |
| 71 | 1578 ± 177.1 | 36.0 ± 0.58 | | |
| 72 | 240.9 ± 56.7 | 37.2 ± 1.80 | | |
| 73 | 3.64 ± 0.88 | 69.4 ± 1.22 | | |
| 74 | 18.4 ± 2.09 | 52.1 ± 1.88 | | |
| 75 | 314.4 ± 30.2 | 24.7 ± 0.17 | | |
| 76 | 28.8 ± 10.5 | 58.5 ± 2.78 | | |
| 77 | 4.61 ± 0.75 | 57.1 ± 2.33 | | |
| 78 | 33.5 ± 4.90 | 71.0 ± 3.61 | | |
| 79 | 19.7 ± 1.11 | 71.6 ± 5.96 | | |
| 80 | 133.7 ± 3.21 | 27.9 ± 0.47 | | |
| 81 | 18.1 ± 4.15 | 10.8 ± 0.96 | | |
| 82 | 19.6 ± 9.39 | 8.90 ± 0.90 | | |
| 83 | 13.6 ± 3.38 | 77.2 ± 3.52 | | |

TABLE 4-continued

Activity Response of Exemplified Compounds of the Invention in HEK-293 or CHO Cells GTPγS (EC$_{50}$: nM, E$_{max}$: %)

| Cpd No. | μ EC$_{50}$ | μ E$_{max}$ | κ EC$_{50}$ | κ E$_{max}$ |
|---|---|---|---|---|
| 84 | 12434 ± 539.7 | 32.4 ± 0.76 | | |
| 85 | 6.51 ± 0.17 | 69.5 ± 2.23 | | |
| 86 | 251.7 ± 23.5 | 48.2 ± 1.26 | | |

TABLE 5

Activity Response of Exemplified Compounds of the Invention in U2OS Cells

GTPγS (EC$_{50}$: nM, E$_{max}$: %)

| Cpd No. | μ EC$_{50}$ | μ E$_{max}$ | κ EC$_{50}$ | κ E$_{max}$ |
|---|---|---|---|---|
| 1 | 163.8 ± 31.6 | 62.0 ± 2.08 | 5.79 ± 0.56 | 103.3 ± 3.53 |
| 2 | 1.89 ± 0.18 | 72.5 ± 1.50 | 4.11 ± 0.25 | 106.0 ± 2.52 |
| 3 | 0.85 ± 0.11 | 16.7 ± 0.33 | 0.32 ± 0.031 | 104.0 ± 2.52 |
| 4 | 521.9 ± 60.1 | 80.2 ± 3.30 | 38.2 ± 4.89 | 97.0 ± 5.29 |
| 5 | 628.9 ± 16.8 | 75.2 ± 1.55 | 63.3 ± 10.2 | 100.0 ± 4.58 |
| 6 | 0.88 ± 0.095 | 30.7 ± 0.88 | 0.072 ± 0.013 | 107.0 ± 2.65 |
| 7 | 83.1 ± 1.96 | 99.0 ± 1.00 | | |
| 8 | 72.7 ± 4.92 | 100.0 ± 3.06 | | |
| 9 | 0.67 ± 0.01 | 27.0 ± 0.00 | | |
| 23 | 0.28 ± 0.073 | 56.0 ± 3.06 | 0.079 ± 0.01 | 103.7 ± 4.06 |
| 24 | 1.94 ± 0.28 | 77.3 ± 3.18 | 0.51 ± 0.072 | 98.3 ± 4.33 |
| 25 | 1.29 ± 0.11 | 48.3 ± 0.67 | 0.17 ± 0.038 | 99.0 ± 4.58 |
| 26 | 0.51 ± 0.054 | 40.0 ± 1.73 | 0.14 ± 0.00 | 101.7 ± 3.48 |
| 27 | 0.27 ± 0.058 | 22.3 ± 2.85 | 0.15 ± 0.023 | 106.3 ± 7.13 |
| 28 | 2.71 ± 0.67 | 57.3 ± 6.57 | 0.49 ± 0.016 | 104.3 ± 2.85 |
| 29 | 2.65 ± 0.89 | 41.3 ± 4.91 | 0.39 ± 0.016 | 107.7 ± 1.20 |
| 30 | 230.4 ± 27.5 | 51.0 ± 3.51 | 13.1 ± 1.48 | 103.7 ± 2.96 |
| 31 | 8.77 ± 1.37 | 58.0 ± 4.73 | 18.5 ± 2.16 | 103.7 ± 3.48 |
| 32 | 2.16 ± 0.38 | 57.3 ± 5.04 | 35.7 ± 5.29 | 97.7 ± 4.67 |
| 33 | 1168 ± 247.3 | 56.0 ± 3.06 | 4.93 ± 1.06 | 108.3 ± 3.38 |
| 38 | 136.8 ± 16.1 | 53.0 ± 3.51 | 2.11 ± 0.23 | 111.7 ± 2.91 |
| 40 | | | 542.4 ± 13.1 | 115.0 ± 1.73 |
| 43 | 99.0 ± 5.84 | 106.8 ± 5.83 | 17.8 ± 1.45 | 102.3 ± 3.71 |
| 44 | | | 327.4 ± 50.5 | 79.3 ± 3.38 |
| 45 | 38.0 ± 2.09 | 103.4 ± 6.47 | 0.95 ± 0.14 | 96.3 ± 5.17 |
| 47 | 8989 ± 1627 | 72.3 ± 3.84 | 3754 ± 206.6 | 99.3 ± 0.67 |
| 48 | 313.5 ± 28.0 | 97.0 ± 2.08 | 104.3 ± 15.8 | 108.0 ± 4.51 |
| 49 | >20 | 21.0 | >20 | 41.0 ± 4.58 |
| 50 | 2395 ± 271.0 | 88.3 ± 7.62 | >2315 ± 291.2 | 103.3 ± 8.41 |
| 51 | 6712 ± 257.4 | 76.7 ± 3.71 | 6285 ± 318.4 | 96.3 ± 0.67 |
| 52 | 68.1 ± 6.57 | 89.0 ± 4.00 | 434.3 ± 39.1 | 99.0 ± 1.73 |
| 53 | 1247 ± 85.4 | 63.3 ± 2.03 | 7000 ± 3063 | 13.3 ± 2.19 |
| 54 | 18655 ± 1893 | 95.0 ± 2.65 | 9862 ± 349.0 | 125.0 ± 1.53 |
| 55 | 14533 ± 652.7 | 82.0 ± 2.65 | 14721 ± 1244 | 113.3 ± 1.45 |
| 56 | 5988 ± 1216 | 72.3 ± 2.85 | 5492 ± 434.2 | 94.7 ± 4.48 |
| 57 | 11256 ± 434.8 | 70.7 ± 2.03 | 11415 ± 993.5 | 118.0 ± 2.00 |
| 58 | 20.3 ± 1.82 | 98.0 ± 2.00 | 11.0 ± 1.59 | 60.0 ± 1.00 |
| 59 | 85.6 ± 9.67 | 74.0 ± 3.51 | 61.2 ± 10.0 | 112.3 ± 7.54 |
| 60 | 4906 ± 1084 | 49.0 ± 3.61 | >20 | 97.7 ± 8.09 |
| 61 | 145.6 ± 24.8 | 78.7 ± 0.33 | 45.4 ± 6.69 | 42.7 ± 2.03 |
| 62 | 171.5 ± 18.7 | 49.7 ± 0.88 | 1118 ± 53.4 | 35.7 ± 1.67 |

TABLE 6

Activity Response of Exemplified Compounds of the Invention in U2OS Cells

β-Arr2 (EC$_{50}$: nM, E$_{max}$: %)

| Cpd No. | μ EC$_{50}$ | μ E$_{max}$ | κ EC$_{50}$ | κ E$_{max}$ |
|---|---|---|---|---|
| 1 | >20 | 25.5 | 63.8 ± 7.23 | 44.2 ± 4.05 |
| 2 | >20 | -1.50 | 8.40 ± 1.86 | 28.7 ± 4.67 |
| 3 | >20 | 0.00 | >20 | -0.33 ± 0.67 |
| 4 | >20 | 1.30 ± 0.77 | 403.2 ± 59.9 | 59.3 ± 4.06 |
| 5 | >20 | -1.00 | 406.9 ± 65.5 | 58.7 ± 5.93 |
| 6 | >20 | -0.33 ± 0.67 | | |
| 7 | 502.8 ± 116.2 | 23.4 ± 1.33 | | |
| 8 | 4710 ± 226.9 | 70.7 ± 6.98 | | |
| 10 | 129.1 ± 34.4 | 2.83 ± 0.27 | 4658 ± 1721 | 17.2 ± 0.97 |
| 11 | >20 | -1.50 | | |
| 12 | 385.8 ± 89.5 | 8.83 ± 0.44 | 5522 ± 4652 | 12.7 ± 1.57 |
| 13 | >20 | -1.00 | | |
| 18 | 0.31 ± 0.063 | 4.38 ± 0.35 | | |
| 21 | 0.38 ± 0.11 | 30.1 ± 0.81 | | |
| 23 | >20 | -1.50 | 0.16 ± 0.055 | 30.0 ± 0.58 |
| 24 | >20 | -0.40 ± 0.60 | 3.56 ± 0.91 | 54.0 ± 4.06 |
| 25 | >20 | -1.40 | 0.10 ± 0.019 | 50.0 ± 0.58 |
| 26 | >20 | 0.00 | 0.081 ± 0.019 | 17.5 ± 2.72 |
| 27 | >20 | 1.00 | 0.27 ± 0.11 | 12.7 ± 1.86 |
| 28 | 30.5 ± 4.44 | 3.70 ± 0.49 | 2.37 ± 0.62 | 45.0 ± 2.08 |
| 29 | >20 | -1.50 | 2.06 ± 0.32 | 45.0 ± 3.00 |
| 30 | >20 | 1.00 ± 0.50 | >20 | -1.00 ± 0.00 |
| 31 | >20 | -1.25 | 53.4 ± 8.62 | 29.7 ± 5.04 |
| 32 | >20 | -1.00 | 26.7 ± 10.5 | 11.3 ± 1.20 |
| 33 | | | 12.8 ± 4.10 | 42.0 ± 4.00 |
| 38 | >20 | -0.17 ± 0.93 | 141.4 ± 45.5 | 70.0 ± 2.00 |
| 43 | >20 | -1.00 | 494.1 ± 140.1 | 59.3 ± 3.18 |
| 44 | | | 10275 ± 1047 | 101.7 ± 11.6 |
| 45 | >20 | 1.33 ± 0.33 | 26.7 ± 8.55 | 84.0 ± 2.08 |
| 48 | 4376 ± 627.1 | 27.7 ± 0.88 | 16286 ± 7601 | 64.3 ± 9.39 |
| 52 | 402.5 ± 109.7 | 6.77 ± 1.13 | >20 | 1.00 |
| 58 | 2143 ± 585.5 | 77.7 ± 7.06 | 8902 ± 1618 | 80.3 ± 7.75 |
| 59 | >20 | -1.00 | >20 | 1.00 ± 0.00 |
| 61 | 649.4 ± 179.9 | 7.67 ± 0.73 | 7295 ± 2063 | 14.7 ± 1.33 |
| 62 | >20 | -1.00 | | |
| 63 | 1.23 ± 0.31 | 21.8 ± 1.31 | | |
| 64 | 7451 ± 929.4 | 51.8 ± 7.76 | | |
| 65 | 3.85 ± 1.26 | 95.0 ± 3.79 | | |
| 66 | 2293 ± 703.0 | 15.9 ± 0.72 | | |
| 68 | 18.9 ± 1.23 | 72.3 ± 0.88 | | |
| 69 | 2.97 ± 0.34 | 14.7 ± 0.88 | | |
| 72 | 266.5 ± 63.3 | 5.80 ± 0.42 | | |
| 76 | 28.4 ± 3.98 | 28.9 ± 1.69 | | |
| 78 | 90.5 ± 15.4 | 67.0 ± 3.71 | | |
| 79 | 39.1 ± 7.13 | 58.9 ± 7.55 | | |
| 80 | 1182 ± 822.2 | 2.62 ± 0.36 | | |
| 83 | 13.8 ± 3.03 | 46.5 ± 1.93 | | |
| 85 | 6.55 ± 2.88 | 39.8 ± 0.77 | | |
| 86 | 288.8 ± 91.8 | 11.2 ± 0.69 | | |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound of Formula II or a pharmaceutically acceptable salt or solvate thereof:

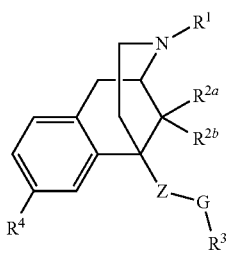

wherein

R¹ is —($C_1$-$C_{10}$)alkyl optionally substituted by —($C_3$-$C_{12}$)cycloalkyl;

$R^{2a}$ and $R^{2b}$, are each independently, hydrogen or —($C_1$-$C_5$)alkyl;

Z is —$(CH^2)_m$— optionally substituted with 1 or 2 independently selected —($C_1$-$C_6$)alkyl;

wherein

1) G is —N($R^a$)C(O)N($R^a$)—, wherein
   each of $R^a$ independently is hydrogen or —($C_1$-$C_5$)alkyl;
   R³ is selected from the group consisting of phenyl, —($C_1$-$C_3$)alkyl-phenyl, and —S(O)₂-phenyl, each of which is optionally substituted with a substituent selected from the group consisting of halo, —COOR⁶, phenyl, and —OPh; and
   R⁶ is hydrogen or —($C_1$-$C_3$)alkyl; or 2) G is —N($R^d$)—, wherein
   $R^d$ is H or —($C_1$-$C_3$)alkyl;
   R³ is selected from the group consisting of —($C_1$-$C_6$)alkyl, —C(=O)—($C_1$-$C_6$)alkyl, —($C_1$-$C_6$)alkyl-(6- to 14-membered)aryl, —($C_1$-$C_6$)alkyl-(5- to 12-membered)heteroaryl, —S(O)₂—($C_1$-$C_6$)alkyl, —S(O)₂-($C_3$-$C_{12}$)cycloalkyl, and -(7- to 12-membered)bicycloheterocyclo; each of which is substituted with one or two substituents independently selected from the group consisting of halo, —COOR⁶, carboxamido, —NH₂, (alkyl)amino, (dialkyl)amino, -(3- to 8- membered)heterocyclo, -(6- to 14-membered)aryl, —SO₂NH₂, and —($C_1$-$C_6$)alkyl-(7- to 12-membered)bicycloheterocyclo optionally substituted by one or two same or different —($C_1$-$C_3$)alkyl; or
   $R^d$ and R³, together with the nitrogen atom to which they are attached, form

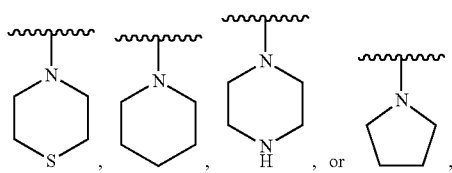

each of which is optionally substituted by one or two substituents independently selected from the group of (=O), —($C_1$-$C_3$)alkyl-phenyl, —C(O)OH, —N($R^a$)SO₂-phenyl, —$(CH_2)_n$—O—$(CH_2)_n$—CH₃, and -(5- to 6-membered)heterocyclo, wherein each of the —($C_1$-$C_3$)alkyl-phenyl, —N($R^a$)SO₂-phenyl, and -(5- to 6-membered)heterocyclo is optionally substituted by one or two substituents independently selected from the group of halogen and phenyl optionally substituted by halogen; and wherein the -(5- to 6-membered)heterocyclo is further optionally fused together with a phenyl group; or 3) G is —C(O)N($R^c$)—, wherein
   $R^c$ is H or —($C_1$-$C_3$)alkyl;
   R³ is selected from the group consisting of hydrogen, —($C_1$-$C_6$)alkyl, -(5- to 6-membered)heterocyclo, phenyl, and —($C_1$-$C_3$)alkyl-phenyl; wherein each of the —($C_1$-$C_6$)alkyl, -(5- to 6-membered)-heterocyclo, phenyl, and —($C_1$-$C_3$)alkyl-phenyl is optionally substituted with one or two substituents independently selected from the group consisting of (=O), halo, —NHC(O)($C_1$-$C_3$)alkyl, —C(O)R⁵, —COOR⁶, —NH₂, and —SO₂NH₂;
   R⁵ is —($C_1$-$C_3$)alkyl; and
   R⁶ is H or —($C_1$-$C_3$)alkyl; or 4) G is —N($R^a$)S(O)₂N($R^b$)—, wherein
   $R^a$ and $R^b$, independently, are hydrogen or —($C_1$-$C_3$)alkyl; and
   R³ is optionally-substituted —($C_1$-$C_{10}$)alkyl; or 5) G is —C(O)—, wherein
   R³ is -(5- to 6-membered)heterocyclo substituted by —N($R^a$)SO₂-phenyl, wherein the —N($R^a$)SO₂-phenyl is further optionally substituted by —($C_1$-$C_3$)alkyl or halogen; and $R^a$ is —($C_3$-$C_6$)cycloalkyl;

Each of $R^a$ independently is hydrogen, —($C_1$-$C_5$)alkyl, or —($C_3$-$C_{12}$)cycloalkyl;

R⁴ is hydrogen, OH, halo, —($C_1$-$C_5$)alkyl, —C(O)NH₂, —($C_1$-$C_5$)alkoxy, —($C_2$-$C_5$)alkenyl, —($C_2$-$C_5$)alkynyl, or —$(CH_2)_n$—O—$(CH_2)_n$—CH₃;

R⁵ is selected from the group consisting of hydrogen, —OH, —NH₂, —($C_1$-$C_6$)alkyl, —($C_2$-$C_5$)alkenyl, —($C_2$-$C_5$)alkynyl, —($C_1$-$C_6$)alkoxy, and —($C_3$-$C_8$)cycloalkyl, each of —NH₂, —($C_1$-$C_6$)alkyl, —($C_2$-$C_5$)alkenyl, —($C_2$-$C_5$)alkynyl, —($C_1$-$C_6$)alkoxy, and —($C_3$-$C_8$)cycloalkyl is optionally substituted with 1, 2, or 3 independently selected R⁶ groups;

R⁶ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)—($C_1$-$C_6$)alkyl-, and (($C_4$-$C_{12}$)cycloalkenyl)—($C_1$-$C_6$)alkyl-;

m is 1, 2, 3, 4, 5, or 6; and n is 0, 1, 2, 3, 4, 5, or 6;

provided that i) when -G-R³ is —C(O)NH₂, then R¹ is —($C_1$-$C_{10}$)alkyl that is either unsubstituted or substituted by cyclobutyl; and ii) when R¹ is cyclopropylmethyl, R⁴ is methoxy, Z is —$(CH_2)_2$—, one of $R^{2a}$ and $R^{2b}$ is H, and the other is methyl, and G is —NHC(O)—, then
   R³ is —($C_1$-$C_6$)alkyl, -(7- to 12-membered)bicycloheterocyclo, or —($C_1$-$C_6$)alkyl-(6- to 14-membered)aryl; each of which is substituted with one, or two substituents independently selected from the group consisting of halo, —NH₂, —COOR⁶, -(3- to 8-membered)-heterocyclo, -(6- to 14-membered)aryl, —SO₂NH₂, and —($C_1$-$C_6$)alkyl-(7- to 12-membered)bicycloheterocyclo; wherein each of the -(6- to 14-membered)aryl, and —($C_1$-$C_6$)alkyl-(7- to 12-membered)bicycloheterocyclo is further optionally substituted by one or two substituents independently selected —($C_1$-$C_3$)alkyl;

iii) when R¹ is unsubstituted —($C_1$-$C_{10}$)alkyl, then R¹ is a straight —($C_1$-$C_{10}$)alkyl chain;

iv) when R¹ is cyclopropylmethyl, Z is —$(CH_2)_2$—, and

133

R³ is
a) —(C₁-C₆)alkyl substituted by —NH₂ or (dialkyl)amino; or
b) —C(=O)—(C₁-C₆)alkyl substituted by —NH₂ or (dialkyl)amino;

then R⁴ is methoxy.

2. The compound of claim 1, wherein said compound is a compound of Formula A:

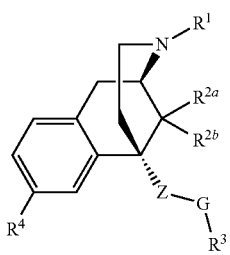

A or a pharmaceutically acceptable salt or solvate thereof.

3. The compound of claim 1, wherein Z is optionally-substituted —(CH2)ₘ—, and m is 1, 2, 3, or 4.

4. The compound of claim 1, wherein G is —N(Rᵃ)C(O)N(Rᵃ)—, and each of Rᵃ independently is hydrogen or —(C₁-C₅)alkyl.

5. The compound of claim 4, wherein R³ is selected from the group consisting of phenyl, —(C₁-C₃)alkyl-phenyl, and —S(O)₂-phenyl, each of which is optionally substituted with a substituent selected from the group consisting of halo, —COOR⁶, phenyl, and —OPh, and wherein R⁶ is hydrogen or —(C₁-C₃)alkyl.

6. The compound of claim 1, wherein G is —N(Rᵈ)—.

7. The compound of claim 6, wherein Rᵈ is H or —(C₁-C₃)alkyl.

8. The compound of claim 6, wherein R³ is selected from the group consisting of —(C₁-C₆)alkyl, —C(=O)—(C₁-C₆)alkyl, —(C₁-C₆)alkyl-(6- to 14-membered)aryl, —(C₁-C₆)alkyl-(5- to 12-membered)heteroaryl, —S(O)₂—(C₁-C₆)alkyl, —S(O)₂—(C₃-C₁₂)cycloalkyl, and -(7- to 12-membered)bicycloheterocyclo; each of which is substituted with one or two substituents independently selected from the group consisting of halo, —COOR⁶, carboxamido, —NH₂, (alkyl)amino, (dialkyl)amino, -(3- to 8-membered)heterocyclo, —(6- to 14-membered)aryl, —SO₂NH₂, and —(C₁-C₆)alkyl-(7- to 12-membered)bicycloheterocyclo optionally substituted by one or two same or different —(C₁-C₃)alkyl.

9. The compound of claim 6, wherein Rᵈ and R³, together with the nitrogen atom to which they are attached, form

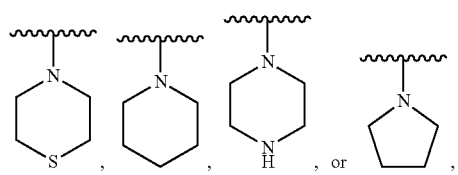

each of which is optionally substituted by one or two substituents independently selected from the group of (=O), —(C₁-C₃)alkyl-phenyl, —C(O)OH, —N(Rᵃ)SO₂-phenyl, —(CH₂)ₙ—O—(CH₂)ₙ—CH₃, and -(5- to 6-membered)heterocyclo, wherein each of the —(C₁-C₃)alkyl-phenyl, —N(Rᵃ)SO₂-phenyl, and -(5- to 6-membered)heterocyclo is

134 optionally substituted by one or two substituents independently selected from the group of halogen and phenyl optionally substituted by halogen; and wherein the -(5- to 6-membered)heterocyclo is further optionally fused together with a phenyl group.

10. The compound of claim 1, wherein G is —C(O)N(Rᶜ)—, and wherein Rᶜ is H or —(C₁-C₃)alkyl.

11. The compound of claim 10, wherein R³ is selected from the group consisting of hydrogen, —(C₁-C₆)alkyl, -(5- to 6-membered)heterocyclo, phenyl, and —(C₁-C₃)alkyl-phenyl; wherein each of the —(C₁-C₆)alkyl, -(5- to 6-membered)-heterocyclo, phenyl, and —(C₁-C₃)alkyl-phenyl is optionally substituted with one or two substituents independently selected from the group consisting of (=O), halo, —NHC(O)(C₁-C₃)alkyl, —C(O)R⁵, —COOR⁶, —NH₂, and —SO₂NH₂, and wherein R⁵ is —(C₁-C₃)alkyl, and R⁶ is H or —(C₁-C₃)alkyl.

12. The compound of claim 1, wherein G is —C(O)—.

13. The compound of claim 12, wherein R³ is —(5- to 6-membered)heterocyclo substituted by —N(Rᵃ)SO₂-phenyl, wherein the —N(Rᵃ)SO₂-phenyl is further optionally substituted by —(C₁-C₃)alkyl or halogen, and wherein Rᵃ is —(C₃-C₆)cycloalkyl.

14. The compound of claim 1, wherein G is —N(Rᵃ)S(O)₂N(Rᵇ)—, and wherein Rᵃ and Rᵇ, independently, are hydrogen or —(C₁-C₃)alkyl.

15. The compound of claim 14, wherein R³ is optionally-substituted —(C₁-C₁₀)alkyl.

16. A compound selected from the group consisting of:

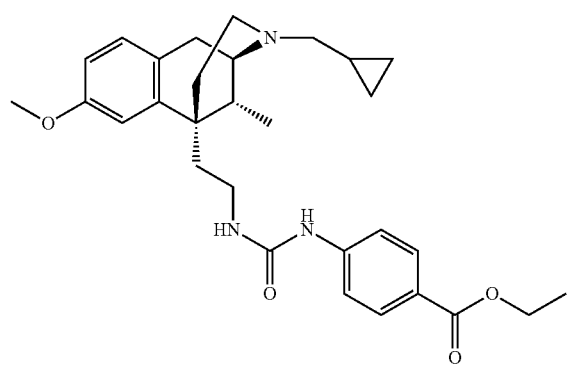

a)

Ethyl 4-(3-(2-((2R,6R,11R)-3-(cyclopropylmethyl)-8-methoxy-11-methyl-2,3,4,5-tetrahydro-2,6-methanobenzo[d]azocin-6(1H)-yl)ethyl)ureido)benzoate;

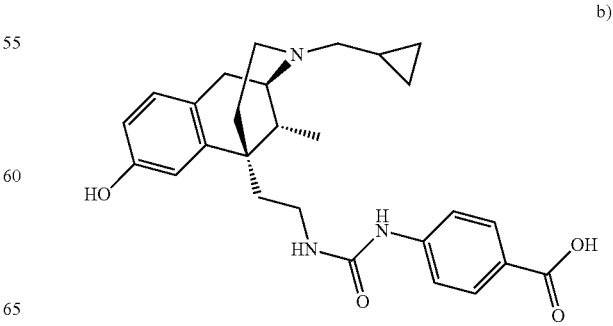

b)

4-(3-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)ureido)benzoic acid;

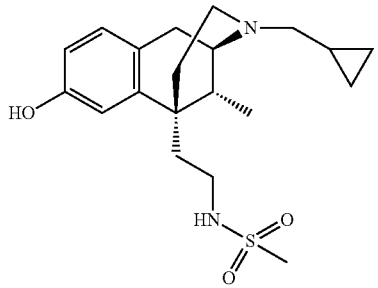

N-(2-((2R,6S,11R)-3-(cyclopropylmethyl)-8-hydroxy-11-methyl-2,3,4,5-tetrahydro-2,6-methanobenzo[d]azocin-6(1H)-yl)ethyl)methanesulfonamide;

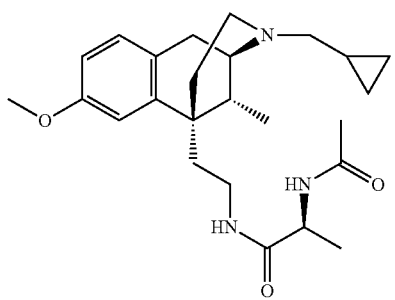

(S)-2-acetamido-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)propanamide;

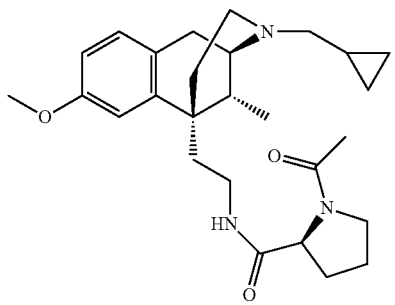

(S)-1-acetyl-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)pyrrolidine-2-caroxamide;

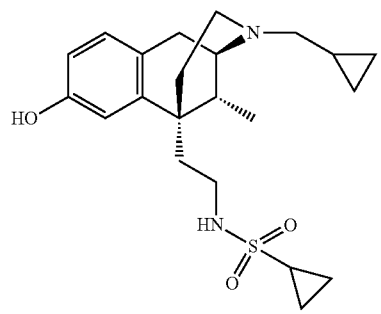

N-(2-((2R,6S,11R)-3-(cyclopropylmethyl)-8-hydroxy-11-methyl-2,3,4,5-tetrahydro-2,6-methanobenzo[d]azocin-6(1H)-yl)ethyl)cyclopropanesulfonamide;

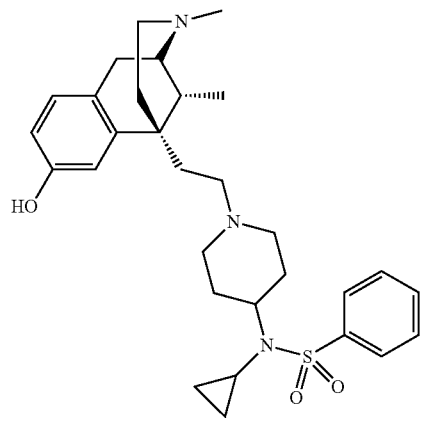

N-cyclopropyl-N-(1-(2-((2R,6R,11R)-8-hydroxy-3,11-dimethyl-2,3,4,5-tetrahydro-2,6-methanobenzo[d]azocin-6(1H)-yl)ethyl)piperidin-4-yl)benzenesulfonamide;

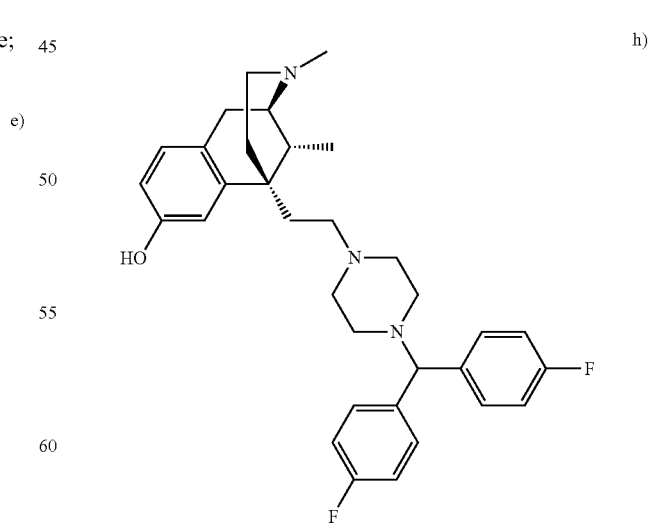

(2R,6R,11R)-6-(2-(4-(bis(4-fluorophenyl)methyl)piperazin-1-yl)ethyl)-3,11-dimethyl-1,2,3,4,5,6-hexahydro-2,6-methanobenzo[d]azocin-8-ol;

i)

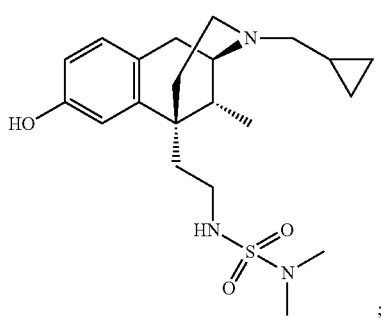

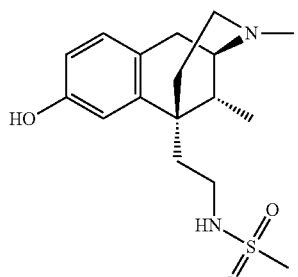

N-(2-((2R,6S,11R)-8-hydroxy-3,11-dimethyl-2,3,4,5-tetrahydro-2,6-methanobenzo-[d]azocin-6(1H)-yl)ethyl)methanesulfonamide;

m)

j)

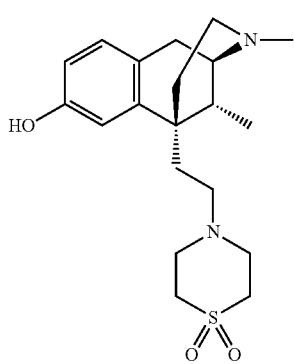

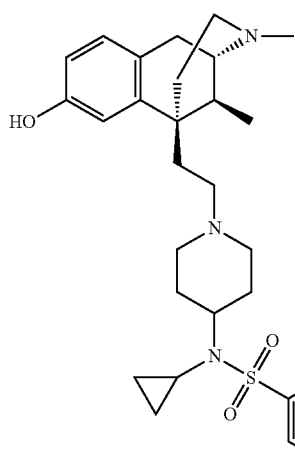

4-(2-((2R,6R,11R)-8-hydroxy-3,11-dimethyl-2,3,4,5-tetrahydro-2,6-methanobenzo-[d]azocin-6(1H)-yl)ethyl)thiomorpholine 1,1-dioxide;

N-cyclopropyl-N-(1-(2-((2S,6S,11S)-8-hydroxy-3,11-dimethyl-2,3,4,5-tetrahydro-2,6-methanobenzo[d]azocin-6(1H)-yl)ethyl)piperidin-4-yl)benzenesulfonamide;

n)

k)

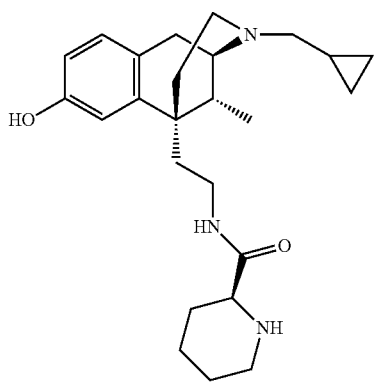

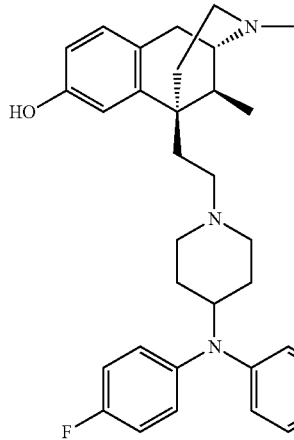

(S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)piperidine-2-carboxamide;

(2S,6S,11S)-6-(2-(4-(bis(4-fluorophenyl)methyl)piperazin-1-yl)ethyl)-3,11-dimethyl-1,2,3,4,5,6-hexahydro-2,6-methanobenzo[d]azocin-8-ol;

o)

139

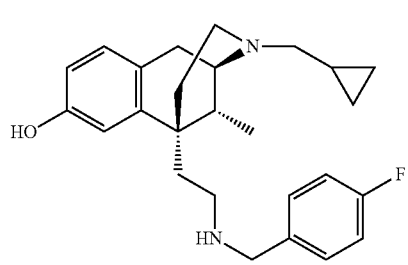

p)

(2R,6R,11R)-3-(cyclopropylmethyl)-6-(2-((4-fluorobenzyl)amino)ethyl)-11-methyl-1,2,3,4,5,6-hexahydro-2,6-methanobenzo[d]azocin-8-ol;

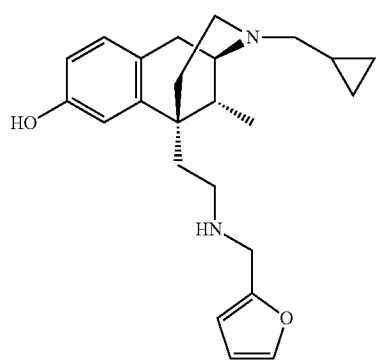

q)

(2R,6R,11R)-3-(cyclopropylmethyl)-6-(2-((furan-2-ylmethyl)amino)ethyl)-11-methyl-1,2,3,4,5,6-hexahydro-2,6-methanobenzo[d]azocin-8-ol;

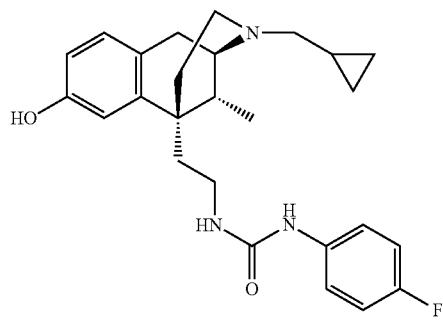

r)

1-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-3-(4-fluorophenyl)urea;

140

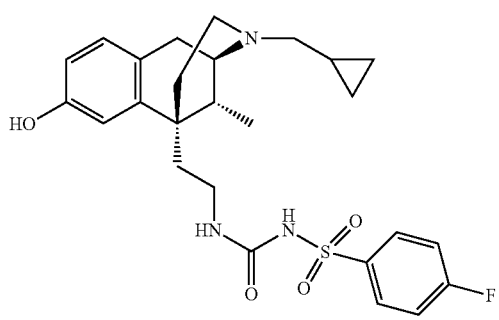

s)

N-((2-((2R,6R,11R)-3-(cyclopropylmethyl)-8-hydroxy-11-methyl-2,3,4,5-tetrahydro-2,6-methanobenzo[d]azocin-6(1H)-yl)ethyl)carbamoyl)-4-fluorobenzenesulfonamide;

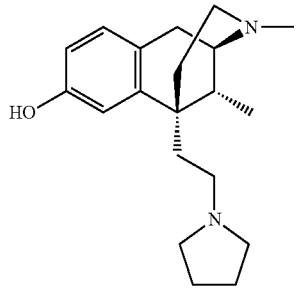

t)

(2R,6R,11R)-3,11-dimethyl-6-(2-(pyrrolidin-1-yl)ethyl)-1,2,3,4,5,6-hexahydro-2,6-methanobenzo[d]azocin-8-ol;

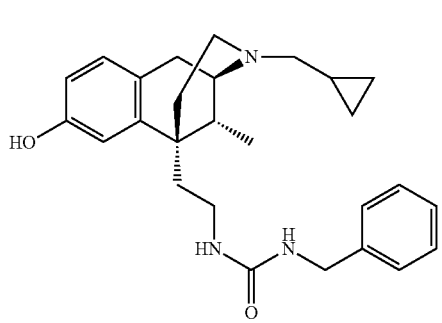

u)

1-Benzyl-3-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)urea;

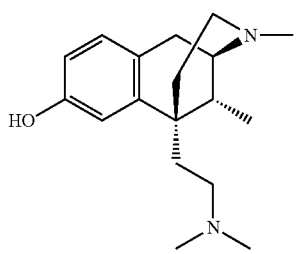

(2R,6R,11R)-6-(2-(dimethylamino)ethyl)-3,11-dimethyl-1,2,3,4,5,6-hexahydro-2,6-methanobenzo[d]azocin-8-ol;

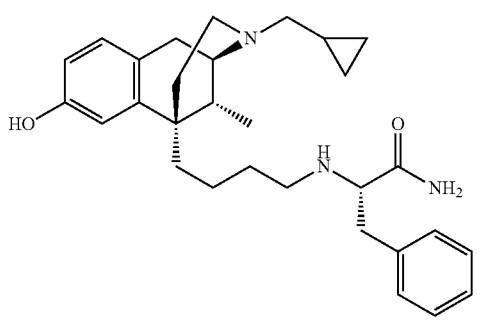

(S)-2-((4-((2R,6R,11R)-3-(cyclopropylmethyl)-8-hydroxy-11-methyl-2,3,4,5-tetrahydro-2,6-methanobenzo[d]azocin-6(1H)-yl)butyl)amino)-3-phenyl-propanamide;

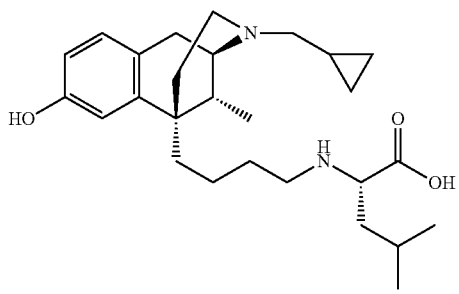

(4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-leucine;

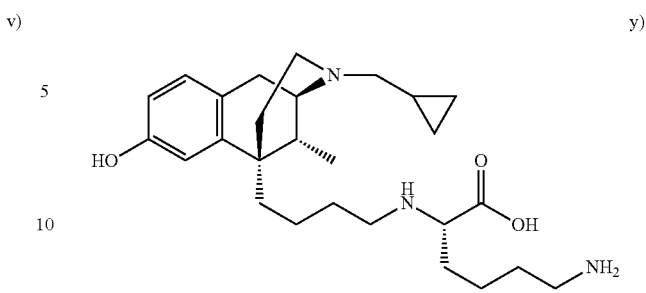

(4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-lysine;

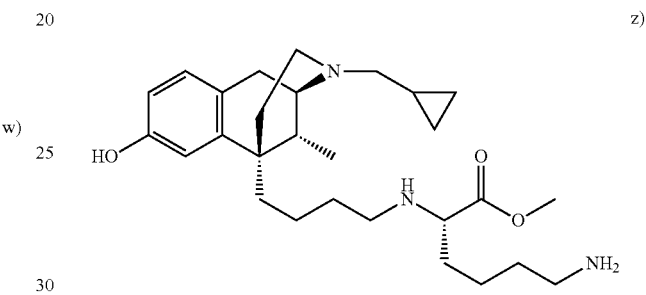

Methyl(4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-lysinate;

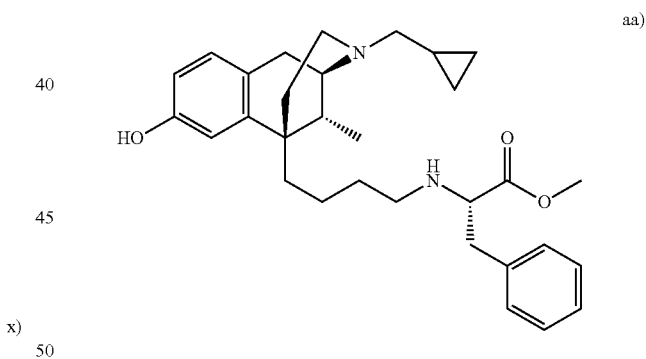

Methyl(4-((2R,6R,11R)-3-(cyclopropylmethyl)-8-hydroxy-11-methyl-2,3,4,5-tetrahydro-2,6-methanobenzo[d]azocin-6(1H)-yl)butyl)-L-phenylalaninate;

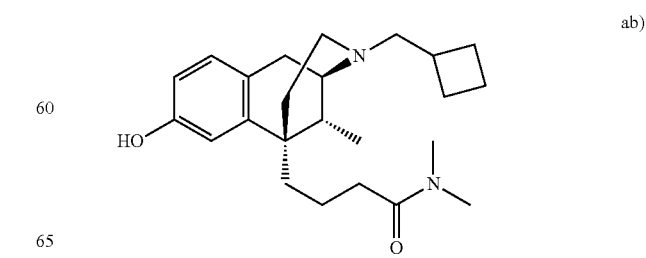

4-((2R,6R,11R)-3-(cyclobutylmethyl)-8-hydroxy-11-methyl-2,3,4,5-tetrahydro-2,6-methanobenzo[d]azocin-6(1H)-yl)-N,N-dimethylbutanamide;

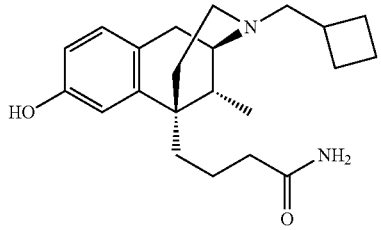

ac)

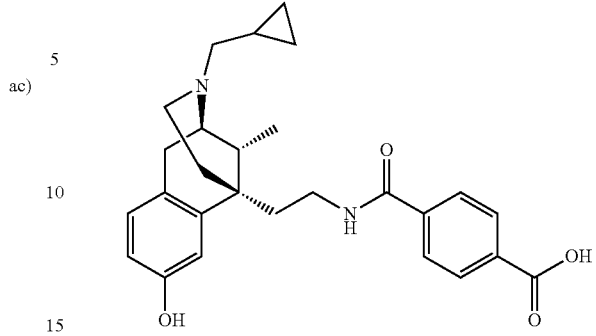

af)

4-((2R,6R,11R)-3-(cyclobutylmethyl)-8-hydroxy-11-methyl-2,3,4,5-tetrahydro-2,6-methanobenzo[d]azocin-6(1H)-yl)butanamide;

4-((2-((2R,6R,11R)-3-(cyclopropylmethyl)-8-hydroxy-11-methyl-2,3,4,5-tetrahydro-2,6-methanobenzo[d]azocin-6(1H)-yl)ethyl)carbamoyl)benzoic acid;

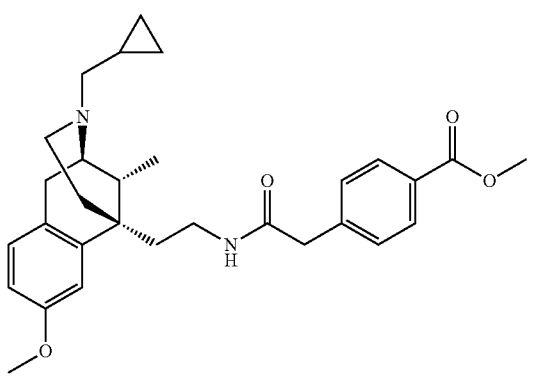

ad)

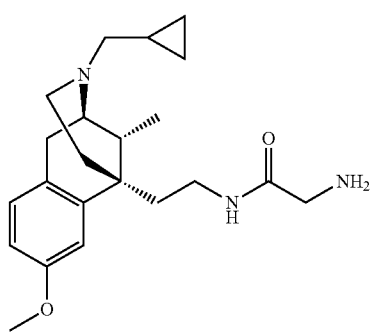

ag)

Methyl 4-(2-((2-((2R,6R,11R)-3-(cyclopropylmethyl)-8-methoxy-11-methyl-2,3,4,5-tetrahydro-2,6-methanobenzo[d]azocin-6(1H)-yl)ethyl)amino)-2-oxoethyl)benzoate;

2-Amino-N-(2-((2R,6R,11R)-3-(cyclopropylmethyl)-8-methoxy-11-methyl-2,3,4,5-tetrahydro-2,6-methanobenzo[d]azocin-6(1H)-yl)ethyl)acetamide;

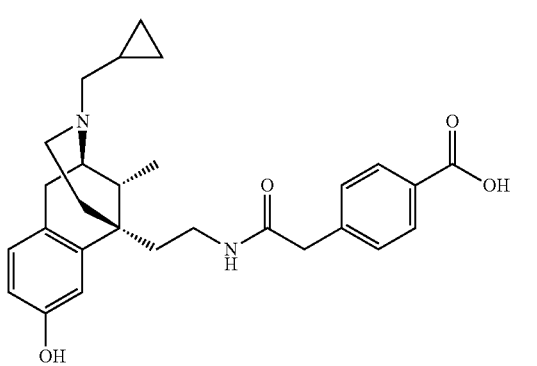

ae)

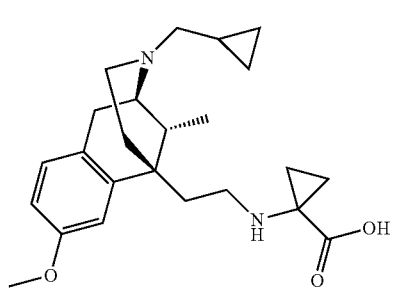

ah)

4-(2-((2-((2R,6R,11R)-3-(cyclopropylmethyl)-8-hydroxy-11-methyl-2,3,4,5-tetrahydro-2,6-methanobenzo[d]azocin-6(1H)-yl)ethyl)amino)-2-oxoethyl)benzoic acid;

1-((2-((2R,6R,11R)-3-(cyclopropylmethyl)-8-methoxy-11-methyl-2,3,4,5-tetrahydro-2,6-methanobenzo[d]azocin-6(1H)-yl)ethyl)amino)cyclopropane-1-carboxylic acid;

145

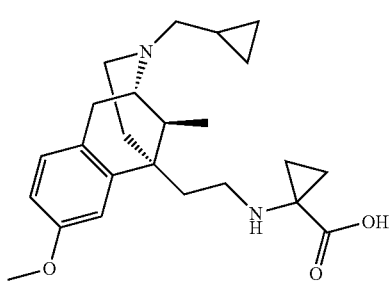

ai)

1-((2-((2S,6S,11S)-3-(cyclopropylmethyl)-8-methoxy-
11-methyl-2,3,4,5-tetrahydro-2,6-methanobenzo[d]
azocin-6(1H)-yl)ethyl)amino)cyclopropane-1-carbox-
ylic acid;

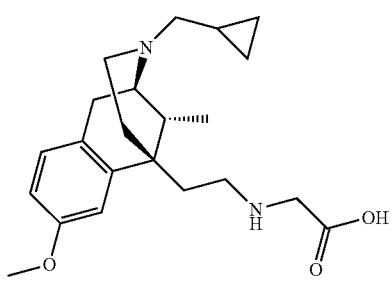

aj)

(2-((2R,6R,11R)-3-(cyclopropylmethyl)-8-methoxy-11-
methyl-2,3,4,5-tetrahydro-2,6-methanobenzo[d]azo-
cin-6(1H)-yl)ethyl)glycine;

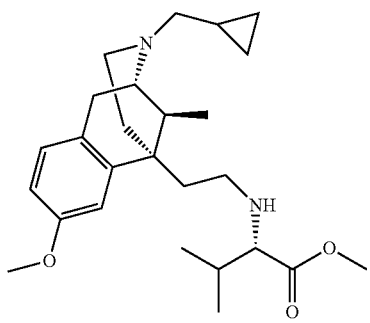

ak)

Methyl(2-((2S,6S,11S)-3-(cyclopropylmethyl)-8-
methoxy-11-methyl-2,3,4,5-tetrahydro-2,6-metha-
nobenzo[d]azocin-6(1H)-yl)ethyl)-L-valinate;

146

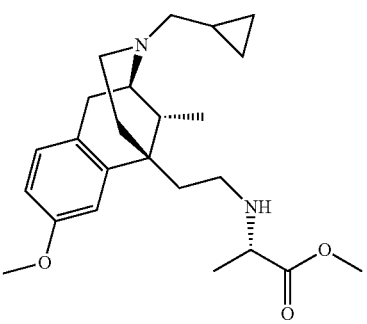

al)

Methyl(2-((2R,6R,11R)-3-(cyclopropylmethyl)-8-
methoxy-11-methyl-2,3,4,5-tetrahydro-2,6-metha-
nobenzo[d]azocin-6(1H)-yl)ethyl)-L-alaninate;

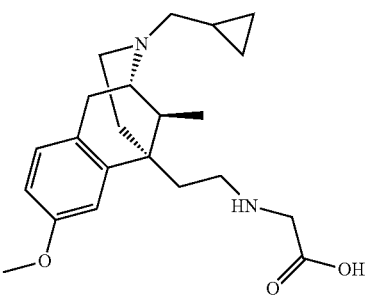

am)

(2-((2S,6S,11S)-3-(cyclopropylmethyl)-8-methoxy-11-
methyl-2,3,4,5-tetrahydro-2,6-methanobenzo[d]azo-
cin-6(1H)-yl)ethyl)glycine;

an)

(2-((2R,6R,11R)-3-(cyclopropylmethyl)-8-methoxy-11-
methyl-2,3,4,5-tetrahydro-2,6-methanobenzo[d]azo-
cin-6(1H)-yl)ethyl)-L-alanine;

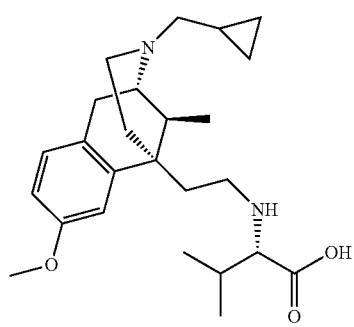

(2-((2S,6S,11S)-3-(cyclopropylmethyl)-8-methoxy-11-methyl-2,3,4,5-tetrahydro-2,6-methanobenzo[d]azocin-6(1H)-yl)ethyl)-L-valine;

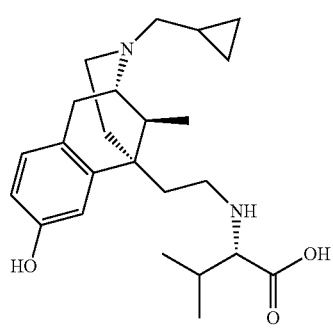

(2-((2S,6S,11S)-3-(cyclopropylmethyl)-8-hydroxy-11-methyl-2,3,4,5-tetrahydro-2,6-methanobenzo[d]azocin-6(1H)-yl)ethyl)-L-valine;

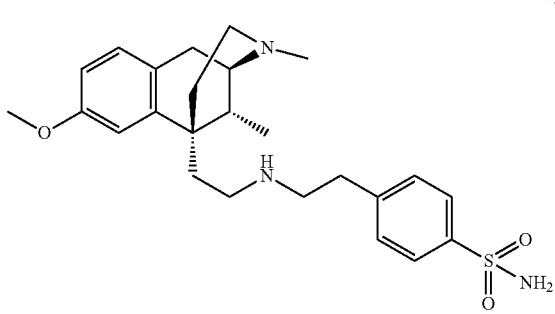

4-(2-((2-((2R,6R,11R)-8-methoxy-3,11-dimethyl-2,3,4,5-tetrahydro-2,6-methanobenzo[d]azocin-6(1H)-yl)ethyl)amino)ethyl)benzenesulfonamide;

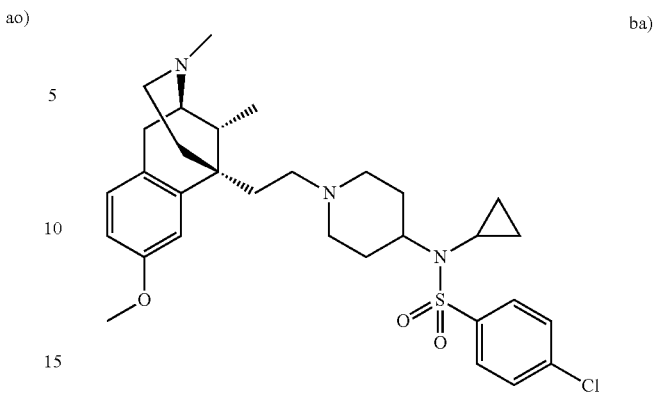

4-Chloro-N-cyclopropyl-N-(1-(2-((2R,6R,11R)-8-methoxy-3,11-dimethyl-2,3,4,5-tetrahydro-2,6-methanobenzo[d]azocin-6(1H)-yl)ethyl)piperidin-4-yl)benzenesulfonamide;

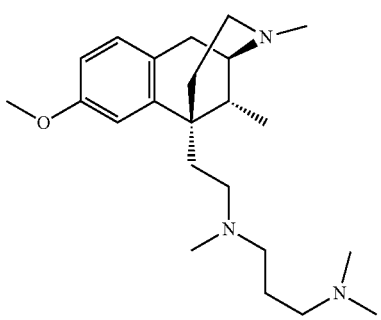

$N^1$-(2-((2R,6R,11R)-8-methoxy-3,11-dimethyl-2,3,4,5-tetrahydro-2,6-methano-benzo[d]azocin-6(1H)-yl)ethyl)-$N^1$,$N^3$,$N^3$-trimethylpropane-1,3-diamine;

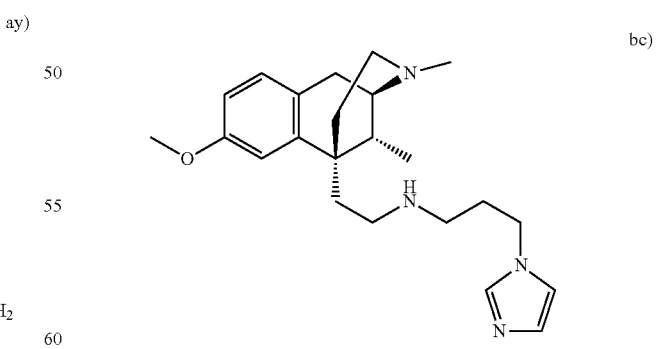

3-(1H-imidazol-1-yl)-N-(2-((2R,6R,11R)-8-methoxy-3,11-dimethyl-2,3,4,5-tetrahydro-2,6-methanobenzo[d]azocin-6(1H)-yl)ethyl)propan-1-amine;

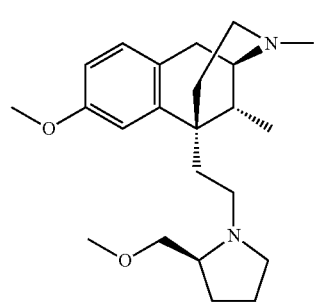

(2R,6S,11R)-8-methoxy-6-(2-((S)-2-(methoxymethyl)
pyrrolidin-1-yl)ethyl)-3,11-dimethyl-1,2,3,4,5,6-hexa-
hydro-2,6-methanobenzo[d]azocine;      bd)

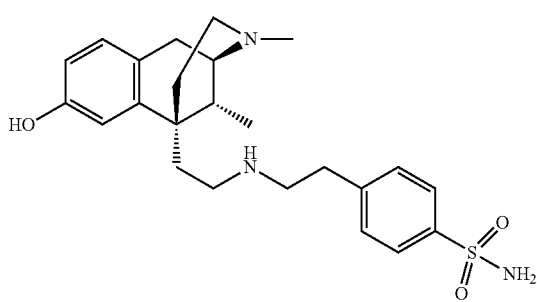

4-(2-((2-((2R,6R,11R)-8-hydroxy-3,11-dimethyl-2,3,4,5-
tetrahydro-2,6-methano-benzo[d]azocin-6(1H)-yl)
ethyl)amino)ethyl)benzenesulfonamide;      bg)

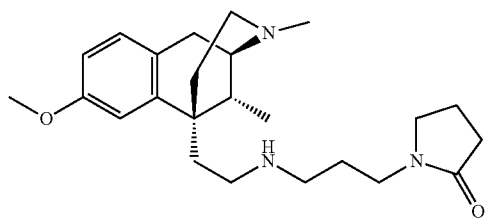

1-(3-((2-((2R,6R,11R)-8-methoxy-3,11-dimethyl-2,3,4,5-
tetrahydro-2,6-methanobenzo-[d]azocin-6(1H)-yl)
ethyl)amino)propyl)pyrrolidin-2-one;      be)

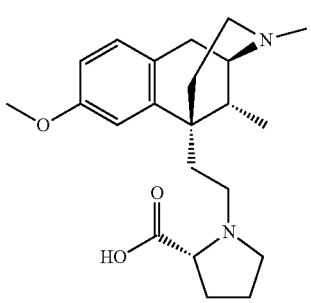

(2-((2R,6S,11R)-8-methoxy-3,11-dimethyl-2,3,4,5-tetra-
hydro-2,6-methanobenzo-[d]azocin-6(1H)-yl)ethyl)-
D-proline;      bh)

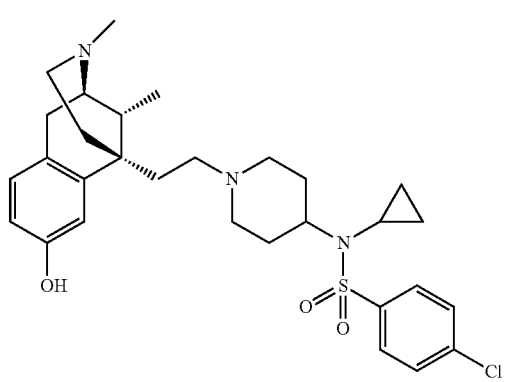

4-Chloro-N-cyclopropyl-N-(1-(2-((2R,6R,11R)-8-hy-
droxy-3,11-dimethyl-2,3,4,5-tetrahydro-2,6-metha-
nobenzo[d]azocin-6(1H)-yl)ethyl)piperidin-4-yl)ben-
zene-sulfonamide;      bf)

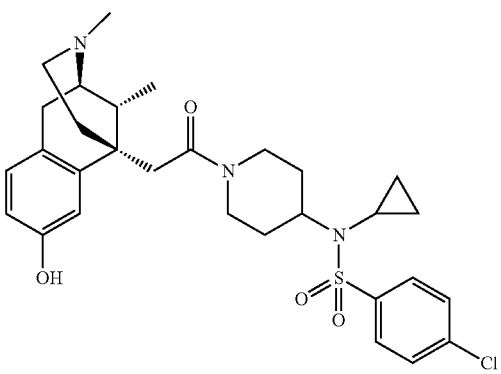

4-Chloro-N-cyclopropyl-N-(1-(2-((2R,6S, 11R)-8-hy-
droxy-3,11-dimethyl-2,3,4,5-tetrahydro-2,6-metha-
nobenzo[d]azocin-6(1H)-yl)acetyl)piperidin-4-yl)ben-
zenesulfonamide;      bi)

151 bj)

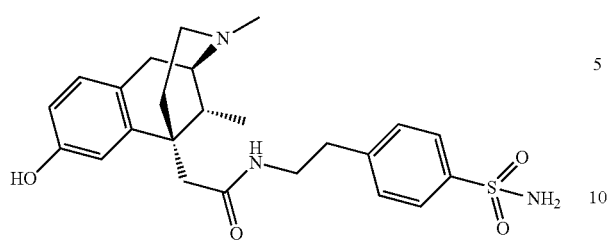

2-((2R,6S,11R)-8-hydroxy-3,11-dimethyl-2,3,4,5-tetra-
hydro-2,6-methanobenzo-[d]azocin-6(1H)-yl)-N-(4-
sulfamoylphenethyl)acetamide;

bk)

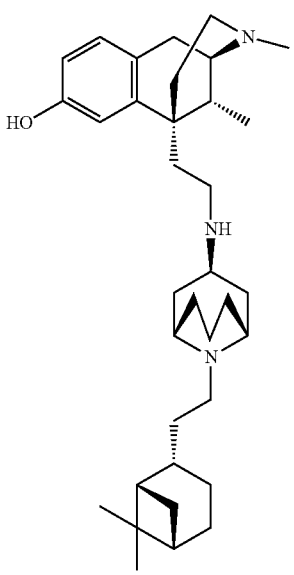

(2R,6R,11R)-6-(2-(((1R,3R,5S)-9-((1R,6S,8r)-bicyclo
[4.3.1]decan-8-yl)-9-azabicyclo[3.3.1]nonan-3-yl)
amino)ethyl)-3,11-dimethyl-1,2,3,4,5,6-hexahydro-2,
6-methanobenzo[d]azocin-8-ol;

bl)

152

(2R,6R,11R)-6-(2-(((1R,3S,5S)-9-(2-((1S,2S,5S)-6,6-di-
methylbicyclo[3.1.1]heptan-2-yl)ethyl)-9-azabicyclo
[3.3.1]nonan-3-yl)amino)ethyl)-3,11-dimethyl-1,2,3,4,
5,6-hexahydro-2,6-methanobenzo[d]azocin-8-ol;

bm)

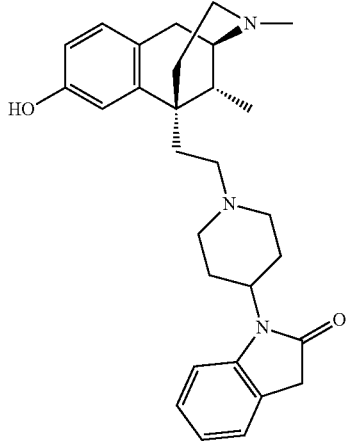

1-(1-(2-((2R,6R,11R)-8-hydroxy-3,11-dimethyl-2,3,4,5-
tetrahydro-2,6-methanobenzo[d]azocin-6(1H)-yl)
ethyl)piperidin-4-yl)indolin-2-one;

bn)

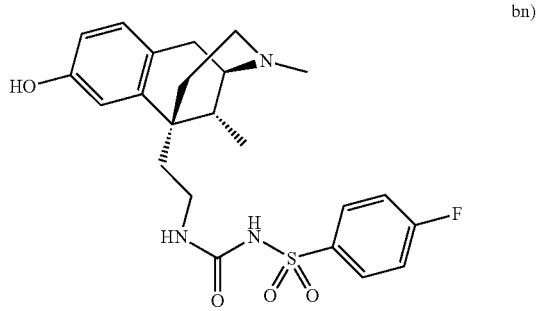

4-Fluoro-N-((2-((2R,6R,11R)-8-hydroxy-3,11-dimethyl-
2,3,4,5-tetrahydro-2,6-methanobenzo[d]azocin-6(1H)-
yl)ethyl)carbamoyl)benzenesulfonamide;

bo)

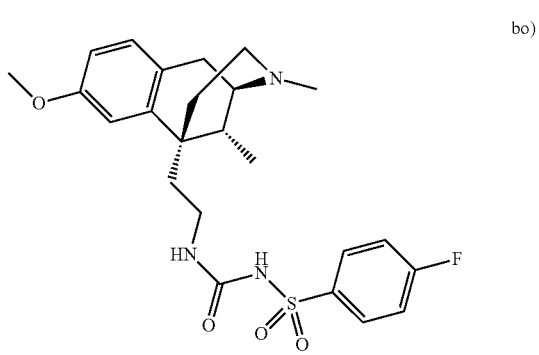

4-Fluoro-N-((2-((2R,6R,11R)-8-methoxy-3,11-dimethyl-
2,3,4,5-tetrahydro-2,6-methanobenzo[d]azocin-6(1H)-
yl)ethyl)carbamoy)benzenesulfonamide;

153

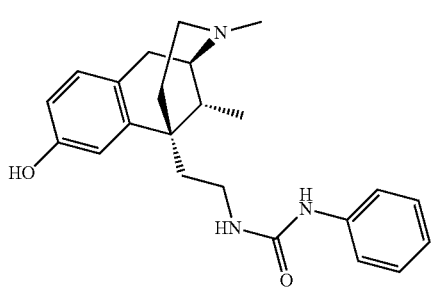 bp)

1-(2-((2R,6R,11R)-8-hydroxy-3,11-dimethyl-2,3,4,5-tetrahydro-2,6-methanobenzo[d]azocin-6(1H)-yl)ethyl)-3-phenylurea;

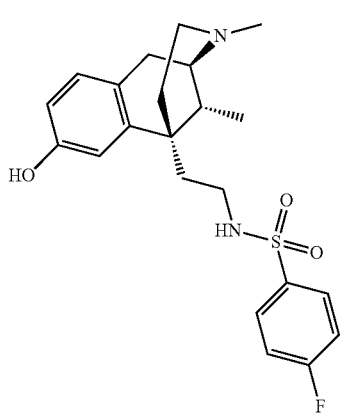 bq)

4-Fluoro-N-(2-((2R,6S,11R)-8-hydroxy-3,11-dimethyl-2,3,4,5-tetrahydro-2,6-methanobenzo[d]azocin-6(1H)-yl)ethyl)benzenesulfonamide;

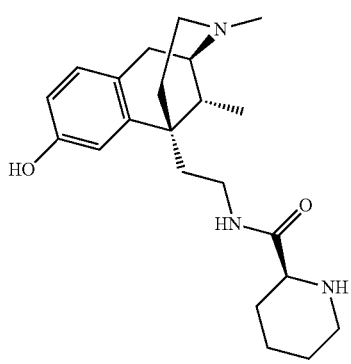 br)

(S)-N-(2-((2R,6R,11R)-8-hydroxy-3,11-dimethyl-2,3,4,5-tetrahydro-2,6-methano-benzo[d]azocin-6(1H)-yl)ethyl)piperidine-2-carboxamide;

154

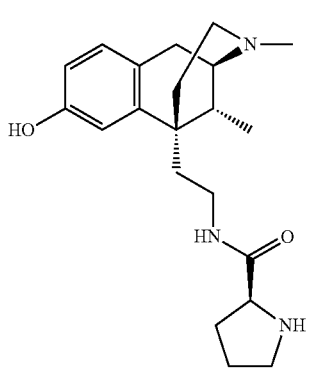 bs)

(S)-N-(2-((2R,6R,11R)-8-hydroxy-3,11-dimethyl-2,3,4,5-tetrahydro-2,6-methano-benzo[d]azocin-6(1H)-yl)ethyl)pyrrolidine-2-carboxamide;

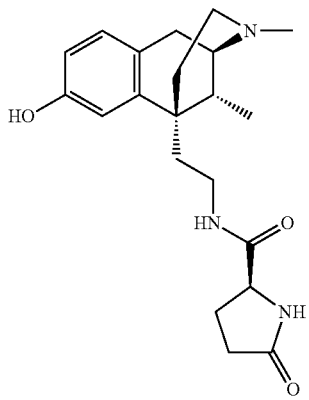 bt)

(S)-N-(2-((2R,6R,11R)-8-hydroxy-3,11-dimethyl-2,3,4,5-tetrahydro-2,6-methano-benzo[d]azocin-6(1H)-yl)ethyl)-5-oxopyrrolidine-2-carboxamide;

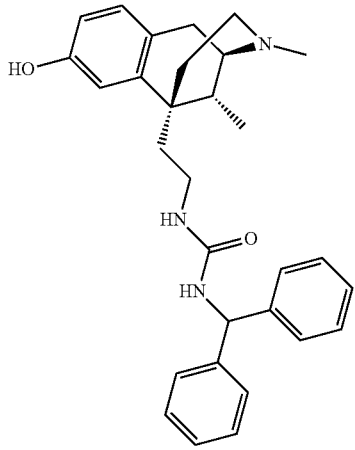 bu)

1-Benzhydryl-3-(2-((2R,6R,11R)-8-hydroxy-3,11-dimethyl-2,3,4,5-tetrahydro-2,6-methanobenzo[d]azocin-6(1H)-yl)ethyl)urea;

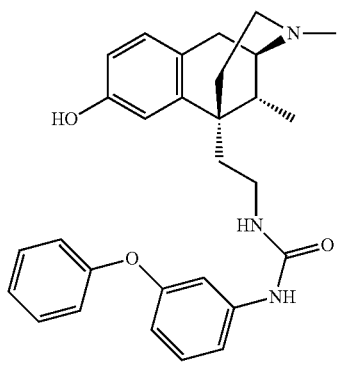

bv)

1-(2-((2R,6R,11R)-8-hydroxy-3,11-dimethyl-2,3,4,5-tetrahydro-2,6-methanobenzo-[d]azocin-6(1H)-yl)ethyl)-3-(3-phenoxyphenyl)urea;

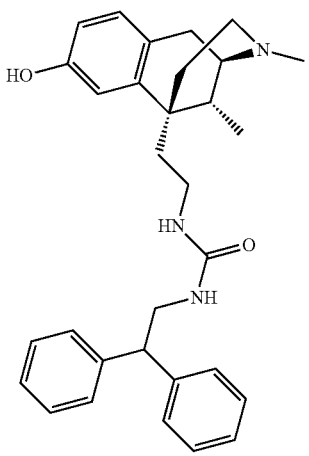

by)

1-(2,2-Diphenylethyl)-3-(2-((2R,6R,11R)-8-hydroxy-3,11-dimethyl-2,3,4,5-tetrahydro-2,6-methanobenzo[d]azocin-6(1H)-yl)ethyl)urea;

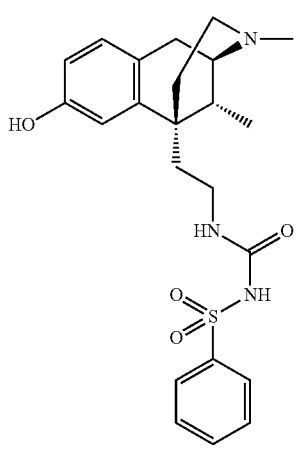

bw)

N-((2-((2R,6R,11R)-8-hydroxy-3,11-dimethyl-2,3,4,5-tetrahydro-2,6-methanobenzo[d]azocin-6(1H)-yl)ethyl)carbamoyl) benzenesulfonamide;

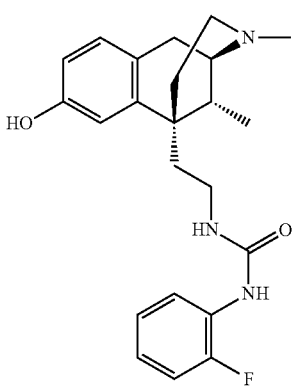

bz)

1-(2-Fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea;

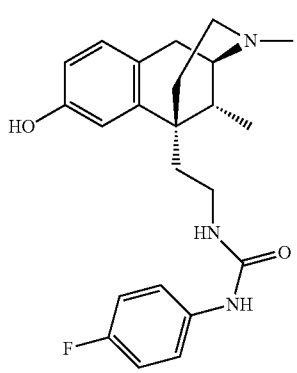

bx)

1-(4-Fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea;

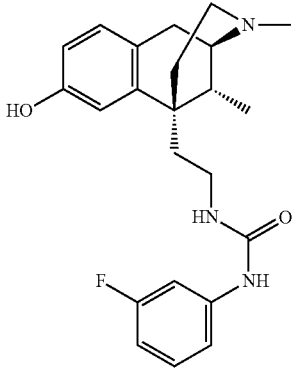

ca)

1-(3-Fluorophenyl)-3-(2-((2R,6R,11R)-8-hydroxy-3,11-dimethyl-2,3,4,5-tetrahydro-2,6-methanobenzo[d]azocin-6(1H)-yl)ethyl)urea;

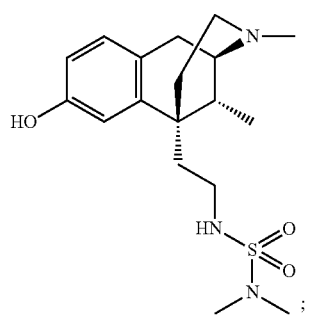

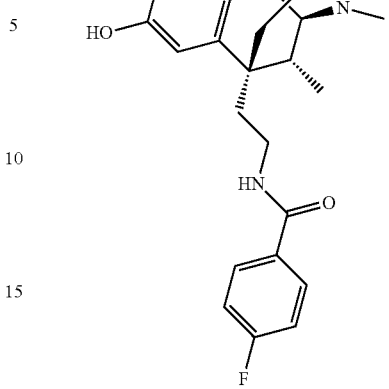

4-Fluoro-N-(2-((2R,6R,11R)-8-hydroxy-3,11-dimethyl-2,3,4,5-tetrahydro-2,6-methanobenzo[d]azocin-6(1H)-yl)ethyl)benzamide;

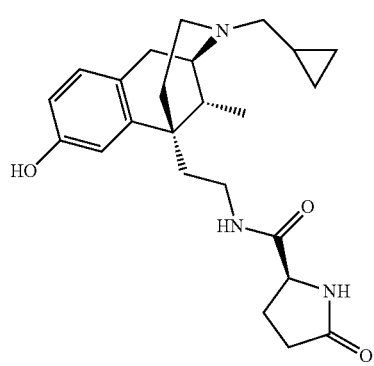

(S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-5-oxopyrrolidine-2-carboxamide;

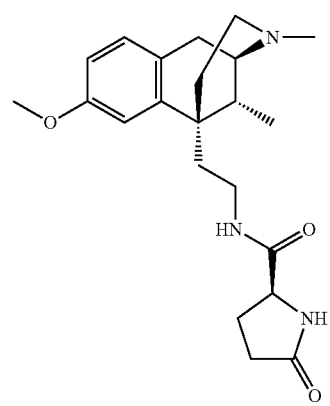

(S)-N-(2-((2R,6R,11R)-8-methoxy-3,11-dimethyl-2,3,4,5-tetrahydro-2,6-methano-benzo[d]azocin-6(1H)-yl)ethyl)-5-oxopyrrolidine-2-carboxamide;

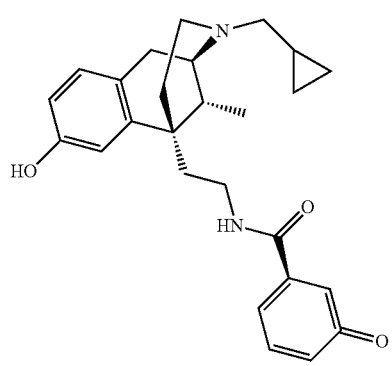

(S)-N-(2-((2R,6R,11R)-3-(cyclopropylmethyl)-8-hydroxy-11-methyl-2,3,4,5-tetrahydro-2,6-methanobenzo[d]azocin-6(1H)-yl)ethyl)-6-oxopiperidine-2-carboxamide;

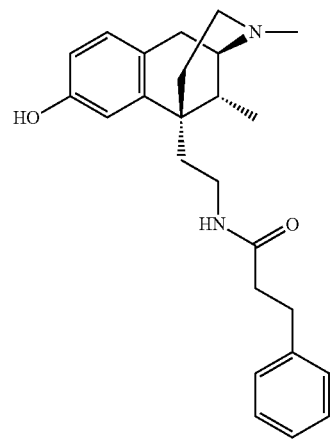

N-(2-((2R,6R,11R)-8-hydroxy-3,11-dimethyl-2,3,4,5-tetrahydro-2,6-methanobenzo[d]azocin-6(1H)-yl)ethyl)-3-phenylpropanamide; and

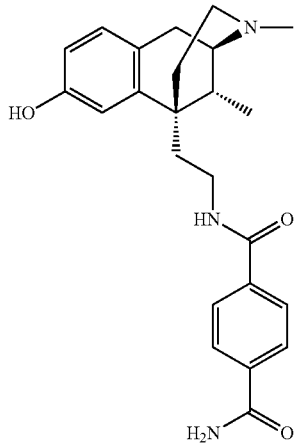

N-(2-((2R,6R,11R)-8-hydroxy-3,11-dimethyl-2,3,4,5-tetrahydro-2,6-methanobenzo-[d]azocin-6(1H)-yl)ethyl)terephthalamide;

and pharmaceutically acceptable salts or solvates thereof.

17. A pharmaceutical composition comprising an effective amount of a compound of claim 1, or a pharmaceutically acceptable salt or solvate thereof, and a pharmaceutically acceptable carrier or excipient.

18. A method for modulating opioid receptor function in a cell, comprising contacting a cell capable of expressing an opioid receptor with an effective amount of a compound of claim 1, or a pharmaceutically acceptable salt or solvate thereof, wherein said opioid receptor is an μ-opioid receptor, an κ-opioid receptor, or ORL-1 receptor.

19. A method of treating a Condition in a mammal, comprising administering to such mammal in need thereof an effective amount of a compound of claim 1, or a pharmaceutically acceptable salt or solvate thereof, wherein said Condition is pain or constipation.

20. The method of claim 19, wherein the Condition is pain, wherein said pain is acute pain, chronic pain or surgical pain, and said chronic pain is neuropathic pain, postoperative pain, or inflammatory pain.

21. A pharmaceutical composition comprising an effective amount of a compound of claim 16, or a pharmaceutically acceptable salt or solvate thereof, and a pharmaceutically acceptable carrier or excipient.

22. A method for modulating opioid receptor function in a cell, comprising contacting a cell capable of expressing an opioid receptor with an effective amount of a compound of claim 16, or a pharmaceutically acceptable salt or solvate thereof, wherein said opioid receptor is an μ-opioid receptor, an κ-opioid receptor, or ORL-1 receptor.

23. A method of treating a Condition in a mammal, comprising administering to such mammal in need thereof an effective amount of a compound of claim 16, or a pharmaceutically acceptable salt or solvate thereof, wherein said Condition is pain or constipation.

* * * * *